(12) United States Patent
Rapp et al.

(10) Patent No.: US 7,312,374 B2
(45) Date of Patent: Dec. 25, 2007

(54) PRODUCTION OF A TRANSGENIC AVIAN BY CYTOPLASMIC INJECTION

(75) Inventors: Jeffrey C. Rapp, Athens, GA (US); Leandro Christmann, Watkinsville, GA (US)

(73) Assignee: AviGenics, Inc, Athens, GA (US)

( * ) Notice: Subject to any disclaimer, the term of this patent is extended or adjusted under 35 U.S.C. 154(b) by 187 days.

(21) Appl. No.: 10/251,364

(22) Filed: Sep. 18, 2002

(65) Prior Publication Data

US 2003/0126629 A1 Jul. 3, 2003

Related U.S. Application Data

(60) Provisional application No. 60/322,969, filed on Sep. 18, 2001, provisional application No. 60/351,550, filed on Jan. 25, 2002.

(51) Int. Cl.
C12N 15/00 (2006.01)
A01K 67/027 (2006.01)
(52) U.S. Cl. .......................... 800/21; 800/19
(58) Field of Classification Search .................. 800/21, 800/19
See application file for complete search history.

(56) References Cited

U.S. PATENT DOCUMENTS

| | | | |
|---|---|---|---|
| 4,997,763 | A | 3/1991 | Hughes et al. |
| 5,011,780 | A | 4/1991 | Perry |
| 5,162,215 | A | 11/1992 | Bosselman et al. |
| 5,175,384 | A | 12/1992 | Krimpenfort et al. |
| 5,340,740 | A | 8/1994 | Petitte et al. |
| 5,656,479 | A | 8/1997 | Petitte et al. |
| 5,731,178 | A | 3/1998 | Sippel et al. |
| 6,027,722 | A | 2/2000 | Hodgson |
| 6,423,488 | B1 | 7/2002 | Harvey |
| 6,573,097 | B2 * | 6/2003 | Cantrell et al. ............. 435/349 |
| 6,730,822 | B1 * | 5/2004 | Ivarie et al. ................... 800/19 |
| 2002/0108132 | A1 | 8/2002 | Rapp |
| 2002/0116732 | A1 | 8/2002 | Christmann |
| 2002/0199214 | A1 | 12/2002 | Rapp |
| 2003/0126628 | A1 | 7/2003 | Harvey et al. |
| 2003/0140363 | A1 | 7/2003 | Rapp |

FOREIGN PATENT DOCUMENTS

| | | |
|---|---|---|
| WO | WO87/05325 A1 | 9/1987 |
| WO | WO90/11355 A1 | 10/1990 |
| WO | WO97/47739 A1 | 12/1997 |
| WO | WO99/10505 A2 | 3/1999 |
| WO | WO99/19472 A1 | 4/1999 |
| WO | WO99/42569 A1 | 8/1999 |
| WO | WO 00/09674 A1 | 2/2000 |
| WO | WO 00/69257 A2 | 11/2000 |
| WO | WO 0220752 A2 | 3/2002 |
| WO | WO 02/064727 A3 | 8/2002 |
| WO | WO 02/079447 A2 | 10/2002 |

OTHER PUBLICATIONS

On-line Medical Dictionary definition of "transgenic".*
Vick, Proc. R. Soc. Lond., 1993, vol. 251, p. 179-182.*
Love, Bio/Technology, 1994, vol. 12, p. 60-63.*
Tanaka (1994, J. Reprod. Fert., vol. 100, p. 447-449).*
Thoraval, Transgenic Research, 1995, vol. 4, p. 369-376).*
Sayegh, Dec. 15, 1999, vol. 72, p. 31-37.*
Mohammed (1998, Immunotechnology, vol. 4, p. 115-125).*
Ishida (2002, Cloning Stem Cells, vol. 4, p. 91-102).*
Harvey (Nature Biotech, Apr. 2002, vol. 19, p. 396-399).*
Ivarie (Trends in Biotechnology, Jan. 2003, vol. 21, p. 14-19).*
Naito (Transgenic Animals: Generation and Use, Ed. By Louis Marie Houdebine, Harwood Academic Publishers, p. 69-73).*
Table of Bird Classification/Families of the Eastern US Birds.*
Harvey (Feb. 2002, Poultry Sci. vol. 81, p. 202-212).*
Mizuarai (Biochemical and Biophysical Res. Comm. Aug. 24, 2001, vol. 286, p. 456-463).*
Proudman, 2001, "The quest for transgenic poultry: birds are not mice with feathers" Biotechnology in Animal Husbandry, vol. 5, Kluwer Academic Publishers, p. 283-299.*
Harvey (Poultry Sci. 2002, vol. 81, p. 202-212).*
Bachiller et al. Liposome-mediated DNA uptake by sperm cells. *Molecular Reproduction and Development*. 1991, 30:194-200, Wiley-Liss, Inc.
Baldari et al., A novel leader peptide which allows efficient secretion of a fragment of human interleukin 1β in *Saccharomyces cerevisiae E.M.B.O.J.*, 1987, 6:229-234.
Cibelli et al. Cloned transgenic calves produced from nonquiescent fetal fibroblasts. *Science*. May 22, 1998; 280:1256-1258.
Collas et al., Nuclear localization signals enhance germline transmission of a transgene in zebrafish, 1998, *Transgenic Research* 7, 303-309.
Etches et al. Strategies for the production of transgenic chickens. *Methods Mol Biol.* 1997;62:433-50.
Eyestone and Campbell. Nuclear transfer from somatic cells: applications in farm animal species. *J. Reprod Fertil Suppl.* 1999;54:489-97.

(Continued)

*Primary Examiner*—Michael C. Wilson
(74) *Attorney, Agent, or Firm*—Kyle D. Yesland

(57) ABSTRACT

This invention provides methods for the stable introduction of heterologous coding sequences into the genome of a bird and expressing the coding sequences to produce desired proteins or to alter the phenotype of the bird. The present invention provides preferred methods for introducing a transgene into the cytoplasm of avian embryonic cells by cytoplasmic microinjection. The embryo then develops into a transgenic adult capable of expressing a heterologous protein and/or capable of generating a line of transgenic birds through breeding. Synthetic vectors and gene promoters useful in the methods are also provided by the present invention, as are transgenic birds that express heterologous protein and avian eggs containing heterologous protein.

41 Claims, 43 Drawing Sheets

OTHER PUBLICATIONS

Eyal-Giladi H. From Cleavage to Primitive Streak Formation: A Complementary Normal Table and a New Look at the First Stages of the Development of the Chick. 1976; *Dev. Biol.*, 49:321-337.

Furuta et al. Proliferation of exogenously injected primordial germ cells (PGCs) into busulfan-treated chicken embryos. *Asian J Androl.* Dec. 1999;1(4):187-90.

Gagne et al. Electroporation of Bovine Spermatozoa to carry foreign DNA in oocytes. 1991 *Mol. Reprod. Dev.* 29: 6-15.

Gilbert and Wood-Gush, A technique for the fistulation of the hen's oviduct through the abdominal wall, with recovery of the ovum. *J. Reprod. Fertil.* 1963, 5:451-453.

Godbey, W. et al. Tracking the intracellular path of poly(ethylenimine)/DNA complexes for gene delivery. Apr. 1999, *Pro Natl Acad Sci USA* 96:5177-5181.

Jaenisch R. Retroviruses and Embryogenesis: Microinjection of Moloney Leukemia Virus into Midgestation Mouse Embryos. *Cell.* Jan. 1980;19(1):181-8.

Lechardeur, D. et al. (1999) Metabolic instability of plasmid DNA in the cytosol: a potential barrier to gene transfer *Gene Ther.* 6:482-97.

Li et al. Ballistic transfection of avian primordial germ cell *in ovo*. *Transgenic Research* 1995, 4:26-9.

Love, et. al. Transgenic Birds by DNA Microinjection. *Bio/Technology.* Jan. 1994; 12:60-63.

Mueller et al. Chimeric pigs following blastocyst injection of transgenic porcine primordial germ cells. *Molecular Reproduction and Development.* 1999, 54:244-254.

Muramatsu et al. Gene gun-mediated in vivo analysis of tissue-specific repression of gene transcription driven by the chicken ovalbumin promoter in the liver and oviduct of laying hens. *Mol Cell Biochem.* Aug. 1998; 185(1-2):27-32.

Naito et al. Introduction of exogenous DNA into somatic and germ cells of chickens by microinjection into the germinal disc of fertilized ova. *Molecular Reproduction and Development.* 1994, 37:167-171.

Naito et al. Production of germline chimeric chickens, with high transmission rate of donor-derived gametes, produced by transfer of primordial germ cells. *Mol Reprod Dev.* Oct. 1994;39 (2):153-61.

Nakanishi and Iritani, Gene transfer in the chicken by sperm-mediated methods. *Molecular Reproduction and Development.* 1993, 36:258-261.

Olsen &Neher, The site of fertilization in the domestic fowl. *J. Exp. Zoo* 1948, 109:355-366.

Page et al. "Transgenesis in mice by cytoplasmic injection of polylysine/DNA mixtures"; *Transgenic Research*, 1995;vol. 4, pp. 353-360.

Pancer et al. Recovery of ova and their re-insertion into the hen's oviduct through a fistula. *Br Poult Sci.* Dec. 1989; 30(4):953-7.

Phi-Van and Stratling, The matrix attachment regions of the chicken lysozyme gene co-map with the boundaries of the chromatin domain. 1988; *E.M.B.O.J.* 7(3): 655-664.

Pollard H., et al., Polyethylenimine but Not Cationic Lipids Promotes Transgene Delivery to the Nucleus in Mammalian Cells*. *J. Biol chem.*, 1998, 273: 7507-11.

Sang and Perry. Episomal Replication of Cloned DNA Injected into the Fertilised Ovum of the Hen, *Gallus domesticus. Mol. Reprod and Devlp.*1989, 1:98-106.

Schiest RH, Petes TD. Integration of DNA fragments by illegitimate recombination in *Saccharomyces cerevisiae. Proc Natl Acad Sci U S A.* Sep. 1, 1991;88(17):7585-9.

Tanaka et al. Chick production by in vitro fertilization of the fowl ovum. *J Reprod Fertil.* 1994, 100:447-449.

Harvey, Validating the hen as a bioreactor for the production of exogenous . . . , Poultry Science, vol. 82, No. 6 p. 927-930 (2003).

Jeong et al., Migration activity of chicken gonadal primordial germ . . . , Asian-Australasian Jounal Animal Sciences vol. 15, No. 9 p. 1227-1231 (2002).

Lampard et al., Secretion of foreign proteins mediated by chicken . . . Biochem. Cell Biol, vol. 80 No. 6 p. 777-788 (2002).

Park et al., Birth of Germline chimeras by transfer of chicken embryonic.. Molecular Reproduction and Development vol. 65, No. 4 p. 389-395 (2003).

* cited by examiner

SEQ ID NO: 6

```
TGCCGCCTTC TTTGATATTC ACTCTGTTGT ATTTCATCTC TTCTTGCCGA TGAAAGGATA  60
TAACAGTCTG TATAACAGTC TGTGAGGAAA TACTTGGTAT TTCTTCTGAT CAGTGTTTTT 120
ATAAGTAATG TTGAATATTG GATAAGGCTG TGTGTCCTTT GTCTTGGGAG ACAAAGCCCA 180
CAGCAGGTGG TGGTTGGGGT GGTGGCAGCT CAGTGACAGG AGAGGTTTTT TTGCCTGTTT 240
TTTTTTTTTT TTTTTTTTTT AAGTAAGGTG TTCTTTTTTC TTAGTAAATT TTCTACTGGA 300
CTGTATGTTT TGACAGGTCA GAAACATTTC TTCAAAAGAA GAACCTTTTG GAAACTGTAC 360
AGCCCTTTTC TTTCATTCCC TTTTTGCTTT CTGTGCCAAT GCCTTTGGTT CTGATTGCAT 420
TATGGAAAAC GTTGATCGGA ACTTGAGGTT TTTATTTATA GTGTGGCTTG AAAGCTTGGA 480
TAGCTGTTGT TACACGAGAT ACCTTATTAA GTTAGGCCA GCTTGATGCT TTATTTTTC 540
CCTTTGAAGT AGTGAGCGTT CTCTGGTTTT TTTCCTTTGA AACTGGTGAG GCTTAGATTT 600
TTCTAATGGG ATTTTTTACC TGATGATCTA GTTGCATACC CAAATGCTTG TAAATGTTTT 660
CCTAGTTAAC ATGTTGATAA CTTCGGATTT ACATGTTGTA TATACTTGTC ATCTGTGTTT 720
CTAGTAAAAA TATATGGCAT TTATAGAAAT ACGTAATTCC TGATTTCCTT TTTTTTTATC 780
TCTATGCTCT GTGTGTACAG GTCAAACAGA CTTCACTCCT ATTTTTATTT ATAGAATTTT 840
ATATGCAGTC TGTCGTTGGT TCTTGTGTTG TAAGGATACA GCCTTAAATT TCCTAGAGCG 900
ATGCTCAGTA AGGCGGGTTG TCACATGGGT TCAAATGTAA AACGGGCACG TTTGGCTGCT 960
GCCTTCCCGA GATCCAGGAC ACTAAACTGC TTCTGCACTG AGGTATAAAT CGCTTCAGAT 1020
CCCAGGGAAG TGCAGATCCA CGTGCATATT CTTAAAGAAG AATGAATACT TTCTAAAATA 1080
TTTTGGCATA GGAAGCAAGC TGCATGGATT TGTTGGGAC TTAAATTATT TTGGTAACGG 1140
AGTGCATAGG TTTTAAACAC AGTTGCAGCA TGCTAACGAG TCACAGCGTT TATGCAGAAG 1200
TGATGCCTGG ATGCCTGTTG CAGCTGTTTA CGGCACTGCC TTGCAGTGAG CATTGCAGAT 1260
AGGGGTGGGG TGCTTTGTGT CGTGTTCCCA CACGCTGCCA CACAGCCACC TCCCGGAACA 1320
CATCTCACCT GCTGGGTACT TTTCAAACCA TCTTAGCAGT AGTAGATGAG TTACTATGAA 1380
ACAGAGAAGT TCCTCAGTTG GATATTCTCA TGGGATGTCT TTTTTCCCAT GTTGGGCAAA 1440
GTATGATAAA GCATCTCTAT TTGTAAATTA TGCACTTGTT AGTTCCTGAA TCCTTTCTAT 1500
AGCACCACTT ATTGCAGCAG GTGTAGGCTC TGGTGTGGCC TGTGTCTGTG CTTCAATCTT 1560
TTAAAGCTTC TTTGGAAATA CACTGACTTG ATTGAAGTCT CTTGAAGATA GTAAACAGTA 1620
CTTACCTTTG ATCCCAATGA AATCGAGCAT TTCAGTTGTA AAAGAATTCC GCCTATTCAT 1680
ACCATGTAAT GTAATTTTAC ACCCCAGTG CTGACACTTT GGAATATATT CAAGTAATAG 1740
ACTTTGGCCT CACCCTCTTG TGTACTGTAT TTTGTAATAG AAAATATTTT AAACTGTGCA 1800
TATGATTATT ACATTATGAA AGAGACATTC TGCTGATCTT CAAATGTAAG AAAATGAGGA 1860
GTGCGTGTGC TTTTATAAAT ACAAGTGATT GCAAATTAGT GCAGGTGTCC TTAAAAAAAA 1920
AAAAAAAAG TAATATAAAA AGGACCAGGT GTTTTACAAG TGAAATACAT TCCTATTTGG 1980
TAAACAGTTA CATTTTATG AAGATTACCA GCGCTGCTGA CTTTCTAAAC ATAAGGCTGT 2040
ATTGTCTTCC TGTACCATTG CATTTCCTCA TTCCCAATTT GCACAAGGAT GTCTGGGTAA 2100
ACTATTCAAG AAATGGCTTT GAAATACAGC ATGGAGCTT GTCTGAGTTG GAATGCAGAG 2160
TTGCACTGCA AAATGTCAGG AAATGGATGT CTCTCAGAAT GCCCAACTCC AAAGGATTTT 2220
ATATGTGTAT ATAGTAAGCA GTTTCCTGAT TCCAGCAGGC CAAAGAGTCT GCTGAATGTT 2280
GTGTTGCCGG AGACCTGTAT TTCTAACAA GGTAAGATGG TATCCTAGCA ACTGCGGATT 2340
TTAATACATT TCAGCAGAA GTACTTAGTT AATCTCTACC TTTAGGGATC GTTTCATCAT 2400
TTTTAGATGT TATACTTGAA ATACTGCATA ACTTTTAGCT TTCATGGGTT CCTTTTTTTC 2460
AGCCTTTAGG AGACTGTTAA GCAATTGCT GTCCAACTTT TGTGTTGGTC TTAAACTGCA 2520
ATAGTAGTTT ACCTTGTATT GAAGAAATAA AGACCATTT TATATTAAAA AATACTTTTG 2580
TCTGTCTTCA TTTTGACTTG TCTGATATCC TTGCAGTGCC CATTATGTCA GTTCTGTCAG 2640
ATATTCAGAC ATCAAAACTT AACGTGAGCT CAGTGGAGTT ACAGCTGCGG TTTTGATGCT 2700
```

FIG. 1A

```
GTTATTATTT CTGAAACTAG AAATGATGTT GTCTTCATCT GCTCATCAAA CACTTCATGC 2760
AGAGTGTAAG GCTAGTGAGA AATGCATACA TTTATTGATA CTTTTTTAAA GTCAACTTTT 2820
TATCAGATTT TTTTTTCATT TGGAAATATA TTGTTTTCTA GACTGCATAG CTTCTGAATC 2880
TGAAATGCAG TCTGATTGGC ATGAAGAAGC ACAGCACTCT TCATCTTACT TAAACTTCAT 2940
TTTGGAATGA AGGAAGTTAA GCAAGGGCAC AGGTCCATGA AATAGAGACA GTGCGCTCAG 3000
GAGAAAGTGA ACCTGGATTT CTTTGGCTAG TGTTCTAAAT CTGTAGTGAG GAAAGTAACA 3060
CCCGATTCCT TGAAAGGGCT CCAGCTTTAA TGCTTCCAAA TTGAAGGTGG CAGGCAACTT 3120
GGCCACTGGT TATTTACTGC ATTATGTCTC AGTTTCGCAG CTAACCTGGC TTCTCCACTA 3180
TTGAGCATGG ACTATAGCCT GGCTTCAGAG GCCAGGTGAA GGTTGGGATG GGTGGAAGGA 3240
GTGCTGGGCT GTGGCTGGGG GGACTGTGGG GACTCCAAGC TGAGCTTGGG GTGGGCAGCA 3300
CAGGGAAAAG TGTGGGTAAC TATTTTAAG TACTGTGTTG CAAACGTCTC ATCTGCAAAT 3360
ACGTAGGGTG TGTACTCTCG AAGATTAACA GTGTGGGTTC AGTAATATAT GGATGAATTC 3420
ACAGTGGAAG CATTCAAGGG TAGATCATCT AACGACACCA GATCATCAAG CTATGATTGG 3480
AAGCGGTATC AGAAGAGCGA GGAAGGTAAG CAGTCTTCAT ATGTTTCCC TCCACGTAAA 3540
GCAGTCTGGG AAAGTAGCAC CCCTTGAGCA GAGACAAGGA AATAATTCAG GAGCATGTGC 3600
TAGGAGAACT TCTTGCTGA ATTCTACTTG CAAGAGCTTT GATGCCTGGC TTCTGGTGCC 3660
TTCTGCAGCA CCTGCAAGGC CCAGAGCCTG TGGTGAGCTG GAGGGAAAGA TTCTGCTCAA 3720
GTCCAAGCTT CAGCAGGTCA TTGTCTTTGC TTCTTCCCCC AGCACTGTGC AGCAGAGTGG 3780
AACTGATGTC GAAGCCTCCT GTCCACTACC TGTTGCTGCA GGCAGACTGC TCTCAGAAAA 3840
AGAGAGCTAA CTCTATGCCA TAGTCTGAAG GTAAATGGG TTTTAAAAAA GAAAACACAA 3900
AGGCAAAACC GGCTGCCCCA TGAGAAGAAA GCAGTGGTAA ACATGGTAGA AAAGGTGCAG 3960
AAGCCCCCAG GCAGTGTGAC AGGCCCCTCC TGCCACCTAG AGGCGGGAAC AAGCTTCCCT 4020
GCCTAGGGCT CTGCCCGCGA AGTGCGTGTT TCTTTGGTGG GTTTTGTTTG GCGTTTGGTT 4080
TTGAGATTTA GACACAAGGG AAGCCTGAAA GGAGGTGTTG GCACTATTT TGGTTTGTAA 4140
AGCCTGTACT TCAAATATAT ATTTTGTGAG GGAGTGTAGC GAATTGGCCA ATTTAAAATA 4200
AAGTTGCAAG AGATTGAAGG CTGAGTAGTT GAGAGGGTAA CACGTTTAAT GAGATCTTCT 4260
GAAACTACTG CTTCTAAACA CTTGTTTGAG TGGTGAGACC TTGGATAGGT GAGTGCTCTT 4320
GTTACATGTC TGATGCACTT GCTTGTCCTT TTCCATCCAC ATCCATGCAT TCCACATCCA 4380
CGCATTTGTC ACTTATCCCA TATCTGTCAT ATCTGACATA CCTGTCTCTT CGTCACTTGG 4440
TCAGAAGAAA CAGATGTGAT AATCCCCAGC CGCCCCAAGT TTGAGAAGAT GGCAGTTGCT 4500
TCTTTCCCTT TTTCCTGCTA AGTAAGGATT TTCCTCTGGC TTTGACACCT CACGAAATAG 4560
TCTTCCTGCC TTACATTCTG GGCATTATTT CAAATATCTT TGGAGTGCGC TGCTCTCAAG 4620
TTTGTGTCTT CCTACTCTTA GAGTGAATGC TCTTAGAGTG AAAGAGAAGG AAGAGAAGAT 4680
GTTGGCCGCA GTTCTCTGAT GAACACACCT CTGAATAATG GCCAAAGGTG GGTGGGTTTC 4740
TCTGAGGAAC GGGCAGCGTT TGCCTCTGAA AGCAAGGAGC TCTGCGGAGT TGCAGTTATT 4800
TTGCAACTGA TGGTGGAACT GGTGCTTAAA GCAGATTCCC TAGGTTCCCT GCTACTTCTT 4860
TTCCTTCTTG GCAGTCAGTT TATTTCTGAC AGACAAACAG CCACCCCAC TGCAGGCTTA 4920
GAAAGTATGT GGCTCTGCCT GGGTGTGTTA CAGCTCTGCC CTGGTGAAAG GGGATTAAAA 4980
CGGGCACCAT TCATCCCAAA CAGGATCCTC ATTCATGGAT CAAGCTGTAA GGAACTTGGG 5040
CTCCAACCTC AAAACATTAA TTGGAGTACG AATGTAATTA AAACTGCATT CTCGCATTCC 5100
TAAGTCATTT AGTCTGGACT CTGCAGCATG TAGGTCGGCA GCTCCACTT TCTCAAAGAC 5160
CACTGATGGA GGAGTAGTAA AAATGGAGAC CGATTCAGAA CAACCAACGG AGTGTTGCCG 5220
AAGAAACTGA TGGAAATAAT GCATGAATTG TGTGGTGGAC ATTTTTTTA AATACATAAA 5280
CTACTTCAAA TGAGGTCGGA GAAGGTCAGT GTTTTATTAG CAGCCATAAA ACCAGGTGAG 5340
CGAGTACCAT TTTTCTCTAC AAGAAAAACG ATTCTGAGCT CTGCGTAAGT ATAAGTTCTC 5400
```

FIG. 1B

```
CATAGCGGCT GAAGCTCCCC CCTGGCTGCC TGCCATCTCA GCTGGAGTGC AGTGCCATTT 5460
CCTTGGGGTT TCTCTCACAG CAGTAATGGG ACAATACTTC ACAAAAATTC TTTCTTTTCC 5520
TGTCATGTGG GATCCCTACT GTGCCCTCCT GGTTTTACGT TACCCCCTGA CTGTTCCATT 5580
CAGCGGTTTG GAAAGAGAAA AAGAATTTGG AAATAAAACA TGTCTACGTT ATCACCTCCT 5640
CCAGCATTTT GGTTTTTAAT TATGTCAATA ACTGGCTTAG ATTTGGAAAT GAGAGGGGGT 5700
TGGGTGTATT ACCGAGGAAC AAAGGAAGGC TTATATAAAC TCAAGTCTTT TATTTAGAGA 5760
ACTGGCAAGC TGTCAAAAAC AAAAAGGCCT TACCACCAAA TTAAGTGAAT AGCCGCTATA 5820
GCCAGCAGGG CCAGCACGAG GGATGGTGCA CTGCTGGCAC TATGCCACGG CCTGCTTGTG 5880
ACTCTGAGAG CAACTGCTTT GGAAATGACA GCACTTGGTG CAATTTCCTT TGTTTCAGAA 5940
TGCGTAGAGC GTGTGCTTGG CGACAGTTTT TCTAGTTAGG CCACTTCTTT TTTCCTTCTC 6000
TCCTCATTCT CCTAAGCATG TCTCCATGCT GGTAATCCCA GTCAAGTGAA CGTTCAAACA 6060
ATGAATCCAT CACTGTAGGA TTCTCGTGGT GATCAAATCT TTGTGTGAGG TCTATAAAAT 6120
ATGGAAGCTT ATTTATTTTT CGTTCTTCCA TATCAGTCTT CTCTATGACA ATTCACATCC 6180
ACCACAGCAA ATTAAGGTG AAGGAGGCTG GTGGGATGAA GAGGGTCTTC TAGCTTTACG 6240
TTCTTCCTTG CAAGGCCACA GGAAATGCT GAGAGCTGTA GAATACAGCC TGGGGTAAGA 6300
AGTTCAGTCT CCTGCTGGGA CAGCTAACCG CATCTTATAA CCCCTTCTGA GACTCATCTT 6360
AGGACCAAAT AGGGTCTATC TGGGGTTTTT GTTCCTGCTG TTCCTCCTGG AAGGCTATCT 6420
CACTATTTCA CTGCTCCCAC GGTTACAAAC CAAAGATACA GCCTGAATTT TTTCTAGGCC 6480
ACATTACATA AATTTGACCT GGTACCAATA TTGTTCTCTA TATAGTTATT TCCTTCCCCA 6540
CTGTGTTTAA CCCCTTAAGG CATTCAGAAC AACTAGAATC ATAGAATGGT TTGGATTGGA 6600
AGGGGCCTTA AACATCATCC ATTTCCAACC CTCTGCCATG GGCTGCTTGC CACCCACTGG 6660
CTCAGGCTGC CCAGGGCCCC ATCCAGCCTG GCCTTGAGCA CCTCCAGGGA TGGGGCACCC 6720
ACAGCTTCTC TGGGCAGCCT GTGCCAACAC CTCACCACTC TCTGGGTAAA GAATTCTCTT 6780
TTAACATCTA ATCTAAATCT CTTCTCTTTT AGTTAAAGC CATTCCTCTT TTTCCCGTTG 6840
CTATCTGTCC AAGAAATGTG TATTGGTCTC CCTCCTGCTT ATAAGCAGGA AGTACTGGAA 6900
GGCTGCAGTG AGGTCTCCCC ACAGCCTTCT CTTCTCCAGG CTGAACAAGC CAGCTCCTT 6960
CAGCCTGTCT TCGTAGGAGA TCATCTTAGT GGCCCTCCTC TGGACCCATT CCAACAGTTC 7020
CACGGCTTTC TTGTGGAGCC CCAGGTCTGG ATGCAGTACT TCAGATGGGG CCTTACAAAG 7080
GCAGAGCAGA TGGGACAAT CGCTTACCCC TCCCTGCTGG CTGCCCCTGT TTTGATGCAG 7140
CCCAGGGTAC TGTTGGCCTT TCAGGCTCCC AGACCCCTTG CTGATTTGTG TCAAGCTTTT 7200
CATCCACCAG AACCCACGCT TCCTGGTTAA TACTTCTGCC CTCACTTCTG TAAGCTTGTT 7260
TCAGGAGACT TCCATTCTTT AGGACAGACT GTGTTACACC TACCTGCCCT ATTCTTGCAT 7320
ATATACATTT CAGTTCATGT TCCTGTAAC AGGACAGAAT ATGTATTCCT CTAACAAAAA 7380
TACATGCAGA ATTCCTAGTG CCATCTCAGT AGGGTTTTCA TGGCAGTATT AGCACATAGT 7440
CAATTTGCTG CAAGTACCTT CCAAGCTGCG GCCTCCCATA AATCCTGTAT TTGGGATCAG 7500
TTACCTTTTG GGGTAAGCTT TTGTATCTGC AGAGACCCTG GGGGTTCTGA TGTGCTTCAG 7560
CTCTGCTCTG TTCTGACTGC ACCATTTTCT AGATCACCCA GTTGTTCCTG TACAACTTCC 7620
TTGTCCTCCA TCCTTTCCCA GCTTGTATCT TTGACAAATA CAGGCCTATT TTTGTGTTTG 7680
CTTCAGCAGC CATTTAATTC TTCAGTGTCA TCTTGTTCTG TTGATGCCAC TGGAACAGGA 7740
TTTTCAGCAG TCTTGCAAAG AACATCTAGC TGAAAACTTT CTGCCATTCA ATATTCTTAC 7800
CAGTTCTTCT TGTTTGAGGT GAGCCATAAA TTACTAGAAC TTCGTCACTG ACAAGTTTAT 7860
GCATTTATT ACTTCTATTA TGTACTTACT TTGACATAAC ACAGACACGC ACATATTTG 7920
CTGGGATTTC CACAGTGTCT CTGTGTCCTT CACATGGTTT TACTGTCATA CTTCCGTTAT 7980
AACCTTGGCA ATCTGCCCAG CTGCCCATCA CAAGAAAGA GATTCCTTTT TTATTACTTC 8040
```

FIG. 1C

```
TCTTCAGCCA ATAAACAAAA TGTGAGAAGC CCAAACAAGA ACTTGTGGGG CAGGCTGCCA 8100
TCAAGGGAGA GACAGCTGAA GGGTTGTGTA GCTCAATAGA ATTAAGAAAT AATAAAGCTG 8160
TGTCAGACAG TTTTGCCTGA TTTATACAGG CACGCCCCAA GCCAGAGAGG CTGTCTGCCA 8220
AGGCCACCTT GCAGTCCTTG GTTTGTAAGA TAAGTCATAG GTAACTTTTC TGGTGAATTG 8280
CGTGGAGAAT CATGATGGCA GTTCTTGCTG TTTACTATGG TAAGATGCTA AAATAGGAGA 8340
CAGCAAAGTA ACACTTGCTG CTGTAGGTGC TCTGCTATCC AGACAGCGAT GGCACTCGCA 8400
CACCAAGATG AGGGATGCTC CCAGCTGACG GATGCTGGGG CAGTAACAGT GGGTCCCATG 8460
CTGCCTGCTC ATTAGCATCA CCTCAGCCCT CACCAGCCCA TCAGAAGGAT CATCCCAAGC 8520
TGAGGAAAGT TGCTCATCTT CTTCACATCA TCAAACCTTT GGCCTGACTG ATGCCTCCCG 8580
GATGCTTAAA TGTGGTCACT GACATCTTTA TTTTTCTATG ATTTCAAGTC AGAACCTCCG 8640
GATCAGGAGG GAACACATAG TGGGAATGTA CCCTCAGCTC CAAGGCCAGA TCTTCCTTCA 8700
ATGATCATGC ATGCTACTTA GGAAGGTGTG TGTGTGTGAA TGTAGAATTG CCTTTGTTAT 8760
TTTTTCTTCC TGCTGTCAGG AACATTTTGA ATACCAGAGA AAAAGAAAAG TGCTCTTCTT 8820
GGCATGGGAG GAGTTGTCAC ACTTGCAAAA TAAAGGATGC AGTCCCAAAT GTTCATAATC 8880
TCAGGGTCTG AAGGAGGATC AGAAACTGTG TATACAATTT CAGGCTTCTC TGAATGCAGC 8940
TTTTGAAAGC TGTTCCTGGC CGAGGCAGTA CTAGTCAGAA CCCTCGGAAA CAGGAACAAA 9000
TGTCTTCAAG GTGCAGCAGG AGGAAACACC TTGCCCATCA TGAAAGTGAA TAACCACTGC 9060
CGCTGAAGGA ATCCAGCTCC TGTTTGAGCA GGTGCTGCAC ACTCCCACAC TGAAACAACA 9120
GTTCATTTTT ATAGGACTTC CAGGAAGGAT CTTCTTCTTA AGCTTCTTAA TTATGGTACA 9180
TCTCCAGTTG GCAGATGACT ATGACTACTG ACAGGAGAAT GAGGAACTAG CTGGGAATAT 9240
TTCTGTTTGA CCACCATGGA GTCACCCATT TCTTTACTGG TATTTGGAAA TAATAATTCT 9300
GAATTGCAAA GCAGGAGTTA GCAAGATCT TCATTTCTTC CATGTTGGTG ACAGCACAGT 9360
TCTGGCTATG AAAGTCTGCT ACAAGGAAG AGGATAAAAA TCATAGGGAT AATAAATCTA 9420
AGTTTGAAGA CAATGAGGTT TTAGCTGCAT TTGACATGAA GAAATTGAGA CCTCTACTGG 9480
ATAGCTATGG TATTTACGTG TCTTTTTGCT TAGTTACTTA TTGACCCCAG CTGAGGTCAA 9540
GTATGAACTC AGGTCTCTCG GGCTACTGGC ATGGATTGAT TACATACAAC TGTAATTTTA 9600
GCAGTGATTT AGGGTTTATG AGTACTTTTG CAGTAAATCA TAGGGTTAGT AATGTTAATC 9660
TCAGGGAAAA AAAAAAAAAG CCAACCCTGA CAGACATCCC AGCTCAGGTG GAAATCAAGG 9720
ATCACAGCTC AGTGCGGTCC CAGAGAACAC AGGGACTCTT CTCTTAGGAC CTTTATGTAC 9780
AGGGCCTCAA GATAACTGAT GTTAGTCAGA AGACTTTCCA TTCTGGCCAC AGTTCAGCTG 9840
AGGCAATCCT GGAATTTTCT CTCCGCTGCA CAGTTCCAGT CATCCCAGTT TGTACAGTTC 9900
TGGCACTTTT TGGGTCAGGC CGTGATCCAA GGAGCAGAAG TTCCAGCTAT GGTCAGGGAG 9960
TGCCTGACCG TCCCAACTCA CTGCACTCAA ACAAAGGCGA AACCACAAGA GTGGCTTTTG 10020
TTGAAATTGC AGTGTGGCCC AGAGGGGCTG CACCAGTACT GGATTGACCA CGAGGCAACA 10080
TTAATCCTCA GCAAGTGCAA TTTGCAGCCA TTAAATTGAA CTAACTGATA CTACAATGCA 10140
ATCAGTATCA ACAAGTGGTT TGGCTTGGAA GATGGAGTCT AGGGGCTCTA CAGGAGTAGC 10200
TACTCTCTAA TGGAGTTGCA TTTTGAAGCA GGACACTGTG AAAAGCTGGC CTCCTAAAGA 10260
GGCTGCTAAA CATTAGGGTC AATTTTCCAG TGCACTTTCT GAAGTGTCTG CAGTTCCCCA 10320
TGCAAAGCTG CCCAAACATA GCACTTCCAA TTGAATACAA TTATATGCAG GCGTACTGCT 10380
TCTTGCCAGC ACTGTCCTTC TCAAATGAAC TCAACAAACA ATTTCAAAGT CTAGTAGAAA 10440
GTAACAAGCT TTGAATGTCA TTAAAAAGTA TATCTGCTTT CAGTAGTTCA GCTTATTTAT 10500
GCCCACTAGA AACATCTTGT ACAAGCTGAA CACTGGGGCT CCAGATTAGT GGTAAAACCT 10560
ACTTTATACA ATCATAGAAT CATAGAATGG CCTGGGTTGG AAGGGACCCC AAGGATCATG 10620
AAGATCCAAC ACCCCCGCCA CAGGCAGGGC CACCAACCTC CAGATCTGGT ACTAGACCAG 10680
GCAGCCCAGG GCTCCATCCA ACCTGGCCAT GAACACCTCC AGGGATGGAG CATCCACAAC 10740
```

FIG. 1D

```
CTCTCTGGGC AGCCTGTGCC AGCACCTCAC CACCCTCTCT GTGAAGAACT TTTCCCTGAC 10800
ATCCAATCTA AGCCTTCCCT CCTTGAGGTT AGATCCACTC CCCCTTGTGC TATCACTGTC 10860
TACTCTTGTA AAAAGTTGAT TCTCCTCCTT TTTGGAAGGT TGCAATGAGG TCTCCTTGCA 10920
GCCTTCTTCT CTTCTGCAGG ATGAACAAGC CCAGCTCCCT CAGCCTGTCT TTATAGGAGA 10980
GGTGCTCCAG CCCTCTGATC ATCTTTGTGG CCCTCCTCTG GACCCGCTCC AAGAGCTCCA 11040
CATCTTTCCT GTACTGGGGG CCCCAGGCCT GAATGCAGTA CTCCAGATGG GGCCTCAAAA 11100
GAGCAGAGTA AAGAGGGACA ATCACCTTCC TCACCCTGCT GGCCAGCCCT CTTCTGATGG 11160
AGCCCTGGAT ACAACTGGCT TTCTGAGCTG CAACTTCTCC TTATCAGTTC CACTATTAAA 11220
ACAGGAACAA TACAACAGGT GCTGATGGCC AGTGCAGAGT TTTTCACACT TCTTCATTTC 11280
GGTAGATCTT AGATGAGGAA CGTTGAAGTT GTGCTTCTGC GTGTGCTTCT TCCTCCTCAA 11340
ATACTCCTGC CTGATACCTC ACCCCACCTG CCACTGAATG GCTCCATGGC CCCCTGCAGC 11400
CAGGGCCCTG ATGAACCCGG CACTGCTTCA GATGCTGTTT AATAGCACAG TATGACCAAG 11460
TTGCACCTAT GAATACACAA ACAATGTGTT GCATCCTTCA GCACTTGAGA AGAAGAGCCA 11520
AATTTGCATT GTCAGGAAAT GGTTTAGTAA TTCTGCCAAT TAAAACTTGT TTATCTACCA 11580
TGGCTGTTTT TATGGCTGTT AGTAGTGGTA CACTGATGAT GAACAATGGC TATGCAGTAA 11640
AATCAAGACT GTAGATATTG CAACAGACTA TAAAATTCCT CTGTGGCTTA GCCAATGTGG 11700
TACTTCCCAC ATTGTATAAG AAATTTGGCA AGTTTAGAGC AATGTTTGAA GTGTTGGGAA 11760
ATTTCTGTAT ACTCAAGAGG GCGTTTTGA CAACTGTAGA ACAGAGGAAT CAAAAGGGGG 11820
TGGGAGGAAG TTAAAAGAAG AGGCAGGTGC AAGAGAGCTT GCAGTCCCGC TGTGTGTACG 11880
ACACTGGCAA CATGAGGTCT TTGCTAATCT TGGTGCTTTG CTTCCTGCCC CTGGCTGCCT 11940
TAGGGTGCGA TCTGCCTCAG ACCCACAGCC TGGGCAGCAG GAGGACCCTG ATGCTGCTGG 12000
CTCAGATGAG GAGAATCAGC CTGTTTAGCT GCCTGAAGGA TAGGCACGAT TTTGGCTTTC 12060
CTCAAGAGGA GTTTGGCAAC CAGTTTCAGA AGGCTGAGAC CATCCCTGTG CTGCACGAGA 12120
TGATCCAGCA GATCTTTAAC CTGTTTAGCA CCAAGGATAG CAGCGCTGCT TGGGATGAGA 12180
CCCTGCTGGA TAAGTTTTAC ACCGAGCTGT ACCAGCAGCT GAACGATCTG GAGGCTTGCG 12240
TGATCCAGGG CGTGGGCGTG ACCGAGACCC CTCTGATGAA GGAGGATAGC ATCCTGGCTG 12300
TGAGGAAGTA CTTTCAGAGG ATCACCCTGT ACCTGAAGGA GAAGAAGTAC AGCCCCTGCG 12360
CTTGGGAAGT CGTGAGGGCT GAGATCATGA GGAGCTTTAG CCTGAGCACC AACCTGCAAG 12420
AGAGCTTGAG GTCTAAGGAG TAAAAAGTCT AGAGTCGGGG CGGCCGGCCG CTTCGAGCAG 12480
ACATGATAAG ATACATTGAT GAGTTTGGAC AAACCACAAC TAGAATGCAG TGAAAAAAAT 12540
GCTTTATTTG TGAAATTTGT GATGCTATTG CTTTATTTGT AACCATTATA AGCTGCAATA 12600
AACAAGTTAA CAACAACAAT TGCATTCATT TTATGTTTCA GGTTCAGGGG GAGGTGTGGG 12660
AGGTTTTTTA AAGCAAGTAA AACCTCTACA AATGTGGTAA AATCGATAAG GATCCGTCGA 12720
GCGGCCGC             12728
```

FIG. 1E

SEQ ID NO: 5

```
TGCGATCTGC CTCAGACCCA CAGCCTGGGC AGCAGGAGGA CCCTGATGCT GCTGGCTCAG   60
ATGAGGAGAA TCAGCCTGTT TAGCTGCCTG AAGGATAGGC ACGATTTTGG CTTTCCTCAA  120
GAGGAGTTTG GCAACCAGTT TCAGAAGGCT GAGACCATCC CTGTGCTGCA CGAGATGATC  180
CAGCAGATCT TTAACCTGTT TAGCACCAAG GATAGCAGCG CTGCTTGGGA TGAGACCCTG  240
CTGGATAAGT TTTACACCGA GCTGTACCAG CAGCTGAACG ATCTGGAGGC TTGCGTGATC  300
CAGGGCGTGG GCGTGACCGA GACCCCTCTG ATGAAGGAGG ATAGCATCCT GGCTGTGAGG  360
AAGTACTTTC AGAGGATCAC CCTGTACCTG AAGGAGAAGA AGTACAGCCC CTGCGCTTGG  420
GAAGTCGTGA GGGCTGAGAT CATGAGGAGC TTTAGCCTGA GCACCAACCT GCAAGAGAGC  480
TTGAGGTCTA AGGAGTAA 498
```

FIG. 2

SEQ ID NO: 7

```
TGCCGCCTTC TTTGATATTC ACTCTGTTGT ATTTCATCTC TTCTTGCCGA TGAAAGGATA   60
TAACAGTCTG TATAACAGTC TGTGAGGAAA TACTTGGTAT TTCTTCTGAT CAGTGTTTTT  120
ATAAGTAATG TTGAATATTG GATAAGGCTG TGTGTCCTTT GTCTTGGGAG ACAAAGCCCA  180
CAGCAGGTGG TGGTTGGGGT GGTGGCAGCT CAGTGACAGG AGAGGTTTTT TTGCCTGTTT  240
TTTTTTTTTT TTTTTTTTTT AAGTAAGGTG TTCTTTTTTC TTAGTAAATT TTCTACTGGA  300
CTGTATGTTT TGACAGGTCA GAAACATTTC TTCAAAAGAA GAACCTTTTG GAAACTGTAC  360
AGCCCTTTTC TTTCATTCCC TTTTTGCTTT CTGTGCCAAT GCCTTTGGTT CTGATTGCAT  420
TATGGAAAAC GTTGATCGGA ACTTGAGGTT TTTATTTATA GTGTGGCTTG AAAGCTTGGA  480
TAGCTGTTGT TACACGAGAT ACCTTATTAA GTTTAGGCCA GCTTGATGCT TTATTTTTC   540
CCTTTGAAGT AGTGAGCGTT CTCTGGTTTT TTTCCTTTGA AACTGGTGAG GCTTAGATTT  600
TTCTAATGGG ATTTTTTACC TGATGATCTA GTTGCATACC CAAATGCTTG TAAATGTTTT  660
CCTAGTTAAC ATGTTGATAA CTTCGGATTT ACATGTTGTA TATACTTGTC ATCTGTGTTT  720
CTAGTAAAAA TATATGGCAT TTATAGAAAT ACGTAATTCC TGATTTCCTT TTTTTTTATC  780
TCTATGCTCT GTGTGTACAG GTCAAACAGA CTTCACTCCT ATTTTTATTT ATAGAATTTT  840
ATATGCAGTC TGTCGTTGGT TCTTGTGTTG TAAGGATACA GCCTTAAATT CCTAGAGCG   900
ATGCTCAGTA AGGCGGGTTG TCACATGGGT TCAAATGTAA AACGGGCACG TTTGGCTGCT  960
GCCTTCCCGA GATCCAGGAC ACTAAACTGC TTCTGCACTG AGGTATAAAT CGCTTCAGAT 1020
CCCAGGGAAG TGCAGATCCA CGTGCATATT CTTAAAGAAG AATGAATACT TTCTAAAATA 1080
TTTTGGCATA GGAAGCAAGC TGCATGGATT TGTTTGGGAC TTAAATTATT TTGGTAACGG 1140
AGTGCATAGG TTTTAAACAC AGTTGCAGCA TGCTAACGAG TCACAGCGTT TATGCAGAAG 1200
TGATGCCTGG ATGCCTGTTG CAGCTGTTTA CGGCACTGCC TTGCAGTGAG CATTGCAGAT 1260
AGGGGTGGGG TGCTTTGTGT CGTGTTCCCA CACGCTGCCA CACAGCCACC TCCCGGAACA 1320
CATCTCACCT GCTGGGTACT TTTCAAACCA TCTTAGCAGT AGTAGATGAG TTACTATGAA 1380
ACAGAGAAGT TCCTCAGTTG GATATTCTCA TGGGATGTCT TTTTTCCCAT GTTGGGCAAA 1440
GTATGATAAA GCATCTCTAT TTGTAAATTA TGCACTTGTT AGTTCCTGAA TCCTTTCTAT 1500
AGCACCACTT ATTGCAGCAG GTGTAGGCTC TGGTGTGGCC TGTGTCTGTG CTTCAATCTT 1560
TTAAAGCTTC TTTGAAATA CACTGACTTG ATTGAAGTCT CTTGAAGATA GTAAACAGTA 1620
CTTACCTTTG ATCCCAATGA AATCGAGCAT TCAGTTGTA AAAGAATTCC GCCTATTCAT 1680
ACCATGTAAT GTAATTTTAC ACCCCAGTG CTGACACTTT GGAATATATT CAAGTAATAG 1740
ACTTTGGCCT CACCCTCTTG TGTACTGTAT TTTGTAATAG AAAATATTTT AAACTGTGCA 1800
TATGATTATT ACATTATGAA AGAGACATTC TGCTGATCTT CAAATGTAAG AAAATGAGGA 1860
GTGCGTGTGC TTTTATAAAT ACAAGTGATT GCAAATTAGT GCAGGTGTCC TTAAAAAAA  1920
AAAAAAAAAG TAATATAAAA AGGACCAGGT GTTTTACAAG TGAAATACAT TCCTATTTGG 1980
TAAACAGTTA CATTTTTATG AAGATTACCA GCGCTGCTGA CTTTCTAAAC ATAAGGCTGT 2040
ATTGTCTTCC TGTACCATTG CATTTCCTCA TTCCCAATTT GCACAAGGAT GTCTGGGTAA 2100
ACTATTCAAG AAATGGCTTT GAAATACAGC ATGGGAGCTT GTCTGAGTTG GAATGCAGAG 2160
TTGCACTGCA AAATGTCAGG AAATGGATGT CTCTCAGAAT GCCCAACTCC AAAGGATTTT 2220
ATATGTGTAT ATAGTAAGCA GTTTCCTGAT TCCAGCAGGC CAAAGAGTCT GCTGAATGTT 2280
GTGTTGCCGG AGACCTGTAT TTCTCAACAA GGTAAGATGG TATCCTAGCA ACTGCGGATT 2340
TTAATACATT TCAGCAGAA GTACTTAGTT AATCTCTACC TTTAGGGATC GTTTCATCAT 2400
TTTAGATGT TATACTTGAA ATACTGCATA ACTTTTAGCT TTCATGGGTT CCTTTTTTC   2460
AGCCTTTAGG AGACTGTTAA GCAATTTGCT GTCCAACTTT TGTGTTGGTC TTAAACTGCA 2520
ATAGTAGTTT ACCTTGTATT GAAGAAATAA AGACCATTTT TATATTAAAA AATACTTTTG 2580
TCTGTCTTCA TTTTGACTTG TCTGATATCC TTGCAGTGCC CATTATGTCA GTTCTGTCAG 2640
ATATTCAGAC ATCAAAACTT AACGTGAGCT CAGTGGAGTT ACAGCTGCGG TTTTGATGCT 2700
```

FIG. 3A

```
GTTATTATTT CTGAAACTAG AAATGATGTT GTCTTCATCT GCTCATCAAA CACTTCATGC 2760
AGAGTGTAAG GCTAGTGAGA AATGCATACA TTTATTGATA CTTTTTTAAA GTCAACTTTT 2820
TATCAGATTT TTTTTTCATT TGGAAATATA TTGTTTTCTA GACTGCATAG CTTCTGAATC 2880
TGAAATGCAG TCTGATTGGC ATGAAGAAGC ACAGCACTCT TCATCTTACT TAAACTTCAT 2940
TTTGGAATGA AGGAAGTTAA GCAAGGGCAC AGGTCCATGA AATAGAGACA GTGCGCTCAG 3000
GAGAAAGTGA ACCTGGATTT CTTTGGCTAG TGTTCTAAAT CTGTAGTGAG GAAAGTAACA 3060
CCCGATTCCT TGAAAGGGCT CCAGCTTTAA TGCTTCCAAA TTGAAGGTGG CAGGCAACTT 3120
GGCCACTGGT TATTTACTGC ATTATGTCTC AGTTTCGCAG CTAACCTGGC TTCTCCACTA 3180
TTGAGCATGG ACTATAGCCT GGCTTCAGAG GCCAGGTGAA GGTTGGGATG GGTGGAAGGA 3240
GTGCTGGGCT GTGGCTGGGG GGACTGTGGG GACTCCAAGC TGAGCTTGGG GTGGGCAGCA 3300
CAGGGAAAAG TGTGGGTAAC TATTTTTAAG TACTGTGTTG CAAACGTCTC ATCTGCAAAT 3360
ACGTAGGGTG TGTACTCTCG AAGATTAACA GTGTGGGTTC AGTAATATAT GGATGAATTC 3420
ACAGTGGAAG CATTCAAGGG TAGATCATCT AACGACACCA GATCATCAAG CTATGATTGG 3480
AAGCGGTATC AGAAGAGCGA GGAAGGTAAG CAGTCTTCAT ATGTTTTCCC TCCACGTAAA 3540
GCAGTCTGGG AAAGTAGCAC CCCTTGAGCA GAGACAAGGA AATAATTCAG GAGCATGTGC 3600
TAGGAGAACT TTCTTGCTGA ATTCTACTTG CAAGAGCTTT GATGCCTGGC TTCTGGTGCC 3660
TTCTGCAGCA CCTGCAAGGC CCAGAGCCTG TGGTGAGCTG GAGGGAAAGA TTCTGCTCAA 3720
GTCCAAGCTT CAGCAGGTCA TTGTCTTTGC TTCTTCCCCC AGCACTGTGC AGCAGAGTGG 3780
AACTGATGTC GAAGCCTCCT GTCCACTACC TGTTGCTGCA GGCAGACTGC TCTCAGAAAA 3840
AGAGAGCTAA CTCTATGCCA TAGTCTGAAG GTAAATGGG TTTTAAAAAA GAAAACACAA 3900
AGGCAAAACC GGCTGCCCCA TGAAGAAGAA GCAGTGGTAA ACATGGTAGA AAAGGTGCAG 3960
AAGCCCCCAG GCAGTGTGAC AGGCCCCTCC TGCCACCTAG AGGCGGGAAC AAGCTTCCCT 4020
GCCTAGGGCT CTGCCGCGA AGTGCGTGTT TCTTTGGTGG GTTTTGTTTG GCGTTTGGTT 4080
TTGAGATTTA GACACAAGGG AAGCCTGAAA GGAGGTGTTG GCACTATTT TGGTTTGTAA 4140
AGCCTGTACT TCAAATATAT ATTTGTGAG GGAGTGTAGC GAATTGGCCA ATTTAAAATA 4200
AAGTTGCAAG AGATTGAAGG CTGAGTAGTT GAGAGGGTAA CACGTTTAAT GAGATCTTCT 4260
GAAACTACTG CTTCTAAACA CTTGTTTGAG TGGTGAGACC TTGGATAGGT GAGTGCTCTT 4320
GTTACATGTC TGATGCACTT GCTTGTCCTT TTCCATCCAC ATCCATGCAT TCCACATCCA 4380
CGCATTTGTC ACTTATCCCA TATCTGTCAT ATCTGACATA CCTGTCTCTT CGTCACTTGG 4440
TCAGAAGAAA CAGATGTGAT AATCCCCAGC CGCCCCAAGT TTGAGAAGAT GGCAGTTGCT 4500
TCTTTCCCTT TTTCCTGCTA AGTAAGGATT TTCTCCTGGC TTTGACACCT CACGAAATAG 4560
TCTTCCTGCC TTACATTCTG GCATTATTT CAAATATCTT TGGAGTGCGC TGCTCTCAAG 4620
TTTGTGTCTT CCTACTCTTA GAGTGAATGC TCTTAGAGTG AAAGAGAAGG AAGAGAAGAT 4680
GTTGGCCGCA GTTCTCTGAT GAACACACCT CTGAATAATG GCCAAAGGTG GGTGGGTTTC 4740
TCTGAGGAAC GGGCAGCGTT TGCCTCTGAA AGCAAGGAGC TCTGCGGAGT TGCAGTTATT 4800
TTGCAACTGA TGGTGGAACT GGTGCTTAAA GCAGATTCCC TAGGTTCCCT GCTACTTCTT 4860
TTCCTTCTTG GCAGTCAGTT TATTTCTGAC AGACAAACAG CCACCCCAC TGCAGGCTTA 4920
GAAAGTATGT GGCTCTGCCT GGGTGTGTTA CAGCTCTGCC CTGGTGAAAG GGGATTAAAA 4980
CGGGCACCAT TCATCCCAAA CAGGATCCTC ATTCATGGAT CAAGCTGTAA GGAACTTGGG 5040
CTCCAACCTC AAAACATTAA TTGGAGTACG AATGTAATTA AAACTGCATT CTCGCATTCC 5100
TAAGTCATTT AGTCTGGACT CTGCAGCATG TAGGTCGGCA GCTCCCACTT TCTCAAAGAC 5160
CACTGATGGA GGAGTAGTAA AAATGGAGAC CGATTCAGAA CAACCAACGG AGTGTTGCCG 5220
AAGAAACTGA TGGAAATAAT GCATGAATTG TGTGGTGGAC ATTTTTTTA AATACATAAA 5280
CTACTTCAAA TGAGGTCGGA GAAGGTCAGT GTTTTATTAG CAGCCATAAA ACCAGGTGAG 5340
CGAGTACCAT TTTTCTCTAC AAGAAAAACG ATTCTGAGCT CTGCGTAAGT ATAAGTTCTC 5400
```

FIG. 3B

```
CATAGCGGCT GAAGCTCCCC CCTGGCTGCC TGCCATCTCA GCTGGAGTGC AGTGCCATTT 5460
CCTTGGGGTT TCTCTCACAG CAGTAATGGG ACAATACTTC ACAAAAATTC TTTCTTTTCC 5520
TGTCATGTGG GATCCCTACT GTGCCCTCCT GGTTTTACGT TACCCCCTGA CTGTTCCATT 5580
CAGCGGTTTG GAAAGAGAAA AAGAATTTGG AAATAAAACA TGTCTACGTT ATCACCTCCT 5640
CCAGCATTTT GGTTTTTAAT TATGTCAATA ACTGGCTTAG ATTTGGAAAT GAGAGGGGGT 5700
TGGGTGTATT ACCGAGGAAC AAAGGAAGGC TTATATAAAC TCAAGTCTTT TATTTAGAGA 5760
ACTGGCAAGC TGTCAAAAAC AAAAAGGCCT TACCACCAAA TTAAGTGAAT AGCCGCTATA 5820
GCCAGCAGGG CCAGCACGAG GGATGGTGCA CTGCTGGCAC TATGCCACGG CCTGCTTGTG 5880
ACTCTGAGAG CAACTGCTTT GGAAATGACA GCACTTGGTG CAATTTCCTT TGTTTCAGAA 5940
TGCGTAGAGC GTGTGCTTGG CGACAGTTTT TCTAGTTAGG CCACTTCTTT TTTCCTTCTC 6000
TCCTCATTCT CCTAAGCATG TCTCCATGCT GGTAATCCCA GTCAAGTGAA CGTTCAAACA 6060
ATGAATCCAT CACTGTAGGA TTCTCGTGGT GATCAAATCT TTGTGTGAGG TCTATAAAAT 6120
ATGGAAGCTT ATTTATTTTT CGTTCTTCCA TATCAGTCTT CTCTATGACA ATTCACATCC 6180
ACCACAGCAA ATTAAGGTGA AGGAGGCTG GTGGGATGAA GAGGGTCTTC TAGCTTTACG 6240
TTCTTCCTTG CAAGGCCACA GGAAATGCT GAGAGCTGTA GAATACAGCC TGGGGTAAGA 6300
AGTTCAGTCT CCTGCTGGGA CAGCTAACCG CATCTTATAA CCCCTTCTGA GACTCATCTT 6360
AGGACCAAAT AGGGTCTATC TGGGGTTTTT GTTCCTGCTG TTCCTCCTGG AAGGCTATCT 6420
CACTATTTCA CTGCTCCCAC GGTTACAAAC CAAAGATACA GCCTGAATTT TTTCTAGGCC 6480
ACATTACATA AATTTGACCT GGTACCAATA TTGTTCTCTA TATAGTTATT TCCTTCCCCA 6540
CTGTGTTTAA CCCCTTAAGG CATTCAGAAC AACTAGAATC ATAGAATGGT TTGGATTGGA 6600
AGGGGCCTTA AACATCATCC ATTTCCAACC CTCTGCCATG GGCTGCTTGC CACCCACTGG 6660
CTCAGGCTGC CCAGGGCCCC ATCCAGCCTG GCCTTGAGCA CCTCCAGGGA TGGGGCACCC 6720
ACAGCTTCTC TGGGCAGCCT GTGCCAACAC CTCACCACTC TCTGGGTAAA GAATTCTCTT 6780
TTAACATCTA ATCTAAATCT CTTCTCTTTT AGTTTAAAGC CATTCCTCTT TTTCCCGTTG 6840
CTATCTGTCC AAGAAATGTG TATTGGTCTC CCTCCTGCTT ATAAGCAGGA AGTACTGGAA 6900
GGCTGCAGTG AGGTCTCCCC ACAGCCTTCT CTTCTCCAGG CTGAACAAGC CCAGCTCCTT 6960
CAGCCTGTCT TCGTAGGAGA TCATCTTAGT GGCCCTCCTC TGGACCCATT CCAACAGTTC 7020
CACGGCTTTC TTGTGGAGCC CCAGGTCTGG ATGCAGTACT TCAGATGGGG CCTTACAAAG 7080
GCAGAGCAGA TGGGGACAAT CGCTTACCCC TCCCTGCTGG CTGCCCCTGT TTTGATGCAG 7140
CCCAGGGTAC TGTTGGCCTT TCAGGCTCCC AGACCCCTTG CTGATTTGTG TCAAGCTTTT 7200
CATCCACCAG AACCCACGCT TCCTGGTTAA TACTTCTGCC CTCACTTCTG TAAGCTTGTT 7260
TCAGGAGACT TCCATTCTTT AGGACAGACT GTGTTACACC TACCTGCCCT ATTCTTGCAT 7320
ATATACATTT CAGTTCATGT TTCCTGTAAC AGGACAGAAT ATGTATTCCT CTAACAAAAA 7380
TACATGCAGA ATTCCTAGTG CCATCTCAGT AGGGTTTTCA TGGCAGTATT AGCACATAGT 7440
CAATTTGCTG CAAGTACCTT .CCAAGCTGCG GCCTCCCATA AATCCTGTAT TTGGGATCAG 7500
TTACCTTTTG GGGTAAGCTT TTGTATCTGC AGAGACCCTG GGGGTTCTGA TGTGCTTCAG 7560
CTCTGCTCTG TTCTGACTGC ACCATTTTCT AGATCACCCA GTTGTTCCTG TACAACTTCC 7620
TTGTCCTCCA TCCTTTCCCA GCTTGTATCT TTGACAAATA CAGGCCTATT TTTGTGTTTG 7680
CTTCAGCAGC CATTTAATTC TTCAGTGTCA TCTTGTTCTG TTGATGCCAC TGGAACAGGA 7740
TTTTCAGCAG TCTTGCAAAG AACATCTAGC TGAAAACTTT CTGCCATTCA ATATTCTTAC 7800
CAGTTCTTCT TGTTTGAGGT GAGCCATAAA TTACTAGAAC TTCGTCACTG ACAAGTTTAT 7860
GCATTTTATT ACTTCTATTA TGTACTTACT TTGACATAAC ACAGACACGC ACATATTTTG 7920
CTGGGATTTC CACAGTGTCT CTGTGTCCTT CACATGGTTT TACTGTCATA CTTCCGTTAT 7980
AACCTTGGCA ATCTGCCCAG CTGCCCATCA AAGAAAAGA GATTCCTTTT TTATTACTTC 8040
TCTTCAGCCA ATAAACAAAA TGTGAGAAGC CCAAACAAGA ACTTGTGGGG CAGGCTGCCA 8100
```

FIG. 3C

```
TCAAGGGAGA GACAGCTGAA GGGTTGTGTA GCTCAATAGA ATTAAGAAAT AATAAAGCTG 8160
TGTCAGACAG TTTTGCCTGA TTTATACAGG CACGCCCAA GCCAGAGAGG CTGTCTGCCA 8220
AGGCCACCTT GCAGTCCTTG GTTTGTAAGA TAAGTCATAG GTAACTTTTC TGGTGAATTG 8280
CGTGGAGAAT CATGATGGCA GTTCTTGCTG TTTACTATGG TAAGATGCTA AAATAGGAGA 8340
CAGCAAAGTA ACACTTGCTG CTGTAGGTGC TCTGCTATCC AGACAGCGAT GGCACTCGCA 8400
CACCAAGATG AGGGATGCTC CCAGCTGACG GATGCTGGGG CAGTAACAGT GGGTCCCATG 8460
CTGCCTGCTC ATTAGCATCA CCTCAGCCCT CACCAGCCCA TCAGAAGGAT CATCCCAAGC 8520
TGAGGAAAGT TGCTCATCTT CTTCACATCA TCAAACCTTT GGCCTGACTG ATGCCTCCCG 8580
GATGCTTAAA TGTGGTCACT GACATCTTTA TTTTTCTATG ATTTCAAGTC AGAACCTCCG 8640
GATCAGGAGG GAACACATAG TGGGAATGTA CCCTCAGCTC CAAGGCCAGA TCTTCCTTCA 8700
ATGATCATGC ATGCTACTTA GGAAGGTGTG TGTGTGTGAA TGTAGAATTG CCTTTGTTAT 8760
TTTTTCTTCC TGCTGTCAGG AACATTTTGA ATACCAGAGA AAAAGAAAAG TGCTCTTCTT 8820
GGCATGGGAG GAGTTGTCAC ACTTGCAAAA TAAAGGATGC AGTCCCAAAT GTTCATAATC 8880
TCAGGGTCTG AAGGAGGATC AGAAACTGTG TATACAATTT CAGGCTTCTC TGAATGCAGC 8940
TTTTGAAAGC TGTTCCTGGC CGAGGCAGTA CTAGTCAGAA CCCTCGGAAA CAGGAACAAA 9000
TGTCTTCAAG GTGCAGCAGG AGGAAACACC TTGCCCATCA TGAAAGTGAA TAACCACTGC 9060
CGCTGAAGGA ATCCAGCTCC TGTTTGAGCA GGTGCTGCAC ACTCCCACAC TGAAACAACA 9120
GTTCATTTTT ATAGGACTTC CAGGAAGGAT CTTCTTCTTA AGCTTCTTAA TTATGGTACA 9180
TCTCCAGTTG GCAGATGACT ATGACTACTG ACAGGAGAAT GAGGAACTAG CTGGGAATAT 9240
TTCTGTTTGA CCACCATGGA GTCACCCATT TCTTTACTGG TATTTGGAAA TAATAATTCT 9300
GAATTGCAAA GCAGGAGTTA GCGAAGATCT TCATTTCTTC CATGTTGGTG ACAGCACAGT 9360
TCTGGCTATG AAAGTCTGCT TACAAGGAAG AGGATAAAAA TCATAGGGAT AATAAATCTA 9420
AGTTTGAAGA CAATGAGGTT TTAGCTGCAT TTGACATGAA GAAATTGAGA CCTCTACTGG 9480
ATAGCTATGG TATTTACGTG TCTTTTTGCT TAGTTACTTA TTGACCCCAG CTGAGGTCAA 9540
GTATGAACTC AGGTCTCTCG GGCTACTGGC ATGGATTGAT TACATACAAC TGTAATTTTA 9600
GCAGTGATTT AGGGTTTATG AGTACTTTTG CAGTAAATCA TAGGGTTAGT AATGTTAATC 9660
TCAGGGAAAA AAAAAAAAAG CCAACCCTGA CAGACATCCC AGCTCAGGTG GAAATCAAGG 9720
ATCACAGCTC AGTGCGGTCC CAGAGAACAC AGGGACTCTT CTCTTAGGAC CTTTATGTAC 9780
AGGGCCTCAA GATAACTGAT GTTAGTCAGA AGACTTTCCA TTCTGGCCAC AGTTCAGCTG 9840
AGGCAATCCT GGAATTTTCT CTCCGCTGCA CAGTTCCAGT CATCCCAGTT TGTACAGTTC 9900
TGGCACTTTT TGGGTCAGGC CGTGATCCAA GGAGCAGAAG TTCCAGCTAT GGTCAGGGAG 9960
TGCCTGACCG TCCCAACTCA CTGCACTCAA ACAAAGGCGA AACCACAAGA GTGGCTTTTG 10020
TTGAAATTGC AGTGTGGCCC AGAGGGGCTG CACCAGTACT GGATTGACCA CGAGGCAACA 10080
TTAATCCTCA GCAAGTGCAA TTTGCAGCCA TTAAATTGAA CTAACTGATA CTACAATGCA 10140
ATCAGTATCA ACAAGTGGTT TGGCTTGGAA GATGGAGTCT AGGGGCTCTA CAGGAGTAGC 10200
TACTCTCTAA TGGAGTTGCA TTTTGAAGCA GGACACTGTG AAAAGCTGGC CTCCTAAAGA 10260
GGCTGCTAAA CATTAGGGTC AATTTTCCAG TGCACTTTCT GAAGTGTCTG CAGTTCCCCA 10320
TGCAAAGCTG CCCAAACATA GCACTTCCAA TTGAATACAA TTATATGCAG GCGTACTGCT 10380
TCTTGCCAGC ACTGTCCTTC TCAAATGAAC TCAACAAACA ATTTCAAAGT CTAGTAGAAA 10440
GTAACAAGCT TTGAATGTCA TTAAAAAGTA TATCTGCTTT CAGTAGTTCA GCTTATTTAT 10500
GCCCACTAGA AACATCTTGT ACAAGCTGAA CACTGGGGCT CCAGATTAGT GGTAAAACCT 10560
ACTTTATACA ATCATAGAAT CATAGAATGG CCTGGGTTGG AAGGGACCCC AAGGATCATG 10620
AAGATCCAAC ACCCCCGCCA CAGGCAGGGC CACCAACCTC CAGATCTGGT ACTAGACCAG 10680
GCAGCCCAGG GCTCCATCCA ACCTGGCCAT GAACACCTCC AGGGATGGAG CATCCACAAC 10740
CTCTCTGGGC AGCCTGTGCC AGCACCTCAC CACCCTCTCT GTGAAGAACT TTCCCTGAC 10800
ATCCAATCTA AGCCTTCCCT CCTTGAGGTT AGATCCACTC CCCCTTGTGC TATCACTGTC 10860
```

FIG. 3D

```
TACTCTTGTA AAAAGTTGAT TCTCCTCCTT TTTGGAAGGT TGCAATGAGG TCTCCTTGCA 10920
GCCTTCTTCT CTTCTGCAGG ATGAACAAGC CCAGCTCCCT CAGCCTGTCT TTATAGGAGA 10980
GGTGCTCCAG CCCTCTGATC ATCTTTGTGG CCCTCCTCTG GACCCGCTCC AAGAGCTCCA 11040
CATCTTTCCT GTACTGGGGG CCCCAGGCCT GAATGCAGTA CTCCAGATGG GGCCTCAAAA 11100
GAGCAGAGTA AAGAGGGACA ATCACCTTCC TCACCCTGCT GGCCAGCCCT CTTCTGATGG 11160
AGCCCTGGAT ACAACTGGCT TTCTGAGCTG CAACTTCTCC TTATCAGTTC CACTATTAAA 11220
ACAGGAACAA TACAACAGGT GCTGATGGCC AGTGCAGAGT TTTTCACACT TCTTCATTTC 11280
GGTAGATCTT AGATGAGGAA CGTTGAAGTT GTGCTTCTGC GTGTGCTTCT TCCTCCTCAA 11340
ATACTCCTGC CTGATACCTC ACCCCACCTG CCACTGAATG GCTCCATGGC CCCCTGCAGC 11400
CAGGGCCCTG ATGAACCCGG CACTGCTTCA GATGCTGTTT AATAGCACAG TATGACCAAG 11460
TTGCACCTAT GAATACACAA ACAATGTGTT GCATCCTTCA GCACTTGAGA AGAAGAGCCA 11520
AATTTGCATT GTCAGGAAAT GGTTTAGTAA TTCTGCCAAT TAAAACTTGT TTATCTACCA 11580
TGGCTGTTTT TATGGCTGTT AGTAGTGGTA CACTGATGAT GAACAATGGC TATGCAGTAA 11640
AATCAAGACT GTAGATATTG CAACAGACTA TAAAATTCCT CTGTGGCTTA GCCAATGTGG 11700
TACTTCCCAC ATTGTATAAG AAATTTGGCA AGTTTAGAGC AATGTTTGAA GTGTTGGGAA 11760
ATTTCTGTAT ACTCAAGAGG GCGTTTTTGA CAACTGTAGA ACAGAGGAAT CAAAAGGGGG 11820
TGGGAGGAAG TTAAAAGAAG AGGCAGGTGC AAGAGAGCTT GCAGTCCCGC TGTGTGTACG 11880
ACACTGGCAA CATGAGGTCT TTGCTAATCT TGGTGCTTTG CTTCCTGCCC CTGGCTGCCT 11940
TAGGG 11945
```

FIG. 3E

SEQ ID NO: 8

```
AAAGTCTAGAGTCGGGGCGGCCGGCCGCTTCGAGCAGACATGATAAGATACATTGATGAG   60
TTTGGACAAACCACAACTAGAATGCAGTGAAAAAAATGCTTTATTTGTGAAATTTGTGAT  120
GCTATTGCTTTATTTGTAACCATTATAAGCTGCAATAAACAAGTTAACAACAACAATTGC  180
ATTCATTTTATGTTTCAGGTTCAGGGGGAGGTGTGGGAGGTTTTTTAAAGCAAGTAAAAC  240
CTCTACAAATGTGGTAAAATCGATAAGGATCCGTCGAGCGGCCGC   285
```

FIG. 4

SEQ ID NO: 42

```
   1 CGCGTGGTAGGTGGCGGGGGGTTCCCAGGAGAGCCCCCAGCGCGGACGGC
     AGCGCCGTCACTCACCGCTCCGTCTCCCTCCGCCCAGGGTCGCCTGGCGC
     AACCGCTGCAAGGGCACCGACGTCCAGGCGTGGATCAGAGGCTGCCGGCT
     GTGAGGAGCTGCCGCGCCCGGCCCGCCCGCTGCACAGCCGGCCGCTTTGC
 200 GAGCGCGACGCTACCCGCTTGGCAGTTTTAAACGCATCCCTCATTAAAAC
     GACTATACGCAAACGCCTTCCCGTCGGTCCGCGTCTCTTTCCGCCGCCAG
     GGCGACACTCGCGGGGAGGGCGGGAAGGGGCCGGGCGGGAGCCCGCGGC
     CAACCGTCGCCCCGTGACGGCACCGCCCCGCCCCCGTGACGCGGTGCGGG
 400 CGCCGGGGCCGTGGGGCTGAGCGCTGCGGCGGGGCCGGGCCGGGCCGGGG
     CGGGAGCTGAGCGCGGCGCGGCTGCGGGCGGCGCCCCTCCGGTGCAATA
     TGTTCAAGAGAATGGCTGAGTTCGGGCCTGACTCCGGGGCAGGGTGAAG
     GTGCGGCGCGGCGGAGGGACGGGGCGGGCGCGGGCCGCCCGGCGGGTG
 600 CCGGGGCCTCTGCCGGCCCGCCCGGCTCGGGCTGCTGCGGCGCTTACGGG
     CGCGCTTCTCGCCGCTGCCGCTTCTCTTCTCTCCCGCGCAAGGGCGTCAC
     CATCGTGAAGCCGGTAGTGTACGGGAACGTGGCGCGGTACTTCGGGAAGA
     AGAGGGAGGAGGACGGGCACACGCATCAGTGGACGGTTTACGTGAAGCCC
 800 TACAGGAACGAGGTAGGGCCCGAGCGCGTCGGCCGCCGTTCTCGGAGCGC
     CGGAGCCGTCAGCGCCGCGCCTGGGTGCGCTGTGGGACACAGCGAGCTTC
     TCTCGTAGGACATGTCCGCCTACGTGAAAAAAATCCAGTTCAAGCTGCAC
     GAGAGCTACGGGAATCCTCTCCGAGGTGGGTGTTGCGTCGGGGGGTTTGC
1000 TCCGCTCGGTCCCGCTGAGGCTCGTCGCCCTCATCTTTCTTTCGTGCCGC
     AGTCGTTACCAAACCGCCGTACGAGATCACCGAAACGGGCTGGGGCGAAT
     TTGAAATCATCATCAAGATATTTTTCATTGATCCAAACGAGCGACCCGTA
     AGTACGCTCAGCTTCTCGTAGTGCTTCCCCCGTCCTGGCGGCCCGGGGCT
1200 GGGCTGCTCGCTGCTGCCGGTCACAGTCCCGCCAGCCGCGGAGCTGACTG
     AGCTCCCTTTCCCGGGACGTGTGCTCTGTGTTCGGTCAGCGAGGCTATCG
     GGAGGGCTTTGGCTGCATTTGGCTTCTCTGGCGCTTAGCGCAGGAGCACG
     TTGTGCTACGCCTGAACTACAGCTGTGAGAAGGCCGTGGAAACCGCTCTC
1400 AAACTGATTTATTGGCGAAATGGCTCTAAACTAAATCGTCTCCTCTCTTT
     GGAAATGCTTTAGAGAAGGTCTCTGTGGTAGTTCTTATGCATCTATCCTA
     AAGCACTTGGCCAGACAATTTAAAGACATCAAGCAGCATTTATAGCAGGC
     ACGTTTAATAACGAATACTGAATTTAAGTAACTCTGCTCACGTTGTATGA
1600 CGTTTATTTTCGTATTCCTGAAAGCCATTAAAATCCTGTGCAGTTGTTTA
     GTAAGAACAGCTGCCACTGTTTTGTATCTAGGAGATAACTGGTGTTTCCC
     TACAGTTCTCAAGCTGATAAAACTCTGTCTTTGTATCTAGGTAACCCTGT
     ATCACTTGCTGAAGCTTTTCAGTCTGACACCAATGCAATCCTGGGAAAG
1800 AAAACTGTAGTTTCTGAATTCTATGATGAAATGGTATGAAAATTTTAATG
     TCAACCGAGCCTGACTTTATTTAAAAAAAATTATTGATGGTGCTGTGTAT
     TTTGGTCCTTCCTTAGATATTTCAAGATCCTACTGCCATGATGCAGCAAC
     TGCTAACGACGTCCCGTCAGCTGACACTTGGTGCTTACAAGCATGAAACA
```

FIG. 5A

2000 GAGTGTAAGTGCAAAATGAGGATACCTTCGCCGACCGTCATTCACTACTA
ATGTTTTCTGTGGGATGTGATCGTACAGTGAGTTTGGCTGTGTGAAATTT
GAATAGCTTGGTATTGGCAGTGATGACGTGATCGATGCCTTGCTTATCAT
GTTTGAAATGAAGTAGAATAAATGCAGCCTGCTTTATTTGAGATAGTTTG
2200 GTTCATTTTATGGAATGCAAGCAAAGATTATACTTCCTCACTGAATTGCA
CTGTCCAAGGTGTGAAATGTGTGGGGATCTGGAGGACGTGACCGAGGG
ACATTGGATCGCTATCTCCCATTTCTTTTGCTGTTACCAGTTCAGATTTT
CTTTTCACCTAGTCTTTAATTCCCAGGGTTTTGTTTTTTCCTTGGTCATA
2400 GTTTTTGTTTTTCACTCTGGCAAATGATGTTGTGAATTACACTGCTTCAG
CCACAAAACTGATGGACTGAATGAGGTCATCAAACAAACTTTTCTTCTTC
CGTATTTCCTTTTTTTTCCCCCACTTATCATTTTTACTGCTGTTGTTGAG
TCTGTAAGGCTAAAAGTAACTGTTTGTGCTTTTTCAGGACGTGTGCTTT
2600 CCAAATTACTGCCACATATATAAAGAAAGGTTGGAATTTTAAAGATAATT
CATGTTTCTTCTTCTTTTTTGCCACCACAGTTGCAGATCTTGAAGTAAAA
ACCAGGGAAAAGCTGGAAGCTGCCAAAAAGAAAACCAGTTTTGAAATTGC
TGAGCTTAAAGAAAGGTTAAAAGCAAGTCGTGAAACCATCAACTGCTTAA
2800 AGAGTGAAATCAGAAAACTCGAAGAGGATGATCAGTCTAAAGATATGTGA
TGAGTGTTGACTTGGCAGGGAGCCTATAATGAGAATGAAAGGACTTCAGT
CGTGGAGTTGTATGCGTTCTCCAATTCTGTAACGGAGACTGTATGAAT
TTCATTTGCAAATCACTGCAGTGTGTGACAACTGACTTTTTATAAATGGC
3000 AGAAAACAAGAATGAATGTATCCTCATTTTATAGTTAAAATCTATGGGTA
TGTACTGGTTTATTTCAAGGAGAATGGATCGTAGAGACTTGGAGGCCAGA
TTGCTGCTTGTATTGACTGCATTTGAGTGGTGTAGGAACATTTTGTCTAT
GGTCCCGTGTTAGTTTACAGAATGCCACTGTTCACTGTTTTGTTTTGTAT
3200 TTTACTTTTTCTACTGCAACGTCAAGGTTTTAAAAGTTGAAAATAAAACA
TGCAGGTTTTTTTTAAATATTTTTTTGTCTCTATCCAGTTTGGGCTTCAA
GTATTATTGTTAACAGCAAGTCCTGATTTAAGTCAGAGGCTGAAGTGTAA
TGGTATTCAAGATGCTTAAGTCTGTTGTCAGCAAAACAAAAGAGAAAACT
3400 TCATAAAATCAGGAAGTTGGCATTTCTAATAACTTCTTTATCAACAGATA
AGAGTTTCTAGCCCTGCATCTACTTTCACTTATGTAGTTGATGCCTTTAT
ATTTTGTGTGTTTGGATGCAGGAAGTGATTCCTACTCTGTTATGTAGATA
TTCTATTTAACACTTGTACTCTGCTGTGCTTAGCCTTTCCCCATGAAAAT
3600 TCAGCGGCTGTAAATCCCCTCTTCTTTTGTAGCCTCATACAGATGGCAG
ACCCTCAGGCTTATAAAGGCTTGGGCATCTTCTTTACTGCTTTGAGATTC
TGTGTTGCAGTAACCTCTGCCAGAGAGGAGAAAAGCCCCACAAACCTCAT
CCCCTTCTTCTATAGCAATCAGTATTACTAATGCTTTGAGAACAGAGCAC
3800 TGGTTTGAAACGTTTGATAATTAGCATTTAACATGGCTTGGTAAAGATGC
AGAACTGAAACAGCTGTGACAGTATGAACTCAGTATGGAGACTTCATTAA
GACAAACAGCTGTTAAAATCAGGCATGTTTCATTGAGGAGGACGGGGCAA
CTTGCACCAGTGGTGCCCACACAAATCCTTCCTGGCGCTGCAGACCAATT

FIG. 5B

4000 TTTCTGGCATTCTGACTGCCGTTGCTGCTGGTCACAGAGAGCAACTATTT
TTATCAGCCACAGGCAATTTGCTTGTAGTATTTTCCAAGTGTTGTAGGTA
AGTATAAATGCATCGGCTCCAGAGCACTTTGAGTATACTTATTAAAAACA
TAAATGAAAGACAAATTAGCTTTGCTTGGGTGCACAGAACATTTTTAGTT
4200 CCAGCCTGCTTTTTGGTAGAAGCCCTCTTCTGAGGCTAGAACTGACTTTG
ACAAGTAGAGAAACTGGCAACGGAGCTATTGCTATCGAAGGATCCTTGTT
AACAAAGTTAATCGTCTTTTAAGGTTTGGTTTATTCATTAAATTTGCTTT
TAAGCTGTAGCTGAAAAGAACGTGCTGTCTTCCATGCACCAGGTGGCAG
4400 CTCTGTGCAAAGTGCTCTCTGGTCTCACCAGCCTTTTAATTGCCGGGATT
CTGGCACGTCTGAGAGGGCTCAGACTGGCTTCGTTTGTTTGAACAGCGTG
TACTGCTTTCTGTAGACATGGCCGGTTTCTCCTGCAGCTTATGAAACT
GTTCACACTGAACACACTGGAACAGGTTGCCCAAGGAGGCCGTGGATGCC
4600 CCATCCCTGGAGGCATTCAAGGCCAGGCTGGATGTGGCTCTGGGCAGCCT
GGTCTGGTGGTTGGCGATCCTGCACATAGCAGCGGGGTTGAAACTCGATG
ATCACTGTGGTCCTTTTCAACCCAGGCTATTCTATGATTCTATGATTCAA
CAGCAAATCATATGTACTGAGAGAGGAAACAAACACAAGTGCTACTGTTT
4800 GCAAGTTTTGTTCATTTGGTAAAGAGTCAGGTTTTAAAATTCAAAATCT
GTCTGGTTTTGGTGTTTTTTTTTTTATTTATTATTTCTTTGGGGTTCT
TTTTGATGCTTTATCTTTCTCTGCCAGGACTGTGTGACAATGGGAACGAA
AAAGAACATGCCAGGCACTGTCCTGGATTGCACACGCTGGTTGCACTCAG
5000 TAGCAGGCTCAGAACTGCCAGTCTTTCCACAGTATTACTTTCTAAACCTA
ATTTTAATAGCGTTAGTAGACTTCCATCACTGGGCAGTGCTTAGTGAATG
CTCTGTGTGAACGTTTTACTTATAAGCATGTTGGAAGTTTTGATGTTCCT
GGATGCAGTAGGGAAGGACAGATTAGCTATGTGAAAGTAGATTCTGAGT
5200 ATCGGGGTTACAAAAGTATAGAAACGATGAGAAATTCTTGTTGTAACTA
ATTGGAATTTCTTTAAGCGTTCACTTATGCTACATTCATAGTATTTCCAT
TTAAAAGTAGGAAAAGGTAAAACGTGAAATCGTGTGATTTTCGGATGGAA
CACCGCCTTCCTATGCACCTGACCAACTTCCAGAGGAAAAGCCTATTGAA
5400 AGCCGAGATTAAGCCACCAAAAGAACTCATTTGCATTGGAATATGTAGTA
TTTGCCCTCTTCCTCCCGGGTAATTACTATACTTTATAGGGTGCTTATAT
GTTAAATGAGTGGCTGGCACTTTTTATTCTCACAGCTGTGGGGAATTCTG
TCCTCTAGGACAGAAACAATTTTAATCTGTTCCACTGGTGACTGCTTTGT
5600 CAGCACTTCCACCTGAAGAGATCAATACACTCTTCAATGTCTAGTTCTGC
AACACTTGGCAAACCTCACATCTTATTTCATACTCTCTTCATGCCTATGC
TTATTAAAGCAATAATCTGGGTAATTTTTGTTTAATCACTGTCCTGACC
CCAGTGATGACCGTGTCCCACCTAAAGCTCAATTCAGGTCCTGAATCTCT
5800 TCAACTCTCTATAGCTAACATGAAGAATCTTCAAAAGTTAGGTCTGAGGG
ACTTAAGGCTAACTGTAGATGTTGTTGCCTGGTTTCTGTGCTGAAGGCCG
TGTAGTAGTTAGAGCATTCAACCTCTAG

FIG. 5C

SEQ ID NO: 43

```
   1 TGCCGCCTTCTTTGATATTCACTCTGTTGTATTTCATCTCTTCTTGCCGA
     TGAAAGGATATAACAGTCTGTATAACAGTCTGTGAGGAAATACTTGGTAT
     TTCTTCTGATCAGTGTTTTTATAAGTAATGTTGAATATTGGATAAGGCTG
 151 TGTGTCCTTTGTCTTGGGAGACAAAGCCCACAGCAGGTGGTGGTTGGGGT
     GGTGGCAGCTCAGTGACAGGAGAGGTTTTTTGCCTGTTTTTTTTTTTT
     TTTTTTTTTAAGTAAGGTGTTCTTTTTTCTTAGTAAATTTTCTACTGGA
 301 CTGTATGTTTGACAGGTCAGAAACATTTCTTCAAAAGAAGAACCTTTTG
     GAAACTGTACAGCCCTTTTCTTTCATTCCCTTTTTGCTTTCTGTGCCAAT
     GCCTTTGGTTCTGATTGCATTATGGAAAACGTTGATCGGAACTTGAGGTT
 451 TTTATTTATAGTGTGGCTTGAAAGCTTGGATAGCTGTTGTTACACGAGAT
     ACCTTATTAAGTTTAGGCCAGCTTGATGCTTTATTTTTTCCCTTTGAAGT
     AGTGAGCGTTCTCTGGTTTTTTCCTTTGAAACTGGTGAGGCTTAGATTT
 601 TTCTAATGGATTTTTTACCTGATGATCTAGTTGCATACCCAAATGCTTG
     TAAATGTTTTCCTAGTTAACATGTTGATAACTTCGGATTTACATGTTGTA
     TATACTTGTCATCTGTGTTTCTAGTAAAATATATGGCATTTATAGAAAT
 751 ACGTAATTCCTGATTTCCTTTTTTTATCTCTATGCTCTGTGTGTACAG
     GTCAAACAGACTTCACTCCTATTTTTATTTATAGAATTTTATATGCAGTC
     TGTCGTTGGTTCTTGTGTTGTAAGGATACAGCCTTAAATTTCCTAGAGCG
 901 ATGCTCAGTAAGGCGGGTTGTCACATGGGTTCAAATGTAAAACGGGCACG
     TTTGGCTGCTGCCTTCCCGAGATCCAGGACACTAAACTGCTTCTGCACTG
     AGGTATAAATCGCTTCAGATCCCAGGGAAGTGCAGATCCACGTGCATATT
1051 CTTAAAGAAGAATGAATACTTTCTAAATATTTTGGCATAGGAAGCAAGC
     TGCATGGATTTGTTTGGGACTTAAATTATTTTGGTAACGGAGTGCATAGG
     TTTTAAACACAGTTGCAGCATGCTAACGAGTCACAGCGTTTATGCAGAAG
1201 TGATGCCTGGATGCCTGTTGCAGCTGTTTACGGCACTGCCTTGCAGTGAG
     CATTGCAGATAGGGGTGGGGTGCTTTGTGTCGTGTTCCCACACGCTGCCA
     CACAGCCACCTCCCGGAACACATCTCACCTGCTGGGTACTTTTCAAACCA
1351 TCTTAGCAGTAGTAGATGAGTTACTATGAAACAGAGAAGTTCCTCAGTTG
     GATATTCTCATGGGATGTCTTTTTTCCCATGTTGGGCAAAGTATGATAAA
     GCATCTCTATTTGTAAATTATGCACTTGTTAGTTCCTGAATCCTTTCTAT
1501 AGCACCACTTATTGCAGCAGGTGTAGGCTCTGGTGTGGCCTGTGTCTGTG
     CTTCAATCTTTTAAAGCTTCTTTGGAAATACACTGACTTGATTGAAGTCT
     CTTGAAGATAGTAAACAGTACTTACCTTTGATCCCAATGAAATCGAGCAT
1651 TTCAGTTGTAAAAGAATTCCGCCTATTCATACCATGTAATGTAATTTTAC
     ACCCCAGTGCTGACACTTTGGAATATATTCAAGTAATAGACTTTGGCCT
     CACCCTCTTGTGTACTGTATTTTGTAATAGAAAATATTTTAAACTGTGCA
1801 TATGATTATTACATTATGAAAGAGACATTCTGCTGATCTTCAAATGTAAG
     AAAATGAGGAGTGCGTGTGCTTTTATAAATACAAGTGATTGCAAATTAGT
     GCAGGTGTCCTTAAAAAAAAAAAAAAAAAAGTAATATAAAAAGGACCAGGT
1951 GTTTTACAAGTGAAATACATTCCTATTTGGTAAACAGTTACATTTTTATG
     AAGATTACCAGCGCTGCTGACTTCTAAACATAAGGCTGTATTGTCTTCC
     TGTACCATTGCATTTCCTCATTCCCAATTTGCACAAGGATGTCTGGGTAA
2101 ACTATTCAAGAAATGGCTTTGAAATACAGCATGGGAGCTTGTCTGAGTTG
     GAATGCAGAGTTGCACTGCAAAATGTCAGGAAATGGATGTCTCTCAGAAT
     GCCCAACTCCAAAGGATTTTATATGTGTATATAGTAAGCAGTTTCCTGAT
```

FIG. 6A

2251 TCCAGCAGGCCAAAGAGTCTGCTGAATGTTGTGTTGCCGGAGACCTGTAT
TTCTCAACAAGGTAAGATGGTATCCTAGCAACTGCGGATTTTAATACATT
TTCAGCAGAAGTACTTAGTTAATCTCTACCTTTAGGGATCGTTTCATCAT
2401 TTTTAGATGTTATACTTGAAATACTGCATAACTTTTAGCTTTCATGGGTT
CCTTTTTTTCAGCCTTTAGGAGACTGTTAAGCAATTTGCTGTCCAACTTT
TGTGTTGGTCTTAAACTGCAATAGTAGTTTACCTTGTATTGAAGAAATAA
2551 AGACCATTTTTATATTAAAAAATACTTTTGTCTGTCTTCATTTTGACTTG
TCTGATATCCTTGCAGTGCCCATTATGTCAGTTCTGTCAGATATTCAGAC
ATCAAAACTTAACGTGAGCTCAGTGGAGTTACAGCTGCGGTTTTGATGCT
2701 GTTATTATTTCTGAAACTAGAAATGATGTTGTCTTCATCTGCTCATCAAA
CACTTCATGCAGAGTGTAAGGCTAGTGAGAAATGCATACATTTATTGATA
CTTTTTTAAAGTCAACTTTTTATCAGATTTTTTTTCATTTGGAAATATA
2851 TTGTTTTCTAGACTGCATAGCTTCTGAATCTGAAATGCAGTCTGATTGGC
ATGAAGAAGCACAGCACTCTTCATCTTACTTAAACTTCATTTGGAATGA
AGGAAGTTAAGCAAGGGCACAGGTCCATGAAATAGAGACAGTGCGCTCAG
3001 GAGAAAGTGAACCTGGATTTCTTTGGCTAGTGTTCTAAATCTGTAGTGAG
GAAAGTAACACCCGATTCCTTGAAAGGGCTCCAGCTTTAATGCTTCCAAA
TTGAAGGTGGCAGGCAACTTGGCCACTGGTTATTTACTGCATTATGTCTC
3151 AGTTTCGCAGCTAACCTGGCTTCTCCACTATTGAGCATGGACTATAGCCT
GGCTTCAGAGGCCAGGTGAAGGTTGGGATGGGTGGAAGGAGTGCTGGGCT
GTGGCTGGGGGGACTGTGGGGACTCCAAGCTGAGCTTGGGGTGGGCAGCA
3301 CAGGGAAAAGTGTGGGTAACTATTTTTAAGTACTGTGTTGCAAACGTCTC
ATCTGCAAATACGTAGGGTGTGTACTCTCGAAGATTAACAGTGTGGGTTC
AGTAATATATGGATGAATTCACAGTGGAAGCATTCAAGGGTAGATCATCT
3451 AACGACACCAGATCATCAAGCTATGATTGGAAGCGGTATCAGAAGAGCGA
GGAAGGTAAGCAGTCTTCATATGTTTTCCCTCCACGTAAAGCAGTCTGGG
AAAGTAGCACCCCTTGAGCAGAGACAAGGAAATAATTCAGGAGCATGTGC
3601 TAGGAGAACTTTCTTGCTGAATTCTACTTGCAAGAGCTTTGATGCCTGGC
TTCTGGTGCCTTCTGCAGCACCTGCAAGGCCCAGAGCCTGTGGTGAGCTG
GAGGGAAAGATTCTGCTCAAGTCCAAGCTTCAGCAGGTCATTGTCTTTGC
3751 TTCTTCCCCCAGCACTGTGCAGCAGAGTGGAACTGATGTCGAAGCCTCCT
GTCCACTACCTGTTGCTGCAGGCAGACTGCTCTCAGAAAAGAGAGCTAA
CTCTATGCCATAGTCTGAAGGTAAAATGGGTTTTAAAAAAGAAAACACAA
3901 AGGCAAAACCGGCTGCCCCATGAGAAGAAAGCAGTGGTAAACATGGTAGA
AAAGGTGCAGAAGCCCCCAGGCAGTGTGACAGGCCCCTCCTGCCACCTAG
AGGCGGGAACAAGCTTCCCTGCCTAGGGCTCTGCCCGCGAAGTGCGTGTT
4051 TCTTTGGTGGGTTTTGTTTGGCGTTTGGTTTTGAGATTTAGACACAAGGG
AAGCCTGAAAGGAGGTGTTGGGCACTATTTTGGTTTGTAAAGCCTGTACT
TCAAATATATATTTTGTGAGGGAGTGTAGCGAATTGGCCAATTTAAAATA
4201 AAGTTGCAAGAGATTGAAGGCTGAGTAGTTGAGGGTAACACGTTTAAT
GAGATCTTCTGAAACTACTGCTTCTAAACACTTGTTTGAGTGGTGAGACC
TTGGATAGGTGAGTGCTCTTGTTACATGTCTGATGCACTTGCTTGTCCTT
4351 TTCCATCCACATCCATGCATTCCACATCCACGCATTTGTCACTTATCCCA
TATCTGTCATATCTGACATACCTGTCTCTTCGTCACTTGGTCAGAAGAAA
CAGATGTGATAATCCCCAGCCGCCCCAAGTTTGAGAAGATGGCAGTTGCT
4501 TCTTTCCCTTTTTCCTGCTAAGTAAGGATTTTCTCCTGGCTTTGACACCT
CACGAAATAGTCTTCCTGCCTTACATTCTGGGCATTATTTCAAATATCTT

FIG. 6B

```
       TGGAGTGCGCTGCTCTCAAGTTTGTGTCTTCCTACTCTTAGAGTGAATGC
 4651  TCTTAGAGTGAAAGAGAAGGAAGAGAAGATGTTGGCCGCAGTTCTCTGAT
       GAACACACCTCTGAATAATGGCCAAAGGTGGGTGGGTTTCTCTGAGGAAC
       GGGCAGCGTTTGCCTCTGAAAGCAAGGAGCTCTGCGGAGTTGCAGTTATT
 4801  TTGCAACTGATGGTGGAACTGGTGCTTAAAGCAGATTCCCTAGGTTCCCT
       GCTACTTCTTTTCCTTCTTGGCAGTCAGTTTATTTCTGACAGACAAACAG
       CCACCCCACTGCAGGCTTAGAAAGTATGTGGCTCTGCCTGGGTGTGTTA
 4951  CAGCTCTGCCCTGGTGAAAGGGGATTAAAACGGGCACCATTCATCCCAAA
       CAGGATCCTCATTCATGGATCAAGCTGTAAGGAACTTGGGCTCCAACCTC
       AAAACATTAATTGGAGTACGAATGTAATTAAAACTGCATTCTCGCATTCC
 5101  TAAGTCATTTAGTCTGGACTCTGCAGCATGTAGGTCGGCAGCTCCCACTT
       TCTCAAAGACCACTGATGGAGGAGTAGTAAAAATGGAGACCGATTCAGAA
       CAACCAACGGAGTGTTGCCGAAGAAACTGATGGAAATAATGCATGAATTG
 5251  TGTGGTGGACATTTTTTTTAAATACATAAACTACTTCAAATGAGGTCGGA
       GAAGGTCAGTGTTTTATTAGCAGCCATAAAACCAGGTGAGCGAGTACCAT
       TTTTCTCTACAAGAAAAACGATTCTGAGCTCTGCGTAAGTATAAGTTCTC
 5401  CATAGCGGCTGAAGCTCCCCCCTGGCTGCCTGCCATCTCAGCTGGAGTGC
       AGTGCCATTTCCTTGGGGTTTCTCTCACAGCAGTAATGGGACAATACTTC
       ACAAAAATTCTTTCTTTTCCTGTCATGTGGGATCCCTACTGTGCCCTCCT
 5551  GGTTTTACGTTACCCCCTGACTGTTCCATTCAGCGGTTTGGAAAGAGAAA
       AAGAATTTGGAAATAAAACATGTCTACGTTATCACCTCCTCCAGCATTTT
       GGTTTTTAATTATGTCAATAACTGGCTTAGATTTGGAAATGAGAGGGGGT
 5701  TGGGTGTATTACCGAGGAACAAAGGAAGGCTTATATAAACTCAAGTCTTT
       TATTTAGAGAACTGGCAAGCTGTCAAAAACAAAAAGGCCTTACCACCAAA
       TTAAGTGAATAGCCGCTATAGCCAGCAGGGCCAGCACGAGGGATGGTGCA
 5851  CTGCTGGCACTATGCCACGGCCTGCTTGTGACTCTGAGAGCAACTGCTTT
       GGAAATGACAGCACTTGGTGCAATTTCCTTTGTTTCAGAATGCGTAGAGC
       GTGTGCTTGGCGACAGTTTTCTAGTTAGGCCACTTCTTTTTCCTTCTC
 6001  TCCTCATTCTCCTAAGCATGTCTCCATGCTGGTAATCCCAGTCAAGTGAA
       CGTTCAAACAATGAATCCATCACTGTAGGATTCTCGTGGTGATCAAATCT
       TTGTGTGAGGTCTATAAAATATGGAAGCTTATTTATTTTTCGTTCTTCCA
 6151  TATCAGTCTTCTCTATGACAATTCACATCCACCACAGCAAATTAAAGGTG
       AAGGAGGCTGGTGGGATGAAGAGGGTCTTCTAGCTTTACGTTCTTCCTTG
       CAAGGCCACAGGAAAATGCTGAGAGCTGTAGAATACAGCCTGGGGTAAGA
 6301  AGTTCAGTCTCCTGCTGGGACAGCTAACCGCATCTTATAACCCCTTCTGA
       GACTCATCTTAGGACCAAATAGGGTCTATCTGGGGTTTTGTTCCTGCTG
       TTCCTCCTGGAAGGCTATCTCACTATTTCACTGCTCCCACGGTTACAAAC
 6451  CAAAGATACAGCCTGAATTTTTTCTAGGCCACATTACATAAATTTGACCT
       GGTACCAATATTGTTCTCTATATAGTTATTTCCTTCCCCACTGTGTTTAA
       CCCCTTAAGGCATTCAGAACAACTAGAATCATAGAATGGTTTGGATTGGA
 6601  AGGGGCCTTAAACATCATCCATTTCCAACCCTCTGCCATGGGCTGCTTGC
       CACCCACTGGCTCAGGCTGCCCAGGGCCCCATCCAGCCTGGCCTTGAGCA
       CCTCCAGGGATGGGGCACCCACAGCTTCTCTGGGCAGCCTGTGCCAACAC
 6751  CTCACCACTCTCTGGGTAAAGAATTCTCTTTTAACATCTAATCTAAATCT
       CTTCTCTTTTAGTTTAAAGCCATTCCTCTTTTTCCCGTTGCTATCTGTCC
       AAGAAATGTGTATTGGTCTCCCTCCTGCTTATAAGCAGGAAGTACTGGAA
 6901  GGCTGCAGTGAGGTCTCCCCACAGCCTTCTCTTCTCCAGGCTGAACAAGC
```

FIG. 6C

```
         CCAGCTCCTTCAGCCTGTCTTCGTAGGAGATCATCTTAGTGGCCCTCCTC
         TGGACCCATTCCAACAGTTCCACGGCTTTCTTGTGGAGCCCCAGGTCTGG
    7051 ATGCAGTACTTCAGATGGGGCCTTACAAGGCAGAGCAGATGGGGACAAT
         CGCTTACCCCTCCCTGCTGGCTGCCCCTGTTTTGATGCAGCCCAGGGTAC
         TGTTGGCCTTTCAGGCTCCAGACCCCTTGCTGATTTGTGTCAAGCTTTT
    7201 CATCCACCAGAACCCACGCTTCCTGGTTAATACTTCTGCCCTCACTTCTG
         TAAGCTTGTTTCAGGAGACTTCCATTCTTTAGGACAGACTGTGTTACACC
         TACCTGCCCTATTCTTGCATATATACATTTCAGTTCATGTTTCCTGTAAC
    7351 AGGACAGAATATGTATTCCTCTAACAAAATACATGCAGAATTCCTAGTG
         CCATCTCAGTAGGGTTTTCATGGCAGTATTAGCACATAGTCAATTTGCTG
         CAAGTACCTTCCAAGCTGCGGCCTCCCATAAATCCTGTATTTGGGATCAG
    7501 TTACCTTTTGGGGTAAGCTTTTGTATCTGCAGAGACCCTGGGGGTTCTGA
         TGTGCTTCAGCTCTGCTCTGTTCTGACTGCACCATTTTCTAGATCACCCA
         GTTGTTCCTGTACAACTTCCTTGTCCTCCATCCTTTCCCAGCTTGTATCT
    7651 TTGACAAATACAGGCCTATTTTGTGTTTGCTTCAGCAGCCATTTAATTC
         TTCAGTGTCATCTTGTTCTGTTGATGCCACTGGAACAGGATTTTCAGCAG
         TCTTGCAAAGAACATCTAGCTGAAAACTTTCTGCCATTCAATATTCTTAC
    7801 CAGTTCTTCTTGTTTGAGGTGAGCCATAAATTACTAGAACTTCGTCACTG
         ACAAGTTTATGCATTTTATTACTTCTATTATGTACTTACTTTGACATAAC
         ACAGACACGCACATATTTTGCTGGGATTTCCACAGTGTCTCTGTGTCCTT
    7951 CACATGGTTTTACTGTCATACTTCCGTTATAACCTTGGCAATCTGCCCAG
         CTGCCCATCACAAGAAAAGAGATTCCTTTTTTATTACTTCTCTTCAGCCA
         ATAAACAAAATGTGAGAAGCCCAAACAAGAACTTGTGGGGCAGGCTGCCA
    8101 TCAAGGGAGAGACAGCTGAAGGGTTGTGTAGCTCAATAGAATTAAGAAAT
         AATAAAGCTGTGTCAGACAGTTTTGCCTGATTTATACAGGCACGCCCCAA
         GCCAGAGAGGCTGTCTGCCAAGGCCACCTTGCAGTCCTTGGTTTGTAAGA
    8251 TAAGTCATAGGTAACTTTTCTGGTGAATTGCGTGGAGAATCATGATGGCA
         GTTCTTGCTGTTTACTATGGTAAGATGCTAAAATAGGAGACAGCAAAGTA
         ACACTTGCTGCTGTAGGTGCTCTGCTATCCAGACAGCGATGGCACTCGCA
    8401 CACCAAGATGAGGGATGCTCCCAGCTGACGGATGCTGGGGCAGTAACAGT
         GGGTCCCATGCTGCCTGCTCATTAGCATCACCTCAGCCCTCACCAGCCCA
         TCAGAAGGATCATCCCAAGCTGAGGAAAGTTGCTCATCTTCTTCACATCA
    8551 TCAAACCTTTGGCCTGACTGATGCCTCCGGATGCTTAAATGTGGTCACT
         GACATCTTTATTTTTCTATGATTTCAAGTCAGAACCTCCGGATCAGGAGG
         GAACACATAGTGGGAATGTACCCTCAGCTCCAAGGCCAGATCTTCCTTCA
    8701 ATGATCATGCATGCTACTTAGGAAGGTGTGTGTGTGTGAATGTAGAATTG
         CCTTTGTTATTTTTCTTCCTGCTGTCAGGAACATTTTGAATACCAGAGA
         AAAAGAAAAGTGCTCTTCTTGGCATGGGAGGAGTTGTCACACTTGCAAAA
    8851 TAAAGGATGCAGTCCCAAATGTTCATAATCTCAGGGTCTGAAGGAGGATC
         AGAAACTGTGTATACAATTTCAGGCTTCTCTGAATGCAGCTTTTGAAAGC
         TGTTCCTGGCCGAGGCAGTACTAGTCAGAACCCTCGGAAACAGGAACAAA
    9001 TGTCTTCAAGGTGCAGCAGGAGGAAACACCTTGCCCATCATGAAAGTGAA
         TAACCACTGCCGCTGAAGGAATCCAGCTCCTGTTTGAGCAGGTGCTGCAC
         ACTCCCACACTGAAACAACAGTTCATTTTTATAGGACTTCCAGGAAGGAT
    9151 CTTCTTCTTAAGCTTCTTAATTATGGTACATCTCCAGTTGGCAGATGACT
         ATGACTACTGACAGGAGAATGAGGAACTAGCTGGGAATATTTCTGTTTGA
         CCACCATGGAGTCACCCATTTCTTTACTGGTATTTGGAAATAATAATTCT
```

FIG. 6D

9301 GAATTGCAAAGCAGGAGTTAGCGAAGATCTTCATTTCTTCCATGTTGGTG
ACAGCACAGTTCTGGCTATGAAAGTCTGCTTACAAGGAAGAGGATAAAAA
9401 TCATAGGGATAATAAATCTAAGTTTGAAGACAATGAGGTTTTAGCTGCAT
TTGACATGAAGAAATTGAGACCTCTACTGGATAGCTATGGTATTTACGTG
TCTTTTTGCTTAGTTACTTATTGACCCCAGCTGAGGTCAAGTATGAACTC
9551 AGGTCTCTCGGGCTACTGGCATGGATTGATTACATACAACTGTAATTTTA
GCAGTGATTTAGGGTTTATGAGTACTTTTGCAGTAAATCATAGGGTTAGT
AATGTTAATCTCAGGGAAAAAAAAAAAAAGCCAACCCTGACAGACATCCC
9701 AGCTCAGGTGGAAATCAAGGATCACAGCTCAGTGCGGTCCCAGAGAACAC
AGGGACTCTTCTCTTAGGACCTTTATGTACAGGGCCTCAAGATAACTGAT
GTTAGTCAGAAGACTTTCCATTCTGGCCACAGTTCAGCTGAGGCAATCCT
9851 GGAATTTTCTCTCCGCTGCACAGTTCCAGTCATCCCAGTTTGTACAGTTC
TGGCACTTTTTGGGTCAGGCCGTGATCCAAGGAGCAGAAGTTCCAGCTAT
GGTCAGGGAGTGCCTGACCGTCCCAACTCACTGCACTCAAACAAAGGCGA
10001 AACCACAAGAGTGGCTTTTGTTGAAATTGCAGTGTGGCCCAGAGGGGCTG
CACCAGTACTGGATTGACCACGAGGCAACATTAATCCTCAGCAAGTGCAA
TTTGCAGCCATTAAATTGAACTAACTGATACTACAATGCAATCAGTATCA
10151 ACAAGTGGTTTGGCTTGGAAGATGGAGTCTAGGGGCTCTACAGGAGTAGC
TACTCTCTAATGGAGTTGCATTTGAAGCAGGACACTGTGAAAAGCTGGC
CTCCTAAAGAGGCTGCTAAACATTAGGGTCAATTTTCCAGTGCACTTTCT
10301 GAAGTGTCTGCAGTTCCCCATGCAAAGCTGCCCAAACATAGCACTTCCAA
TTGAATACAATTATATGCAGGCGTACTGCTTCTTGCCAGCACTGTCCTTC
TCAAATGAACTCAACAAACAATTTCAAAGTCTAGTAGAAAGTAACAAGCT
10451 TTGAATGTCATTAAAAAGTATATCTGCTTTCAGTAGTTCAGCTTATTTAT
GCCCACTAGAAACATCTTGTACAAGCTGAACACTGGGGCTCCAGATTAGT
GGTAAAACCTACTTTATACAATCATAGAATCATAGAATGGCCTGGGTTGG
10601 AAGGGACCCCAAGGATCATGAAGATCCAACACCCCGCCACAGGCAGGGC
CACCAACCTCCAGATCTGGTACTAGACCAGGCAGCCCAGGGCTCCATCCA
ACCTGGCCATGAACACCTCCAGGGATGGAGCATCCACAACCTCTCTGGGC
10751 AGCCTGTGCCAGCACCTCACCACCCTCTCTGTGAAGAACTTTTCCCTGAC
ATCCAATCTAAGCCTTCCCTCCTTGAGGTTAGATCCACTCCCCCTTGTGC
TATCACTGTCTACTCTTGTAAAAGTTGATTCTCCTCCTTTTGGAAGGT
10901 TGCAATGAGGTCTCCTTGCAGCCTTCTTCTCTTCTGCAGGATGAACAAGC
CCAGCTCCCTCAGCCTGTCTTTATAGGAGAGGTGCTCCAGCCCTCTGATC
ATCTTTGTGGCCCTCCTCTGGACCCGCTCCAAGAGCTCCACATCTTTCCT
11051 GTACTGGGGGCCCCAGGCCTGAATGCAGTACTCCAGATGGGGCCTCAAAA
GAGCAGAGTAAAGAGGGACAATCACCTTCCTCACCCTGCTGGCCAGCCCT
CTTCTGATGGAGCCCTGGATACAACTGGCTTTCTGAGCTGCAACTTCTCC
11201 TTATCAGTTCCACTATTAAAACAGGAACAATACAACAGGTGCTGATGGCC
AGTGCAGAGTTTTTCACACTTCTTCATTTCGGTAGATCTTAGATGAGGAA
CGTTGAAGTTGTGCTTCTGCGTGTGCTTCTTCCTCCTCAAATACTCCTGC
11351 CTGATACCTCACCCCACCTGCCACTGAATGGCTCCATGGCCCCTGCAGC
CAGGGCCCTGATGAACCCGGCACTGCTTCAGATGCTGTTTAATAGCACAG
TATGACCAAGTTGCACCTATGAATACACAAACAATGTGTTGCATCCTTCA
11501 GCACTTGAGAAGAAGAGCCAAATTTGCATTGTCAGGAAATGGTTTAGTAA
TTCTGCCAATTAAAACTTGTTTATCTACCATGGCTGTTTTATGGCTGTT
AGTAGTGGTACACTGATGATGAACAATGGCTATGCAGTAAAATCAAGACT

FIG. 6E

11651 GTAGATATTGCAACAGACTATAAAATTCCTCTGTGGCTTAGCCAATGTGG
      TACTTCCCACATTGTATAAGAAATTTGGCAAGTTTAGAGCAATGTTTGAA
      GTGTTGGGAAATTTCTGTATACTCAAGAGGGCGTTTTTGACAACTGTAGA
11801 ACAGAGGAATCAAAAGGGGGTGGGAGGAAGTTAAAAGAAGAGGCAGGTGC
      AAGAGAGCTTGCAGTCCCGCTGTGTGTACGACACTGGCAACATGAGGTCT
      TTGCTAATCTTGGTGCTTTGCTTCCTGCCCCTGGCTGCCTTAGGGTGCGA
11951 TCTGCCTCAGACCCACAGCCTGGGCAGCAGGAGGACCCTGATGCTGCTGG
      CTCAGATGAGGAGAATCAGCCTGTTTAGCTGCCTGAAGGATAGGCACGAT
      TTTGGCTTTCCTCAAGAGGAGTTTGGCAACCAGTTTCAGAAGGCTGAGAC
12101 CATCCCTGTGCTGCACGAGATGATCCAGCAGATCTTTAACCTGTTTAGCA
      CCAAGGATAGCAGCGCTGCTTGGGATGAGACCCTGCTGGATAAGTTTTAC
      ACCGAGCTGTACCAGCAGCTGAACGATCTGGAGGCTTGCGTGATCCAGGG
12251 CGTGGGCGTGACCGAGACCCCTCTGATGAAGGAGGATAGCATCCTGGCTG
      TGAGGAAGTACTTTCAGAGGATCACCCTGTACCTGAAGGAGAAGAAGTAC
      AGCCCCTGCGCTTGGGAAGTCGTGAGGGCTGAGATCATGAGGAGCTTTAG
12401 CCTGAGCACCAACCTGCAAGAGAGCTTGAGGTCTAAGGAGTAAAAAGTCT
      AGAGTCGGGGCGGCGCGTGGTAGGTGGCGGGGGGTTCCCAGGAGAGCCCC
      CAGCGCGGACGGCAGCGCCGTCACTCACCGCTCCGTCTCCCTCCGCCCAG
12551 GGTCGCCTGGCGCAACCGCTGCAAGGGCACCGACGTCCAGGCGTGGATCA
      GAGGCTGCCGGCTGTGAGGAGCTGCCGCGCCCGGCCCGCCCGCTGCACAG
      CCGGCCGCTTTGCGAGCGCGACGCTACCCGCTTGGCAGTTTTAAACGCAT
12701 CCCTCATTAAAACGACTATACGCAAACGCCTTCCCGTCGGTCCGCGTCTC
      TTTCCGCCGCCAGGGCGACACTCGCGGGGAGGGCGGGAAGGGGCCGGGC
      GGGAGCCCGCGGCCAACCGTCGCCCCGTGACGGCACCGCCCCGCCCCCGT
12851 GACGCGGTGCGGGCGCCGGGGCCGTGGGCTGAGCGCTGCGGCGGGGCCG
      GGCCGGGCCGGGGCGGGAGCTGAGCGCGGCGCGGCTGCGGGCGGCGCCCC
      CTCCGGTGCAATATGTTCAAGAGAATGGCTGAGTTCGGGCCTGACTCCGG
13001 GGGCAGGGTGAAGGTGCGGCGCGGGCGGAGGGACGGGCGGGCGCGGGGC
      CGCCCGGCGGGTGCCGGGGCCTCTGCCGGCCCGCCCGGCTCGGGCTGCTG
      CGGCGCTTACGGGCGCGCTTCTCGCCGCTGCCGCTTCTCTTCTCTCCCGC
13151 GCAAGGGCGTCACCATCGTGAAGCCGGTAGTGTACGGGAACGTGGCGCGG
      TACTTCGGGAAGAAGAGGGAGGAGGACGGGCACACGCATCAGTGGACGGT
      TTACGTGAAGCCCTACAGGAACGAGGTAGGGCCCGAGCGCGTCGGCCGCC
13301 GTTCTCGGAGCGCCGGAGCCGTCAGCGCCGCGCCTGGGTGCGCTGTGGGA
      CACAGCGAGCTTCTCTCGTAGGACATGTCCGCCTACGTGAAAAAAATCCA
      GTTCAAGCTGCACGAGAGCTACGGGAATCCTCTCCGAGGTGGGTGTTGCG
13451 TCGGGGGGTTTGCTCCGCTCGGTCCCGCTGAGGCTCGTCGCCCTCATCTT
      TCTTTCGTGCCGCAGTCGTTACCAAACCGCCGTACGAGATCACCGAAACG
13551 GGCTGGGGCGAATTTGAAATCATCATCAAGATATTTTTCATTGATCCAAA
      CGAGCGACCCGTAAGTACGCTCAGCTTCTCGTAGTGCTTCCCCCGTCCTG
      GCGGCCCGGGGCTGGGCTGCTCGCTGCTGCCGGTCACAGTCCCGCCAGCC
13701 GCGGAGCTGACTGAGCTCCCTTTCCCGGGACGTGTGCTCTGTGTTCGGTC
      AGCGAGGCTATCGGGAGGCTTTGGCTGCATTTGGCTTCTCTGGCGCTTA
      GCGCAGGAGCACGTTGTGCTACGCCTGAACTACAGCTGTGAGAAGGCCGT
13851 GGAAACCGCTCTCAAACTGATTTATTGGCGAAATGGCTCTAAACTAAATC
      GTCTCCTCTCTTTGGAAATGCTTTAGAGAAGGTCTCTGTGGTAGTTCTTA
      TGCATCTATCCTAAAGCACTTGGCCAGACAATTTAAAGACATCAAGCAGC

FIG. 6F

14001 ATTTATAGCAGGCACGTTTAATAACGAATACTGAATTTAAGTAACTCTGC
TCACGTTGTATGACGTTTATTTTCGTATTCCTGAAAGCCATTAAAATCCT
GTGCAGTTGTTTAGTAAGAACAGCTGCCACTGTTTTGTATCTAGGAGATA
14151 ACTGGTGTTTCCCTACAGTTCTCAAGCTGATAAAACTCTGTCTTTGTATC
TAGGTAACCCTGTATCACTTGCTGAAGCTTTTCAGTCTGACACCAATGC
AATCCTGGGAAAGAAAACTGTAGTTTCTGAATTCTATGATGAAATGGTAT
14301 GAAAATTTTAATGTCAACCGAGCCTGACTTTATTTAAAAAAAATTATTGA
TGGTGCTGTGTATTTTGGTCCTTCCTTAGATATTTCAAGATCCTACTGCC
ATGATGCAGCAACTGCTAACGACGTCCCGTCAGCTGACACTTGGTGCTTA
14451 CAAGCATGAAACAGAGTGTAAGTGCAAAATGAGGATACCTTCGCCGACCG
TCATTCACTACTAATGTTTTCTGTGGGATGTGATCGTACAGTGAGTTTGG
CTGTGTGAAATTTGAATAGCTTGGTATTGGCAGTGATGACGTGATCGATG
14601 CCTTGCTTATCATGTTTGAAATGAAGTAGAATAAATGCAGCCTGCTTTAT
TTGAGATAGTTTGGTTCATTTTATGGAATGCAAGCAAAGATTATACTTCC
TCACTGAATTGCACTGTCCAAAGGTGTGAAATGTGTGGGGATCTGGAGGA
14751 CCGTGACCGAGGGACATTGGATCGCTATCTCCCATTTCTTTTGCTGTTAC
CAGTTCAGATTTTCTTTTCACCTAGTCTTTAATTCCCAGGGTTTTGTTTT
TTCCTTGGTCATAGTTTTTGTTTTCACTCTGGCAAATGATGTTGTGAAT
14901 TACACTGCTTCAGCCACAAAACTGATGGACTGAATGAGGTCATCAAACAA
ACTTTTCTTCTTCCGTATTTCCTTTTTTTTCCCCCACTTATCATTTTTAC
TGCTGTTGTTGAGTCTGTAAGGCTAAAAGTAACTGTTTTGTGCTTTTTCA
15051 GGACGTGTGCTTTCCAAATTACTGCCACATATATAAAGAAAGGTTGGAAT
TTTAAAGATAATTCATGTTTCTTCTTCTTTTTTGCCACCACAGTTGCAGA
TCTTGAAGTAAAAACCAGGGAAAAGCTGGAAGCTGCCAAAAAGAAAACCA
15201 GTTTTGAAATTGCTGAGCTTAAAGAAAGGTTAAAAGCAAGTCGTGAAACC
ATCAACTGCTTAAAGAGTGAAATCAGAAAACTCGAAGAGGATGATCAGTC
TAAAGATATGTGATGAGTGTTGACTTGGCAGGGAGCCTATAATGAGAATG
15351 AAAGGACTTCAGTCGTGGAGTTGTATGCGTTCTCTCCAATTCTGTAACGG
AGACTGTATGAATTTCATTTGCAAATCACTGCAGTGTGTGACAACTGACT
TTTTATAAATGGCAGAAAACAAGAATGAATGTATCCTCATTTTATAGTTA
15501 AAATCTATGGGTATGTACTGGTTTATTTCAAGGAGAATGGATCGTAGAGA
CTTGGAGGCCAGATTGCTGCTTGTATTGACTGCATTTGAGTGGTGTAGGA
ACATTTTGTCTATGGTCCCGTGTTAGTTTACAGAATGCCACTGTTCACTG
15651 TTTTGTTTTGTATTTTACTTTTCTACTGCAACGTCAAGGTTTTAAAAGT
TGAAAATAAAACATGCAGGTTTTTTTTAAATATTTTTTGTCTCTATCCA
GTTTGGGCTTCAAGTATTATTGTTAACAGCAAGTCCTGATTTAAGTCAGA
15801 GGCTGAAGTGTAATGGTATTCAAGATGCTTAAGTCTGTTGTCAGCAAAAC
AAAAGAGAAAACTTCATAAAATCAGGAAGTTGGCATTTCTAATAACTTCT
TTATCAACAGATAAGAGTTTCTAGCCCTGCATCTACTTTCACTTATGTAG
15951 TTGATGCCTTTATATTTGTGTGTTTGGATGCAGGAAGTGATTCCTACTC
TGTTATGTAGATATTCTATTTAACACTTGTACTCTGCTGTGCTTAGCCTT
16051 TCCCCATGAAAATTCAGCGGCTGTAAATCCCCCTCTTCTTTTGTAGCCTC
ATACAGATGGCAGACCCTCAGGCTTATAAAGGCTTGGGCATCTTCTTTAC
TGCTTTGAGATTCTGTGTTGCAGTAACCTCTGCCAGAGAGGAGAAAAGCC
16201 CCACAAACCTCATCCCCTTCTTCTATAGCAATCAGTATTACTAATGCTTT
GAGAACAGAGCACTGGTTTGAAACGTTTGATAATTAGCATTTAACATGGC
TTGGTAAAGATGCAGAACTGAAACAGCTGTGACAGTATGAACTCAGTATG

FIG. 6G

16351 GAGACTTCATTAAGACAAACAGCTGTTAAAATCAGGCATGTTTCATTGAG
      GAGGACGGGGCAACTTGCACCAGTGGTGCCCACACAAATCCTTCCTGGCG
      CTGCAGACCAATTTTTCTGGCATTCTGACTGCCGTTGCTGCTGGTCACAG
16501 AGAGCAACTATTTTATCAGCCACAGGCAATTTGCTTGTAGTATTTTCCA
      AGTGTTGTAGGTAAGTATAAATGCATCGGCTCCAGAGCACTTTGAGTATA
      CTTATTAAAAACATAAATGAAAGACAAATTAGCTTTGCTTGGGTGCACAG
16651 AACATTTTTAGTTCCAGCCTGCTTTTTGGTAGAAGCCCTCTTCTGAGGCT
      AGAACTGACTTTGACAAGTAGAGAAACTGGCAACGGAGCTATTGCTATCG
16751 AAGGATCCTTGTTAACAAAGTTAATCGTCTTTTAAGGTTTGGTTTATTCA
      TTAAATTTGCTTTTAAGCTGTAGCTGAAAAAGAACGTGCTGTCTTCCATG
16851 CACCAGGTGGCAGCTCTGTGCAAAGTGCTCTCTGGTCTCACCAGCCTTTT
      AATTGCCGGGATTCTGGCACGTCTGAGAGGGCTCAGACTGGCTTCGTTTG
      TTTGAACAGCGTGTACTGCTTTCTGTAGACATGGCCGGTTTCTCTCCTGC
17001 AGCTTATGAAACTGTTCACACTGAACACACTGGAACAGGTTGCCCAAGGA
      GGCCGTGGATGCCCCATCCCTGGAGGCATTCAAGGCCAGGCTGGATGTGG
      CTCTGGGCAGCCTGGTCTGGTGGTTGGCGATCCTGCACATAGCAGCGGGG
17151 TTGAAACTCGATGATCACTGTGGTCCTTTTCAACCCAGGCTATTCTATGA
      TTCTATGATTCAACAGCAAATCATATGTACTGAGAGAGGAAACAAACACA
      AGTGCTACTGTTTGCAAGTTTTGTTCATTTGGTAAAAGAGTCAGGTTTTA
17301 AAATTCAAAATCTGTCTGGTTTTGGTGTTTTTTTTTTTATTTATTATT
      TCTTTGGGGTTCTTTTTGATGCTTTATCTTTCTCTGCCAGGACTGTGTGA
      CAATGGGAACGAAAAGAACATGCCAGGCACTGTCCTGGATTGCACACGC
17451 TGGTTGCACTCAGTAGCAGGCTCAGAACTGCCAGTCTTTCCACAGTATTA
      CTTTCTAAACCTAATTTTAATAGCGTTAGTAGACTTCCATCACTGGGCAG
      TGCTTAGTGAATGCTCTGTGTGAACGTTTTACTTATAAGCATGTTGGAAG
17601 TTTTGATGTTCCTGGATGCAGTAGGGAAGGACAGATTAGCTATGTGAAAA
      GTAGATTCTGAGTATCGGGGTTACAAAAGTATAGAAACGATGAGAAATT
      CTTGTTGTAACTAATTGGAATTTCTTTAAGCGTTCACTTATGCTACATTC
17751 ATAGTATTTCCATTTAAAAGTAGGAAAAGGTAAAACGTGAAATCGTGTGA
      TTTTCGGATGGAACACCGCCTTCCTATGCACCTGACCAACTTCCAGAGGA
      AAAGCCTATTGAAAGCCGAGATTAAGCCACCAAAAGAACTCATTTGCATT
17901 GGAATATGTAGTATTTGCCCTCTTCCTCCCGGGTAATTACTATACTTTAT
      AGGGTGCTTATATGTTAAATGAGTGGCTGGCACTTTTTATTCTCACAGCT
      GTGGGGAATTCTGTCCTCTAGGACAGAAACAATTTTAATCTGTTCCACTG
18051 GTGACTGCTTTGTCAGCACTTCCACCTGAAGAGATCAATACACTCTTCAA
      TGTCTAGTTCTGCAACACTTGGCAAACCTCACATCTTATTTCATACTCTC
      TTCATGCCTATGCTTATTAAAGCAATAATCTGGGTAATTTTGTTTTAAT
18201 CACTGTCCTGACCCCAGTGATGACCGTGTCCCACCTAAAGCTCAATTCAG
      GTCCTGAATCTCTTCAACTCTCTATAGCTAACATGAAGAATCTTCAAAAG
      TTAGGTCTGAGGGACTTAAGGCTAACTGTAGATGTTGTTGCCTGGTTTCT
18351 GTGCTGAAGGCCGTGTAGTAGTTAGAGCATTCAACCTCTAGAAGAAGCTT
      GGCCAGCTGGTCGACCTGCAGATCCGGCCCTCGAGGGGGGGCCCGGTACC
      CAGCTTTTGTTCCCTTTAGTGAGGGTTAATTTCGAGCTTGGCGTAATCAT
18501 GGTCATAGCTGTTTCCTGTGTGAAATTGTTATCCGCTCACAATTCCACAC
      AACATACGAGCCGGAAGCATAAAGTGTAAAGCCTGGGGTGCCTAATGAGT
      GAGCTAACTCACATTAATTGCGTTGCGCTCACTGCCCGCTTTCCAGTCGG
18651 GAAACCTGTCGTGCCAGCTGCATTAATGAATCGGCCAACGCGCGGGGAGA

FIG. 6H

```
      GGCGGTTTGCGTATTGGGCGCTCTTCCGCTTCCTCGCTCACTGACTCGCT
      GCGCTCGGTCGTTCGGCTGCGGCGAGCGGTATCAGCTCACTCAAAGGCGG
18801 TAATACGGTTATCCACAGAATCAGGGGATAACGCAGGAAAGAACATGTGA
      GCAAAAGGCCAGCAAAAGGCCAGGAACCGTAAAAAGGCCGCGTTGCTGGC
      GTTTTTCCATAGGCTCCGCCCCCCTGACGAGCATCACAAAAATCGACGCT
18951 CAAGTCAGAGGTGGCGAAACCCGACAGGACTATAAAGATACCAGGCGTTT
      CCCCCTGGAAGCTCCCTCGTGCGCTCTCCTGTTCCGACCCTGCCGCTTAC
      CGGATACCTGTCCGCCTTTCTCCCTTCGGGAAGCGTGGCGCTTTCTCATA
19101 GCTCACGCTGTAGGTATCTCAGTTCGGTGTAGGTCGTTCGCTCCAAGCTG
      GGCTGTGTGCACGAACCCCCCGTTCAGCCCGACCGCTGCGCCTTATCCGG
      TAACTATCGTCTTGAGTCCAACCCGGTAAGACACGACTTATCGCCACTGG
19251 CAGCAGCCACTGGTAACAGGATTAGCAGAGCGAGGTATGTAGGCGGTGCT
      ACAGAGTTCTTGAAGTGGTGGCCTAACTACGGCTACACTAGAAGGACAGT
      ATTTGGTATCTGCGCTCTGCTGAAGCCAGTTACCTTCGGAAAAAGAGTTG
19401 GTAGCTCTTGATCCGGCAAACAAACCACCGCTGGTAGCGGTGGTTTTTTT
      GTTTGCAAGCAGCAGATTACGCGCAGAAAAAAAGGATCTCAAGAAGATCC
      TTTGATCTTTTCTACGGGGTCTGACGCTCAGTGGAACGAAAACTCACGTT
19551 AAGGGATTTTGGTCATGAGATTATCAAAAAGGATCTTCACCTAGATCCTT
      TTAAATTAAAAATGAAGTTTTAAATCAATCTAAAGTATATATGAGTAAAC
      TTGGTCTGACAGTTACCAATGCTTAATCAGTGAGGCACCTATCTCAGCGA
19701 TCTGTCTATTTCGTTCATCCATAGTTGCCTGACTCCCCGTCGTGTAGATA
      ACTACGATACGGGAGGGCTTACCATCTGGCCCCAGTGCTGCAATGATACC
      GCGAGACCCACGCTCACCGGCTCCAGATTTATCAGCAATAAACCAGCCAG
19851 CCGGAAGGGCCGAGCGCAGAAGTGGTCCTGCAACTTTATCCGCCTCCATC
      CAGTCTATTAATTGTTGCCGGGAAGCTAGAGTAAGTAGTTCGCCAGTTAA
      TAGTTTGCGCAACGTTGTTGCCATTGCTACAGGCATCGTGGTGTCACGCT
20001 CGTCGTTTGGTATGGCTTCATTCAGCTCCGGTTCCCAACGATCAAGGCGA
      GTTACATGATCCCCCATGTTGTGCAAAAAAGCGGTTAGCTCCTTCGGTCC
      TCCGATCGTTGTCAGAAGTAAGTTGGCCGCAGTGTTATCACTCATGGTTA
20151 TGGCAGCACTGCATAATTCTCTTACTGTCATGCCATCCGTAAGATGCTTT
      TCTGTGACTGGTGAGTACTCAACCAAGTCATTCTGAGAATAGTGTATGCG
      GCGACCGAGTTGCTCTTGCCCGGCGTCAATACGGGATAATACCGCGCCAC
20301 ATAGCAGAACTTTAAAAGTGCTCATCATTGGAAAACGTTCTTCGGGGCGA
      AAACTCTCAAGGATCTTACCGCTGTTGAGATCCAGTTCGATGTAACCCAC
      TCGTGCACCCAACTGATCTTCAGCATCTTTTACTTTCACCAGCGTTTCTG
20451 GGTGAGCAAAAACAGGAAGGCAAAATGCCGCAAAAAAGGGAATAAGGGCG
      ACACGGAAATGTTGAATACTCATACTCTTCCTTTTTCAATATTATTGAAG
      CATTTATCAGGGTTATTGTCTCATGAGCGGATACATATTTGAATGTATTT
20601 AGAAAAATAAACAAATAGGGGTTCCGCGCACATTTCCCCGAAAAGTGCCA
      CCTAAATTGTAAGCGTTAATATTTTGTTAAAATTCGCGTTAAATTTTTGT
      TAAATCAGCTCATTTTTTAACCAATAGGCCGAAATCGGCAAAATCCCTTA
20751 TAAATCAAAAGAATAGACCGAGATAGGGTTGAGTGTTGTTCCAGTTTGGA
      ACAAGAGTCCACTATTAAAGAACGTGGACTCCAACGTCAAAGGGCGAAAA
      ACCGTCTATCAGGGCGATGGCCCACTACGTGAACCATCACCCTAATCAAG
20901 TTTTTTGGGGTCGAGGTGCCGTAAAGCACTAAATCGGAACCCTAAAGGGA
      GCCCCCGATTTAGAGCTTGACGGGGAAAGCCGGCGAACGTGGCGAGAAAG
      GAAGGGAAGAAAGCGAAAGGAGCGGGCGCTAGGGCGCTGGCAAGTGTAGC
```

FIG. 61

21051 GGTCACGCTGCGCGTAACCACCACACCCGCCGCGCTTAATGCGCCGCTAC
      AGGGCGCGTCCCATTCGCCATTCAGGCTGCGCAACTGTTGGGAAGGGCGA
      TCGGTGCGGGCCTCTTCGCTATTACGCCAGCTGGCGAAAGGGGGATGTGC
21201 TGCAAGGCGATTAAGTTGGGTAACGCCAGGGTTTTCCCAGTCACGACGTT
      GTAAAACGACGGCCAGTGAATTGTAATACGACTCACTATAGGGCGAATTG
21301 GAGCTCCACCGCGGTGGCGGCCGCTCTAG

FIG. 6J

SEQ ID NO: 11

```
GTACCGGGCCCCCCCTCGAGGTGAATATCCAAGAATGCAGAACTGCATGGAAAGCAGAGCTG
CAGGCACGATGGTGCTGAGCCTTAGCTGCTTCCTGCTGGGAGATGTGGATGCAGAGACGAAT
GAAGGACCTGTCCCTTACTCCCCTCAGCATTCTGTGCTATTTAGGGTTCTACCAGAGTCCTT
AAGAGGTTTTTTTTTTTTTGGTCCAAAAGTCTGTTTGTTTGGTTTTGACCACTGAGAGCAT
GTGACACTTGTCTCAAGCTATTAACCAAGTGTCCAGCCAAAATCGATGTCACAACTTGGGAA
TTTTCCATTTGAAGCCCCTTGCAAAAACAAAGAGCACCTTGCCTGCTCCAGCTCCTGGCTGT
GAAGGGTTTTGGTGCCAAAGAGTGAAAGGCTTCCTAAAAATGGGCTGAGCCGGGGAAGGGGG
GCAACTTGGGGGCTATTGAGAAACAAGGAAGGACAAACAGCGTTAGGTCATTGCTTCTGCAA
ACACAGCCAGGGCTGCTCCTCTATAAAGGGGAAGAAAGAGGCTCCGCAGCCATCACAGACC
CAGAGGGGACGGTCTGTGAATCAAGCTT
```

FIG. 14

SEQ ID NO: 17
IFN-A
ATGGCTTTGACCTTTGCCTTACTGGTGGCTCTCCTGGTGCTGAGCTGCAAGAGCAGCTGCTCTGT
GGGCTGCGATCTGCCTCA

SEQ ID NO: 18
IFN-B
GACCCACAGCCTGGGCAGCAGGAGGACCCTGATGCTGCTGGCTCAGATGAGGAGAATCAGCCTGT
TTAGCTGCCTGAAGGATAGGCACGATTTTGGCTTT

SEQ ID NO: 19
IFN-C
CTCAAGAGGAGTTTGGCAACCAGTTTCAGAAGGCTGAGACCATCCCTGTGCTGCACGAGATG

SEQ ID NO: 20
IFN-D
TCCAGCAGATCTTTAACCTGTTTAGCACCAAGGATAGCAGCGCTGCTTGGGATGAGACCCTGCTG
GATAAGTTTTACACCGAGCTGTACCAGCA

SEQ ID NO: 21
IFN-E
CTGAACGATCTGGAGGCTTGCGTGATCCAGGGCGTGGGCGTGACCGAGACCCCTCTGATGAAGGA
GGATAGCATCCT

SEQ ID NO: 22
IFN-F
GCTGTGAGGAAGTACTTTCAGAGGATCACCCTGTACCTGAAGGAGAAGAAGTACAGCCCTTGCGC
TTGGGAAGTCGTGAGGG

SEQ ID NO: 23
IFN-G
CTGAGATCATGAGGAGCTTTAGCCTGAGCACCAACCTGCAAGAGAGCTTGAGGTCTAAGGAGTAA

SEQ ID NO: 24
IFN-1
CCCAAGCTTTCACCATGGCTTTGACCTTTGCCTT

SEQ ID NO: 25
IFN-2b
ATCTGCCTCAGACCCACAG

FIG. 15A

SEQ ID NO: 26
IFN-3c
GATTTTGGCTTTCCTCAAGAGGAGTT

SEQ ID NO: 27
IFN-4b
GCACGAGATGATCCAGCAGAT

SEQ ID NO: 28
IFN-5
ATCGTTCAGCTGCTGGTACA

SEQ ID NO: 29
IFN-6
CCTCACAGCCAGGATGCTAT

SEQ ID NO: 30
IFN-7
ATGATCTCAGCCCTCACGAC

SEQ ID NO: 31
IFN-2
CTGTGGGTCTGAGGCAGAT

SEQ ID NO: 32
IFN-3b
AACTCCTCTTGAGGAAAGCCAAAATC

SEQ ID NO: 33
IFN-4
ATCTGCTGGATCATCTCGTGC

SEQ ID NO: 34
IFN-8
TGCTCTAGACTTTTACTCCTTAGACCTCAAGCTCT

FIG. 15B

SEQ ID NO: 38
Oligo 1. TCACTCGAGGTGAATATCCAAGAAT

SEQ ID NO: 39
Oligo 2. GAGATCGATTTTGGCTGGACACTTG

SEQ ID NO: 40
Oligo 3. CACATCGATGTCACAACTTGGGAAT

SEQ ID NO: 41
Oligo 4. TCTAAGCTTCGTCACAGACCGTCCC

FIG. 22

SEQUENCE LISTING

<160> NUMBER OF SEQ ID NOS: 41

<210> SEQ ID NO 1
<211> LENGTH: 20
<212> TYPE: DNA
<213> ORGANISM: Artificial sequence
<220> FEATURE:
<223> OTHER INFORMATION: Primer 5pLMAR2

<400> SEQUENCE: 1
tgccgccttc tttgatattc                                                  20

<210> SEQ ID NO 2
<211> LENGTH: 20
<212> TYPE: DNA
<213> ORGANISM: Artificial sequence
<220> FEATURE:
<223> OTHER INFORMATION: Primer LE-6.1kbrev1

<400> SEQUENCE: 2
ttggtggtaa ggccttttg                                                   20

<210> SEQ ID NO 3
<211> LENGTH: 20
<212> TYPE: DNA
<213> ORGANISM: Artificial sequence
<220> FEATURE:
<223> OTHER INFORMATION: Primer lys-6.1

<400> SEQUENCE: 3
ctggcaagct gtcaaaaaca                                                  20

<210> SEQ ID NO 4
<211> LENGTH: 20
<212> TYPE: DNA
<213> ORGANISM: Artificial sequence
<220> FEATURE:
<223> OTHER INFORMATION: Primer LysE1rev

<400> SEQUENCE: 4
cagctcacat cgtccaaaga                                                  20

<210> SEQ ID NO 5
<211> LENGTH: 498
<212> TYPE: DNA
<213> ORGANISM: Artificial sequence

```
<220> FEATURE:
<223> OTHER INFORMATION: IFNMAGMAX
<220> FEATURE:
<221> NAME/KEY: misc_feature
<222> LOCATION: (1)..(498)
<223> OTHER INFORMATION:

<400> SEQUENCE: 5
tgcgatctgc ctcagaccca cagcctgggc agcaggagga ccctgatgct gctggctcag      60
atgaggagaa tcagcctgtt tagctgcctg aaggataggc acgattttgg ctttcctcaa     120
gaggagtttg caaccagtt tcagaaggct gagaccatcc ctgtgctgca cgagatgatc      180
cagcagatct ttaacctgtt tagcaccaag gatagcagcg ctgcttggga tgagaccctg     240
ctggataagt tttacaccga gctgtaccag cagctgaacg atctggaggc ttgcgtgatc     300
cagggcgtgg gcgtgaccga gacccctctg atgaaggagg atagcatcct ggctgtgagg     360
aagtactttc agaggatcac cctgtacctg aaggagaaga agtacagccc ctgcgcttgg     420
gaagtcgtga gggctgagat catgaggagc tttagcctga gcaccaacct gcaagagagc     480
ttgaggtcta aggagtaa                                                   498

<210> SEQ ID NO 6
<211> LENGTH: 12728
<212> TYPE: DNA
<213> ORGANISM: Gallus gallus
<220> FEATURE:
<221> NAME/KEY: misc_feature
<222> LOCATION: (1)..(237)
<223> OTHER INFORMATION: 5prime matrix (scaffold) attachment region
      (MAR)
<220> FEATURE:
<221> NAME/KEY: misc_feature
<222> LOCATION: (261)..(1564)
<223> OTHER INFORMATION: 5prime matrix (scaffold) attachment region
      (MAR)
<220> FEATURE:
<221> NAME/KEY: misc_feature
<222> LOCATION: (1565)..(1912)
<223> OTHER INFORMATION: 5prime matrix (scaffold) attachment region
      (MAR)
<220> FEATURE:
<221> NAME/KEY: misc_feature
<222> LOCATION: (1930)..(2012)
<223> OTHER INFORMATION: 5prime matrix (scaffold) attachment region
      (MAR)
<220> FEATURE:
<221> NAME/KEY: misc_feature
<222> LOCATION: (2013)..(2671)
<223> OTHER INFORMATION: Intrinsically curved DNA
<220> FEATURE:
<221> NAME/KEY: misc_feature
<222> LOCATION: (5848)..(5934)
<223> OTHER INFORMATION: Transcription Enhancer
<220> FEATURE:
<221> NAME/KEY: misc_feature
<222> LOCATION: (9160)..(9325)
<223> OTHER INFORMATION: Transcription Enhancer
<220> FEATURE:
<221> NAME/KEY: misc_feature
<222> LOCATION: (9326)..(9626)
<223> OTHER INFORMATION: Negative Regulatory Element
<220> FEATURE:
<221> NAME/KEY: misc_feature
<222> LOCATION: (9621)..(9660)
<223> OTHER INFORMATION: Hormone Response Element
<220> FEATURE:
<221> NAME/KEY: misc_feature
<222> LOCATION: (9680)..(10060)
<223> OTHER INFORMATION: Hormone Response Element
<220> FEATURE:
<221> NAME/KEY: misc_feature
<222> LOCATION: (10576)..(10821)
```

<223> OTHER INFORMATION: Chicken CR1 Repeat Sequence
<220> FEATURE:
<221> NAME/KEY: misc_feature
<222> LOCATION: (10926)..(11193)
<223> OTHER INFORMATION: Chicken CR1 Repeat Sequence
<220> FEATURE:
<221> NAME/KEY: misc_feature
<222> LOCATION: (11424)..(11938)
<223> OTHER INFORMATION: Lysozyme Proximal Promoter and Lysozyme Signal
    Peptide
<220> FEATURE:
<221> NAME/KEY: misc_feature
<222> LOCATION: (11946)..(12443)
<223> OTHER INFORMATION: Human Interferon alpha 2d encoding region codon
    optimized for exp
    ression in chicken cells (IFNMAGMAX)
<220> FEATURE:
<221> NAME/KEY: polyA_signal
<222> LOCATION: (12444)..(12728)
<223> OTHER INFORMATION:

<400> SEQUENCE: 6

```
tgccgccttc tttgatattc actctgttgt atttcatctc ttcttgccga tgaaaggata      60
taacagtctg tataacagtc tgtgaggaaa tacttggtat ttcttctgat cagtgttttt     120
ataagtaatg ttgaatattg gataaggctg tgtgtccttt gtcttgggag acaaagccca     180
cagcaggtgg tggttggggt ggtggcagct cagtgacagg agaggttttt ttgcctgttt     240
tttttttttt tttttttttt aagtaaggtg ttcttttttc ttagtaaatt ttctactgga     300
ctgtatgttt tgacaggtca gaaacatttc ttcaaaagaa gaacctttttg gaaactgtac    360 agcccttttc tttcattccc tttttgcttt ctgtgccaat gcctttggtt ctgattgcat     420
tatggaaaac gttgatcgga acttgaggtt tttatttata gtgtggcttg aaagcttgga     480
tagctgttgt tacacgagat accttattaa gtttaggcca gcttgatgct ttatttttttc    540 cctttgaagt agtgagcgtt ctctggtttt tttcctttga aactggtgag gcttagattt     600
ttctaatggg attttttacc tgatgatcta gttgcatacc caaatgcttg taaatgtttt     660
cctagttaac atgttgataa cttcggattt acatgttgta tatacttgtc atctgtgttt     720
ctagtaaaaa tatatggcat ttatagaaat acgtaattcc tgatttcctt ttttttttatc    780 tctatgctct gtgtgtacag gtcaaacaga cttcactcct attttttattt atagaatttt    840 atatgcagtc tgtcgttggt tcttgtgttg taaggataca gccttaaatt tcctagagcg     900
atgctcagta aggcgggttg tcacatgggt tcaaatgtaa aacgggcacg tttggctgct     960
gccttcccga gatccaggac actaaactgc ttctgcactg aggtataaat cgcttcagat    1020
cccagggaag tgcagatcca cgtgcatatt cttaaagaag aatgaatact ttctaaaata    1080
ttttggcata ggaagcaagc tgcatggatt tgtttgggac ttaaattatt ttggtaacgg    1140
agtgcatagg ttttaaacac agttgcagca tgctaacgag tcacagcgtt tatgcagaag    1200
tgatgcctgg atgcctgttg cagctgttta cggcactgcc ttgcagtgag cattgcagat    1260 agggggtgggg tgctttgtgt cgtgttccca cacgctgcca cacagccacc tcccggaaca    1320
catctcacct gctgggtact tttcaaacca tcttagcagt agtagatgag ttactatgaa    1380
acagagaagt tcctcagttg gatattctca tgggatgtct tttttcccat gttgggcaaa    1440
gtatgataaa gcatctctat ttgtaaatta tgcacttgtt agttcctgaa tcctttctat    1500
agcaccactt attgcagcag gtgtaggctc tggtgtggcc tgtgtctgtg cttcaatctt    1560
ttaaagcttc tttggaaata cactgacttg attgaagtct cttgaagata gtaaacagta    1620
cttacctttg atcccaatga aatcgagcat ttcagttgta aagaattcc gcctattcat     1680
```

```
accatgtaat gtaattttac accccagtg ctgacacttt ggaatatatt caagtaatag      1740
actttggcct caccctcttg tgtactgtat tttgtaatag aaaatatttt aaactgtgca      1800
tatgattatt acattatgaa agagacattc tgctgatctt caaatgtaag aaaatgagga      1860
gtgcgtgtgc ttttataaat acaagtgatt gcaaattagt gcaggtgtcc ttaaaaaaaa      1920
aaaaaaaaag taatataaaa aggaccaggt gttttacaag tgaaatacat tcctatttgg      1980
taaacagtta cattttatg aagattacca gcgctgctga ctttctaaac ataaggctgt      2040
attgtcttcc tgtaccattg catttcctca ttcccaattt gcacaaggat gtctgggtaa      2100
actattcaag aaatggcttt gaaatacagc atggagctt gtctgagttg gaatgcagag      2160
ttgcactgca aaatgtcagg aaatggatgt ctctcagaat gcccaactcc aaaggatttt      2220
atatgtgtat atagtaagca gtttcctgat tccagcaggc caaagagtct gctgaatgtt      2280
gtgttgccgg agacctgtat ttctcaacaa ggtaagatgg tatcctagca actgcggatt      2340
ttaatacatt ttcagcagaa gtacttagtt aatctctacc tttagggatc gtttcatcat      2400
ttttagatgt tatacttgaa atactgcata acttttagct ttcatgggtt cctttttttc      2460
agcctttagg agactgttaa gcaatttgct gtccaacttt tgtgttggtc ttaaactgca      2520
atagtagttt accttgtatt gaagaaataa agaccatttt tatattaaaa aatacttttg      2580
tctgtcttca ttttgacttg tctgatatcc ttgcagtgcc cattatgtca gttctgtcag      2640
atattcagac atcaaaactt aacgtgagct cagtggagtt acagctgcgg ttttgatgct      2700
gttattattt ctgaaactag aaatgatgtt gtcttcatct gctcatcaaa cacttcatgc      2760
agagtgtaag gctagtgaga aatgcataca tttattgata cttttttaaa gtcaacttt      2820
tatcagattt ttttttcatt tggaaatata ttgttttcta gactgcatag cttctgaatc      2880
tgaaatgcag tctgattggc atgaagaagc acagcactct tcatcttact taaacttcat      2940
tttggaatga aggaagttaa gcaagggcac aggtccatga aatagagaca gtgcgctcag      3000
gagaaagtga acctggattt ctttggctag tgttctaaat ctgtagtgag aaagtaaca      3060
cccgattcct tgaaagggct ccagctttaa tgcttccaaa ttgaaggtgg caggcaactt      3120
ggccactggt tatttactgc attatgtctc agtttcgcag ctaacctggc ttctccacta      3180
ttgagcatgg actatagcct ggcttcagag gccaggtgaa ggttgggatg ggtggaagga      3240
gtgctgggct gtggctgggg gactgtggg gactccaagc tgagcttggg gtgggcagca      3300
cagggaaaag tgtgggtaac tattttaag tactgtgttg caaacgtctc atctgcaaat      3360
acgtagggtg tgtactctcg aagattaaca gtgtgggttc agtaatatat ggatgaattc      3420
acagtggaag cattcaaggg tagatcatct aacgacacca gatcatcaag ctatgattgg      3480
aagcggtatc agaagagcga ggaaggtaag cagtcttcat atgttttccc tccacgtaaa      3540
gcagtctggg aaagtagcac cccttgagca gagacaagga ataattcag gagcatgtgc      3600
taggagaact tccttgctga attctacttg caagagcttt gatgcctggc ttctggtgcc      3660
ttctgcagca cctgcaaggc ccagagcctg tggtgagctg gagggaaaga ttctgctcaa      3720
gtccaagctt cagcaggtca ttgtctttgc ttcttccccc agcactgtgc agcagagtgg      3780
aactgatgtc gaagcctcct gtccactacc tgttgctgca ggcagactgc tctcagaaaa      3840
agagagctaa ctctatgcca tagtctgaag gtaaaatggg ttttaaaaaa gaaacacaa      3900
aggcaaaacc ggctgccca tgagaagaaa gcagtggtaa acatggtaga aaaggtgcag      3960
aagcccccag gcagtgtgac aggccctcc tgccacctag aggcgggaac aagcttccct      4020
gcctagggct ctgcccgcga agtgcgtgtt tctttggtgg gttttgtttg gcgtttggtt      4080
```

```
ttgagattta gacacaaggg aagcctgaaa ggaggtgttg ggcactattt tggtttgtaa    4140
agcctgtact tcaaatatat attttgtgag ggagtgtagc gaattggcca atttaaaata    4200
aagttgcaag agattgaagg ctgagtagtt gagagggtaa cacgtttaat gagatcttct    4260
gaaactactg cttctaaaca cttgtttgag tggtgagacc ttggataggt gagtgctctt    4320
gttacatgtc tgatgcactt gcttgtcctt ttccatccac atccatgcat tccacatcca    4380
cgcatttgtc acttatccca tatctgtcat atctgacata cctgtctctt cgtcacttgg    4440
tcagaagaaa cagatgtgat aatccccagc cgccccaagt tgagaagat ggcagttgct     4500 tctttccctt tttcctgcta agtaaggatt ttctcctggc tttgacacct cacgaaatag    4560
tcttcctgcc ttacattctg ggcattattt caaatatctt tggagtgcgc tgctctcaag    4620
tttgtgtctt cctactctta gagtgaatgc tcttagagtg aaagagaagg aagagaagat    4680
gttggccgca gttctctgat gaacacacct ctgaataatg ccaaaggtg ggtgggtttc     4740 tctgaggaac gggcagcgtt tgcctctgaa agcaaggagc tctgcggagt tgcagttatt    4800
ttgcaactga tggtggaact ggtgcttaaa gcagattccc taggttccct gctacttctt    4860
ttccttcttg gcagtcagtt tatttctgac agacaaacag ccaccccac tgcaggctta     4920 gaaagtatgt ggctctgcct gggtgtgtta cagctctgcc ctggtgaaag gggattaaaa    4980
cgggcaccat tcatcccaaa caggatcctc attcatggat caagctgtaa ggaacttggg    5040
ctccaacctc aaaacattaa ttggagtacg aatgtaatta aaactgcatt ctcgcattcc    5100
taagtcattt agtctggact ctgcagcatg taggtcggca gctcccactt tctcaaagac    5160
cactgatgga ggagtagtaa aaatggagac cgattcagaa caaccaacgg agtgttgccg    5220
aagaaactga tggaaataat gcatgaattg tgtggtggac attttttta aatacataaa     5280 ctacttcaaa tgaggtcgga gaaggtcagt gttttattag cagccataaa accaggtgag    5340
cgagtaccat ttttctctac aagaaaaacg attctgagct ctgcgtaagt ataagttctc    5400
catagcggct gaagctcccc cctggctgcc tgccatctca gctggagtgc agtgccattt    5460
ccttggggtt tctctcacag cagtaatggg acaatacttc acaaaaattc tttcttttcc    5520
tgtcatgtgg gatccctact gtgccctcct ggttttacgt taccccctga ctgttccatt    5580
cagcggtttg gaaagagaaa aagaatttgg aaataaaaca tgtctacgtt atcacctcct    5640
ccagcatttt ggttttttaat tatgtcaata actggcttag atttggaaat gagaggggt    5700 tgggtgtatt accgaggaac aaaggaaggc ttatataaac tcaagtcttt tatttagaga    5760
actggcaagc tgtcaaaaac aaaaaggcct taccaccaaa ttaagtgaat agccgctata    5820
gccagcaggg ccagcacgag ggatggtgca ctgctggcac tatgccacgg cctgcttgtg    5880
actctgagag caactgcttt ggaaatgaca gcacttggtg caatttcctt tgtttcagaa    5940
tgcgtagagc gtgtgcttgg cgacagtttt tctagttagg ccacttcttt tttccttctc    6000
tcctcattct cctaagcatg tctccatgct ggtaatccca gtcaagtgaa cgttcaaaca    6060
atgaatccat cactgtagga ttctcgtggt gatcaaatct ttgtgtgagg tctataaaat    6120
atggaagctt atttatttt cgttcttcca tatcagtctt ctctatgaca attcacatcc      6180
accacagcaa attaaggtg aaggaggctg gtgggatgaa gagggtcttc tagctttacg      6240
ttcttccttg caaggccaca ggaaaatgct gagagctgta gaatacagcc tggggtaaga    6300
agttcagtct cctgctggga cagctaaccg catcttataa cccttctga gactcatctt      6360 aggaccaaat agggtctatc tgggttttt gttcctgctg ttcctcctgg aaggctatct     6420
```

```
cactatttca ctgctcccac ggttacaaac caaagataca gcctgaattt tttctaggcc    6480
acattacata aatttgacct ggtaccaata ttgttctcta tatagttatt tccttcccca    6540
ctgtgtttaa cccottaagg cattcagaac aactagaatc atagaatggt ttggattgga    6600
aggggcctta aacatcatcc atttccaacc ctctgccatg ggctgcttgc cacccactgg    6660
ctcaggctgc ccagggcccc atccagcctg gccttgagca cctccaggga tggggcaccc    6720
acagcttctc tgggcagcct gtgccaacac ctcaccactc tctgggtaaa gaattctctt    6780
ttaacatcta atctaaatct cttctctttt agtttaaagc cattcctctt tttcccgttg    6840
ctatctgtcc aagaaatgtg tattggtctc cctcctgctt ataagcagga agtactggaa    6900
ggctgcagtg aggtctcccc acagccttct cttctccagg ctgaacaagc ccagctcctt    6960
cagcctgtct tcgtaggaga tcatcttagt ggccctcctc tggacccatt ccaacagttc    7020
cacggctttc ttgtggagcc ccaggtctgg atgcagtact tcagatgggg ccttacaaag    7080
gcagagcaga tggggacaat cgcttacccc tccctgctgg ctgcccctgt tttgatgcag    7140
cccagggtac tgttggcctt tcaggctccc agaccccttg ctgatttgtg tcaagctttt    7200
catccaccag aacccacgct tcctggttaa tacttctgcc ctcacttctg taagcttgtt    7260
tcaggagact tccattcttt aggacagact gtgttacacc tacctgccct attcttgcat    7320
atatacattt cagttcatgt ttcctgtaac aggacagaat atgtattcct ctaacaaaaa    7380
tacatgcaga attcctagtg ccatctcagt agggttttca tggcagtatt agcacatagt    7440
caatttgctg caagtacctt ccaagctgcg gcctcccata aatcctgtat ttgggatcag    7500 ttacctttg gggtaagctt ttgtatctgc agagaccctg ggggttctga tgtgcttcag    7560
ctctgctctg ttctgactgc accattttct agatcaccca gttgttcctg tacaacttcc    7620
ttgtcctcca tcctttccca gcttgtatct ttgacaaata caggcctatt tttgtgtttg    7680
cttcagcagc catttaattc ttcagtgtca tcttgttctg ttgatgccac tggaacagga    7740
ttttcagcag tcttgcaaag aacatctagc tgaaaacttt ctgccattca atattcttac    7800
cagttcttct tgtttgaggt gagccataaa ttactagaac ttcgtcactg acaagtttat    7860
gcattttatt acttctatta tgtacttact ttgacataac acagacacgc acatattttg    7920
ctgggatttc cacagtgtct ctgtgtcctt cacatggttt tactgtcata cttccgttat    7980
aaccttggca atctgcccag ctgcccatca caagaaaaga gattcctttt ttattacttc    8040
tcttcagcca ataaacaaaa tgtgagaagc ccaaacaaga acttgtgggg caggctgcca    8100
tcaagggaga gacagctgaa gggttgtgta gctcaataga attaagaaat aataaagctg    8160
tgtcagacag ttttgcctga tttatacagg cacgccccaa gccagagagg ctgtctgcca    8220
aggccacctt gcagtccttg gtttgtaaga taagtcatag gtaacttttc tggtgaattg    8280
cgtggagaat catgatggca gttcttgctg tttactatgg taagatgcta aaataggaga    8340
cagcaaagta acacttgctg ctgtaggtgc tctgctatcc agacagcgat ggcactcgca    8400
caccaagatg agggatgctc ccagctgacg gatgctgggg cagtaacagt gggtcccatg    8460
ctgcctgctc attagcatca cctcagccct caccagccca tcagaaggat catcccaagc    8520
tgaggaaagt tgctcatcct cttcacatca tcaaaccttt ggcctgactg atgcctcccg    8580
gatgcttaaa tgtggtcact gacatcttta tttttctatg atttcaagtc agaacctccg    8640
gatcaggagg gaacacatag tgggaatgta ccctcagctc caaggccaga tcttccttca    8700
atgatcatgc atgctactta ggaaggtgtg tgtgtgtgaa tgtagaattg cctttgttat    8760
tttttcttcc tgctgtcagg aacatttttga ataccagaga aaaagaaaag tgctcttctt    8820
```

```
ggcatgggag gagttgtcac acttgcaaaa taaaggatgc agtcccaaat gttcataatc   8880
tcagggtctg aaggaggatc agaaactgtg tatacaattt caggcttctc tgaatgcagc   8940
ttttgaaagc tgttcctggc cgaggcagta ctagtcagaa ccctcggaaa caggaacaaa   9000
tgtcttcaag gtgcagcagg aggaaacacc ttgcccatca tgaaagtgaa taaccactgc   9060
cgctgaagga atccagctcc tgtttgagca ggtgctgcac actcccacac tgaaacaaca   9120
gttcattttt ataggacttc caggaaggat cttcttctta agcttcttaa ttatggtaca   9180
tctccagttg gcagatgact atgactactg acaggagaat gaggaactag ctgggaatat   9240
ttctgtttga ccaccatgga gtcacccatt tctttactgg tatttggaaa taataattct   9300
gaattgcaaa gcaggagtta gcgaagatct tcatttcttc catgttggtg acagcacagt   9360
tctggctatg aaagtctgct tacaaggaag aggataaaaa tcatagggat aataaatcta   9420
agtttgaaga caatgaggtt ttagctgcat ttgacatgaa gaaattgaga cctctactgg   9480
atagctatgg tatttacgtg tcttttttgct tagttactta ttgaccccag ctgaggtcaa   9540
gtatgaactc aggtctctcg ggctactggc atggattgat tacatacaac tgtaatttta   9600
gcagtgattt agggtttatg agtacttttg cagtaaatca tagggttagt aatgttaatc   9660
tcagggaaaa aaaaaaaaag ccaaccctga cagacatccc agctcaggtg gaaatcaagg   9720
atcacagctc agtgcggtcc cagagaacac agggactctt ctcttaggac ctttatgtac   9780
agggcctcaa gataactgat gttagtcaga agactttcca ttctggccac agttcagctg   9840
aggcaatcct ggaattttct ctccgctgca cagttccagt catcccagtt tgtacagttc   9900
tggcactttt tgggtcaggc cgtgatccaa ggagcagaag ttccagctat ggtcagggag   9960
tgcctgaccg tcccaactca ctgcactcaa acaaaggcga aaccacaaga gtggcttttg   10020
ttgaaattgc agtgtggccc agaggggctg caccagtact ggattgacca cgaggcaaca   10080
ttaatcctca gcaagtgcaa tttgcagcca ttaaattgaa ctaactgata ctacaatgca   10140
atcagtatca acaagtggtt tggcttggaa gatggagtct aggggctcta caggagtagc   10200
tactctctaa tggagttgca ttttgaagca ggacactgtg aaaagctggc ctcctaaaga   10260
ggctgctaaa cattagggtc aattttccag tgcactttct gaagtgtctg cagttcccca   10320
tgcaaagctg cccaaacata gcacttccaa ttgaatacaa ttatatgcag gcgtactgct   10380
tcttgccagc actgtccttc tcaaatgaac tcaacaaaca atttcaaagt ctagtagaaa   10440
gtaacaagct ttgaatgtca ttaaaaagta tatctgcttt cagtagttca gcttatttat   10500
gcccactaga aacatcttgt acaagctgaa cactggggct ccagattagt ggtaaaacct   10560
actttataca atcatagaat catagaatgg cctgggttgg aagggacccc aaggatcatg   10620
aagatccaac accccgcca caggcagggc caccaacctc cagatctggt actagaccag   10680
gcagcccagg gctccatcca acctggccat gaacacctcc agggatggag catccacaac   10740
ctctctgggc agcctgtgcc agcacctcac caccctctct gtgaagaact tttccctgac   10800
atccaatcta agccttccct ccttgaggtt agatccactc ccccttgtgc tatcactgtc   10860
tactcttgta aaaagttgat tctcctcctt tttggaaggt tgcaatgagg tctccttgca   10920
gccttcttct cttctgcagg atgaacaagc ccagctccct cagcctgtct ttataggaga   10980
ggtgctccag ccctctgatc atctttgtgg ccctcctctg gacccgctcc aagagctcca   11040
catctttcct gtactggggg ccccaggcct gaatgcagta ctccagatgg ggcctcaaaa   11100
gagcagagta aagagggaca atcaccttcc tcaccctgct ggccagccct cttctgatgg   11160
```

```
agccctggat acaactggct ttctgagctg caacttctcc ttatcagttc cactattaaa    11220
acaggaacaa tacaacaggt gctgatggcc agtgcagagt ttttcacact tcttcatttc    11280
ggtagatctt agatgaggaa cgttgaagtt gtgcttctgc gtgtgcttct tcctcctcaa    11340
atactcctgc ctgatacctc accccacctg ccactgaatg gctccatggc ccctgcagc     11400 cagggccctg atgaacccgg cactgcttca gatgctgttt aatagcacag tatgaccaag    11460
ttgcacctat gaatacacaa acaatgtgtt gcatccttca gcacttgaga agaagagcca    11520
aatttgcatt gtcaggaaat ggtttagtaa ttctgccaat taaaacttgt ttatctacca    11580
tggctgtttt tatggctgtt agtagtggta cactgatgat gaacaatggc tatgcagtaa    11640
aatcaagact gtagatattg caacagacta taaaattcct ctgtggctta gccaatgtgg    11700
tacttcccac attgtataag aaatttggca agtttagagc aatgtttgaa gtgttgggaa    11760
atttctgtat actcaagagg gcgttttttga caactgtaga acagaggaat caaaaggggg    11820
tgggaggaag ttaaaagaag aggcaggtgc aagagagctt gcagtcccgc tgtgtgtacg    11880
acactggcaa catgaggtct ttgctaatct tggtgctttg cttcctgccc ctggctgcct    11940
tagggtgcga tctgcctcag acccacagcc tgggcagcag gaggaccctg atgctgctgg    12000
ctcagatgag gagaatcagc ctgtttagct gcctgaagga taggcacgat tttggcttc     12060 ctcaagagga gtttggcaac cagtttcaga aggctgagac catccctgtg ctgcacgaga    12120
tgatccagca gatctttaac ctgtttagca ccaaggatag cagcgctgct tgggatgaga    12180
ccctgctgga taagttttac accgagctgt accagcagct gaacgatctg gaggcttgcg    12240
tgatccaggg cgtgggcgtg accgagaccc ctctgatgaa ggaggatagc atcctggctg    12300
tgaggaagta ctttcagagg atcacccctg acctgaagga gaagaagtac agcccctgcg    12360
cttgggaagt cgtgagggct gagatcatga ggagctttag cctgagcacc aacctgcaag    12420
agagcttgag gtctaaggag taaaaagtct agagtcgggg cggccggccg cttcgagcag    12480
acatgataag atacattgat gagtttggac aaaccacaac tagaatgcag tgaaaaaaat    12540
gctttatttg tgaaatttgt gatgctattg ctttatttgt aaccattata agctgcaata    12600
aacaagttaa caacaacaat tgcattcatt ttatgtttca ggttcagggg gaggtgtggg    12660 aggttttta aagcaagtaa aacctctaca aatgtggtaa aatcgataag gatccgtcga    12720
gcggccgc                                                             12728
```

<210> SEQ ID NO 7
<211> LENGTH: 11945
<212> TYPE: DNA
<213> ORGANISM: Gallus gallus
<220> FEATURE:
<221> NAME/KEY: misc_feature
<222> LOCATION: (1)..(237)
<223> OTHER INFORMATION: 5prime matrix attachment region (MAR)
<220> FEATURE:
<221> NAME/KEY: misc_feature
<222> LOCATION: (261)..(1564)
<223> OTHER INFORMATION: 5prime matrix attachment region (MAR)
<220> FEATURE:
<221> NAME/KEY: misc_feature
<222> LOCATION: (1565)..(1912)
<223> OTHER INFORMATION: 5prime matrix attachment region (MAR)
<220> FEATURE:
<221> NAME/KEY: misc_feature
<222> LOCATION: (1930)..(2012)
<223> OTHER INFORMATION: 5prime matrix attachment region (MAR)
<220> FEATURE:
<221> NAME/KEY: misc_feature
<222> LOCATION: (2013)..(2671)
<223> OTHER INFORMATION: Intrinsically Curved DNA

```
<220> FEATURE:
<221> NAME/KEY: misc_feature
<222> LOCATION: (5848)..(5934)
<223> OTHER INFORMATION: Transcription Enhancer
<220> FEATURE:
<221> NAME/KEY: misc_feature
<222> LOCATION: (9160)..(9325)
<223> OTHER INFORMATION: Transcription Enhancer
<220> FEATURE:
<221> NAME/KEY: misc_feature
<222> LOCATION: (9326)..(9626)
<223> OTHER INFORMATION: Negative Regulatory Element
<220> FEATURE:
<221> NAME/KEY: misc_feature
<222> LOCATION: (9621)..(9660)
<223> OTHER INFORMATION: Hormone Response Element
<220> FEATURE:
<221> NAME/KEY: misc_feature
<222> LOCATION: (9680)..(10060)
<223> OTHER INFORMATION: Hormone Response Element
<220> FEATURE:
<221> NAME/KEY: misc_feature
<222> LOCATION: (10576)..(10821)
<223> OTHER INFORMATION: Chicken CR1 Repeat
<220> FEATURE:
<221> NAME/KEY: misc_feature
<222> LOCATION: (10926)..(11193)
<223> OTHER INFORMATION: Chicken CR1 Repeat
<220> FEATURE:
<221> NAME/KEY: misc_feature
<222> LOCATION: (11424)..(11938)
<223> OTHER INFORMATION: Proximal promoter and lysozyme signal peptide

<400> SEQUENCE: 7
tgccgccttc tttgatattc actctgttgt atttcatctc ttcttgccga tgaaaggata      60
taacagtctg tataacagtc tgtgaggaaa tacttggtat ttcttctgat cagtgttttt     120
ataagtaatg ttgaatattg gataaggctg tgtgtccttt gtcttgggag acaaagccca     180
cagcaggtgg tggttggggt ggtggcagct cagtgacagg agaggttttt ttgcctgttt     240
tttttttttt tttttttttt aagtaaggtg ttctttttc ttagtaaatt ttctactgga      300
ctgtatgttt tgacaggtca gaaacatttc ttcaaaagaa gaaccttttg gaaactgtac     360 agccctttc tttcattccc ttttgctttt ctgtgccaat gcctttggtt ctgattgcat      420
tatggaaaac gttgatcgga acttgaggtt tttatttata gtgtggcttg aaagcttgga    480
tagctgttgt tacacgagat accttattaa gtttaggcca gcttgatgct ttattttttc     540
cctttgaagt agtgagcgtt ctctggtttt tttcctttga aactggtgag cttagatttt    600
ttctaatggg attttttacc tgatgatcta gttgcatacc caaatgcttg taaatgtttt     660
cctagttaac atgttgataa cttcggattt acatgttgta tatacttgtc atctgtgttt     720
ctagtaaaaa tatatggcat ttatagaaat acgtaattcc tgatttcctt ttttttatc     780 tctatgctct gtgtgtacag gtcaaacaga cttcactcct attttattt atagaattt     840 atatgcagtc tgtcgttggt tcttgtgttg taaggataca gccttaaatt tcctagagcg    900
atgctcagta aggcgggttg tcacatgggt tcaaatgtaa aacgggcacg tttggctgct     960
gccttcccga gatccaggac actaaactgc ttctgcactg aggtataaat cgcttcagat   1020
cccagggaag tgcagatcca cgtgcatatt cttaaagaag aatgaatact ttctaaaata   1080
ttttggcata ggaagcaagc tgcatggatt tgtttgggac ttaaattatt ttggtaacgg   1140
agtgcatagg ttttaaacac agttgcagca tgctaacgag tcacagcgtt tatgcagaag   1200
tgatgcctgg atgcctgttg cagctgttta cggcactgcc ttgcagtgag cattgcagat   1260 agggggtgggg tgctttgtgt cgtgttccca cacgctgcca cacagccacc tcccggaaca  1320
```

```
catctcacct gctgggtact tttcaaacca tcttagcagt agtagatgag ttactatgaa    1380
acagagaagt tcctcagttg gatattctca tgggatgtct ttttccccat gttgggcaaa    1440
gtatgataaa gcatctctat ttgtaaatta tgcacttgtt agttcctgaa tcctttctat    1500
agcaccactt attgcagcag gtgtaggctc tggtgtggcc tgtgtctgtg cttcaatctt    1560
ttaaagcttc tttggaaata cactgacttg attgaagtct cttgaagata gtaaacagta    1620
cttacctttg atcccaatga aatcgagcat ttcagttgta aaagaattcc gcctattcat    1680
accatgtaat gtaattttac accccagtg ctgacactt ggaatatatt caagtaatag      1740
actttggcct caccctcttg tgtactgtat tttgtaatag aaaatatttt aaactgtgca    1800
tatgattatt acattatgaa agagacattc tgctgatctt caaatgtaag aaaatgagga    1860
gtgcgtgtgc ttttataaat acaagtgatt gcaaattagt gcaggtgtcc ttaaaaaaaa    1920
aaaaaaaag taatataaaa aggaccaggt gttttacaag tgaaatacat tcctatttgg     1980
taaacagtta catttttatg aagattacca gcgctgctga ctttctaaac ataaggctgt    2040
attgtcttcc tgtaccattg catttcctca ttcccaattt gcacaaggat gtctgggtaa    2100
actattcaag aaatggcttt gaaatacagc atgggagctt gtctgagttg gaatgcagag    2160
ttgcactgca aaatgtcagg aaatggatgt ctctcagaat gcccaactcc aaaggatttt    2220
atatgtgtat atagtaagca gtttcctgat tccagcaggc caaagagtct gctgaatgtt    2280
gtgttgccgg agacctgtat ttctcaacaa ggtaagatgg tatcctagca actgcggatt    2340
ttaatacatt ttcagcagaa gtacttagtt aatctctacc tttagggatc gtttcatcat    2400
ttttagatgt tatacttgaa atactgcata acttttagct ttcatgggtt cctttttttc    2460
agcctttagg agactgttaa gcaatttgct gtccaacttt tgtgttggtc ttaaactgca    2520
atagtagttt accttgtatt gaagaaataa agaccatttt tatattaaaa aatacttttg    2580
tctgtcttca ttttgacttg tctgatatcc ttgcagtgcc cattatgtca gttcgtcag    2640
atattcagac atcaaaactt aacgtgagct cagtggagtt acagctgcgg ttttgatgct    2700
gttattattt ctgaaactag aaatgatgtt gtcttcatct gctcatcaaa cacttcatgc    2760
agagtgtaag gctagtgaga aatgcataca tttattgata cttttttaaa gtcaactttt    2820
tatcagattt ttttttcatt tggaaatata ttgttttcta gactgcatag cttctgaatc    2880
tgaaatgcag tctgattggc atgaagaagc acagcactct tcatcttact taaacttcat    2940
tttggaatga aggaagttaa gcaagggcac aggtccatga aatagagaca gtgcgctcag    3000
gagaaagtga acctggattt ctttggctag tgttctaaat ctgtagtgag gaaagtaaca    3060
cccgattcct tgaaagggct ccagctttaa tgcttccaaa ttgaaggtgg caggcaactt    3120
ggccactggt tatttactgc attatgtctc agtttcgcag ctaacctggc ttctccacta    3180
ttgagcatgg actatagcct ggcttcagag gccaggtgaa ggttgggatg ggtggaagga    3240
gtgctgggct gtggctgggg ggactgtggg gactccaagc tgagcttggg gtgggcagca    3300
cagggaaaag tgtgggtaac tattttttaag tactgtgttg caaacgtctc atctgcaaat    3360
acgtagggtg tgtactctcg aagattaaca gtgtgggttc agtaatatat ggatgaattc    3420
acagtggaag cattcaaggg tagatcatct aacgacacca gatcatcaag ctatgattgg    3480
aagcggtatc agaagagcga ggaagtaag cagtcttcat atgttttccc tccacgtaaa     3540
gcagtctggg aaagtagcac cccttgagca gagacaagga aataattcag gagcatgtgc    3600
taggagaact tccttgctga attctacttg caagagcttt gatgcctggc ttctggtgcc    3660
ttctgcagca cctgcaaggc ccagagcctg tggtgagctg gagggaaaga ttctgctcaa    3720
```

```
gtccaagctt cagcaggtca ttgtctttgc ttcttccccc agcactgtgc agcagagtgg    3780
aactgatgtc gaagcctcct gtccactacc tgttgctgca ggcagactgc tctcagaaaa    3840
agagagctaa ctctatgcca tagtctgaag gtaaaatggg ttttaaaaaa gaaaacacaa    3900
aggcaaaacc ggctgcccca tgagaagaaa gcagtggtaa acatggtaga aaaggtgcag    3960
aagcccccag gcagtgtgac aggccccctcc tgccacctag aggcgggaac aagcttccct    4020
gcctagggct ctgcccgcga agtgcgtgtt tctttggtgg gttttgtttg gcgtttggtt    4080
ttgagattta gacacaaggg aagcctgaaa ggaggtgttg ggcactattt tggtttgtaa    4140
agcctgtact tcaaatatat attttgtgag ggagtgtagc gaattggcca atttaaaata    4200
aagttgcaag agattgaagg ctgagtagtt gagagggtaa cacgtttaat gagatcttct    4260
gaaactactg cttctaaaca cttgtttgag tggtgagacc ttggataggt gagtgctctt    4320
gttacatgtc tgatgcactt gcttgtcctt ttccatccac atccatgcat tccacatcca    4380
cgcatttgtc acttatccca tatctgtcat atctgacata cctgtctctt cgtcacttgg    4440
tcagaagaaa cagatgtgat aatccccagc cgccccaagt ttgagaagat ggcagttgct    4500 tctttcccctt tttcctgcta agtaaggatt ttctcctggc tttgacacct cacgaaatag    4560
tcttcctgcc ttacattctg ggcattattt caaatatctt tggagtgcgc tgctctcaag    4620
tttgtgtctt cctactctta gagtgaatgc tcttagagtg aaagagaagg aagagaagat    4680
gttggccgca gttctctgat gaacacacct ctgaataatg ccaaaggtg ggtgggtttc    4740 tctgaggaac gggcagcgtt tgcctctgaa agcaaggagc tctgcggagt tgcagttatt    4800
ttgcaactga tggtggaact ggtgcttaaa gcagattccc taggttccct gctacttctt    4860
ttccttcttg gcagtcagtt tatttctgac agacaaacag ccaccccac tgcaggctta    4920 gaaagtatgt ggctctgcct gggtgtgtta cagctctgcc ctggtgaaag gggattaaaa    4980
cgggcaccat tcatcccaaa caggatcctc attcatggat caagctgtaa ggaacttggg    5040
ctccaacctc aaaacattaa ttggagtacg aatgtaatta aaactgcatt ctcgcattcc    5100
taagtcattt agtctggact ctgcagcatg taggtcggca gctcccactt tctcaaagac    5160
cactgatgga ggagtagtaa aaatggagac cgattcagaa caaccaacgg agtgttgccg    5220
aagaaactga tggaaataat gcatgaattg tgtggtggac attttttta aatacataaa    5280 ctacttcaaa tgaggtcgga gaaggtcagt gttttattag cagccataaa accaggtgag    5340
cgagtaccat ttttctctac aagaaaaacg attctgagct ctgcgtaagt ataagttctc    5400
catagcggct gaagctcccc cctggctgcc tgccatctca gctggagtgc agtgccattt    5460 ccttggggt tctctcacag cagtaatggg acaatacttc acaaaaattc tttcttttcc    5520
tgtcatgtgg gatccctact gtgccctcct ggttttacgt taccccctga ctgttccatt    5580
cagcggtttg gaaagagaaa aagaatttgg aaataaaaca tgtctacgtt atcacctcct    5640
ccagcatttt ggttttttaat tatgtcaata actggcttag atttggaaat gagaggggt    5700 tgggtgtatt accgaggaac aaaggaaggc ttatataaac tcaagtcttt tatttagaga    5760
actggcaagc tgtcaaaaac aaaaaggcct taccaccaaa ttaagtgaat agccgctata    5820
gccagcaggg ccagcacgag ggatggtgca ctgctggcac tatgccacgg cctgcttgtg    5880
actctgagag caactgcttt ggaaatgaca gcacttggtg caatttcctt tgtttcagaa    5940
tgcgtagagc gtgtgcttgg cgacagtttt tctagttagg ccacttcttt tttccttctc    6000
tcctcattct cctaagcatg tctccatgct ggtaatccca gtcaagtgaa cgttcaaaca    6060
```

```
atgaatccat cactgtagga ttctcgtggt gatcaaatct ttgtgtgagg tctataaaat    6120
atggaagctt atttattttt cgttcttcca tatcagtctt ctctatgaca attcacatcc    6180
accacagcaa attaaaggtg aaggaggctg gtgggatgaa gagggtcttc tagctttacg    6240
ttcttccttg caaggccaca ggaaaatgct gagagctgta gaatacagcc tggggtaaga    6300
agttcagtct cctgctggga cagctaaccg catcttataa cccttctga gactcatctt    6360 aggaccaaat agggtctatc tggggttttt gttcctgctg ttcctcctgg aaggctatct    6420
cactatttca ctgctcccac ggttacaaac caaagataca gcctgaattt tttctaggcc    6480
acattacata aatttgacct ggtaccaata ttgttctcta tatagttatt tccttcccca    6540
ctgtgtttaa ccccttaagg cattcagaac aactagaatc atagaatggt ttggattgga    6600
aggggcctta aacatcatcc atttccaacc ctctgccatg ggctgcttgc cacccactgg    6660
ctcaggctgc ccagggcccc atccagcctg gccttgagca cctccaggga tggggcaccc    6720
acagcttctc tgggcagcct gtgccaacac ctcaccactc tctgggtaaa gaattctctt    6780
ttaacatcta atctaaatct cttctctttt agtttaaagc cattcctctt tttcccgttg    6840
ctatctgtcc aagaaatgtg tattggtctc cctcctgctt ataagcagga agtactggaa    6900
ggctgcagtg aggtctcccc acagccttct cttctccagg ctgaacaagc ccagctcctt    6960
cagcctgtct tcgtaggaga tcatcttagt ggccctcctc tggacccatt ccaacagttc    7020
cacggctttc ttgtggagcc ccaggtctgg atgcagtact tcagatgggg ccttacaaag    7080
gcagagcaga tggggacaat cgcttacccc tccctgctgg ctgcccctgt tttgatgcag    7140
cccagggtac tgttggcctt tcaggctccc agacccttg ctgatttgtg tcaagctttt    7200
catccaccag aacccacgct tcctggttaa tacttctgcc ctcacttctg taagcttgtt    7260
tcaggagact tccattcttt aggacagact gtgttacacc tacctgccct attcttgcat    7320
atatacattt cagttcatgt ttcctgtaac aggacagaat atgtattcct ctaacaaaaa    7380
tacatgcaga attcctagtg ccatctcagt agggttttca tggcagtatt agcacatagt    7440
caatttgctg caagtacctt ccaagctgcg gcctcccata aatcctgtat ttgggatcag    7500
ttaccttttg gggtaagctt ttgtatctgc agagaccctg ggggtctga tgtgcttcag    7560 ctctgctctg ttctgactgc accattttct agatcaccca gttgttcctg tacaacttcc    7620
ttgtcctcca tcctttccca gcttgtatct ttgacaaata caggcctatt tttgtgtttg    7680
cttcagcagc catttaattc ttcagtgtca tcttgttctg ttgatgccac tggaacagga    7740
ttttcagcag tcttgcaaag aacatctagc tgaaaacttt ctgccattca atattcttac    7800
cagttcttct tgtttgaggt gagccataaa ttactagaac ttcgtcactg acaagtttat    7860
gcattttatt acttctatta tgtacttact ttgacataac acagacacgc acatattttg    7920
ctgggatttc cacagtgtct ctgtgtcctt cacatggttt tactgtcata cttccgttat    7980
aaccttggca atctgcccag ctgcccatca caagaaaaga gattccttt ttattacttc    8040 tcttcagcca ataaacaaaa tgtgagaagc ccaaacaaga acttgtgggg caggctgcca    8100
tcaagggaga gacagctgaa gggttgtgta gctcaataga attaagaaat aataaagctg    8160
tgtcagacag ttttgcctga tttatacagg cacgccccaa gccagagagg ctgtctgcca    8220
aggccacctt gcagtccttg gtttgtaaga taagtcatag gtaacttttc tggtgaattg    8280
cgtggagaat catgatggca gttcttgctg tttactatgg taagatgcta aaataggaga    8340
cagcaaagta acacttgctg ctgtaggtgc tctgctatcc agacagcgat ggcactcgca    8400
caccaagatg agggatgctc ccagctgacg gatgctgggg cagtaacagt gggtcccatg    8460
```

-continued

```
ctgcctgctc attagcatca cctcagccct caccagccca tcagaaggat catcccaagc    8520
tgaggaaagt tgctcatctt cttcacatca tcaaaccttt ggcctgactg atgcctccg     8580
gatgcttaaa tgtggtcact gacatcttta tttttctatg atttcaagtc agaacctccg    8640
gatcaggagg gaacacatag tgggaatgta ccctcagctc caaggccaga tcttccttca    8700
atgatcatgc atgctactta ggaaggtgtg tgtgtgtgaa tgtagaattg cctttgttat    8760
ttttcttcc tgctgtcagg aacatttga ataccagaga aaagaaaag tgctcttctt       8820
ggcatgggag gagttgtcac acttgcaaaa taaaggatgc agtcccaaat gttcataatc    8880
tcagggtctg aaggaggatc agaaactgtg tatacaattt caggcttctc tgaatgcagc    8940
ttttgaaagc tgttcctggc cgaggcagta ctagtcagaa ccctcggaaa caggaacaaa    9000
tgtcttcaag gtgcagcagg aggaaacacc ttgcccatca tgaaagtgaa taaccactgc   9060
cgctgaagga atccagctcc tgtttgagca ggtgctgcac actcccacac tgaaacaaca   9120
gttcattttt ataggacttc caggaaggat cttcttctta agcttcttaa ttatggtaca   9180
tctccagttg gcagatgact atgactactg acaggagaat gaggaactag ctgggaatat   9240
ttctgtttga ccaccatgga gtcacccatt tctttactgg tatttggaaa taataattct   9300
gaattgcaaa gcaggagtta gcgaagatct tcatttcttc catgttggtg acagcacagt   9360
tctggctatg aaagtctgct tacaaggaag aggataaaaa tcatagggat aataaatcta   9420
agtttgaaga caatgaggtt ttagctgcat ttgacatgaa gaaattgaga cctctactgg   9480
atagctatgg tatttacgtg tcttttttgct tagttactta ttgaccccag ctgaggtcaa   9540
gtatgaactc aggtctctcg ggctactggc atggattgat tacatacaac tgtaatttta   9600
gcagtgattt agggttatg agtacttttg cagtaaatca tagggttagt aatgttaatc    9660
tcagggaaaa aaaaaaaag ccaaccctga cagacatccc agctcaggtg gaaatcaagg    9720
atcacagctc agtgcggtcc cagagaacac agggactctt ctcttaggac ctttatgtac   9780
agggcctcaa gataactgat gttagtcaga agactttcca ttctggccac agttcagctg   9840
aggcaatcct ggaattttct ctccgctgca cagttccagt catcccagtt tgtacagttc   9900
tggcactttt tgggtcaggc cgtgatccaa ggagcagaag ttccagctat ggtcagggag   9960
tgcctgaccg tcccaactca ctgcactcaa acaaaggcga aaccacaaga gtggcttttg   10020
ttgaaattgc agtgtggccc agaggggctg caccagtact ggattgacca cgaggcaaca   10080
ttaatcctca gcaagtgcaa tttgcagcca ttaaattgaa ctaactgata ctacaatgca   10140
atcagtatca acaagtggtt tggcttggaa gatggagtct aggggctcta caggagtagc   10200
tactctctaa tggagttgca ttttgaagca ggacactgtg aaaagctggc ctcctaaaga   10260
ggctgctaaa cattagggtc aattttccag tgcactttct gaagtgtctg cagttcccca   10320
tgcaaagctg cccaaacata gcacttccaa ttgaatacaa ttatatgcag gcgtactgct   10380
tcttgccagc actgtccttc tcaaatgaac tcaacaaaca atttcaaagt ctagtagaaa   10440
gtaacaagct ttgaatgtca ttaaaaagta tatctgcttt cagtagttca gcttattttat  10500
gcccactaga aacatcttgt acaagctgaa cactggggct ccagattagt ggtaaaacct   10560
actttataca atcatagaat catagaatgg cctgggttgg aagggacccc aaggatcatg   10620
aagatccaac accccgcca caggcagggc caccaacctc cagatctggt actagaccag    10680
gcagcccagg gctccatcca acctggccat gaacacctcc agggatggag catccacaac   10740
ctctctgggc agcctgtgcc agcacctcac caccctctct gtgaagaact tttccctgac   10800
```

-continued

```
atccaatcta agccttccct ccttgaggtt agatccactc ccccttgtgc tatcactgtc    10860
tactcttgta aaaagttgat tctcctcctt tttggaaggt tgcaatgagg tctccttgca    10920
gccttcttct cttctgcagg atgaacaagc ccagctccct cagcctgtct ttataggaga    10980
ggtgctccag ccctctgatc atctttgtgg ccctcctctg gacccgctcc aagagctcca    11040
catctttcct gtactggggg ccccaggcct gaatgcagta ctccagatgg ggcctcaaaa    11100
gagcagagta aagagggaca atcaccttcc tcaccctgct ggccagccct cttctgatgg    11160
agccctggat acaactggct ttctgagctg caacttctcc ttatcagttc cactattaaa    11220
acaggaacaa tacaacaggt gctgatggcc agtgcagagt ttttcacact tcttcatttc    11280
ggtagatctt agatgaggaa cgttgaagtt gtgcttctgc gtgtgcttct tcctcctcaa    11340
atactcctgc ctgatacctc accccacctg ccactgaatg gctccatggc cccctgcagc    11400
cagggccctg atgaacccgg cactgcttca gatgctgttt aatagcacag tatgaccaag    11460
ttgcacctat gaatacacaa acaatgtgtt gcatccttca gcacttgaga agaagagcca    11520
aatttgcatt gtcaggaaat ggtttagtaa ttctgccaat taaaacttgt ttatctacca    11580
tggctgtttt tatggctgtt agtagtggta cactgatgat gaacaatggc tatgcagtaa    11640
aatcaagact gtagatattg caacagacta taaaattcct ctgtggctta gccaatgtgg    11700
tacttcccac attgtataag aaatttggca agtttagagc aatgtttgaa gtgttgggaa    11760
atttctgtat actcaagagg gcgttttttga caactgtaga acagaggaat caaaagggg    11820 tgggaggaag ttaaagaag aggcaggtgc aagagagctt gcagtcccgc tgtgtgtacg    11880
acactggcaa catgaggtct tgctaatct tggtgctttg cttcctgccc ctggctgcct    11940
taggg                                                              11945
```

<210> SEQ ID NO 8
<211> LENGTH: 285
<212> TYPE: DNA
<213> ORGANISM: SV40
<220> FEATURE:
<221> NAME/KEY: misc_feature
<222> LOCATION: (1)..(285)
<223> OTHER INFORMATION: SV40 Polyadenylation Sequence

<400> SEQUENCE: 8

```
aaagtctaga gtcggggcgg ccggccgctt cgagcagaca tgataagata cattgatgag     60
tttggacaaa ccacaactag aatgcagtga aaaaaatgct ttatttgtga aatttgtgat    120
gctattgctt tatttgtaac cattataagc tgcaataaac aagttaacaa caacaattgc    180
attcatttta tgtttcaggt tcaggggggag gtgtgggagg ttttttaaag caagtaaaac    240
ctctacaaat gtggtaaaat cgataaggat ccgtcgagcg gccgc                    285
```

<210> SEQ ID NO 9
<211> LENGTH: 5972
<212> TYPE: DNA
<213> ORGANISM: Gallus gallus
<220> FEATURE:
<221> NAME/KEY: misc_feature
<222> LOCATION: (1)..(5972)
<223> OTHER INFORMATION: Lysozyme 3prime domain

<400> SEQUENCE: 9

```
cgcgtggtag gtggcggggg gttcccagga gagcccccag cgcggacggc agcgccgtca     60
ctcaccgctc cgtctccctc cgcccagggt cgcctggcgc aaccgctgca agggcaccga    120
cgtccaggcg tggatcagag gctgccggct gtgaggagct gccgcgcccg gccgcccgc    180
```

```
tgcacagccg gccgctttgc gagcgcgacg ctacccgctt ggcagtttta aacgcatccc      240
tcattaaaac gactatacgc aaacgccttc ccgtcggtcc gcgtctcttt ccgccgccag      300
ggcgacactc gcggggaggg cgggaagggg gccgggcggg agcccgcggc caaccgtcgc      360
cccgtgacgg caccgccccg cccccgtgac gcggtgcggg cgccggggcc gtgggctga      420 gcgctgcggc ggggccgggc cgggccgggg cgggagctga gcgcgcgcg gctgcgggcg      480 gcgccccctc cggtgcaata tgttcaagag aatggctgag ttcgggcctg actccggggg      540
cagggtgaag gtgcgcgcg ggcggaggga cgggcgggc gcggggccgc ccggcgggtg      600
ccggggcctc tgccggcccg cccggctcgg gctgctgcgg cgcttacggg cgcgcttctc      660
gccgctgccg cttctcttct ctcccgcgca agggcgtcac catcgtgaag ccggtagtgt      720
acgggaacgt ggcgcggtac ttcgggaaga gagggagga ggacgggcac acgcatcagt      780
ggacggttta cgtgaagccc tacaggaacg aggtagggcc cgagcgcgtc ggccgccgtt      840
ctcggagcgc cggagccgtc agcgccgcgc ctgggtgcgc tgtgggacac agcgagcttc      900
tctcgtagga catgtccgcc tacgtgaaaa aatccagtt caagctgcac gagagctacg      960
ggaatcctct ccgaggtggg tgttgcgtcg ggggtttgc tccgctcggt cccgctgagg     1020
ctcgtcgccc tcatctttct ttcgtgccgc agtcgttacc aaaccgccgt acgagatcac     1080
cgaaacgggc tgggcgaat ttgaaatcat catcaagata ttttcattg atccaaacga     1140 gcgacccgta agtacgctca gcttctcgta gtgcttcccc cgtcctggcg gcccggggct     1200
gggctgctcg ctgctgccgg tcacagtccc gccagccgcg gagctgactg agctcccttt     1260
cccgggacgt gtgctctgtg ttcggtcagc gaggctatcg ggagggcttt ggctgcattt     1320
ggcttctctg gcgcttagcg caggagcacg ttgtgctacg cctgaactac agctgtgaga     1380
aggccgtgga aaccgctctc aaactgattt attggcgaaa tggctctaaa ctaaatcgtc     1440
tcctctcttt ggaaatgctt tagagaaggt ctctgtggta gttcttatgc atctatccta     1500
aagcacttgg ccagacaatt taaagacatc aagcagcatt tatagcaggc acgtttaata     1560
acgaatactg aatttaagta actctgctca cgttgtatga cgtttatttt cgtattcctg     1620
aaagccatta aaatcctgtg cagttgttta gtaagaacag ctgccactgt tttgtatcta     1680
ggagataact ggtgtttccc tacagttctc aagctgataa aactctgtct ttgtatctag     1740
gtaaccctgt atcacttgct gaagcttttt cagtctgaca ccaatgcaat cctgggaaag     1800
aaaactgtag tttctgaatt ctatgatgaa atggtatgaa aattttaatg tcaaccgagc     1860
ctgactttat ttaaaaaaa ttattgatgg tgctgtgtat tttggtcctt ccttagatat     1920
ttcaagatcc tactgccatg atgcagcaac tgctaacgac gtcccgtcag ctgacacttg     1980
gtgcttacaa gcatgaaaca gagtgtaagt gcaaatgag gataccttcg ccgaccgtca     2040
ttcactacta atgttttctg tgggatgtga tcgtacagtg agtttggctg tgtgaaattt     2100
gaatagcttg gtattggcag tgatgacgtg atcgatgcct tgcttatcat gtttgaaatg     2160
aagtagaata aatgcagcct gctttatttg agatagtttg gttcattta tggaatgcaa     2220 gcaaagatta tacttcctca ctgaattgca ctgtccaaag gtgtgaaatg tgtggggatc     2280
tggaggaccg tgaccgaggg acattggatc gctatctccc atttcttttg ctgttaccag     2340
ttcagatttt cttttcacct agtctttaat tcccagggtt ttgttttttc cttggtcata     2400 gttttttgttt ttcactctgg caaatgatgt tgtgaattac actgcttcag ccacaaaact     2460
gatggactga atgaggtcat caaacaaact tttcttcttc cgtatttcct tttttttccc     2520
```

```
ccacttatca ttttttactgc tgttgttgag tctgtaaggc taaaagtaac tgttttgtgc   2580 ttttttcagga cgtgtgcttt ccaaattact gccacatata taaagaaagg ttggaatttt   2640
aaagataatt catgtttctt cttctttttt gccaccacag ttgcagatct tgaagtaaaa   2700
accagggaaa agctggaagc tgccaaaaag aaaaccagtt ttgaaattgc tgagcttaaa   2760
gaaaggttaa aagcaagtcg tgaaaccatc aactgcttaa agagtgaaat cagaaaactc   2820
gaagaggatg atcagtctaa agatatgtga tgagtgttga cttggcaggg agcctataat   2880
gagaatgaaa ggacttcagt cgtggagttg tatgcgttct ctccaattct gtaacggaga   2940
ctgtatgaat ttcatttgca aatcactgca gtgtgtgaca actgactttt tataaatggc   3000
agaaaacaag aatgaatgta tcctcatttt atagttaaaa tctatgggta tgtactggtt   3060
tatttcaagg agaatggatc gtagagactt ggaggccaga ttgctgcttg tattgactgc   3120
atttgagtgg tgtaggaaca ttttgtctat ggtcccgtgt tagtttacag aatgccactg   3180
ttcactgttt tgttttgtat tttacttttt ctactgcaac gtcaaggttt taaaagttga   3240
aaataaaaca tgcaggtttt ttttaaatat ttttttgtct ctatccagtt tgggcttcaa   3300
gtattattgt taacagcaag tcctgattta agtcagaggc tgaagtgtaa tggtattcaa   3360
gatgcttaag tctgttgtca gcaaaacaaa agagaaaact tcataaaatc aggaagttgg   3420
catttctaat aacttcttta tcaacagata agagtttcta gccctgcatc tactttcact   3480
tatgtagttg atgcctttat attttgtgtg tttggatgca ggaagtgatt cctactctgt   3540
tatgtagata ttctatttaa cacttgtact ctgctgtgct tagcctttcc ccatgaaaat   3600
tcagcggctg taaatccccc tcttcttttg tagcctcata cagatggcag accctcaggc   3660
ttataaaggc ttgggcatct tctttactgc tttgagattc tgtgttgcag taacctctgc   3720
cagagaggag aaaagcccca caaacctcat ccccttcttc tatagcaatc agtattacta   3780
atgctttgag aacagagcac tggttttgaaa cgtttgataa ttagcattta acatggcttg   3840
gtaaagatgc agaactgaaa cagctgtgac agtatgaact cagtatggag acttcattaa   3900
gacaaacagc tgttaaaatc aggcatgttt cattgaggag gacggggcaa cttgcaccag   3960
tggtgcccac acaaatcctt cctggcgctg cagaccaatt tttctggcat tctgactgcc   4020
gttgctgctg gtcacagaga gcaactattt ttatcagcca caggcaattt gcttgtagta   4080
ttttccaagt gttgtaggta agtataaatg catcggctcc agagcacttt gagtatactt   4140
attaaaaaca taaatgaaag acaaattagc tttgcttggg tgcacagaac attttttagtt   4200 ccagcctgct ttttggtaga agccctcttc tgaggctaga actgactttg acaagtagag   4260
aaactggcaa cggagctatt gctatcgaag gatccttgtt aacaaagtta atcgtctttt   4320
aaggtttggt ttattcatta aatttgcttt taagctgtag ctgaaaaaga acgtgctgtc   4380
ttccatgcac caggtggcag ctctgtgcaa agtgctctct ggtctcacca gccttttaat   4440
tgccgggatt ctggcacgtc tgagagggct cagactggct tcgtttgttt gaacagcgtg   4500
tactgctttc tgtagacatg gccggtttct ctcctgcagc ttatgaaact gttcacactg   4560
aacacactgg aacaggttgc ccaaggaggc cgtggatgcc ccatccctgg aggcattcaa   4620
ggccaggctg gatgtggctc tgggcagcct ggtctggtgg ttggcgatcc tgcacatagc   4680 agcgggggttc aaactcgatg atcactgtgg tccttttcaa cccaggctat tctatgattc   4740
tatgattcaa cagcaaatca tatgtactga gagaggaaac aaacacaagt gctactgttt   4800
gcaagttttc ttcatttggt aaaagagtca ggttttaaaa ttcaaaatct gtctggtttt   4860 ggtgttttttt tttttttatt tattatttct ttggggttct ttttgatgct ttatctttct   4920
```

```
ctgccaggac tgtgtgacaa tgggaacgaa aagaacatg ccaggcactg tcctggattg      4980
cacacgctgg ttgcactcag tagcaggctc agaactgcca gtctttccac agtattactt     5040
tctaaaccta attttaatag cgttagtaga cttccatcac tgggcagtgc ttagtgaatg     5100
ctctgtgtga acgttttact tataagcatg ttggaagttt tgatgttcct ggatgcagta     5160
gggaaggaca gattagctat gtgaaaagta gattctgagt atcggggtta caaaaagtat     5220
agaaacgatg agaaattctt gttgtaacta attggaattt ctttaagcgt tcacttatgc     5280
tacattcata gtatttccat ttaaaagtag gaaaaggtaa aacgtgaaat cgtgtgattt     5340
tcggatggaa caccgccttc ctatgcacct gaccaacttc cagaggaaaa gcctattgaa     5400
agccgagatt aagccaccaa agaactcat ttgcattgga atatgtagta tttgccctct      5460
tcctcccggg taattactat actttatagg gtgcttatat gttaaatgag tggctggcac     5520
tttttattct cacagctgtg gggaattctg tcctctagga cagaaacaat tttaatctgt     5580
tccactggtg actgctttgt cagcacttcc acctgaagag atcaatacac tcttcaatgt     5640
ctagttctgc aacacttggc aaacctcaca tcttatttca tactctcttc atgcctatgc     5700
ttattaaagc aataatctgg gtaattttg ttttaatcac tgtcctgacc ccagtgatga      5760
ccgtgtccca cctaaagctc aattcaggtc ctgaatctct tcaactctct atagctaaca     5820
tgaagaatct tcaaaagtta ggtctgaggg acttaaggct aactgtagat gttgttgcct     5880
ggtttctgtg ctgaaggccg tgtagtagtt agagcattca acctctagaa gaagcttggc    5940
cagctggtcg acctgcagat ccggccctcg ag                                   5972
```

<210> SEQ ID NO 10
<211> LENGTH: 18391
<212> TYPE: DNA
<213> ORGANISM: Gallus gallus
<220> FEATURE:
<221> NAME/KEY: misc_feature
<222> LOCATION: (1)..(237)
<223> OTHER INFORMATION: 5prime matrix (scaffold) attachment region
       (MAR)
<220> FEATURE:
<221> NAME/KEY: misc_feature
<222> LOCATION: (261)..(1564)
<223> OTHER INFORMATION: 5prime matrix (scaffold) attachment region
       (MAR)
<220> FEATURE:
<221> NAME/KEY: misc_feature
<222> LOCATION: (1565)..(1912)
<223> OTHER INFORMATION: 5prime matrix (scaffold) attachment region
       (MAR)
<220> FEATURE:
<221> NAME/KEY: misc_feature
<222> LOCATION: (1930)..(2012)
<223> OTHER INFORMATION: 5prime matrix (scaffold) attachment region
       (MAR)
<220> FEATURE:
<221> NAME/KEY: misc_feature
<222> LOCATION: (2013)..(2671)
<223> OTHER INFORMATION: Intrinsically curved DNA
<220> FEATURE:
<221> NAME/KEY: misc_feature
<222> LOCATION: (5848)..(5934)
<223> OTHER INFORMATION: Transcription enhancer
<220> FEATURE:
<221> NAME/KEY: misc_feature
<222> LOCATION: (9160)..(9325)
<223> OTHER INFORMATION: Transcription enhancer
<220> FEATURE:
<221> NAME/KEY: misc_feature
<222> LOCATION: (9326)..(9626)
<223> OTHER INFORMATION: Negative regulatory element
<220> FEATURE:

```
<221> NAME/KEY: misc_feature
<222> LOCATION: (9621)..(9660)
<223> OTHER INFORMATION: Hormone response element
<220> FEATURE:
<221> NAME/KEY: misc_feature
<222> LOCATION: (9680)..(10060)
<223> OTHER INFORMATION: Hormone response element
<220> FEATURE:
<221> NAME/KEY: misc_feature
<222> LOCATION: (10576)..(10821)
<223> OTHER INFORMATION: Chicken CR1 Repeat Sequence
<220> FEATURE:
<221> NAME/KEY: misc_feature
<222> LOCATION: (10926)..(11193)
<223> OTHER INFORMATION: Chicken CR1 Repeat Sequence
<220> FEATURE:
<221> NAME/KEY: misc_feature
<222> LOCATION: (11424)..(11938)
<223> OTHER INFORMATION: Lysozyme Proximal Promoter and Lysozyme Signal
      Peptide
<220> FEATURE:
<221> NAME/KEY: misc_feature
<222> LOCATION: (11946)..(12443)
<223> OTHER INFORMATION: human interferon alpha 2b codon-optimized for
      expression in chickens
<220> FEATURE:
<221> NAME/KEY: misc_feature
<222> LOCATION: (12464)..(18391)
<223> OTHER INFORMATION: Chicken Lysozyme 3prime domain

<400> SEQUENCE: 10
tgccgccttc tttgatattc actctgttgt atttcatctc ttcttgccga tgaaaggata      60
taacagtctg tataacagtc tgtgaggaaa tacttggtat ttcttctgat cagtgttttt     120
ataagtaatg ttgaatattg gataaggctg tgtgtccttt gtcttgggag acaaagccca     180
cagcaggtgg tggttggggt ggtggcagct cagtgacagg agaggttttt ttgcctgttt     240
tttttttttt tttttttttt aagtaaggtg ttcttttttc ttagtaaatt ttctactgga     300
ctgtatgttt tgacaggtca gaaacatttc ttcaaaagaa gaacctttg gaaactgtac      360 agccctttc tttcattccc tttttgcttt ctgtgccaat gcctttggtt ctgattgcat      420
tatggaaaac gttgatcgga acttgaggtt tttatttata gtgtggcttg aaagcttgga     480
tagctgttgt tacacgagat accttattaa gtttaggcca gcttgatgct ttattttttc     540
cctttgaagt agtgagcgtt ctctggtttt tttccttga aactggtgag cttagattt       600 ttctaatggg attttttacc tgatgatcta gttgcatacc caaatgcttg taaatgtttt     660
cctagttaac atgttgataa cttcggattt acatgttgta tatacttgtc atctgtgttt     720
ctagtaaaaa tatatggcat ttatagaaat acgtaattcc tgatttcctt ttttttatc     780 tctatgctct gtgtgtacag gtcaaacaga cttcactcct attttattt atagaatttt      840 atatgcagtc tgtcgttggt tcttgtgttg taaggataca gccttaaatt tcctagagcg     900
atgctcagta aggcgggttg tcacatgggt tcaaatgtaa aacgggcacg tttggctgct     960
gccttcccga gatccaggac actaaactgc ttctgcactg aggtataaat cgcttcagat    1020
cccagggaag tgcagatcca cgtgcatatt cttaaagaag aatgaatact ttctaaaata    1080
ttttggcata ggaagcaagc tgcatggatt tgtttgggac ttaaattatt ttggtaacgg    1140
agtgcatagg ttttaaacac agttgcagca tgctaacgag tcacagcgtt tatgcagaag    1200
tgatgcctgg atgcctgttg cagctgttta cggcactgcc ttgcagtgag cattgcagat    1260
aggggtgggg tgctttgtgt cgtgttccca cacgctgcca cacagccacc tcccggaaca    1320
catctcacct gctgggtact tttcaaacca tcttagcagt agtagatgag ttactatgaa    1380
acagagaagt tcctcagttg gatattctca tgggatgtct tttttcccat gttgggcaaa    1440
```

-continued

```
gtatgataaa gcatctctat ttgtaaatta tgcacttgtt agttcctgaa tcctttctat    1500
agcaccactt attgcagcag gtgtaggctc tggtgtggcc tgtgtctgtg cttcaatctt    1560
ttaaagcttc tttggaaata cactgacttg attgaagtct cttgaagata gtaaacagta    1620
cttacctttg atcccaatga aatcgagcat ttcagttgta aaagaattcc gcctattcat    1680
accatgtaat gtaattttac accccagtg ctgacacttt ggaatatatt caagtaatag    1740
actttggcct caccctcttg tgtactgtat tttgtaatag aaaatatttt aaactgtgca    1800
tatgattatt acattatgaa agagacattc tgctgatctt caaatgtaag aaaatgagga    1860
gtgcgtgtgc ttttataaat acaagtgatt gcaaattagt gcaggtgtcc ttaaaaaaaa    1920
aaaaaaaaag taatataaaa aggaccaggt gttttacaag tgaaatacat tcctatttgg    1980
taaacagtta cattttatg aagattacca gcgctgctga ctttctaaac ataaggctgt    2040
attgtcttcc tgtaccattg catttcctca ttcccaattt gcacaaggat gtctgggtaa    2100
actattcaag aaatggcttt gaaatacagc atgggagctt gtctgagttg aatgcagag    2160
ttgcactgca aaatgtcagg aaatggatgt ctctcagaat gcccaactcc aaaggatttt    2220
atatgtgtat atagtaagca gtttcctgat tccagcaggc caaagagtct gctgaatgtt    2280
gtgttgccgg agacctgtat ttctcaacaa ggtaagatgg tatcctagca actgcggatt    2340
taatacatt tcagcagaa gtacttagtt aatctctacc tttagggatc gtttcatcat    2400
ttttagatgt tatacttgaa atactgcata acttttagct ttcatgggtt ccttttttc    2460
agcctttagg agactgttaa gcaatttgct gtccaacttt tgtgttggtc ttaaactgca    2520
atagtagttt accttgtatt gaagaaataa agaccatttt tatattaaaa aatacttttg    2580
tctgtcttca ttttgacttg tctgatatcc ttgcagtgcc cattatgtca gttctgtcag    2640
atattcagac atcaaaactt aacgtgagct cagtggagtt acagctgcgg ttttgatgct    2700
gttattattt ctgaaactag aaatgatgtt gtcttcatct gctcatcaaa cacttcatgc    2760
agagtgtaag gctagtgaga aatgcataca tttattgata ctttttttaaa gtcaacttt    2820
tatcagattt ttttttcatt tggaaatata ttgttttcta gactgcatag cttctgaatc    2880
tgaaatgcag tctgattggc atgaagaagc acagcactct tcatcttact taaacttcat    2940
tttggaatga aggaagttaa gcaagggcac aggtccatga aatagagaca gtgcgctcag    3000
gagaaagtga acctggattt cttttggctag tgttctaaat ctgtagtgag gaaagtaaca    3060
cccgattcct tgaaagggct ccagcttaa tgcttccaaa ttgaaggtgg caggcaactt    3120
ggccactggt tatttactgc attatgtctc agtttcgcag ctaacctggc ttctccacta    3180
ttgagcatgg actatagcct ggcttcagag gccaggtgaa ggttgggatg ggtggaagga    3240
gtgctgggct gtggctgggg ggactgtggg gactccaagc tgagcttggg gtgggcagca    3300
cagggaaaag tgtgggtaac tattttttaag tactgtgttg caaacgtctc atctgcaaat    3360
acgtagggtg tgtactctcg aagattaaca gtgtgggttc agtaatatat ggatgaattc    3420
acagtggaag cattcaaggg tagatcatct aacgacacca gatcatcaag ctatgattgg    3480
aagcggtatc agaagagcga ggaaggtaag cagtcttcat atgttttccc tccacgtaaa    3540
gcagtctggg aaagtagcac cccttgagca gagacaagga aataattcag gagcatgtgc    3600
taggagaact ttcttgctga attctacttg caagagcttt gatgcctggc ttctggtgcc    3660
ttctgcagca cctgcaaggc ccagagcctg tggtgagctg gagggaaaga ttctgctcaa    3720
gtccaagctt cagcaggtca ttgtctttgc ttcttccccc agcactgtgc agcagagtgg    3780
```

```
aactgatgtc gaagcctcct gtccactacc tgttgctgca ggcagactgc tctcagaaaa   3840
agagagctaa ctctatgcca tagtctgaag gtaaaatggg ttttaaaaaa gaaaacacaa   3900
aggcaaaacc ggctgcccca tgagaagaaa gcagtggtaa acatggtaga aaaggtgcag   3960
aagcccccag gcagtgtgac aggcccctcc tgccacctag aggcgggaac aagcttccct   4020
gcctagggct ctgcccgcga agtgcgtgtt tctttggtgg gttttgtttg gcgtttggtt   4080
ttgagattta gacacaaggg aagcctgaaa ggaggtgttg ggcactattt tggtttgtaa   4140
agcctgtact tcaaatatat attttgtgag ggagtgtagc gaattggcca atttaaaata   4200
aagttgcaag agattgaagg ctgagtagtt gagagggtaa cacgtttaat gagatcttct   4260
gaaactactg cttctaaaca cttgtttgag tggtgagacc ttggataggt gagtgctctt   4320
gttacatgtc tgatgcactt gcttgtcctt ttccatccac atccatgcat tccacatcca   4380
cgcatttgtc acttatccca tatctgtcat atctgacata cctgtctctt cgtcacttgg   4440
tcagaagaaa cagatgtgat aatccccagc cgccccaagt tgagaagat ggcagttgct    4500 tctttccctt tttcctgcta agtaaggatt ttctcctggc tttgacacct cacgaaatag   4560
tcttcctgcc ttacattctg ggcattattt caaatatctt tggagtgcgc tgctctcaag   4620
tttgtgtctt cctactctta gagtgaatgc tcttagagtg aaagagaagg aagagaagat   4680
gttggccgca gttctctgat gaacacacct ctgaataatg ccaaaggtg ggtgggtttc    4740 tctgaggaac gggcagcgtt tgcctctgaa agcaaggagc tctgcggagt tgcagttatt   4800
ttgcaactga tggtggaact ggtgcttaaa gcagattccc taggttccct gctacttctt   4860
ttccttcttg gcagtcagtt tatttctgac agacaaacag ccaccccac tgcaggctta    4920 gaaagtatgt ggctctgcct gggtgtgtta cagctctgcc ctggtgaaag gggattaaaa   4980
cgggcaccat tcatcccaaa caggatcctc attcatggat caagctgtaa ggaacttggg   5040
ctccaacctc aaaacattaa ttggagtacg aatgtaatta aaactgcatt ctcgcattcc   5100
taagtcattt agtctggact ctgcagcatg taggtcggca gctcccactt tctcaaagac   5160
cactgatgga ggagtagtaa aaatggagac cgattcagaa caaccaacgg agtgttgccg   5220
aagaaactga tggaaataat gcatgaattg tgtggtggac attttttta aatacataaa    5280 ctacttcaaa tgaggtcgga gaaggtcagt gttttattag cagccataaa accaggtgag   5340
cgagtaccat ttttctctac aagaaaaacg attctgagct ctgcgtaagt ataagttctc   5400
catagcggct gaagctcccc cctggctgcc tgccatctca gctggagtgc agtgccattt   5460
ccttggggtt tctctcacag cagtaatggg acaatacttc acaaaaattc tttcttttcc   5520
tgtcatgtgg gatccctact gtgccctcct ggttttacgt tacccctga ctgttccatt    5580 cagcggtttg gaaagagaaa aagaatttgg aaataaaaca tgtctacgtt atcacctcct   5640
ccagcatttt ggttttaat tatgtcaata actggcttag atttggaaat gagaggggt     5700 tgggtgtatt accgaggaac aaaggaaggc ttatataaac tcaagtcttt tatttagaga   5760
actggcaagc tgtcaaaaac aaaaaggcct taccaccaaa ttaagtgaat agccgctata   5820
gccagcaggg ccagcacgag ggatggtgca ctgctggcac tatgccacgg cctgcttgtg   5880
actctgagag caactgcttt ggaaatgaca gcacttggtg caatttcctt tgtttcagaa   5940
tgcgtagagc gtgtgcttgg cgacagtttt tctagttagg ccacttcttt tttccttctc   6000
tcctcattct cctaagcatg tctccatgct ggtaatccca gtcaagtgaa cgttcaaaca   6060
atgaatccat cactgtagga ttctcgtggt gatcaaatct ttgtgtgagg tctataaaat   6120
atggaagctt atttattttt cgttcttcca tatcagtctt ctctatgaca attcacatcc   6180
```

```
accacagcaa attaaaggtg aaggaggctg gtgggatgaa gagggtcttc tagctttacg    6240
ttcttccttg caaggccaca ggaaaatgct gagagctgta gaatacagcc tggggtaaga    6300
agttcagtct cctgctggga cagctaaccg catcttataa ccccttctga gactcatctt    6360
aggaccaaat agggtctatc tggggttttt gttcctgctg ttcctcctgg aaggctatct    6420
cactatttca ctgctcccac ggttacaaac caaagataca gcctgaattt tttctaggcc    6480
acattacata aatttgacct ggtaccaata ttgttctcta tatagttatt tccttcccca    6540
ctgtgtttaa ccccttaagg cattcagaac aactagaatc atagaatggt ttggattgga    6600
aggggcctta aacatcatcc atttccaacc ctctgccatg ggctgcttgc cacccactgg    6660
ctcaggctgc ccagggcccc atccagcctg gccttgagca cctccaggga tggggcaccc    6720
acagcttctc tgggcagcct gtgccaacac ctcaccactc tctgggtaaa gaattctctt    6780
ttaacatcta atctaaatct cttctctttt agtttaaagc cattcctctt tttcccgttg    6840
ctatctgtcc aagaaatgtg tattggtctc cctcctgctt ataagcagga agtactggaa    6900
ggctgcagtg aggtctcccc acagccttct cttctccagg ctgaacaagc ccagctcctt    6960
cagcctgtct tcgtaggaga tcatcttagt ggccctcctc tggacccatt ccaacagttc    7020
cacggctttc ttgtggagcc ccaggtctgg atgcagtact tcagatgggg ccttacaaag    7080
gcagagcaga tggggacaat cgcttacccc tccctgctgg ctgcccctgt tttgatgcag    7140
cccagggtac tgttggcctt tcaggctccc agacccctgc tgatttgtg tcaagctttt    7200 catccaccag aacccacgct tcctggttaa tacttctgcc ctcacttctg taagcttgtt    7260
tcaggagact tccattcttt aggacagact gtgttacacc tacctgccct attcttgcat    7320
atatacattt cagttcatgt ttcctgtaac aggacagaat atgtattcct ctaacaaaaa    7380
tacatgcaga attcctagtg ccatctcagt agggttttca tggcagtatt agcacatagt    7440
caatttgctg caagtacctt ccaagctgcg gcctcccata aatcctgtat ttgggatcag    7500 ttacctttg gggtaagctt ttgtatctgc agagaccctg ggggttctga tgtgcttcag    7560
ctctgctctg ttctgactgc accattttct agatcaccca gttgttcctg tacaacttcc    7620
ttgtcctcca tccttttccca gcttgtatct ttgacaaata caggcctatt tttgtgtttg    7680
cttcagcagc catttaattc ttcagtgtca tcttgttctg ttgatgccac tggaacagga    7740
ttttcagcag tcttgcaaag aacatctagc tgaaaacttt ctgccattca atattcttac    7800
cagttcttct tgtttgaggt gagccataaa ttactagaac ttcgtcactg acaagtttat    7860
gcattttatt acttctatta tgtacttact ttgacataac acagacacgc acatattttg    7920
ctgggatttc cacagtgtct ctgtgtcctt cacatggttt tactgtcata cttccgttat    7980
aaccttggca atctgcccag ctgcccatca aagaaaaga gattcctttt ttattacttc    8040
tcttcagcca ataaacaaaa tgtgagaagc ccaaacaaga acttgtgggg caggctgcca    8100
tcaagggaga gacagctgaa gggttgtgta gctcaataga attaagaaat aataaagctg    8160
tgtcagacag ttttgcctga tttatacagg cacgccccaa gccagagagg ctgtctgcca    8220
aggccacctt gcagtccttg gtttgtaaga taagtcatag gtaacttttc tggtgaattg    8280
cgtggagaat catgatggca gttccttgctg tttactatgg taagatgcta aaataggaga    8340
cagcaaagta acacttgctg ctgtaggtgc tctgctatcc agacagcgat ggcactcgca    8400
caccaagatg agggatgctc ccagctgacg gatgctgggg cagtaacagt gggtcccatg    8460
ctgcctgctc attagcatca cctcagccct caccagccca tcagaaggat catcccaagc    8520
```

```
tgaggaaagt tgctcatctt cttcacatca tcaaacctttt ggcctgactg atgcctcccg   8580
gatgcttaaa tgtggtcact gacatcttta tttttctatg atttcaagtc agaacctccg   8640
gatcaggagg gaacacatag tgggaatgta ccctcagctc caaggccaga tcttccttca   8700
atgatcatgc atgctactta ggaaggtgtg tgtgtgtgaa tgtagaattg cctttgttat   8760
tttttcttcc tgctgtcagg aacattttga ataccagaga aaaagaaaag tgctcttctt   8820
ggcatgggag gagttgtcac acttgcaaaa taaaggatgc agtcccaaat gttcataatc   8880
tcagggtctg aaggaggatc agaaactgtg tatacaattt caggcttctc tgaatgcagc   8940
ttttgaaagc tgttcctggc cgaggcagta ctagtcagaa ccctcggaaa caggaacaaa   9000
tgtcttcaag gtgcagcagg aggaaacacc ttgcccatca tgaaagtgaa taaccactgc   9060
cgctgaagga atccagctcc tgtttgagca ggtgctgcac actcccacac tgaaacaaca   9120
gttcattttt ataggacttc caggaaggat cttcttctta agcttcttaa ttatggtaca   9180
tctccagttg gcagatgact atgactactg acaggagaat gaggaactag ctgggaatat   9240
ttctgtttga ccaccatgga gtcacccatt tctttactgg tatttggaaa taataattct   9300
gaattgcaaa gcaggagtta gcgaagatct tcatttcttc catgttggtg acagcacagt   9360
tctggctatg aaagtctgct tacaaggaag aggataaaaa tcatagggat aataaatcta   9420
agtttgaaga caatgaggtt ttagctgcat ttgacatgaa gaaattgaga cctctactgg   9480
atagctatgg tatttacgtg tctttttgct tagttactta ttgaccccag ctgaggtcaa   9540
gtatgaactc aggtctctcg ggctactggc atggattgat tacatacaac tgtaatttta   9600
gcagtgattt agggtttatg agtacttttg cagtaaatca tagggttagt aatgttaatc   9660
tcagggaaaa aaaaaaaaag ccaaccctga cagacatccc agctcaggtg gaaatcaagg   9720
atcacagctc agtgcggtcc cagagaacac agggactctt ctcttaggac ctttatgtac   9780
agggcctcaa gataactgat gttagtcaga agactttcca ttctggccac agttcagctg   9840
aggcaatcct ggaattttct ctccgctgca cagttccagt catcccagtt tgtacagttc   9900
tggcactttt tgggtcaggc cgtgatccaa ggagcagaag ttccagctat ggtcagggag   9960
tgcctgaccg tcccaactca ctgcactcaa acaaaggcga aaccacaaga gtggcttttg  10020
ttgaaattgc agtgtggccc agaggggctg caccagtact ggattgacca cgaggcaaca  10080
ttaatcctca gcaagtgcaa tttgcagcca ttaaattgaa ctaactgata ctacaatgca  10140
atcagtatca acaagtggtt tggcttggaa gatggagtct aggggctcta caggagtagc  10200
tactctctaa tggagttgca ttttgaagca ggacactgtg aaaagctggc ctcctaaaga  10260
ggctgctaaa cattagggtc aattttccag tgcactttct gaagtgtctg cagttcccca  10320
tgcaaagctg cccaaacata gcacttccaa ttgaatacaa ttatatgcag gcgtactgct  10380
tcttgccagc actgtccttc tcaaatgaac tcaacaaaca atttcaaagt ctagtagaaa  10440
gtaacaagct ttgaatgtca ttaaaaagta tatctgcttt cagtagttca gcttatttat  10500
gcccactaga aacatcttgt acaagctgaa cactggggct ccagattagt ggtaaaacct  10560
actttataca atcatagaat catagaatgg cctgggttgg aagggacccc aaggatcatg  10620
aagatccaac accccgcca caggcagggc caccaacctc cagatctggt actagaccag  10680
gcagcccagg gctccatcca acctggccat gaacacctcc agggatggag catccacaac  10740
ctctctgggc agcctgtgcc agcacctcac cacccctctct gtgaagaact tttccctgac  10800
atccaatcta agccttccct ccttgaggtt agatccactc ccccttgtgc tatcactgtc  10860
tactcttgta aaaagttgat tctcctcctt tttggaaggt tgcaatgagg tctccttgca  10920
```

```
gccttcttct cttctgcagg atgaacaagc ccagctccct cagcctgtct ttataggaga    10980
ggtgctccag ccctctgatc atctttgtgg ccctcctctg gacccgctcc aagagctcca    11040
catctttcct gtactggggg ccccaggcct gaatgcagta ctccagatgg ggcctcaaaa    11100
gagcagagta agagggaca atcaccttcc tcaccctgct ggccagccct cttctgatgg     11160
agccctggat acaactggct ttctgagctg caacttctcc ttatcagttc cactattaaa    11220
acaggaacaa tacaacaggt gctgatggcc agtgcagagt ttttcacact tcttcatttc    11280
ggtagatctt agatgaggaa cgttgaagtt gtgcttctgc gtgtgcttct tcctcctcaa    11340
atactcctgc ctgataccte acccacctg ccactgaatg gctccatggc ccctgcagc     11400
cagggccctg atgaacccgg cactgcttca gatgctgttt aatagcacag tatgaccaag    11460
ttgcacctat gaatacacaa acaatgtgtt gcatccttca gcacttgaga agaagagcca    11520
aatttgcatt gtcaggaaat ggtttagtaa ttctgccaat taaaacttgt ttatctacca    11580
tggctgtttt tatggctgtt agtagtggta cactgatgat gaacaatggc tatgcagtaa    11640
aatcaagact gtagatattg caacagacta taaaattcct ctgtggctta gccaatgtgg    11700
tacttcccac attgtataag aaatttggca agtttagagc aatgtttgaa gtgttgggaa    11760
atttctgtat actcaagagg gcgttttga caactgtaga acagaggaat caaaaggggg     11820
tgggaggaag ttaaaagaag aggcaggtgc aagagagctt gcagtcccgc tgtgtgtacg    11880
acactggcaa catgaggtct ttgctaatct tggtgctttg cttcctgccc ctggctgcct    11940
tagggtgcga tctgcctcag acccacagcc tgggcagcag gaggaccctg atgctgctgg    12000
ctcagatgag gagaatcagc ctgtttagct gcctgaagga taggcacgat tttggctttc    12060
ctcaagagga gtttggcaac cagtttcaga aggctgagac catccctgtg ctgcacgaga    12120
tgatccagca gatctttaac ctgtttagca ccaaggatag cagcgctgct tgggatgaga    12180
ccctgctgga taagttttac accgagctgt accagcagct gaacgatctg gaggcttgcg    12240
tgatccaggg cgtgggcgtg accgagaccc tctgatgaa ggaggatagc atcctggctg     12300
tgaggaagta ctttcagagg atcacccctgt acctgaagga gaagaagtac agcccctgcg   12360
cttgggaagt cgtgagggct gagatcatga ggagctttag cctgagcacc aacctgcaag    12420
agagcttgag gtctaaggag taaaaagtct agagtcgggg cggcgcgtgg taggtggcgg    12480
ggggttccca ggagagcccc cagcgcggac ggcagcgccg tcactcaccg ctccgtctcc    12540
ctccgcccag gtcgcctgg cgcaaccgct gcaagggcac cgacgtccag gcgtggatca     12600
gaggctgccg gctgtgagga gctgccgcgc ccggcccgcc cgctgcacag ccggccgctt    12660
tgcgagcgcg acgctacccg cttggcagtt ttaaacgcat ccctcattaa acgactata    12720
cgcaaacgcc ttcccgtcgg tccgcgtctc tttccgccgc cagggcgaca ctcgcgggga    12780
gggcgggaag gggccgggc gggagcccgc ggccaaccgt cgccccgtga cggcaccgcc     12840
ccgcccccgt gacgcggtgc gggcgccggg gccgtggggc tgagcgctgc ggcggggccg    12900
ggccgggccg gggcgggagc tgagcgcggc gcggctgcgg gcggcgcccc ctccggtgca    12960
atatgttcaa gagaatggct gagttcgggc ctgactccgg gggcagggtg aaggtgcggc    13020
gcggcggag ggacggggcg ggcgcgggc cgcccggcgg gtgccgggc ctctgccggc       13080
ccgcccggct cgggctgctg cggcgcttac gggcgcgctt ctcgccgctg ccgcttctct    13140
tctctcccgc gcaagggcgt caccatcgtg aagccggtag tgtacgggaa cgtggcgcgg    13200
tacttcggga agaagaggga ggaggacggg cacacgcatc agtggacggt ttacgtgaag    13260
```

-continued

```
ccctacagga acgaggtagg gcccgagcgc gtcggccgcc gttctcggag cgccggagcc    13320
gtcagcgccg cgcctgggtg cgctgtggga cacagcgagc ttctctcgta ggacatgtcc    13380
gcctacgtga aaaaaatcca gttcaagctg cacgagagct acgggaatcc tctccgaggt    13440
gggtgttgcg tcgggggtt tgctccgctc ggtcccgctg aggctcgtcg ccctcatctt     13500
tctttcgtgc cgcagtcgtt accaaaccgc cgtacgagat caccgaaacg ggctggggcg    13560
aatttgaaat catcatcaag atatttttca ttgatccaaa cgagcgaccc gtaagtacgc    13620
tcagcttctc gtagtgcttc ccccgtcctg gcggcccggg gctgggctgc tcgctgctgc    13680
cggtcacagt cccgccagcc gcggagctga ctgagctccc tttcccggga cgtgtgctct    13740
gtgttcggtc agcgaggcta tcgggagggc tttggctgca tttggcttct ctggcgctta    13800
gcgcaggagc acgttgtgct acgcctgaac tacagctgtg agaaggccgt ggaaaccgct    13860
ctcaaactga tttattggcg aaatggctct aaactaaatc gtctcctctc tttggaaatg    13920
ctttagagaa ggtctctgtg gtagttctta tgcatctatc ctaaagcact tggccagaca    13980
atttaaagac atcaagcagc atttatagca ggcacgttta ataacgaata ctgaatttaa    14040
gtaactctgc tcacgttgta tgacgtttat tttcgtattc ctgaaagcca ttaaaatcct    14100
gtgcagttgt ttagtaagaa cagctgccac tgttttgtat ctaggagata actggtgttt    14160
ccctacagtt ctcaagctga taaaactctg tctttgtatc taggtaaccc tgtatcactt    14220
gctgaagctt tttcagtctg acaccaatgc aatcctggga agaaaactg tagtttctga     14280
attctatgat gaaatggtat gaaaatttta atgtcaaccg agcctgactt tatttaaaaa    14340
aaattattga tggtgctgtg tattttggtc cttccttaga tatttcaaga tcctactgcc    14400
atgatgcagc aactgctaac gacgtcccgt cagctgacac ttggtgctta caagcatgaa    14460
acagagtgta agtgcaaaat gaggatacct tcgccgaccg tcattcacta ctaatgtttt    14520
ctgtgggatg tgatcgtaca gtgagtttgg ctgtgtgaaa tttgaatagc ttggtattgg    14580
cagtgatgac gtgatcgatg ccttgcttat catgtttgaa atgaagtaga ataaatgcag    14640
cctgctttat ttgagatagt ttggttcatt ttatggaatg caagcaaaga ttatacttcc    14700
tcactgaatt gcactgtcca aaggtgtgaa atgtgtgggg atctggagga ccgtgaccga    14760
gggacattgg atcgctatct cccatttctt ttgctgttac cagttcagat tttcttttca    14820
cctagtcttt aattcccagg gttttgtttt ttccttggtc atagtttttg tttttcactc    14880
tggcaaatga tgttgtgaat tacactgctt cagccacaaa actgatggac tgaatgaggt    14940
catcaaacaa acttttcttc ttccgtattt cctttttttt ccccacctta tcattttac     15000
tgctgttgtt gagtctgtaa ggctaaaagt aactgttttg tgcttttca ggacgtgtgc     15060
tttccaaatt actgccacat atataaagaa aggttggaat tttaaagata attcatgttt    15120
cttcttcttt tttgccacca cagttgcaga tcttgaagta aaaccaggg aaaagctgga     15180
agctgccaaa agaaaaacca gttttgaaat tgctgagctt aagaaaggt taaaagcaag     15240
tcgtgaaacc atcaactgct aaagagtga atcagaaaa ctcgaagagg atgatcagtc      15300
taaagatatg tgatgagtgt tgacttggca gggagcctat aatgagaatg aaaggacttc    15360
agtcgtggag ttgtatgcgt tctctccaat tctgtaacgg agactgtatg aatttcattt    15420
gcaaatcact gcagtgtgtg acaactgact ttttataaat ggcagaaaac aagaatgaat    15480
gtatcctcat tttatagtta aaatctatgg gtatgtactg gtttatttca aggagaatgg    15540
atcgtagaga cttggaggcc agattgctgc ttgtattgac tgcatttgag tggtgtagga    15600
acattttgtc tatggtcccg tgttagttta cagaatgcca ctgttcactg ttttgttttg    15660
```

```
tattttactt tttctactgc aacgtcaagg ttttaaaagt tgaaaataaa acatgcaggt      15720 ttttttttaaa tattttttg tctctatcca gtttgggctt caagtattat tgttaacagc     15780
aagtcctgat ttaagtcaga ggctgaagtg taatggtatt caagatgctt aagtctgttg      15840
tcagcaaaac aaaagagaaa acttcataaa atcaggaagt tggcatttct ataacttct      15900 ttatcaacag ataagagttt ctagccctgc atctactttc acttatgtag ttgatgcctt      15960
tatattttgt gtgtttggat gcaggaagtg attcctactc tgttatgtag atattctatt      16020
taacacttgt actctgctgt gcttagcctt tccccatgaa aattcagcgg ctgtaaatcc      16080
ccctcttctt ttgtagcctc atacagatgg cagaccctca ggcttataaa ggcttgggca      16140
tcttctttac tgctttgaga ttctgtgttg cagtaacctc tgccagagag gagaaaagcc      16200
ccacaaacct catccccttc ttctatagca atcagtatta ctaatgcttt gagaacagag      16260
cactggtttg aaacgtttga taattagcat ttaacatggc ttggtaaaga tgcagaactg      16320
aaacagctgt gacagtatga actcagtatg gagacttcat taagacaaac agctgttaaa      16380
atcaggcatg tttcattgag gaggacgggg caacttgcac cagtggtgcc cacacaaatc      16440
cttcctggcg ctgcagacca attttttctgg cattctgact gccgttgctg ctggtcacag      16500
agagcaacta tttttatcag ccacaggcaa tttgcttgta gtattttcca agtgttgtag      16560
gtaagtataa atgcatcggc tccagagcac tttgagtata cttattaaaa acataaatga      16620
aagacaaatt agctttgctt gggtgcacag aacatttta gttccagcct gcttttggt      16680 agaagccctc ttctgaggct agaactgact ttgacaagta gagaaactgg caacggagct      16740
attgctatcg aaggatcctt gttaacaaag ttaatcgtct tttaaggttt ggtttattca      16800
ttaaatttgc ttttaagctg tagctgaaaa agaacgtgct gtcttccatg caccaggtgg      16860
cagctctgtg caaagtgctc tctggtctca ccagcctttt aattgccggg attctggcac      16920
gtctgagagg gctcagactg gcttcgtttg tttgaacagc gtgtactgct ttctgtagac      16980
atggccggtt tctctcctgc agcttatgaa actgttcaca ctgaacacac tggaacaggt      17040
tgcccaagga ggccgtggat gccccatccc tggaggcatt caaggccagg ctggatgtgg      17100
ctctgggcag cctggtctgg tggttggcga tcctgcacat agcagcgggg ttgaaactcg      17160
atgatcactg tggtccttt caacccaggc tattctatga ttctatgatt caacagcaaa      17220
tcatatgtac tgagagagga aacaaacaca agtgctactg tttgcaagtt ttgttcattt      17280
ggtaaaagag tcaggtttta aaattcaaaa tctgtctggt tttggtgttt ttttttttt      17340 atttattatt tctttggggt tctttttgat gctttatctt tctctgccag gactgtgtga      17400
caatgggaac gaaaaagaac atgccaggca ctgtcctgga ttgcacacgc tggttgcact      17460
cagtagcagg ctcagaactg ccagtctttc cacagtatta ctttctaaac ctaatttaa      17520 tagcgttagt agacttccat cactgggcag tgcttagtga atgctctgtg tgaacgtttt      17580
acttataagc atgttggaag ttttgatgtt cctggatgca gtagggaagg acagattagc      17640
tatgtgaaaa gtagattctg agtatcgggg ttacaaaaag tatagaaacg atgagaaatt      17700
cttgttgtaa ctaattggaa tttctttaag cgttcactta tgctacattc atagtatttc      17760
catttaaaag taggaaaagg taaaacgtga atcgtgtga ttttcggatg gaacaccgcc      17820
ttcctatgca cctgaccaac ttccagagga aaagcctatt gaaagccgag attaagccac      17880
caaaagaact catttgcatt ggaatatgta gtatttgccc tcttcctccc gggtaattac      17940
tatactttat agggtgctta tatgttaaat gagtggctgg cacttttat tctcacagct      18000
```

-continued

```
gtggggaatt ctgtcctcta ggacagaaac aatttaatc tgttccactg gtgactgctt    18060
tgtcagcact tccacctgaa gagatcaata cactcttcaa tgtctagttc tgcaacactt    18120
ggcaaacctc acatcttatt tcatactctc ttcatgccta tgcttattaa agcaataatc    18180
tgggtaattt ttgttttaat cactgtcctg accccagtga tgaccgtgtc ccacctaaag    18240
ctcaattcag gtcctgaatc tcttcaactc tctatagcta acatgaagaa tcttcaaaag    18300
ttaggtctga gggacttaag gctaactgta gatgttgttg cctggtttct gtgctgaagg    18360
ccgtgtagta gttagagcat tcaacctcta g                                  18391
```

<210> SEQ ID NO 11
<211> LENGTH: 586
<212> TYPE: DNA
<213> ORGANISM: Artificial sequence
<220> FEATURE:
<223> OTHER INFORMATION: MDOT artificial promoter

<400> SEQUENCE: 11

```
gtaccgggcc cccctcgag gtgaatatcc aagaatgcag aactgcatgg aaagcagagc      60
tgcaggcacg atggtgctga gccttagctg cttcctgctg ggagatgtgg atgcagagac     120
gaatgaagga cctgtccctt actcccctca gcattctgtg ctatttaggg ttctaccaga    180
gtccttaaga ggttttttt ttttttggtc caaaagtctg tttgtttggt tttgaccact    240
gagagcatgt gacacttgtc tcaagctatt aaccaagtgt ccagccaaaa tcgatgtcac    300
aacttgggaa ttttccattt gaagccccctt gcaaaaacaa agagcacctt gcctgctcca    360
gctcctggct gtgaagggtt ttggtgccaa agagtgaaag gcttcctaaa aatgggctga    420
gccggggaag gggggcaact tgggggctat tgagaaacaa ggaaggacaa acagcgttag    480
gtcattgctt ctgcaaacac agccagggct gctcctctat aaaagggaa gaaagaggct    540 ccgcagccat cacagaccca gagggacgg tctgtgaatc aagctt                   586
```

<210> SEQ ID NO 12
<211> LENGTH: 11
<212> TYPE: PRT
<213> ORGANISM: Artificial sequence
<220> FEATURE:
<223> OTHER INFORMATION: SV40 terminator

<400> SEQUENCE: 12

```
Cys Gly Gly Pro Lys Lys Lys Arg Lys Val Gly
1               5                   10
```

<210> SEQ ID NO 13
<211> LENGTH: 20
<212> TYPE: DNA
<213> ORGANISM: Artificial sequence
<220> FEATURE:
<223> OTHER INFORMATION: Lys051

<400> SEQUENCE: 13

```
tgcatccttc agcacttgag                                                 20
```

<210> SEQ ID NO 14
<211> LENGTH: 20
<212> TYPE: DNA
<213> ORGANISM: Artificial sequence
<220> FEATURE:
<223> OTHER INFORMATION: Primer IFN-3rev

<400> SEQUENCE: 14

```
aactcctctt gaggaaagcc                                                20

<210> SEQ ID NO 15
<211> LENGTH: 34
<212> TYPE: DNA
<213> ORGANISM: Artificial sequence
<220> FEATURE:
<223> OTHER INFORMATION: Primer LYSBSU

<400> SEQUENCE: 15
ccccccccta aggcagccag gggcaggaag caaa                                34

<210> SEQ ID NO 16
<211> LENGTH: 12
<212> TYPE: DNA
<213> ORGANISM: Artificial sequence
<220> FEATURE:
<223> OTHER INFORMATION: Primer SaltoNotI

<400> SEQUENCE: 16
tcgagcggcc gc                                                        12

<210> SEQ ID NO 17
<211> LENGTH: 83
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 17
atggctttga cctttgcctt actggtggct ctcctggtgc tgagctgcaa gagcagctgc    60
tctgtgggct gcgatctgcc tca                                            83

<210> SEQ ID NO 18
<211> LENGTH: 100
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 18
gacccacagc ctgggcagca ggaggaccct gatgctgctg gctcagatga ggagaatcag    60
cctgtttagc tgcctgaagg ataggcacga ttttggcttt                         100

<210> SEQ ID NO 19
<211> LENGTH: 62
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 19
ctcaagagga gtttggcaac cagtttcaga aggctgagac catccctgtg ctgcacgaga    60
tg                                                                   62

<210> SEQ ID NO 20
<211> LENGTH: 94
<212> TYPE: DNA
<213> ORGANISM: Artificial Sequence
```

```
<220> FEATURE:
<223> OTHER INFORMATION: primer used in the formation
      of the chicken codon optimized human interferon
      2b-encoding nucleic acid

<400> SEQUENCE: 20
tccagcagat ctttaacctg tttagcacca aggatagcag cgctgcttgg gatgagaccc      60
tgctggataa gttttacacc gagctgtacc agca                                 94

<210> SEQ ID NO 21
<211> LENGTH: 77
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 21
ctgaacgatc tggaggcttg cgtgatccag ggcgtgggcg tgaccgagac ccctctgatg      60
aaggaggata gcatcct                                                    77

<210> SEQ ID NO 22
<211> LENGTH: 82
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 22
gctgtgagga agtactttca gaggatcacc ctgtacctga aggagaagaa gtacagccct      60
tgcgcttggg aagtcgtgag gg                                              82

<210> SEQ ID NO 23
<211> LENGTH: 65
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 23
ctgagatcat gaggagcttt agcctgagca ccaacctgca agagagcttg aggtctaagg      60
agtaa                                                                 65

<210> SEQ ID NO 24
<211> LENGTH: 34
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 24
cccaagcttt caccatggct ttgacctttg cctt                                 34

<210> SEQ ID NO 25
<211> LENGTH: 19
<212> TYPE: DNA
<213> ORGANISM: Artificial Sequence
<220> FEATURE:
```

```
<223> OTHER INFORMATION: primer used in the formation
      of the chicken codon optimized human interferon
      2b-encoding nucleic acid

<400> SEQUENCE: 25
atctgcctca gacccacag                                                  19

<210> SEQ ID NO 26
<211> LENGTH: 26
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 26
gattttggct ttcctcaaga ggagtt                                          26

<210> SEQ ID NO 27
<211> LENGTH: 21
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 27
gcacgagatg atccagcaga t                                               21

<210> SEQ ID NO 28
<211> LENGTH: 20
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 28
atcgttcagc tgctggtaca                                                 20

<210> SEQ ID NO 29
<211> LENGTH: 20
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 29
cctcacagcc aggatgctat                                                 20

<210> SEQ ID NO 30
<211> LENGTH: 20
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 30
atgatctcag ccctcacgac                                                 20
```

```
<210> SEQ ID NO 31
<211> LENGTH: 19
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 31
ctgtgggtct gaggcagat                                                   19

<210> SEQ ID NO 32
<211> LENGTH: 26
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 32
aactcctctt gaggaaagcc aaaatc                                           26

<210> SEQ ID NO 33
<211> LENGTH: 21
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 33
atctgctgga tcatctcgtg c                                                21

<210> SEQ ID NO 34
<211> LENGTH: 36
<212> TYPE: DNA
<213> ORGANISM: Artificial Sequence
<220> FEATURE:
<223> OTHER INFORMATION: primer used in the formation
      of the chicken codon optimized human interferon
      2b-encoding nucleic acid

<400> SEQUENCE: 34
tgctctagac tttttactcc ttagacctca agctct                                36

<210> SEQ ID NO 35
<211> LENGTH: 19
<212> TYPE: DNA
<213> ORGANISM: Artificial Sequence
<220> FEATURE:
<223> OTHER INFORMATION: neo for-1 primer for detecting the interferon
      transgene

<400> SEQUENCE: 35
tggattgcac gcaggttct                                                   19

<210> SEQ ID NO 36
<211> LENGTH: 20
<212> TYPE: DNA
<213> ORGANISM: Artificial Sequence
<220> FEATURE:
<223> OTHER INFORMATION: neo rev-1 primer for detecting the interferon
      transgene

<400> SEQUENCE: 36
```

```
gtgcccagtc atagccgaat                                          20

<210> SEQ ID NO 37
<211> LENGTH: 20
<212> TYPE: DNA
<213> ORGANISM: Artificial Sequence
<220> FEATURE:
<223> OTHER INFORMATION: FAM labeled NEO-PROBE1 for detecting the
      interferon transgene

<400> SEQUENCE: 37
cctctccacc caagcggccg                                          20

<210> SEQ ID NO 38
<211> LENGTH: 25
<212> TYPE: DNA
<213> ORGANISM: Artificial Sequence
<220> FEATURE:
<223> OTHER INFORMATION: primer used in the synthesis of the MDOT
      promoter

<400> SEQUENCE: 38
tcactcgagg tgaatatcca agaat                                    25

<210> SEQ ID NO 39
<211> LENGTH: 25
<212> TYPE: DNA
<213> ORGANISM: Artificial Sequence
<220> FEATURE:
<223> OTHER INFORMATION: primer used in the synthesis of the MDOT
      promoter

<400> SEQUENCE: 39
gagatcgatt ttggctggac acttg                                    25

<210> SEQ ID NO 40
<211> LENGTH: 25
<212> TYPE: DNA
<213> ORGANISM: Artificial Sequence
<220> FEATURE:
<223> OTHER INFORMATION: primer used in the synthesis of the MDOT
      promoter

<400> SEQUENCE: 40
cacatcgatg tcacaacttg ggaat                                    25

<210> SEQ ID NO 41
<211> LENGTH: 25
<212> TYPE: DNA
<213> ORGANISM: Artificial Sequence
<220> FEATURE:
<223> OTHER INFORMATION: primer used in the synthesis of the MDOT
      promoter

<400> SEQUENCE: 41
tctaagcttc gtcacagacc gtccc                                    25
```

PRODUCTION OF A TRANSGENIC AVIAN BY CYTOPLASMIC INJECTION

This application claims the benefit of U.S. Provisional Application No. 60/322,969, filed Sep. 18, 2001, and U.S. Provisional Application No. 60/351,550, filed Jan. 25, 2002, both of which are incorporated by reference herein in their entireties.

1. FIELD OF THE INVENTION

The present invention relates to methods of producing a transgenic avian by introducing a nucleic acid encoding a heterologous protein into an avian embryo preferably by cytoplasmic injection, but also by other methods of introducing nucleic acids into embryonic cells, including but not limited to, nuclear transfer, retroviral vector infection, and fertilization with sperm containing the nucleic acid. The present invention further relates to a transgenic avian expressing a heterologous polypeptide, which, preferably, is deposited into the white of the avian egg. The invention further provides vectors containing coding sequences for heterologous proteins, the expression of which is under the control of a promoter and other regulatory elements that cause expression of the heterologous protein and preferably, lead to deposition of the protein in the avian egg. Also included in the invention are avian eggs derived from the transgenic avians and the heterologous proteins isolated therefrom.

2. BACKGROUND

The field of transgenics was initially developed to understand the action of a single gene in the context of the whole animal and the phenomena of gene activation, expression, and interaction. This technology has also been used to produce models for various diseases in humans and other animals and is amongst the most powerful tools available for the study of genetics, and the understanding of genetic mechanisms and function. From an economic perspective, the use of transgenic technology for the production of specific proteins or other substances of pharmaceutical interest (Gordon et al., 1987, *Biotechnology* 5: 1183-1187; Wilmut et al., 1990, *Theriogenology* 33: 113-123) offers significant advantages over more conventional methods of protein production by gene expression.

Heterologous nucleic acids have been engineered so that an expressed protein may be joined to a protein or peptide that will allow secretion of the transgenic expression product into milk or urine, from which the protein may then be recovered. These procedures have had limited success and may require lactating animals, with the attendant costs of maintaining individual animals or herds of large species, including cows, sheep, or goats.

The hen oviduct offers outstanding potential as a protein bioreactor because of the high levels of protein production, the promise of proper folding and post-translation modification of the target protein, the ease of product recovery, and the shorter developmental period of chickens compared to other potential animal species. The production of an avian egg begins with formation of a large yolk in the ovary of the hen. The unfertilized oocyte or ovum is positioned on top of the yolk sac. After ovulation, the ovum passes into the infundibulum of the oviduct where it is fertilized, if sperm are present, and then moves into the magnum of the oviduct, lined with tubular gland cells. These cells secrete the egg-white proteins, including ovalbumin, lysozyme, ovomucoid, conalbumin and ovomucin, into the lumen of the magnum where they are deposited onto the avian embryo and yolk.

2.1 Microinjection

Historically, transgenic animals have been produced almost exclusively by microinjection of the fertilized egg. Mammalian pronuclei from fertilized eggs are microinjected in vitro with foreign, i.e., xenogeneic or allogeneic, heterologous DNA or hybrid DNA molecules. The microinjected fertilized eggs are then transferred to the genital tract of a pseudopregnant female (e.g., Krimpenfort et al., in U.S. Pat. No. 5,175,384). However, the production of a transgenic avian using microinjection techniques is more difficult than the production of a transgenic mammal. In avians, the opaque yolk is positioned such that visualization of the pronucleus, or nucleus of a single-cell embryo, is impaired thus preventing efficient injection of the these structures with heterologous DNA. What is therefore needed is an efficient method of introducing a heterologous nucleic acid into a recipient avian embryonic cell.

Cytoplasmic DNA injection has previously been described for introduction of DNA directly into the germinal disk of a chick embryo by Sang and Perry, 1989, *Mol. Reprod. Dev.* 1: 98-106, Love et al., 1994, Biotechnology 12: 60-3, and Naito et al., 1994, *Mol. Reprod. Dev.* 37:167-171; incorporated herein by reference in their entireties. Sang and Perry described only episomal replication of the injected cloned DNA, while Love et al. suggested that the injected DNA becomes integrated into the cell's genome and Naito et al. showed no direct evidence of integration. In all these cases, the germinal disk was not visualized during microinjection, i.e., the DNA was injected "blind" into the germinal disk. Such prior efforts resulted in poor and unstable transgene integration. None of these methods were reported to result in expression of the transgene in eggs and the level of mosaicism in the one transgenic chicken reported to be obtained was one copy per 10 genome equivalents.

2.2 Retroviral Vectors

Other techniques have been used in efforts to create transgenic chickens expressing heterologous proteins in the oviduct. Previously, this has been attempted by microinjection of replication defective retroviral vectors near the blastoderm (PCT Publication WO 97/47739, entitled Vectors and Methods for Tissue Specific Synthesis of Protein in Eggs of Transgenic Hens, by MacArthur). Bosselman et al. in U.S. Pat. No. 5,162,215 also describes a method for introducing a replication-defective retroviral vector into a pluripotent stem cell of an unincubated chick embryo, and further describes chimeric chickens whose cells express a heterologous vector nucleic acid sequence. However, the percentage of $G_1$ transgenic offspring (progeny from vector-positive male $G_0$ birds) was low and varied between 1% and approximately 8%. Such retroviral vectors have other significant limitations, for example, only relatively small fragments of nucleic acid can be inserted into the vectors precluding, in most instances, the use of large portions of the regulatory regions and/or introns of a genomic locus which, as described herein, can be useful in obtaining significant levels of heterologous protein expression. Additionally, retroviral vectors are generally not appropriate for generating transgenics for the production of pharmaceuticals due to safety and regulatory issues.

2.3 Transfection of Male Germ Cells, Followed by Transfer to Recipient Testis Other methods include in vitro stable transfection of male germ cells, followed by transfer to a recipient testis. PCT Publication WO 87/05325 discloses a method of transferring organic and/or inorganic material into sperm or egg cells by using liposomes. Bachiller et al. (1991, *Mol. Reprod. Develop*. 30: 194-200) used Lipofectin-based liposomes to transfer DNA into mice sperm, and provided evidence that the liposome transfected DNA was overwhelmingly contained within the sperm's nucleus although no transgenic mice could be produced by this technique. Nakanishi & Iritani (1993, *Mol. Reprod. Develop*. 36: 258-261) used Lipofectin-based liposomes to associate heterologous DNA with chicken sperm, which were in turn used to artificially inseminate hens. There was no evidence of genomic integration of the heterologous DNA either in the DNA-liposome treated sperm or in the resultant chicks.

Several methods exist for transferring DNA into sperm cells. For example, heterologous DNA may also be transferred into sperm cells by electroporation that creates temporary, short-lived pores in the cell membrane of living cells by exposing them to a sequence of brief electrical pulses of high field strength. The pores allow cells to take up heterologous material such as DNA, while only slightly compromising cell viability. Gagne et al. (1991, *Mol. Reprod. Dev*. 29: 6-15) disclosed the use of electroporation to introduce heterologous DNA into bovine sperm subsequently used to fertilize ova. However, there was no evidence of integration of the electroporated DNA either in the sperm nucleus or in the nucleus of the egg subsequent to fertilization by the sperm.

Another method for transferring DNA into sperm cells was initially developed for integrating heterologous DNA into yeasts and slime molds, and later adapted to sperm, is restriction enzyme mediated integration (REMI) (Shemesh et al., PCT International Publication WO 99/42569). REMI utilizes a linear DNA derived from a plasmid DNA by cutting that plasmid with a restriction enzyme that generates single-stranded cohesive ends. The linear, cohesive-ended DNA together with the restriction enzyme used to produce the cohesive ends is then introduced into the target cells by electroporation or liposome transfection. The restriction enzyme is then thought to cut the genomic DNA at sites that enable the heterologous DNA to integrate via its matching cohesive ends (Schiestl and Petes, 1991, *Proc. Natl. Acad. Sci. USA* 88: 7585-7589).

It is advantageous, before the implantation of the transgenic germ cells into a testis of a recipient male, to depopulate the testis of untransfected male germ cells. Depopulation of the testis has commonly been by exposing the whole animal to gamma irradiation by localized irradiation of the testis. Gamma radiation-induced spermatogonial degeneration is probably related to the process of apoptosis. (Hasegawa et al., 1998, *Radiat. Res*. 149:263-70). Alternatively, a composition containing an alkylating agent such as busulfan (MYLERAN™) can be used, as disclosed in Jiang F. X., 1998, *Anat. Embryol*. 198(1):53-61; Russell and Brinster, 1996, *J. Androl*. 17(6):615-27; Boujrad et al., *Andrologia* 27(4), 223-28 (1995); Linder et al., 1992, *Reprod. Toxicol*. 6(6):491-505; Kasuga and Takahashi, 1986, *Endocrinol. Jpn* 33(1):105-15. These methods likewise have not resulted in efficient transgenesis or heterologous protein production in avian eggs.

2.5 Nuclear Transfer

Nuclear transfer from cultured cell populations provides an alternative method of genetic modification, whereby donor cells may be sexed, optionally genetically modified, and then selected in culture before their use. The resultant transgenic animal originates from a single transgenic nucleus and mosaics are avoided. The genetic modification is easily transmitted to the offspring. Nuclear transfer from cultured somatic cells also provides a route for directed genetic manipulation of animal species, including the addition or "knock-in" of genes, and the removal or inactivation or "knock-out" of genes or their associated control sequences (Polejaeva et al., 2000, *Theriogenology*, 53: 117-26). Gene targeting techniques also promise the generation of transgenic animals in which specific genes coding for endogenous proteins have been replaced by exogenous genes such as those coding for human proteins.

The nuclei of donor cells are transferred to oocytes or zygotes and, once activated, result in a reconstructed embryo. After enucleation and introduction of donor genetic material, the reconstructed embryo is cultured to the morula or blastocyte stage, and transferred to a recipient animal, either in vitro or in vivo (Eyestone and Campbell, 1999, *J. Reprod Fertil Suppl*. 54:489-97). Double nuclear transfer has also been reported in which an activated, previously transferred nucleus is removed from the host unfertilized egg and transferred again into an enucleated fertilized embryo.

The embryos are then transplanted into surrogate mothers and develop to term. In some mammalian species (mice, cattle and sheep) the reconstructed embryos can be grown in culture to the blastocyst stage before transfer to a recipient female. The total number of offspring produced from a single embryo, however, is limited by the number of available blastomeres (embryos at the 32-64 cell stage are the most widely used) and the efficiency of the nuclear transfer procedure. Cultured cells can also be frozen and stored indefinitely for future use.

Two types of recipient cells are commonly used in nuclear transfer procedures: oocytes arrested at the metaphase of the second meiotic division (MII) and which have a metaphase plate with the chromosomes arranged on the meiotic spindle, and pronuclear zygotes. Enucleated two-cell stage blastomeres of mice have also been used as recipients. In agricultural mammals, however, development does not always occur when pronuclear zygotes are used, and, therefore, MII-arrested oocytes are the preferred recipient cells.

Although gene targeting techniques combined with nuclear transfer hold tremendous promise for nutritional and medical applications, current approaches suffer from several limitations, including long generation times between the founder animal and production transgenic herds, and extensive husbandry and veterinary costs. It is therefore desirable to use a system where cultured somatic cells for nuclear transfer are more efficiently employed.

What is needed, therefore, is an efficient method of generating transgenic avians that express a heterologous protein encoded by a transgene, particularly in the oviduct for deposition into egg whites.

3. SUMMARY OF THE INVENTION

This invention provides methods for the stable introduction of heterologous coding sequences into the genome of a bird and expressing those heterologous coding sequences to produce desired proteins. Synthetic vectors and gene promoters useful in the methods are also provided by the present invention, as are transgenic birds that express a heterologous protein and avian eggs containing a heterologous protein. In a preferred embodiment, the vectors useful in methods of the invention are not eukaryotic viral, more preferably not retroviral, vectors (although the vectors may contain transcriptional regulatory elements, such as promoters, from eukaryotic viruses). In other embodiments, however, the vectors are eukaryotic viral vectors or are retroviral vectors.

One aspect of the present invention is a method of producing a transgenic avian capable of expressing a heterologous protein. The method comprises isolating an early stage embryo from a fertilized hen, and microinjecting into the isolated embryo a selected nucleic acid that encodes the desired heterologous protein. The microinjected avian embryo is transferred to the oviduct of a recipient hen for in vivo development and to be laid as a shelled egg (or, alternatively, cultured ex vivo). The shelled egg is incubated to hatch a transgenic chick that has incorporated, preferably, integrated into its genome, the selected nucleic acid.

The present invention provides methods for introducing a transgene into the cytoplasm of avian embryonic cells by cytoplasmic microinjection. The cells may be embryonic cells as, for example, from a single cell embryo visualized through overlying yolk or tissue by using, for example, light microscopy, or a camera system such as a CCD camera with a microscopic lens (e.g., as disclosed in PCT International Publication WO 02/064727 by Christmann, which is incorporated by reference herein in its entirety). Microelectroporation can optionally be used to enhance the uptake of exogenous DNA into the cell nucleus and improving the efficiency of DNA integration. The cytoplasmically microinjected embryo is then, preferably, returned to a female bird to be laid as a hard-shell egg or, as an alternative, cultured ex vivo. After hatching from the hard-shelled egg, a transgenic chick is produced that expresses a heterologous protein and/or that can be bred to generate a line of transgenic birds expressing a heterologous protein.

In alternative embodiments, the nucleic acid is introduced by infection or injection of the nucleic acid contained within a retroviral vector, sperm-mediated transgenesis, or nuclear transfer.

In one embodiment, the present invention provides methods for producing heterologous proteins in avians. Transgenes are introduced by, most preferably, cytoplasmic microinjection into one embryonic cell, preferably the germinal disk of an early stage embryo, that then develop into a transgenic bird. The protein of interest may be expressed in the tubular gland cells of the magnum of the oviduct, secreted into the lumen, or deposited within the egg white onto the egg yolk or expressed, for example, in the serum of the bird. Such transgenic birds can also be bred to identify birds that carry the transgene in their germ line. The exogenous genes can therefore be transmitted to birds by both cytoplasmic microinjection of the exogenous gene into bird embryonic cells, and by subsequent stable transmission of the exogenous gene to the bird's offspring in a Mendelian fashion.

The present invention provides for a method of producing a heterologous protein in an avian oviduct. The method comprises, as a first step, providing a vector containing a coding sequence and a promoter that functions in avians, preferably in the avian magnum, operably linked to the coding sequence, so that the promoter can effect expression of the nucleic acid in the tubular gland cells of the magnum of an avian oviduct and/or in any other desired tissue of the avian. In a preferred embodiment, the vector containing the transgene is not a eukaryotic viral vector (preferably, not a retroviral vector, such as but not limited to reticuloendotheliosis virus (REV), ALV or MuLV) or derived from a eukaryotic virus (but, in certain embodiments, may contain promoter and/or other gene expression regulatory sequences from a eukaryotic virus, such as, but not limited to, a Rous sarcoma virus viral promoter or a cytomegalovirus promoter). Next, the vector is introduced into avian embryonic cells by cytoplasmic microinjection so that the vector sequence may be randomly inserted into the avian genome. Finally, a mature transgenic avian that expresses the exogenous protein in its oviduct is derived from the transgenic embryonic cells or by breeding a transgenic avian derived from the transgenic embryonic cells.

In particular embodiments, the level of mosaicism of the transgene (percentage of cells containing the transgene) in avians hatched from microinjected embryos (i.e., the $G_0$s) is greater than 5%, 10%, 25%, 50%, 75% or 90%, or is the equivalent of one copy per one genome, two genomes, five genomes, seven genomes or eight genomes, as determined by any number of techniques known in the art and described infra. In additional particular embodiments, the percentage of $G_0$s that transmit the transgene to progeny ($G_1$s) is greater than 5%, preferably, greater than 10%, 20%, 30%, 40%, and, most preferably, greater than 50%. In other embodiments, the efficiency of transgenesis (i.e., number of $G_0$s containing the transgene) is greater than 2%, 5%, 10%, 20%, 30%, 40%, 50%, 60%, 70%, 80% or 99%.

This method can also be used to produce an avian egg containing an exogenous protein when the exogenous protein, that is expressed for example, in the tubular gland cells or fibroblast cells, is also secreted into the oviduct lumen and deposited, e.g., into the white of an egg. In other embodiments of the invention, the exogenous protein is expressed in the liver, or secreted into the blood, and deposited into the yolk. In preferred embodiments, the level of expression of the heterologous protein in the egg white of eggs laid by $G_0$ and/or $G_1$ chicks and/or their progeny is greater than 5 µg, 10 µg, 50 µg, 100 µg, 250 µg, 500 µg, o 750 µg, more preferably greater than 1 mg, 2 mg, 5 mg, 10 mg, 20 mg, 50 mg, 100 mg, 200 mg, 500 mg, 700 mg, 1 gram, 2 grams, 3 grams, 4 grams or 5 grams.

The present invention further provides promoters useful for expression of the heterologous protein in the egg. For example, the promoter comprises regions of at least two promoters derived from an avian including, but not limited to, an ovomucoid, ovalbumin, conalbumin, lysozyme, or ovotransferrin, or any other promoter that directs expression of a gene in an avian, particularly in a specific-tissue of interest, such as the magnum. Alternatively, the promoter used in the expression vector may be derived from that of the lysozyme gene that is expressed in both the oviduct and macrophages. In other embodiments the promoter is a viral or non-avian promoter, e.g., cytomegalovirus or Rous sarcoma virus promoter. In certain embodiments, the promoter is constitutive in avian cells. In other embodiments, the promoter is inducible. In particular embodiments, the gene regulatory sequences are flanked by matrix attachment regions (MARs), preferably, but not limited to those associated with the lysozyme gene in chickens or other avian. The nucleic acid encoding the polypeptide may be operably linked to a transcription promoter and/or a transcription terminator. In other embodiments, prior to microinjection, the vector is mixed with a nuclear localization signal peptide to facilitate targeting of the injected vector to the nucleus.

Other embodiments of the invention provide for transgenic avians, such as chickens or quail, carrying a transgene in the genetic material of their germ-line tissue, preferably where the transgene was not introduced into the avian genome using a eukaryotic viral promoter. The transgene incorporated into the genomic DNA of a recipient bird can encode at least one polypeptide that may be, for example, but is not limited to, a cytokine, a growth factor, enzyme, structural protein, immunoglobulin, or any other polypeptide of interest that is capable of being expressed by an avian cell or tissue. Preferably, the heterologous protein is a mammalian, or preferably a human, protein or derived from a mammalian, or preferably a human, protein (e.g., a derivative or variant thereof). In particular embodiments, the invention provides heterologous proteins isolated or purified from an avian tissue, preferably serum, more preferably eggs, most preferably egg whites, and pharmaceutical compositions comprising such heterologous proteins. In a more preferred embodiment, the heterologous protein is an antibody that is human (including antibodies produced from human immunoglobulin sequences in mice or in antibody libraries or synthetically produced but having variable domain framework regions that are the same as or homologous to human framework regions) or humanized.

The present invention further relates to nucleic acid vectors (preferably, not derived from eukaryotic viruses, except, in certain embodiments, for eukaryotic viral promoters and/or enhancers) and transgenes inserted therein that incorporate multiple polypeptide-encoding regions, wherein a first polypeptide-encoding region is operatively linked to a transcription promoter and a second polypeptide-encoding region is operatively linked to an Internal Ribosome Entry Sequence (IRES). For example, the vector may contain coding sequences for two different heterologous proteins (e.g., the heavy and light chains of an immunoglobulin) or the coding sequences for all or a significant part of the genomic sequence for the gene from which the promoter driving expression of the transgene is derived, and the heterologous protein desired to be expressed (e.g., a construct containing the genomic coding sequences, including introns; of the avian lysozyme gene when the avian lysozyme promoter is used to drive expression of the transgene, an IRES, and the coding sequence for the heterologous protein desired to be expressed downstream (i.e., 3' on the RNA transcript of the IRES)). Thus, in certain embodiments, the nucleic acid encoding the heterologous protein is introduced into the 5' untranslated or 3' untranslated regions of an endogenous gene, such as but not limited to, lysozyme, ovalbumin, ovotransferrin, and ovomucoid, with an IRES sequence directing translation of the heterologous sequence.

Such nucleic acid constructs, when inserted into the genome of a bird and expressed therein, will generate individual polypeptides that may be post-translationally modified, for example, glycosylated or, in certain embodiments, be present as complexes, such as heterodimers with each other in the white of the avian egg. Alternatively, the expressed polypeptides may be isolated from an avian egg and combined in vitro, or expressed in a non-reproductive tissue such as serum. In other embodiments, for example, but not limited to, when expression of both heavy and light chains of an antibody is desired, two separate constructs, each containing a coding sequence for one of the heterologous proteins operably linked to a promoter (either the same or different promoters), are introduced by microinjection into cytoplasm of one or more embryonic cells and transgenic avians harboring both transgenes in their genomes and expressing both heterologous proteins are identified. Alternatively, two transgenic avians each containing one of the two heterologous proteins (e.g., one transgenic avian having a transgene encoding the light chain of an antibody and a second transgenic avian having a transgene encoding the heavy chain of the antibody) can be bred to obtain an avian containing both transgenes in its germline and expressing both transgene encoded proteins, preferably in eggs.

In other embodiments, the present invention further provides methods for the introduction to an avian genome of at least one transgene encoding at least one heterologous polypeptide including sperm-mediated transfer where nucleic acids are incorporated into avian sperm by liposomes, electroporation, restriction enzyme mediated integration (REMI), or similar methods. The modified sperm may then be returned to the testis of a male bird which then may be mated with a female to generate transgenic offspring, or the modified sperm may be used directly to fertilize the female bird by artificial insemination to generate transgenic offspring.

The present invention further provides methods for incorporating a transgene into the nucleus of an avian cell cultured in vitro including by transfection, cytoplasmic microinjection or pronuclear microinjection. The transgenic cell nucleus may then be transferred to a fertilized enucleated cell. The enucleated cell may be an embryonic cell of a bird egg visualized through overlying yolk or tissue by using two photon laser scanning microscopy.

For convenience, certain terms employed in the specification, examples, and appended claims are collected here.

3.1 Definitions

The term "avian" as used herein is intended to refer to any species, subspecies or race of organism of the taxonomic class ava, such as, but not limited to, such organisms as chicken, turkey, duck, goose, quail, pheasants, parrots, finches, hawks, crows and ratites including ostrich, emu and cassowary. The term includes the various known strains of *Gallus gallus*, or chickens, (for example, White Leghorn, Brown Leghorn, Barred-Rock, Sussex, New Hampshire, Rhode Island, Ausstralorp, Minorca, Amrox, Calif. Gray, Italian Partidge-colored), as well as strains of turkeys, pheasants, quails, duck, ostriches and other poultry commonly bred.

The term "embryonic cells" as used herein refers to cells that are typically single cell embryos, or the equivalent thereof, and is meant to encompass dividing embryos, such as two-cell, four-cell, or even later stages as described by Eyal-Giladi and Kochav (1976, *Dev. Biol.* 49:321-337) and ova 1, 2, 3, 4, 5, 6, 7, 8, 9, 10, 12, 14, 16, 18, or 20 hours after the preceding lay. The embryonic cells may be isolated freshly, maintained in culture, or reside within an embryo. Although the present invention is generally described in terms of microinjection of a single-cell embryo, it should be recognized that other cells from an early stage embryo are suitable for cytoplasmic injection in the methods of the present injection. For example, cells obtained from a stage later than a stage I embryo, up to and including a stage X embryo, i.e., stages II-X, may be useful in the present invention. Chick developmental stages are described in the following reference, Eyal-Giladi and Kochav, 1976, *Dev. Biol.* 49(2):321-37, which is hereby incorporated by reference in its entirety.

The term "nucleic acid" as used herein refers to any natural and synthetic linear and 15 sequential arrays of nucleotides and nucleosides, for example cDNA, genomic DNA, mRNA, tRNA, oligonucleotides, oligonucleosides and derivatives thereof. Representative examples of the nucleic acids of the present invention include bacterial plasmid vectors including expression, cloning, cosmid and transformation vectors such as, but not limited to, pBR322, animal viral vectors such as, but not limited to, modified adenovirus, influenza virus, polio virus, pox virus, retrovirus, and the like, vectors derived from bacteriophage nucleic acid, e.g, plasmids and cosmids, artificial chromosomes, such as but not limited to, Yeast Artificial Chromosomes (YACs) and Bacterial Artificial Chromosomes (BACs), and synthetic oligonucleotides like chemically synthesized DNA or RNA. The term "nucleic acid" further includes modified or derivatised nucleotides and nucleosides such as, but not limited to, halogenated nucleotides such as, but not only, 5-bromouracil, and derivatised nucleotides such as biotin-labeled nucleotides.

As used herein the terms "polypeptide" and "protein" refer to a polymer of amino acids of three or more amino acids in a serial array, linked through peptide bonds. The term "polypeptide" includes proteins, protein fragments, protein analogues, oligopeptides and the like. The term "polypeptides" contemplates polypeptides as defined above that are encoded by nucleic acids, produced through recombinant technology, isolated from an appropriate source such as a bird, or are synthesized. The term "polypeptides" further contemplates polypeptides as defined above that include chemically modified amino acids or amino acids covalently or noncovalently linked to labeling ligands.

The term "fragment" as used herein to refers to an at least 10, 20, 50, 75, 100, 150, 200, 250, 300, 500, 1000, 2000 or 5000 nucleotide long portion of a nucleic acid (e.g., cDNA) that has been constructed artificially (e.g., by chemical synthesis) or by cleaving a natural product into multiple pieces, using restriction endonucleases or mechanical shearing, or enzymatically, for example, by PCR or any other polymerizing technique known in the art, or expressed in a host cell by recombinant nucleic acid technology known to one of skill in the art. The term "fragment" as used herein may also refer to an at least 5, 10, 20, 30, 40, 50, 75, 100, 150, 200, 250, 300, 400, 500, 1000, 2000, or 5000 amino acid portion of a polypeptide, which portion is cleaved from a naturally occurring polypeptide by proteolytic cleavage by at least one protease, or is a portion of the naturally occurring polypeptide synthesized by chemical methods or using recombinant DNA technology (e.g., expressed from a portion of the nucleotide sequence encoding the naturally occurring polypeptide) known to one of skill in the art.

The term "isolated nucleic acid" as used herein refers to a nucleic acid that has been removed from other components of the cell containing the nucleic acid or from other components of chemical/synthetic reaction used to generate the nucleic acid. In specific embodiments, the nucleic acid is 50%, 60%, 70%, 80%, 90%, 95%, 99% or 100% pure. The techniques used to isolate and characterize the nucleic acids and proteins of the present invention are well known to those of skill in the art and standard molecular biology and biochemical manuals may be consulted to select suitable protocols without undue experimentation. See, for example, Sambrook et al, 2001, Molecular Cloning: A Laboratory Manual, 3rd ed., Cold Spring Harbor Press; the content of which is herein incorporated by reference in its entirety.

By the use of the term "enriched" in reference to nucleic acid it is meant that the specific DNA or RNA sequence constitutes a significantly higher fraction of the total DNA or RNA present in the cells or solution of interest than in normal or diseased cells or in the cells from which the sequence was taken. Enriched does not imply that there are no other DNA or RNA sequences present, just that the relative amount of the sequence of interest has been significantly increased, for example, by 1 fold, 2 fold, 5 fold, 10 fold, 50 fold, 100 fold, 500 fold, 1000 fold, 10,000 fold, 100,000 fold, or 1,000,000 fold. The other DNA may, for example, be derived from a yeast or bacterial genome, or a cloning vector, such as a plasmid or a viral vector.

The terms "transcription regulatory sequences" and "gene expression control regions" as used herein refer to nucleotide sequences that are associated with a gene nucleic acid sequence and which regulate the transcriptional expression of the gene. Exemplary transcription regulatory sequences include enhancer elements, hormone response elements, steroid response elements, negative regulatory elements, and the like. The "transcription regulatory sequences" may be isolated and incorporated into a vector nucleic acid to enable regulated transcription in appropriate cells of portions of the vector DNA. The "transcription regulatory sequence" may precede, but is not limited to, the region of a nucleic acid sequence that is in the region 5' of the end of a protein coding sequence that may be transcribed into mRNA. Transcriptional regulatory sequences may also be located within a protein coding region, in regions of a gene that are identified as "intron" regions, or may be in regions of nucleic acid sequence that are in the region of nucleic acid.

The term "promoter" as used herein refers to the DNA sequence that determines the site of transcription initiation by an RNA polymerase. A "promoter-proximal element" may be a regulatory sequence within about 200 base pairs of the transcription start site. A "magnum-specific" promoter, as used herein, is a promoter that is primarily or exclusively active in the tubular gland cells of the avian magnum. Useful promoters also include exogenously inducible promoters. These are promoters that can be "turned on" in response to an exogenously supplied agent or stimulus, which is generally not an endogenous metabolite or cytokine. Examples include an antibiotic-inducible promoter, such as a tetracycline-inducible promoter, a heat-inducible promoter, a light-inducible promoter, or a laser inducible promoter. (e.g., Halloran et al., 2000, *Development* 127: 1953-1960; Gemer et al., 2000, *Int. J. Hyperthermia* 16: 171-81; Rang and Will, 2000, *Nucleic Acids Res*. 28: 1120-5; Hagihara et al., 1999, *Cell Transplant* 8: 4314; Huang et al., 1999, *Mol. Med*. 5: 129-37; Forster et al., 1999, *Nucleic Acids Res*. 27: 708-10; Liu et al., 1998, *Biotechniques* 24: 624-8, 630-2; the contents of which have been incorporated herein by reference in their entireties).

To facilitate manipulation and handling of the nucleic acid to be administered, the nucleic acid is preferably inserted into a cassette where it is operably linked to a promoter. The promoter should be capable of driving expression in the desired cells. The selection of appropriate promoters can be readily accomplished. For some applications, a high expression promoter is preferred such as the cytomegalovirus (CMV) promoter. Other promoters useful in the present invention include the Rous Sarcoma Virus (RSV) promoter (Davis et al., 1993, *Hum. Gene Therap*. 4:151). In other embodiments, all or a portion of the, for example, lysozyme, ovomucoid, ovalbumin, albumin, conalbumin or ovotransferrin promoters, which direct expression of proteins present in egg white, are used, as detailed infra, or synthetic promoters such as the MDOT promoter described infra.

The terms "operably" or "operatively linked" refer to the configuration of the coding and control sequences so as to perform the desired function. Thus, control sequences operably linked to a coding sequence are capable of effecting the expression of the coding sequence and regulating in which tissues, at what developmental timepoints, or in response to which signals, etc., a gene is expressed. A coding sequence is operably linked to or under the control of transcriptional regulatory regions in a cell when DNA polymerase will bind the promoter sequence and transcribe the coding sequence into mRNA that can be translated into the encoded protein. The control sequences need not be contiguous with the coding sequence, so long as they function to direct the expression thereof. Thus, for example, intervening untranslated yet transcribed sequences, can be present between a promoter sequence and the coding sequence and the promoter sequence can still be considered "operably linked" to the coding sequence. Such intervening sequences include but are not limited to enhancer sequences which are not transcribed or are not bound by polymerase.

The term "expressed" or "expression" as used herein refers to the transcription from a gene to give an RNA nucleic acid molecule complementary at least in part to a region of one of the two nucleic acid strands of the gene. The term "expressed" or "expression" as used herein also refers to the translation from said RNA nucleic acid molecule to give a protein or polypeptide or a portion thereof.

The term "matrix attachment region" or "MAR" as used herein refers to a DNA sequence having an affinity or intrinsic binding ability for the nuclear scaffold or matrix. The MAR elements of the chicken lysozyme locus are described by Phi-Van et al., 1996, E.M.B.O.J. 76:665-664 and Phi-Van, L. and Stratling, W. H., 1996, Biochem. 35:10735-10742; incorporated herein by reference in their entireties.

The term "probe" as used herein, when referring to a nucleic acid, refers to a nucleotide sequence that can be used to hybridize with and thereby identify the presence of a complementary sequence, or a complementary sequence differing from the probe sequence but not to a degree that prevents hybridization under the hybridization stringency conditions used. The probe may be modified with labels such as, but not only, radioactive groups, biotin, and the like.

The term "nucleic acid vector" as used herein refers to a natural or synthetic single or double stranded plasmid or viral nucleic acid molecule, or any other nucleic acid molecule, such as but not limited to YACs, BACs, bacteriophage-derived artificial chromosome (BBPAC), cosmid or P1 derived artificial chromosome (PAC), that can be transfected or transformed into cells and replicate independently of, or within, the host cell genome. A circular double stranded vector can be linearized by treatment with an appropriate restriction enzyme based on the nucleotide sequence of the vector. A nucleic acid can be inserted into a vector by cutting the vector with restriction enzymes and ligating the pieces together. The nucleic acid molecule can be RNA or DNA.

The term "expression vector" as used herein refers to a nucleic acid vector that comprises regulatory sequences operably linked to a nucleotide sequence coding at least one polypeptide. As used herein, the term "regulatory sequences" includes promoters, enhancers, and other elements that may control gene expression.

The term "recombinant cell" refers to a cell that has a new combination of nucleic acid segments that are not covalently linked to each other in nature in that particular configuration. A new configuration of nucleic acid segments can be introduced into an organism using a wide array of nucleic acid manipulation techniques available to those skilled in the art. A recombinant cell can be a single eukaryotic cell, such as a mammalian cell, or a single prokaryotic cell. The recombinant cell may harbor a vector that is extragenomic. An extragenomic nucleic acid vector does not insert into the cell's genome. A recombinant cell may further harbor a vector or a portion thereof (e.g., the portion containing the regulatory sequences and the coding sequence) that is intragenomic. The term intragenomic defines a nucleic acid construct incorporated within the recombinant cell's genome.

The terms "recombinant nucleic acid" and "recombinant DNA" as used herein refer a combination of at least two nucleic acids that is not naturally found in a eukaryotic or prokaryotic cell in that particular configuration. The nucleic acids may include, but are not limited to, nucleic acid vectors, gene expression regulatory elements, origins of replication, suitable gene sequences that when expressed confer antibiotic resistance, protein-encoding sequences and the like. The term "recombinant polypeptide" is meant to include a polypeptide produced by recombinant DNA techniques such that it is distinct from a naturally occurring polypeptide either in its location, purity or structure. Generally, such a recombinant polypeptide will be present in a cell in an amount different from that normally observed in nature.

As used herein, the term "transgene" means a nucleic acid sequence (encoding, for example, a human interferon polypeptide) that is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location that differs from that of the natural gene or its insertion results in a knockout). A trangene also includes a regulatory sequence designed to be inserted into the genome such that it regulates the expression of an endogenous coding sequence, e.g., to increase expression and or to change the timing and or tissue specificity of expression, etc. (e.g., to effect "gene activation").

As used herein, a "transgenic avian" is any avian species, including the chicken, in which one or more of the cells of the avian may contain heterologous nucleic acid introduced by way of human intervention, such as by transgenic techniques known in the art, and particularly, as described herein. The nucleic acid is introduced into a cell, directly or indirectly by introduction into a precursor of the cell, by way of deliberate genetic manipulation, such as by microinjection or by infection with a recombinant virus. The term genetic manipulation does not include classical cross-breeding, or in vitro fertilization (although it does include fertilization with sperm into which a transgene has been introduced, but rather is directed to the introduction of a recombinant DNA molecule. This molecule may be integrated within a chromosome, or it may be extrachromosomally replicating DNA. In the typical transgenic avian, the transgene causes cells to express a recombinant form of the subject polypeptide, e.g. either agonistic or antagonistic forms, or a form in which the gene has been disrupted. The terms "chimeric avian" or "mosaic avian" are used herein to refer to avians in which the recombinant gene is found, or in which the recombinant is expressed in some but not all cells of the avian. The term "tissue-specific chimeric avian" indicates that the recombinant gene is present and/or expressed in some tissues but not others.

The term "chromosomal positional effect (CPE)" as used herein refers to the variation in the degree of gene transcription as a function of the location of the transcribed locus within the cell genome. Random transgenesis may result in a transgene being inserted at different locations in the genome so that individual cells of a population of transgenic cells may each have at least one transgene, each at a different location and therefore each in a different genetic environment. Each cell, therefore, may express the transgene at a level specific for that particular cell and dependant upon the immediate genetic environment of the transgene. In a transgenic avian, as a consequence, different tissues may exhibit different levels of transgene expression.

The term "cytokine" as used herein refers to any secreted polypeptide that affects the functions of cells and is a molecule that modulates interactions between cells in the immune, inflammatory or hematopoietic response. A cytokine includes, but is not limited to, monokines and lymphokines regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-alpha) and Tumor Necrosis Factor beta (TNF-beta).

The term "antibody" as used herein refers to polyclonal and monoclonal antibodies and fragments thereof, and immunologic binding equivalents thereof. The term "antibody" refers to a homogeneous molecular entity, or a mixture such as a polyclonal serum product made up of a plurality of different molecular entities, and may further comprise any modified or derivatised variant thereof that retains the ability to specifically bind an epitope. A monoclonal antibody is capable of selectively binding to a target antigen or epitope. Antibodies may include, but are not limited to polyclonal antibodies, monoclonal antibodies (mAbs), humanized or chimeric antibodies, camelized single chain antibodies (scFvs), Fab fragments, F(ab')$_2$ fragments, disulfide-linked Fvs (sdFv) fragments produced by a Fab expression library, anti-idiotypic (anti-Id) antibodies, intrabodies, synthetic antibodies, and epitope-binding fragments of any of the above.

The term "immunoglobulin polypeptide" as used herein refers to a polypeptide derived from a constituent polypeptide of an immunoglobulin. An "immunoglobulin polypeptide" may be, but is not limited to, an immunoglobulin (preferably an antibody) heavy or light chain and may include a variable region, adiversity region, joining region and a constant region or any combination, variant or truncated form thereof. The term "immunoglobulin polypeptides" further includes single-chain antibodies comprised of, but not limited to, an immunoglobulin heavy chain variable region, an immunoglobulin light chain variable region and optionally a peptide linker.

The term "male germ cells" as used herein refers to spermatozoa (i.e., male gametes) and developmental precursors thereof. In fetal development, primordial germ cells are thought to arise from the embryonic ectoderm, and are first seen in the epithelium of the endodermal yolk sac at the E8 stage. From there they migrate through the hindgut endoderm to the genital ridges. In the sexually mature male vertebrate animal, there are several types of cells that are precursors of spermatozoa, and which can be genetically modified, including the primitive spermatogonial stem cells, known as A0/As, which differentiate into type B spermatogonia. The latter further differentiate to form primary spermatocytes, and enter a prolonged meiotic prophase during which homologous chromosomes pair and recombine. Useful precursor cells at several morphological/developmental stages are also distinguishable: preleptotene spermatocytes, leptotene spermatocytes, zygotene spermatocytes, pachytene spermatocytes, secondary, spermatocytes, and the haploid spermatids. The latter undergo further morphological changes during spermatogenesis, including the reshaping of their nucleus, the formation of aerosome, and assembly of the tail. The final changes in the spermatozoon (i.e., male gamete) take place in the genital tract of the female, prior to fertilization.

The terms "ovum" and "oocyte" are used interchangeably herein. Although only one ovum matures at a time, an animal is born with a finite number of ova. In avian species, such as a chicken, ovulation, which is the shedding of an egg from the ovarian follicle, occurs when the brain's pituitary gland releases a luteinizing hormone. Mature follicles form a stalk or pedicle of connective tissue and smooth muscle. Immediately after ovulation the follicle becomes a thin-walled sac, the post-ovulatory follicle. The mature ovum erupts from its sac and starts its journey through the oviduct. Eventually, the ovum enters the infundibulum where fertilization occurs. Fertilization must take place within 15 minutes of ovulation, before the ovum becomes covered by albumen. During fertilization, sperm (avians have polyspermic fertilization) penetrate the blastodisc. When the sperm lodges within this germinal disk, an embryo begins to form as a "blastoderm" or "zygote."

The term "donor cell" is used herein to describe the source of the nuclear structure that is transplanted to the recipient enucleated cytoplast. All cells of normal karyotype, including embryonic, fetal, and adult somatic cells, preferably in a quiescent state, may be nuclear donors. The use of non-quiescent cells as nuclear donors has been described by Cibelli, et al., 1998, *Science* 280: 1256-8.

This application uses gene nomenclature accepted by the Cucurbit Genetics Cooperative as it appears in the *Cucurbit Genetics Cooperative Report*, 1995, 18:85; herein incorporated by reference in its entirety. Using this gene nomenclature, genes are symbolized by italicized Roman letters. If a mutant gene is recessive to the normal type, then the symbol and name of the mutant gene appear in italicized lower case letters.

3.2 Abbreviations

Abbreviations used in the present specification include the following: aa, amino acid(s); bp, base pair(s); cDNA, DNA complementary to RNA; nt, nucleotide(s); SSC, sodium chloride-sodium citrate; MAR, matrix attachment region; DMSO, dimethyl sulfoxide; TPLSM, two photon laser scanning microscopy; REMI, restriction enzyme mediated integration; mAb, monoclonal antibody, WEFs, whole embryo fibroblasts.

4. BRIEF DESCRIPTION OF THE FIGURES

FIGS. 1A-E illustrate the nucleotide sequence (SEQ ID NO: 6) comprising the chicken lysozyme gene expression control region (SEQ ID NO: 7), the nucleotide sequence encoding the chicken expression optimized human interferon α2b (IFNMAGMAX; SEQ ID NO: 5) and a SV40 polyadenylation signal sequence (SEQ ID NO: 8).

FIG. 2 illustrates the nucleotide sequence SEQ ID NO: 5 encoding the chicken expression optimized human interferon α2b (IFNMAGMAX).

FIGS. 3A-E illustrate the nucleotide sequence SEQ ID NO: 7 encoding the chicken lysozyme gene expression control region.

FIG. 4 illustrates the nucleotide sequence SEQ ID NO: 8 encoding the SV40 polyadenylation signal sequence.

FIGS. 5A-C illustrate the nucleotide sequence SEQ ID NO: 9 encoding the chicken lysozyme 3' domain.

FIGS. 6A-J illustrate the nucleotide sequence SEQ ID NO: 10 encoding the lysozyme gene expression control region (SEQ ID NO: 7) linked to the nucleic acid insert SEQ ID NO: 5 encoding the chicken expression-optimized human interferon α2b (IFNMAGMAX) and the chicken lysozyme 3' domain SEQ ID NO: 9.

FIG. 7 illustrates the results of the PCR analysis of chick blood DNA. Lanes 4 and 5 and lanes 11 and 12 contain PCR products from blood DNA collected from bird #8305.

Figure 11:
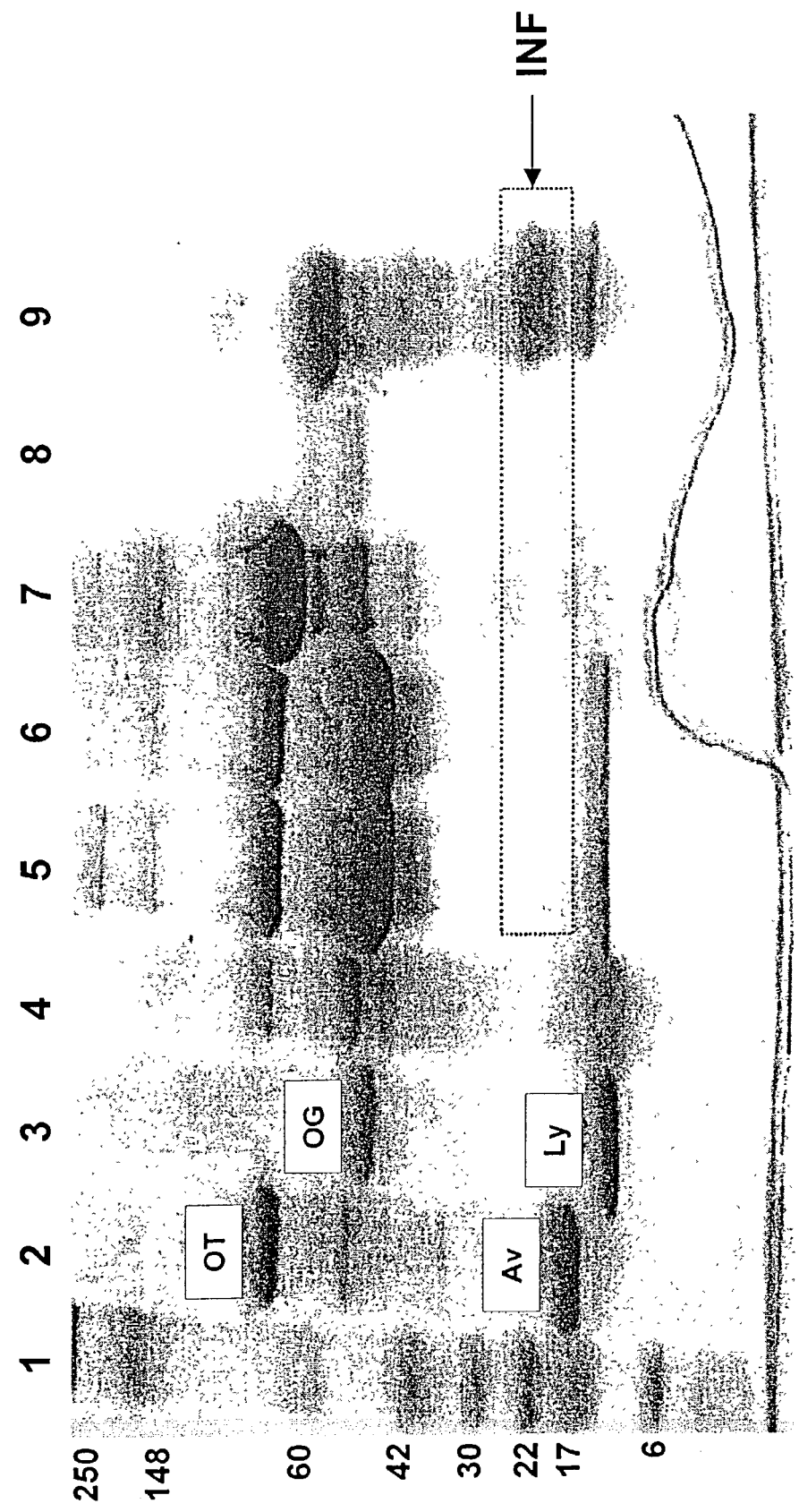

FIG. 11 illustrates the results of a Western blot analysis of the protein contents of fractions from the purification of human IFN-α2b purified from the pooled egg whites obtained from transgenic chicken AVI-029.1, HIC pool (artifact); 2, HIC pool; 3, cation exchange Pool #2; 4, cation exchange Pool #1; 5, solubilized egg white; 6, pooled egg white; 7, ovoglobulins; 8, ovalbumin/lysozyme markers; 9, transferrin/avidin markers; 10, molecular weight markers.

Figure 12:
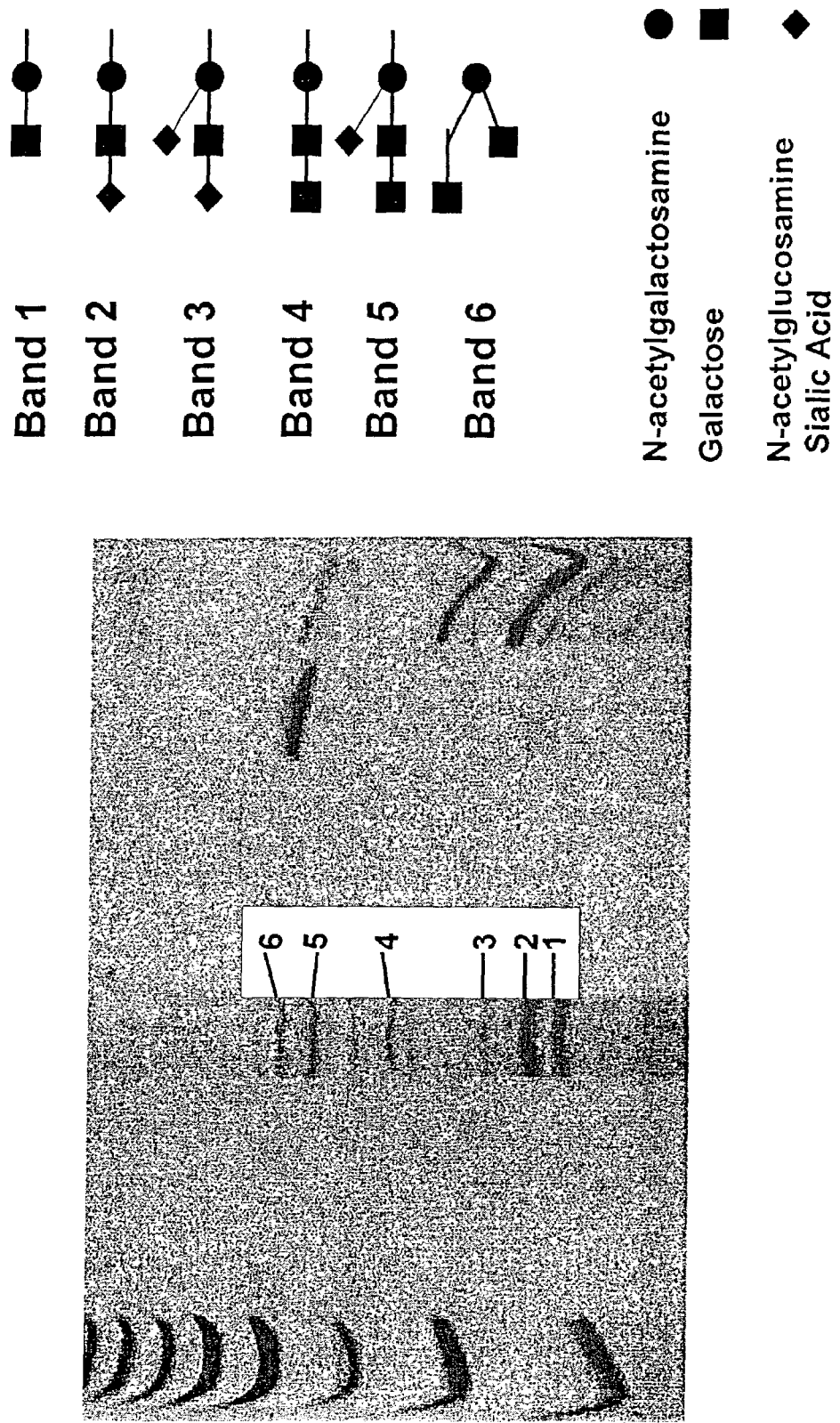

FIG. 12 illustrates the glycosylation analysis of IFN-α2b purified from the pooled egg whites obtained from transgenic chicken AVI-029.

Figure 13:
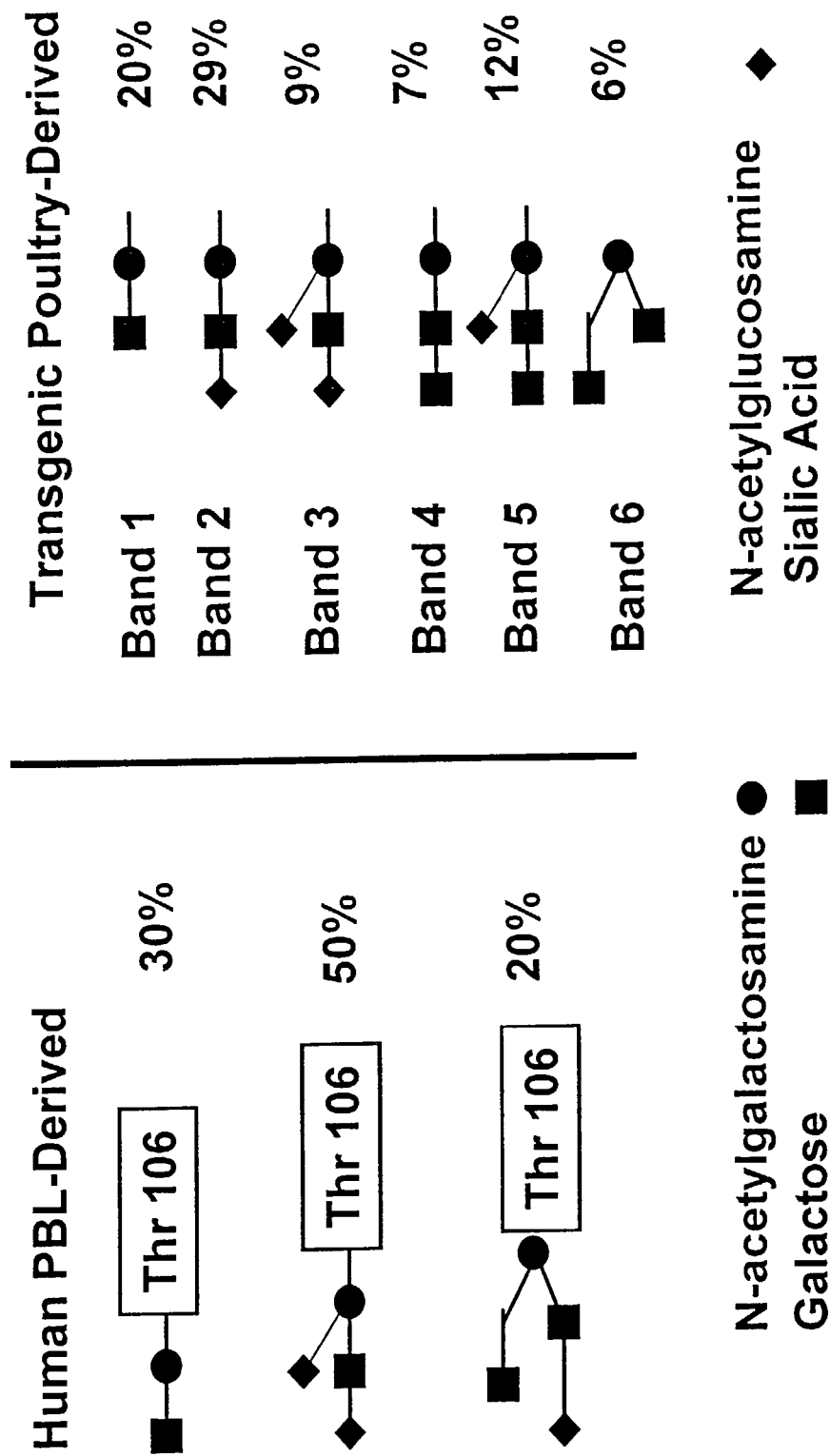

FIG. 13 compares the identities and relative proportions of glycosylated side-chains of human and transgenic chicken human IFN-α2b.

FIG. 14 illustrates the nucleic acid sequence SEQ ID NO: 11 of the combinatorial promoter MDOT.

FIGS. 15A-B illustrate the oligonucleotides and primers (SEQ ID NOS: 17-34) used in the formation of the chicken codon optimized human interferon α2b-encoding nucleic acid.

Figure 16:
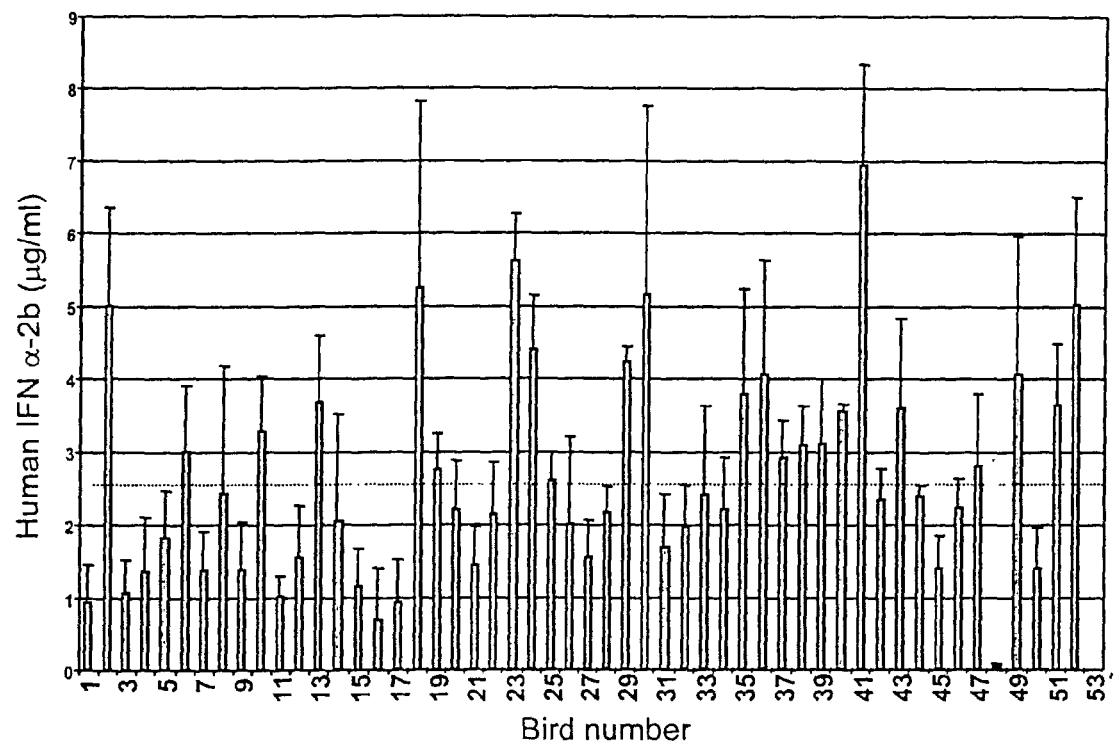

FIG. 16 illustrates the levels of expression of human α2b in eggs as determined by ELISA.

Figure 17:
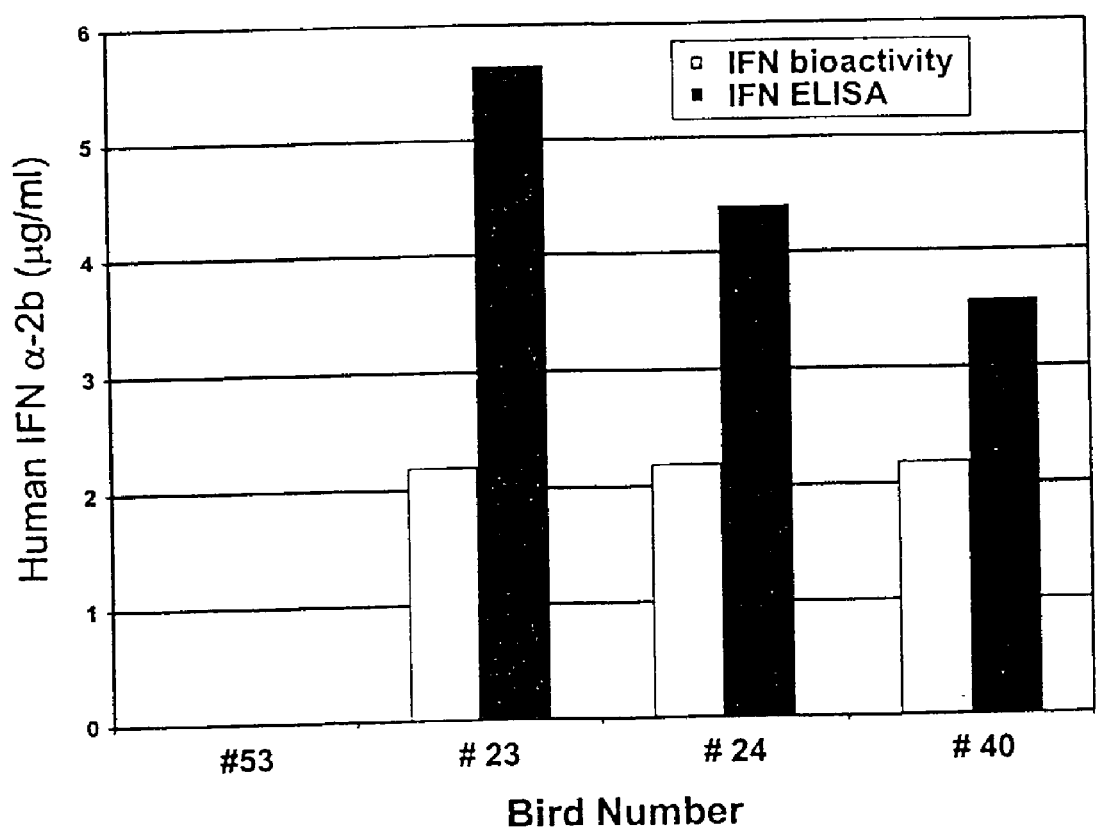

FIG. 17 illustrates the bioactivity versus the mass of human interferon α2b in $G_2$ hen egg whites.

Figure 18:
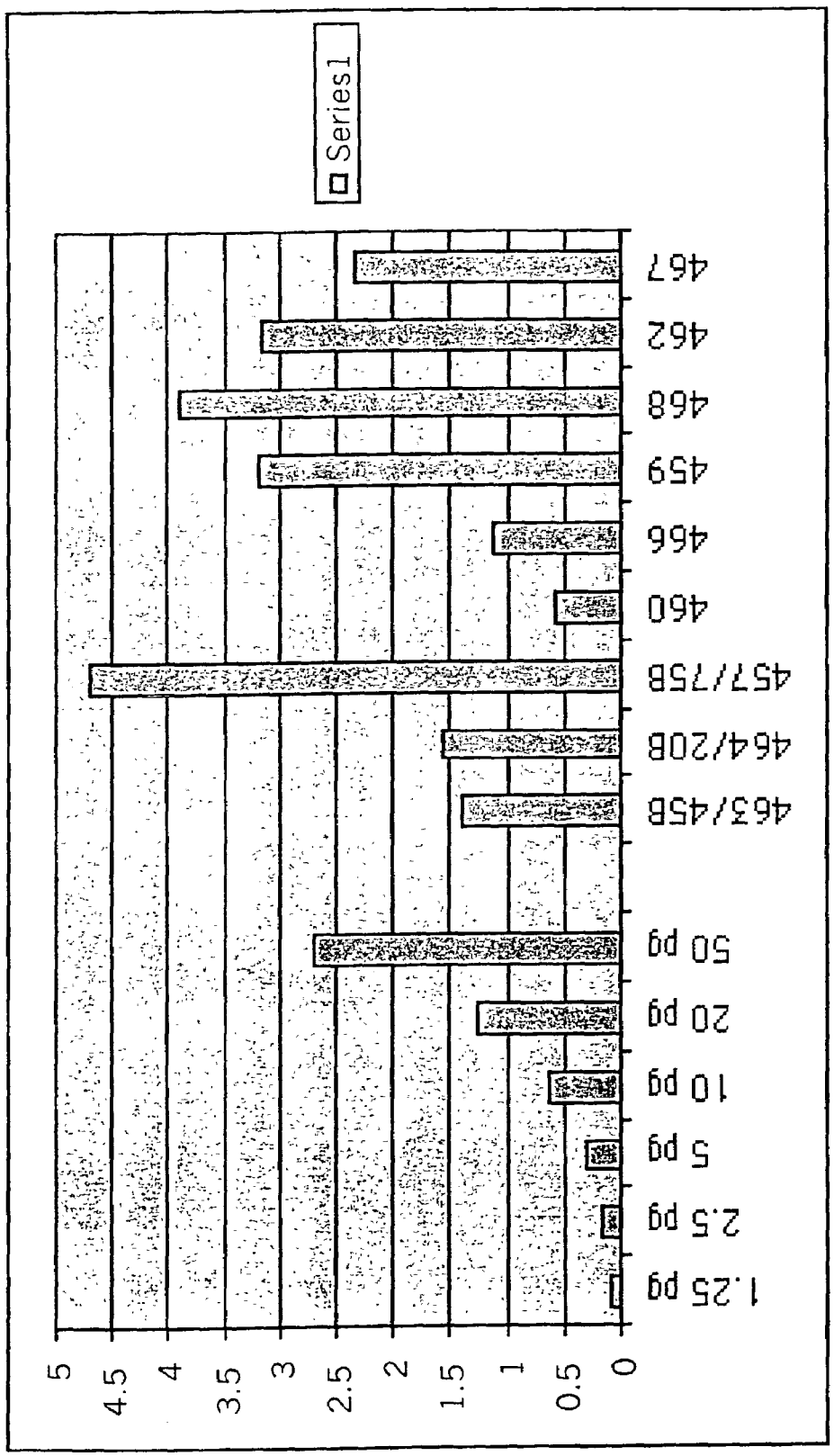

FIG. 18 illustrates interferon serum levels in chicks producing human interferon α2b.

Figure 19:
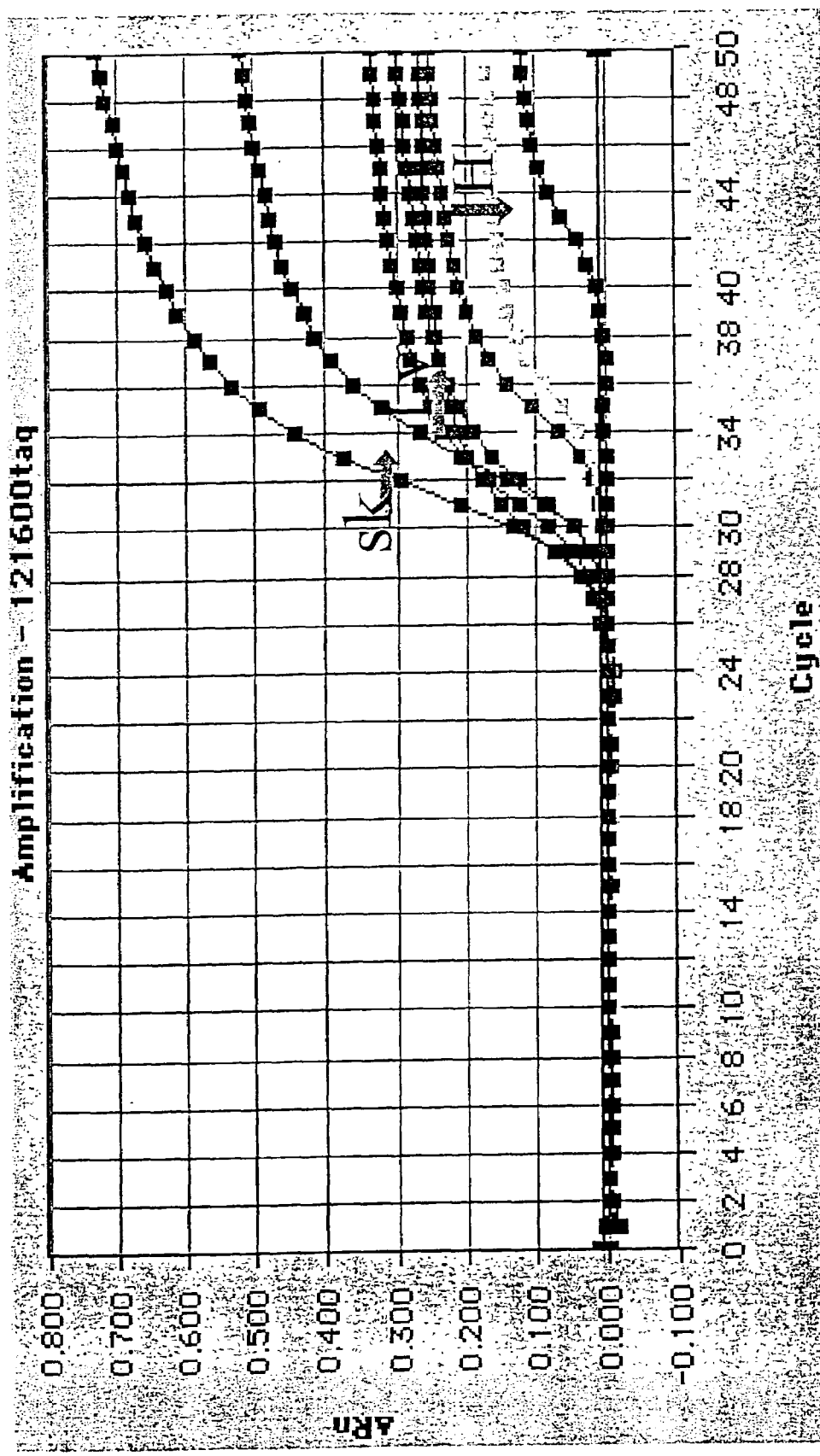

FIG. 19 illustrates the presence of a pLNHX-MDOT-IFN transgene in chicks.

Figure 20:
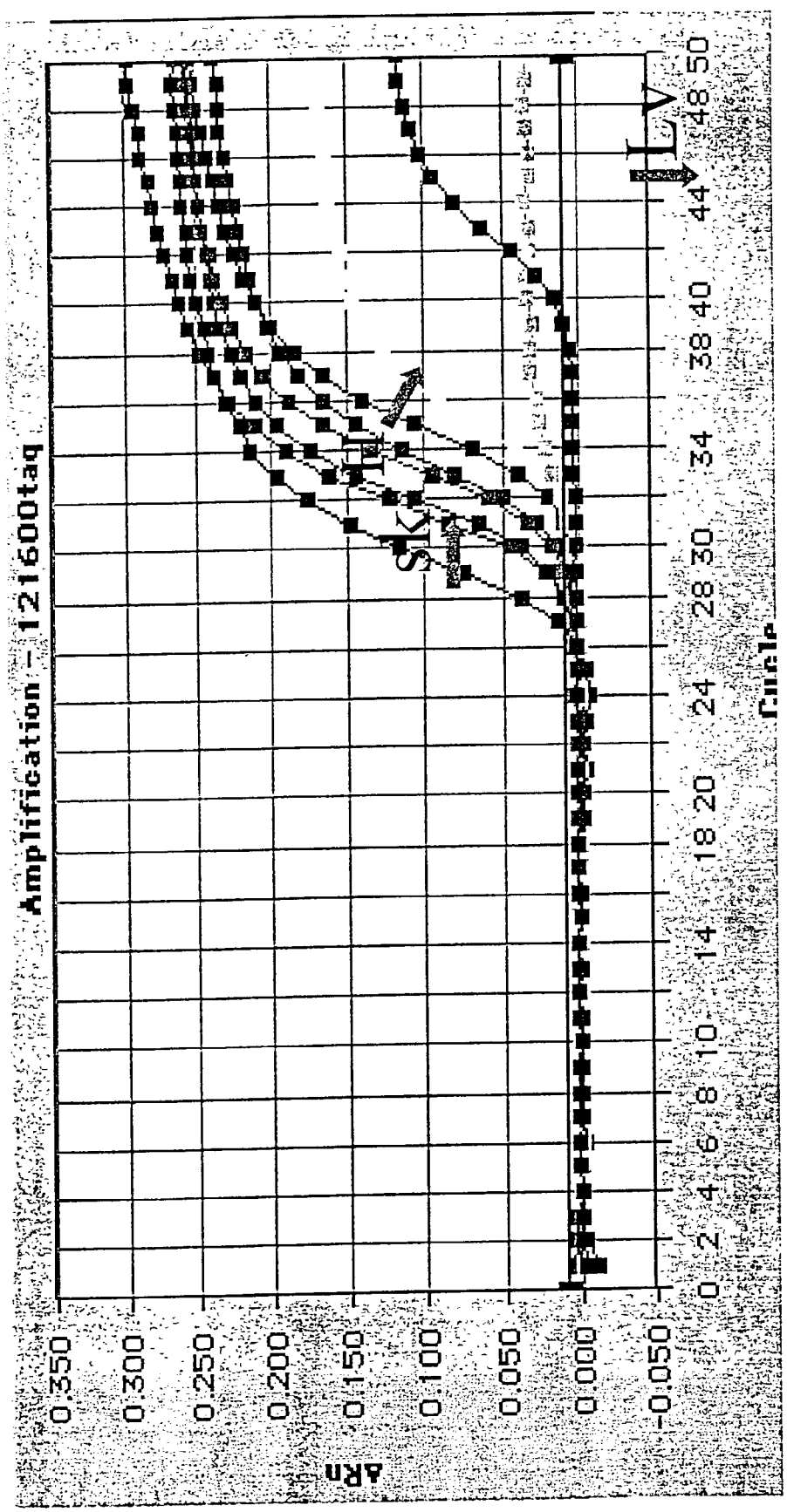

FIG. 20 illustrates the presence of a pLNHX-MDOT-IFN transgene in chicks.

Figure 21:
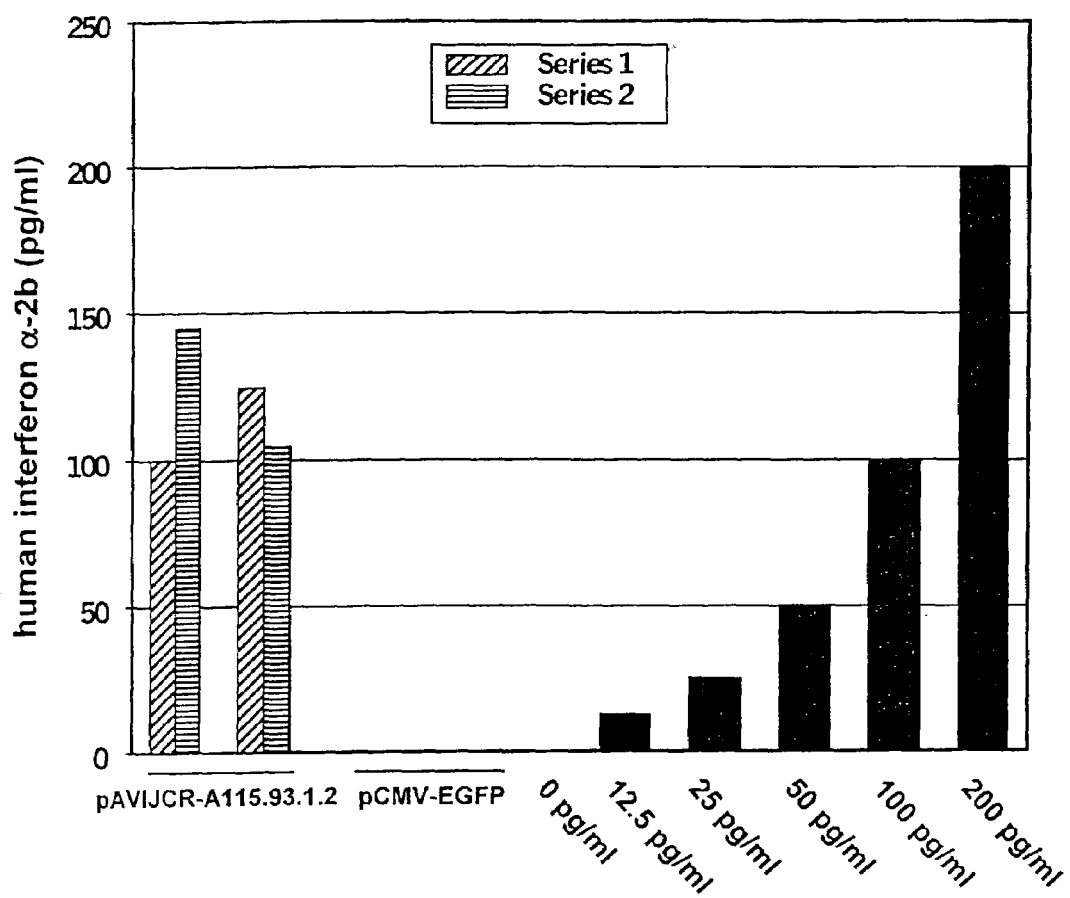

FIG. 21 illustrates the production of human interferon by quail oviduct cells transfected with pAVIJCR-A115.93.1.2.

FIG. 22 illustrates the primers (SEQ ID NOS: 38-41) used in the synthesis of the MDOT promoter.

Figure 23:
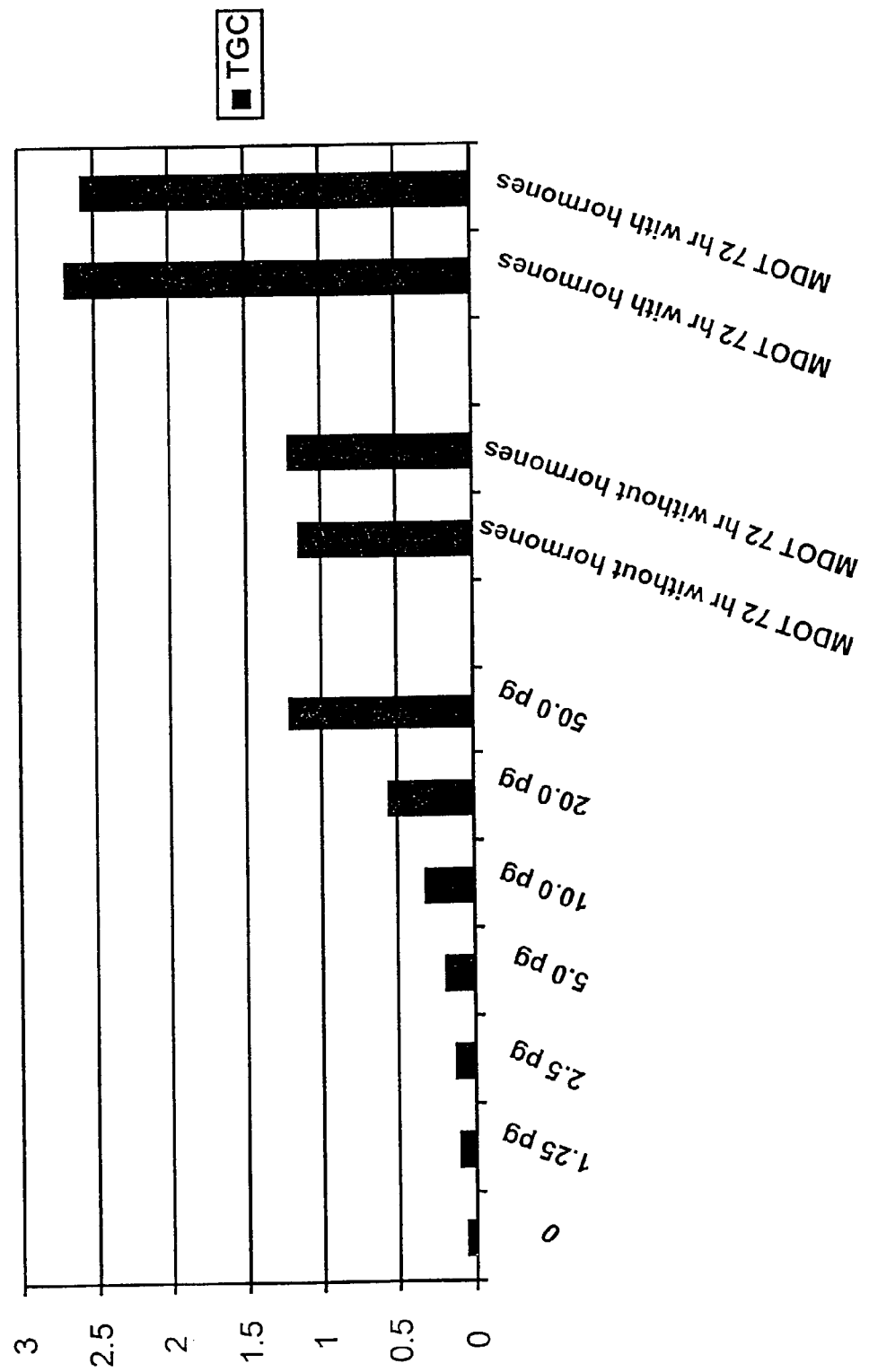

FIG. 23 illustrates the induction of human interferon α2b by hormonally treated transfected cells.

5. DETAILED DESCRIPTION OF THE INVENTION

The present invention relates to methods of introducing nucleic acids into avian embryonic cells to produce a transgenic chicken, or other avian species, carrying the transgene in the genetic material in all or most of its tissue, including germ-line tissue. The methods and vectors of the present invention further generate transgenic avians that express heterologous genes in the serum of the avian and/or are deposited into an avian egg, preferably in the egg white. Vectors containing promoters that direct high level of expression of the heterologous protein in the avian, particularly in the magnum for deposition into the avian egg are provided. Additional regulatory elements, such as MAR's, IRES's, enhancers, polyadenlyation signals, etc., may be included in the vectors of the invention to improve expression and efficiency.

Using the methods of the invention, transgenic avians that express significant quantities of useful heterologous proteins, e.g., therapeutic and diagnostic proteins, including immunoglobulins, industrially useful proteins and other biologics etc. in the avian egg white are produced. The heterologous protein can then be readily purified from the avian egg. The methods of the invention provide improved efficiencies of transgenesis, transmission of the transgene and/or level of heterologous protein expression.

The transgenic avians of the invention are most preferably generated using cytoplasmic microinjection of nucleic acid into avian embryonic cells. Other methods contemplated by the invention include sperm-mediated transgenesis, nuclear transfer and injection or infection with a retroviral vector. Once the nucleic acid has been introduced into the embryo (or ovum which is then fertilized in vitro), the embryo is preferably returned to the avian using ovum transfer or, alternatively, is cultured ex vivo.

5.1 Methods of Transgenesis 5.1.1 Cytoplasmic Injection

The present invention provides methods of introducing nucleic acids containing a transgene, preferably, nucleic acid vectors of the invention as described in Section 5.2, infra, into an embryonic avian cell or an avian ovum by microinjection into the cell. In preferred embodiments, the nucleic acid is introduced by microinjection into the cytoplasm of the cell; however, in other embodiments of the invention, the nucleic acid is introduced into a nucleus or pronucleus, or is deposited in the perinuclear space.

In the method of the present invention, fertilized ova, and preferably stage I embryos, are isolated from euthanized hens between forty-five minutes and four hours after oviposition of the previous egg. It is, however, contemplated that the methods of the present invention may be applied to recipient cells of other stages of embryonic development such as stage I-X, as described by Eyal-Giladi and Kochav (1976, Dev. Biol. 49:321-337). Alternatively, eggs may be isolated from hens whose oviducts have been fistulated as described by Gilbert and Woodgush, 1963, J of Reprod. and Fertility 5: 451-453 and Pancer et al., 1989, Br. Poult. Sci. 30: 953-7; incorporated herein in their entireties. Also, unfertilized eggs can be injected by in-vitro fertilization performed by any method known in the art, for example, but not limited to, the method of Tanaka et al., 1994, J. Reprod. Fertility 100:447-449 (the content of which is incorporated herein in its entirety).

In particular, microinjection into the germinal disk can be accomplished as described in Example 6.1, infra. Briefly, once the fertilized ovum or embryo has been obtained, the albumen capsule is optionally removed and the ovum placed in a dish with the germinal disk facing upwards. Remnants of the albumen capsule may be removed from over the germinal disk if necessary and/or desired. Phosphate buffered saline (PBS) or any other appropriate physiological solution may be added to the dish to prevent drying of the ovum.

Preferably, prior to microinjection, the surface of the embryo is visualized using a lateral imaging system described previously (International Patent Publication WO 02/064,727), this system allows precise imaging of the injection site and facilitates accurate needle placement and injection within the germinal disk of the recipient embryo.

In one embodiment, allowing the visualization of the embryo's pronuclear or nuclear structures, a dye such as MITOTRACKER® (300 nM, Molecular Probes catalog number M-7510), can be added to the cylinder. Other dyes, such as DAPI (4', 6'-diamidino-2-phenylindole hydrochloride), HOECHST® 33342 (bis-benzimide), or Syto 59, can also be used in methods of the invention. Visualization generally is performed after approximately 20 minutes of incubation. Imaging using the MITOTRACKER® dye shows intense labeling of the region around the nucleus while the nucleus itself does not take up the dye. This allows localization of the embryo's nuclear structures for injection while not causing excessive damage to its structure since the content of the pronuclei are not labeled and therefore are not bleached during imaging. The nucleic acid solution (generally 1-100 nanoliters) is then injected into the cytoplasm or, alternatively, into the pronucleus or perinuclear space.

Any suitable microinjection assembly and methods for microinjecting and reimplanting avian eggs are contemplated as useful in the method of cytoplasmic injection of the present invention. A particularly suitable apparatus and method for use in the present invention is fully described in U.S. patent application Ser. No. 09/919,143 by Christmann and PCT Publication WO 02/064727, incorporated herein by reference in their entireties. The microscope/micromanipulation unit may be an IM-16 microinjector and a MM-188NE micromanipulator, both from NIKON®/NARISHIGE, adapted to an upright Nikon Eclipse E800 microscope adapted to operate under both transmitted and reflected light conditions. This unique configuration allows the loading of a DNA solution into a micropipette while observing the pipette with a dry or water immersion lenses under diascopic illumination or transmitted light. Pipette loading is followed by the prompt localization and positioning of the germinal disk under the microscope and subsequent guided injection of DNA solution into the germinal disk using dry or water-immersion lenses under fiber optic, as well as episcopic, illumination (through the objectives and onto the embryo surface).

In certain embodiments, the microinjected cell will also be subjected to microelectroporation. The application of electrical current, e.g., microelectroporation, enhances the uptake of exogenous DNA fragments by cultured cells and the uptake of nucleic acids in the cytoplasm of a cell into the nucleus. Enhancement of nuclear uptake of the heterologous DNA will promote earlier chromosomal integration of the exogenous DNA molecules, thus reducing the degree of genetic mosaicism observed in transgenic avian founders.

Accordingly, in specific embodiments, a sample of nucleic acid will be microinjected using the methods described immediately above, and then, delivered to a recipient cell nucleus by microelectroporation. In a system suitable for use in microelectroporating early stage avian cells, a cathode will be located within the lumen of the DNA delivery micropipette. Alternatively, the cathode electrode may be located on the exterior surface of the micropipette. For either option, the electrode is situated close or adjacent to the exit orifice of the pipette so that the electrode and the micropipette may be introduced into the recipient cell together. Alternatively, the micropipette will be introduced into the cytoplasm and used to guide a cathode to make electrical contact with the cytoplasm of the targeted cell.

In one arrangement of the electrodes of the microelectroporation system, the anode is located on the micropipette and, therefore, will enter the cell or cells with the micropipette and the cathode. In another arrangement, an anode is in electrical contact with the solution that surrounds the targeted recipient early stage avian cell. In yet another version, the anode is individually positioned within the cytoplasm, or the nucleus, of the recipient cell. The anode and cathode are electrically connected to an electrical pulse generator capable of delivering a timed electrical pulse to the electrodes. One suitable apparatus for generating a timed electrical pulse according to the present invention is a Kation Scientific Iontaphorsis pump BAB-500 or ECM 830 manufactured by BTX®. After microinjection of the nucleic acid, the recipient cell will be pulsed at least once with about 0.1 to about 20.0 microamps for about 0.1 to about 60 secs.

After injection and, optionally, microelectroporation, the embryo is allowed to proceed through the natural in vivo cycle of albumen deposition and hard-shell formation. In preferred embodiments, the embryo is surgically transferred into the infundibulum of a recipient hen, where it is allowed to move into the infundibulum and into the anterior. magnum by gravity feed, such that the recipient hen produces a hard shell egg that is incubated to produce a transgenic chick See, e.g., Olsen and Neher, 1948, *J. Exp. Zoo* 109: 355-366, which is incorporated by reference in its entirety. The transgenic embryo is then laid as a hard-shell egg and may be incubated to hatch a transgenic chick. In an alternate embodiment of the present invention, the injected embryo is transferred into the oviduct of a recipient hen, a soft-shell egg is collected between 12 and 24 hours after ovum transfer by injecting the hen with sufficient oxytocin to induce ovipositioning. The soft shell egg can subsequently be incubated, and a chick hatched, using an in-vitro culture system as, for example, that described by Perry in U.S. Pat. No. 5,011,780 (the contents of which is incorporated herein in its entirety). In either case, the hatched chick may be allowed to attain sexual maturity whereupon it can be used, for example, to breed new generations of heterozygous or homozygous transgenic progeny. Sexually mature female transgenic avians are particularly useful for the expression of a heterologous nucleic acid to yield a heterologous polypeptide in the white of an egg.

The hatched chick can then be tested for presence of the transgene and/or expression of the heterologous protein encoded by the transgene using methods well known in the art. In a particular embodiment, blood cells of the hatched chick are screened using methods disclosed in U.S. Pat. No. 6,423,488, issued Jul. 3, 2002, which is hereby incorporated by reference in its entirety.

5.1.2 Transgenesis of Blastodermal Cells

In alternative embodiments, a transgene can be introduced into avian embryonic blastodermal cells, to produce a transgenic chicken, or other avian species, that carries the transgene in the genetic material of its germ-line tissue. The methods and vectors of the present invention further generate transgenic avians capable of expressing heterologous genes in the serum of the avian and/or deposited in an avian egg. The blastodermal cells are typically stage VII-XII cells, or the equivalent thereof, and preferably are near stage X. The cells useful in the present invention include embryonic germ (EG) cells, embryonic stem (ES) cells & primordial germ cells (PGCs). The embryonic blastodermal cells may be isolated freshly, maintained in culture, or reside within an embryo.

A variety of vectors useful in carrying out the methods of the present invention are described herein, in Section 5.2 infra. These vectors may be used for stable introduction of an exogenous coding sequence into the genome of a bird. In alternative embodiments, the vectors may be used to produce exogenous proteins in specific tissues of an avian, and in the oviduct in particular. In still further embodiments, the vectors are used in methods to produce avian eggs which contain exogenous protein.

In some cases, introduction of a vector of the present invention into the embryonic blastodermal cells is performed with embryonic blastodermal cells that are either freshly isolated or in culture. The transgenic cells are then typically injected into the subgerminal cavity beneath a recipient blastoderm in an egg. In some cases, however, the vector is delivered directly to the cells of a blastodermal embryo.

In one embodiment of the invention, vectors used for transfecting blastodermal cells and generating random, stable integration into the avian genome contain a coding sequence and a magnum-specific promoter in operational and positional relationship to express the coding sequence in the tubular gland cell of the magnum of the avian oviduct. The magnum-specific promoter may optionally be a segment of the ovalbumin promoter region which is sufficiently large to direct expression of the coding sequence in the tubular gland cells. Other exemplary promoters include the promoter regions of the ovalbumin, lysozyme, conalbumin, ovomucoid, or ovomucin genes. Alternatively, the promoter may be a promoter that is largely, but not entirely, specific to the magnum, such as the lysozyme promoter. Other suitable promoters may be artificial constructs such as a combination of nucleic acid regions derived from at least two avian gene promoters. One such embodiment of the present invention is the MDOT construct comprising regions derived from the chicken ovomucin and ovotransferrin promoters In an alternative embodiment of the invention, transgenes containing constitutive promoters are used, but the transgenes are engineered so that expression of the transgene effectively becomes magnum-specific. Thus, a method for producing an exogenous protein in an avian oviduct provided by the present invention involves generating a transgenic avian that bears two transgenes in its tubular gland cells. One transgene comprises a first coding sequence operably linked to a constitutive promoter. The second transgene comprises a second coding sequence that is operably linked to a magnum-specific promoter, where expression of the first coding sequence is either directly or indirectly dependent upon the cellular presence of the protein expressed by the second coding sequence.

Optionally, site-specific recombination systems, such as the Cre-loxP or FLP-FRT systems, are utilized to implement the magnum-specific activation of an engineered constitutive promoter. In one embodiment, the first transgene contains an FRT-bounded blocking sequence which blocks expression of the first coding sequence in the absence of FTP, and the second coding sequence encodes FTP. In another embodiment, the first transgene contains a loxP-bounded blocking sequence which blocks expression of the first coding sequence in the absence of the Cre enzyme, and the second coding sequence encodes Cre. The loxP-bounded blocking sequence may be positioned in the 5' untranslated region of the first coding sequence and the loxP-bounded sequence may optionally contain an open reading frame.

For instance, in one embodiment of the invention, magnum-specific expression is conferred on a constitutive transgene, by linking a cytomegalovirus (CMV) promoter to the coding sequence of the protein to be secreted (CDS). The 5' untranslated region (UTR) of the coding sequence contains a loxP-bounded blocking sequence. The loxP-bounded blocking sequence contains two loxP sites, between which is a start codon (ATG) followed by a stop codon, creating a short, nonsense open reading frame (ORF). Note that the loxP sequence contains two start codons in the same orientation. Therefore, to prevent them from interfering with translation of the coding sequence after loxP excision, the loxP sites must be orientated such that the ATGs are in the opposite strand.

In the absence of Cre enzyme, the cytomegalovirus promoter drives expression of a small open reading frame (ORF). Ribosomes will initiate at the first ATG, the start codon of the ORF, then terminate without being able to reinitiate translation at the start codon of the coding sequence. To be certain that the coding sequence is not translated, the first ATG is out of frame with the coding sequence's ATG. If the Cre enzyme is expressed in cells containing the CMV-cDNA transgene, the Cre enzyme will recombine the loxP sites, excising the intervening ORF. Translation will begin at the start codon of the coding sequence, resulting in synthesis of the desired protein.

To make this system tissue specific, the Cre enzyme is expressed under the control of a tissue-specific promoter, such as the magnum-specific ovalbumin promoter, in the same cell as the CMV-loxP-coding sequence transgene. Although a truncated ovalbumin promoter may be fairly weak, it is still tissue-specific and will express sufficient amounts of the Cre enzyme to induce efficient excision of the interfering ORF. In fact, low levels of recombinase should allow higher expression of the recombinant protein since it does not compete against coding sequence transcripts for translation machinery.

Alternate methods of blocking translation of the coding sequence include inserting a transcription termination signal and/or a splicing signal between the loxP sites. These can be inserted along with the blocking ORF or alone. In another embodiment of the invention, a stop codon can be inserted between the loxP sites in the signal peptide of the coding sequence. Before recombinase is expressed, the peptide terminates before the coding sequence. After recombinase is expressed (under the direction of a tissue specific promoter), the stop codon is excised, allowing translation of the coding sequence. The loxP site and coding sequence are juxtaposed such that they are in frame and the loxP stop codons are out of frame. Since signal peptides are able to accept additional sequence (Brown et al., *Mol. Gen. Genet.* 197:351-7 (1984)), insertion of loxP or other recombinase target sequences (i.e. FRT) is unlikely to interfere with secretion of the desired coding sequence. In one expression vector, the loxP site is present in the signal peptide such that the amino acids encoded by loxP are not present in the mature, secreted protein. Before Cre enzyme is expressed, translation terminates at the stop codon, preventing expression of β-lactamase. After recombinase is expressed (only in magnum cells), the loxP sites recombine and excise the first stop codon. Therefore, β-lactamase is expressed selectively only in magnum cells.

In the aforementioned embodiments, the blocking ORF can be any peptide that is not harmful to chickens. The blocking ORF can also be a gene that is useful for production of the ALV-transduction particles and/or transgenic birds. In one embodiment, the blocking ORF is a marker gene.

For instance, the blocking ORF could be the neomycin resistance gene, which is required for production of transduction particles. Once the transgene is integrated into the chicken genome, the neomycin resistance gene is not required and can be excised.

Alternatively, β-lactamase can be used as the blocking ORF as it is an useful marker for production of transgenic birds. (For specific examples of the use of β-lactamase as a marker in transgenic birds, see Example 22, below.) As an example, the blocking ORF is replaced by β-lactamase and the downstream coding sequence now encodes a secreted biopharmaceutical. β-Lactamase will be expressed in blood and other tissues; it will not be expressed in the magnum after magnum-specific expression of Cre and recombination-mediated excision of β-lactamase, allowing expression of the desired protein.

The Cre and loxP transgenes could be inserted into the chicken genome via mediated transgenesis either simultaneously or separately. Any method of transgenesis that results in stable integration into the chicken genome is suitable including, but not limited to, viral integration and sperm-mediated integration. Both the ovalbumin promoter-recombinase and CMV-loxP-CDS transgenes could be placed simultaneously into chickens. However, the efficiencies of transgenesis are low and therefore the efficiency of getting both transgenes into the chicken genome simultaneously is low. In an alternative and preferred method, one flock is produced that carries the magnum-specific promoter/recombinase transgene and a second is produced that carries the CMV-loxP-CDS transgene. The flocks would then be crossed to each other. Hens resulting from this outbreeding will express the coding sequence and only in their magnum.

As mentioned above, the vectors produced according to the methods of the invention may optionally be provided with a 3' UTR containing a polyadenylation site to confer stability to the RNA produced. In a preferred embodiment, the 3' UTR may be that of the exogenous gene, or selected from the group consisting of the ovalbumin, lysozyme, or SV40 late region. However, the ovalbumin 3' UTR is not suitable in a PMGI vector that is to be inserted into the endogenous ovalbumin gene because the addition of ovalbumin sequences to the PMGI vector will interfere with proper targeting.

5.1.3 Viral Host Cell Transformation

In another embodiment, a method of introducing a nucleic acid comprising a nucleic acid sequence encoding one of the subject polypeptides and the associated gene expression control regions into a cell is using of a viral vector containing nucleic acid, e.g. a cDNA, encoding the gene product. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid. Retrovirus vectors and adeno-associated virus vectors are generally understood to be the recombinant gene delivery system of choice for the transfer of heterologous genes in vivo. These vectors provide efficient delivery of genes into cells, and the transferred nucleic acids are stably integrated into the chromosomal DNA of the host. Recombinant retrovirus can be constructed wherein the retroviral coding sequences (gag, pol, env) have been replaced by nucleic acid encoding a polypeptide, thereby rendering the retrovirus replication defective. Protocols for producing recombinant retroviruses and for infecting cells in vitro or in vivo with such viruses can be found in Current Protocols in Molecular Biology, Ausubel et al., (1989) (eds.) Greene Publishing Associates, Sections 9.10-9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include psiCrip, psiCre, psi2 and psiAm.

Furthermore, it is possible to limit the infection spectrum of retroviruses and consequently of retroviral-based vectors, by modifying the viral packaging proteins on the surface of the viral particle (see, for example PCT publications WO 93/25234, WO 94/06920, and WO 94/11524). For instance, strategies for the modification of the infection spectrum of retroviral vectors include coupling antibodies specific for cell surface antigens to the viral env protein (Roux et al., 1989, Proc. Natl. Acad. Sci. 86: 9079-9083; Julan et al., J. Gen. Virol. 73: 3251-3255 (1992); and Goud et al., 1993, Virology 163: 251-254); or coupling cell surface ligands to the viral env proteins (Neda et al., 1991, J. Biol. Chem. 266, 14143-14146), and which are incorporated herein by reference in their entireties. Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector into an amphotropic vector. Moreover, use of retroviral gene delivery can be further enhanced by the use of tissue- or cell-specific transcriptional regulatory sequences that control expression of the nucleic acid encoding an immunoglobulin polypeptide of the retroviral vector.

One retrovirus for randomly introducing a transgene into the avian genome is the replication-deficient ALV retrovirus. To produce an appropriate ALV retroviral vector, a pNLB vector is modified by inserting a region of the ovalbumin promoter and one or more exogenous genes between the 5' and 3' long terminal repeats (LTRs) of the retrovirus genome. Any coding sequence placed downstream of the ovalbumin promoter will be expressed at high levels and only in the tubular gland cells of the oviduct magnum because the ovalbumin promoter drives the high level of expression of the ovalbumin protein and is only active in the oviduct tubular gland cells. While a 7.4 kb ovalbumin promoter has been found to produce the most active construct when assayed in cultured oviduct tubular gland cells, the ovalbumin promoter must be shortened for use in the retroviral vector. In a preferred embodiment, the retroviral vector comprises a 1.4 kb segment of the ovalbumin promoter; a 0.88 kb segment would also suffice.

Any of the vectors of the present invention may also optionally include a coding sequence encoding a signal peptide that will direct secretion of the protein expressed by the vector's coding sequence from the tubular gland cells of the oviduct. This aspect of the invention effectively broadens the spectrum of exogenous proteins that may be deposited in avian eggs using the methods of the invention. Where an exogenous protein would not otherwise be secreted, the vector bearing the coding sequence is modified to comprise a DNA sequence comprising about 60 bp encoding a signal peptide from the lysozyme gene. The DNA sequence encoding the signal peptide is inserted in the vector such that it is located at the N-terminus of the protein encoded by the cDNA.

Construction of one vector is reported in Example 19, below. β-lactamase may be expressed from the CMV promoter and utilizes a poly adenylation signal (PA) in the 3' long terminal repeat (LTR). β-Lactamase has a natural signal peptide; thus, it is found in blood and in egg white.

Avian embryos have been successfully transduced with pNLB-CMV-BL transduction particles (see Examples 11 and 12, below). The egg whites of eggs from the resulting stably transduced hens were found to contain up to 20 mg of secreted, active β-lactamase per egg (see Examples 13 and 14, below).

Another viral gene delivery system useful in the present invention utilizes adenovirus-derived vectors. The genome of an adenovirus can be manipulated such that it encodes a gene product of interest, but is inactivated in terms of its ability to replicate in a normal lytic viral life cycle (see, for example, Berkner et al. BioTechniques 6, 616 (1988); Rosenfeld et al. Science 252, 43 1434 (1991); and Rosenfeld et al. Cell 68, 143-155 (1992)), incorporated herein by reference in their entireties. Suitable adenoviral vectors derived from the adenovirus strain Ad type 5 dl324 or other strains of adenovirus (e.g., Ad2, Ad3, Ad7 etc.) are well known to those skilled in the art. The virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Most replication-defective adenoviral vectors currently in use and therefore favored by the present invention are deleted for all or parts of the viral E1 and E3 genes but retain as much as 80% of the adenoviral genetic material (see, for example, Jones et al., (1979) Cell 16, 683; Berkner et al., supra; and Graham et al., in Methods in Molecular Biology, E. J Murray, (1991) Ed. (Humana, Clifton, N.J.) vol. 7. pp. 109-127), and which are incorporated herein by reference in their entireties. Expression of an inserted nucleic acid encoding a polypeptide such as IFNMAGMAX, an immunoglobulin, EPO, GM-CSF, can be under control of, for example, the lysozyme promoter, the ovalbumin promoter, artificial promoter construct sequences and the like.

Yet another viral vector system useful for delivery of, for example, the subject nucleic acid encoding an immunoglobulin polypeptide, is the adeno-associated virus (AAV). Vectors containing as little as 300 base pairs of AAV can be packaged and can integrate. Space for heterologous DNA is limited to about 4.5 kb. An AAV vector such as that described in Tratschin et al., Mol. Cell. Biol. 5, 3251-3260 (1985) can be used to introduce DNA into cells. A variety of nucleic acids have been introduced into different cell types using AAV vectors (see, for example Hermonat et al., Proc. Natl. Acad. Sci. 81, 6466-6470 (1984); Tratschin et al., Mol. Cell. Biol. 4, 2072-2081 (1985); Wondisford et al., Mol. Endocrinol. 2, 32-39 (1988); Tratschin et al., J. Virol. 51, 611-619 (1984); and Flotte et al., J. Biol. Chem. 268, 3781-3790 (1993)), incorporated herein by reference in their entireties.

Other viral vector systems that may have application in the methods according to the present invention have been derived from, but are not limited to, herpes virus, vaccinia virus, avian leucosis virus and several RNA viruses.

5.1.4 Generation of Transgenic Avian Zygotes by Nuclear Transfer and TPLSM

In another embodiment, transgenes may be introduced into the ovum of an animal, according to the present invention, by nuclear transfer via two-photon visualization and ablation, wherein the nuclear donor contains a desired heterologous DNA sequence in its genome. One of ordinary skill in the art will be able to readily adapt conventional methods to insert the desired transgene into the genome of the nuclear donor prior to injection of the nuclear donor into the recipient cytoplast, or prior to fusion of the nuclear donor cell with the recipient cell. For example, a vector that contains one or more transgene(s) encoding at least one polypeptide chain of an antibody, may be delivered into the nuclear donor cell through the use of a delivery vehicle. The transgene is then transferred along with the nuclear donor into the recipient ovum. Following zygote reconstruction, the ovum is transferred into the reproductive tract of a recipient hen. In one embodiment of the present invention, the ovum is transferred into the infundibulum of the recipient hen. After reconstruction, the embryo containing the transgene develops inside the recipient hen and travels through the oviduct thereof where it is encapsulated by natural egg white proteins and a natural egg shell. The egg is laid and can be incubated and hatched to produce a transgenic chick. The resulting transgenic chick will carry one or more desired transgene(s) in its gern line. Following maturation, the transgenic avian may lay eggs that contain one or more desired heterologous protein(s) that can be easily harvested.

In another embodiment of the present invention, a nuclear donor cell is transfected with a vector construct that contains a transgene encoding at least one polypeptide chain. Methods for transfection of somatic cell nuclei are well known in the art and include, by way of example, the use of retroviral vectors, retrotransposons, adenoviruses, adeno-associated viruses, naked DNA, lipid-mediated transfection, electroporation and direct injection into the nucleus. Such techniques, particularly as applied to avians, are disclosed in Bosselman (U.S. Pat. No. 5,162,215), Etches (PCT Publication No. WO 99/10505), Hodgson (U.S. Pat. No. 6,027,722), Hughes (U.S. Pat. No. 4,997,763), Ivarie (PCT Publication No. WO 99/19472), MacArthur (PCT Publication No. WO 97/47739), Perry (U.S. Pat. No. 5,011,780), Petitte (U.S. Pat. Nos. 5,340,740 and 5,656,749), and Simkiss (PCT Publication No. WO 90/11355), the disclosures of which are incorporated by reference herein in their entireties.

Nuclear transfer allows the cloning of animal species, wherein individual steps are common to the procedures of embryonic, fetal and adult cell cloning. These steps include, but are not limited to, preparation of a cytoplast, donor cell nucleus (nuclear donor) isolation and transfer to the cytoplast to produce a reconstructed embryo, optional reconstructed embryo culture, and embryo transfer to a synchronized host animal.

The present invention may use this approach to nuclear transfer in animals by employing two-photon visualization. In embodiments of the invention, the recipient animal is an avian including, but not limited to, chickens, ducks, turkeys, quails, pheasants and ratites. In this method, a fertilized or unfertilized egg is removed from an animal and manipulated in vitro, wherein the genetic material of the egg is visualized and removed and the ablated nucleus replaced with a donor nucleus. Optionally, the donor nucleus may be genetically modified with, for example, a transgene encoding an immunoglobulin polypeptide. Two-photon laser scanning microscopy (TPLSM) may be used to visualize the nuclear structures. Following visualization, the nucleus in the recipient cell, such as a fertilized or unfertilized egg, is removed or ablated, optionally using TPLSM.

TPLSM is based on two-photon excited fluorescence in which two photons collide simultaneously with a fluorescent molecule. Their combined energy is absorbed by the fluorophore, inducing fluorescent emission that is detected by a photomultiplier tube and converted into a digital image. See Squirrell et al., Nature Biotechnol. 17, 763-7, (1999) and Piston et al., Trends Cell Biol. 9, 66-9, (1999) incorporated herein by reference in their entireties. TPLSM generates images of living, optically dense structures for prolonged periods of time, while not affecting their viability. TPLSM utilizes biologically innocuous pulsed near-infrared light, usually at a wavelength of about 700 nm to about 1000 mm, which is able to penetrate deep into light-scattering specimens. TPLSM may employ different lasers, such as a mode-locked laser, where the wavelength is fixed, or a tunable laser that can be tuned to wavelengths between about 700 nm and about 1000 nm, depending upon the range of emission of the dye used. For DAPI and Hoescht 33342 dyes, 720-770 nm is preferred. New fluorophores are being produced with different ranges of emission and the invention is not limited to the presently available dyes and their respective emission ranges.

Furthermore, lasers used in TPLSM can be grouped into femtosecond and picosecond lasers. These lasers are distinguished by their pouse duration. A femtosecond laser is preferred since it is particularly suitable for visualization without harming the specimen.

TPLSM produces noninvasive, three-dimensional, real-time images of the optically dense avian egg. Visualization of the metaphase plate or pronucleus in avian eggs during nuclear transfer has been prevented by the yolk. Two-photon imaging with femtosecond lasers operating in the near infrared, however, allows visualization of nuclear structures without damaging cellular constituents. Prior to visualization, specimens may be incubated or injected with DNA-specific dyes such as DAPI (4', 6'-diamidino-2-phenylindole hydrochloride) or Hoescht 33342 (bis-benzimide), the albumen capsule is removed and the ovum placed in a dish with the germinal disk facing the top. Remnants of the albumen capsule are removed from the top of the germinal disk.

An aqueous solution, for example phosphate-buffered saline (PBS), is added to prevent drying of the ovum. A cloning cylinder is placed around the germinal disk and DAPI in PBS is added to the cylinder. Alternatively, a DAPI-PBS solution may be injected into the germinal disk with a glass pipette, whereupon the dye enters the nuclear structures. For dye injection, removal of the albumen capsule is not necessary, whereas injection of nuclei into the disk is facilitated in the absence of the capsule.

Images of the inside of the early avian embryo can be generated through the use of TPLSM. Visualization may be performed after about 10 to 15 minutes of incubation or about 10 minutes after dye injection. During visualization, the germinal disk is placed under the microscope objective and the pronuclear structures are searched within the central area of the disk using relatively low laser powers of about 3-6 milliwatts. Once the structures are found they may be ablated by using higher laser power or mechanically removed, guided by TPLSM.

Nuclear transfer also requires the destruction or enucleation of the pronucleus before a nuclear donor can be introduced into the oocyte cytoplast. Two-photon laser-mediated ablation of nuclear structures provides an alternative to microsurgery to visualize the pronucleus lying about 25 μm beneath the ovum's vitelline membrane within the germinal disk. Higher laser powers than those used for imaging are used for enucleation, with minimal collateral damage to the cell. The wavelength for ablation generally ranges from about 700 nm to 1000 nm, at about 30 to about 70 milliwatts. TPLSM and two-photon laser-mediated ablation are more efficient than alternative methods because they are less operator dependent and less invasive, which results in improved viability of the recipient cell.

A nucleus from a cultured somatic cell (nuclear donor) may thee be injected into the enucleated recipient cytoplast by a micromanipulation unit comprising a microinjector and a micromanipulator. The donor nucleus is introduced into the germinal disk though guided injection using episcopic illumination (i.e., light coming through the objective onto the sample). Alternatively, a donor cell may be fused to the recipient cell using methods well known in the art, e.g. by means of fusion-promoting chemicals, such as polyethylene glycol, inactivated viruses, such as Sendai virus, or electrical stimulation. The reconstructed zygote may then be surgically transferred to the oviduct of a recipient hen to produce a hard shell egg. Alternatively, the reconstructed embryo may be cultured for 24 hours and screened for development prior to surgical transfer.

The egg can be harvested after laying and before hatching of a chick, or further incubated to generate a cloned chick, optionally genetically modified. The cloned chick may carry a transgene in all or most of its cells. After maturation, the transgenic avian may lay eggs that contain one or more desired, heterologous protein(s). The cloned chick may also be a knock-in chick expressing an alternative phenotype or capable of laying eggs having an heterologous protein therein. The reconstructed egg may also be cultured to term using the ex ovo method described by Perry et al. (supra).

5.1.5 Zygote Reconstruction by Ovum Transfer

Another embodiment of the invention provides for a method of producing a cloned animal comprising nuclear transfer in combination with ovum transfer. Two-photon visualization and ablation may be used to perform nuclear transfer, as described above. Accordingly, the replacement of the recipient cell's nucleus with the donor cell's nucleus results in a reconstructed zygote. Preferably, pronuclear stage eggs are used as recipient cytoplasts already activated by fertilization. Alternatively, unactivated metaphase II eggs may serve as recipient cytoplast and activation induced after renucleation. The ovum may be cultured via ovum transfer, wherein the ovum containing the reconstructed zygote is transferred to a recipient hen. The ovum is surgically transferred into the oviduct of the recipient hen shortly after oviposition. This is accomplished according to normal husbandry procedures (oviposition, incubation, and hatching; see Tanaka et al., supra).

Alternatively, the ovum may be cultured to stage X prior to transfer into a recipient hen. More specifically, reconstructed stage I embryos are cultured for 24-48 hours to stage X. This allows for developmental screening of the reconstructed embryo prior to surgical transfer. Stage I embryos are enclosed within a thick albumen capsule. In this novel procedure, the albumen capsule is removed, after which the nuclear donor is injected into the germinal disk. Subsequently, the capsule-and germinal disk are recombined by placing the thick capsule in contact with the germinal disk on top of the yolk. Embryos develop to stage X at similar rates as those cultured with their capsules intact. At stage X, the embryo is transferred to the oviduct of a recipient hen.

Once transferred, the embryo develops inside the recipient hen and travels through the oviduct of the hen where it is encapsulated by natural egg white proteins and a natural egg shell. The egg which contains endogenous yolk and an embryo from another hen, is laid and can then be incubated and hatched like a normal chick. The resulting chick may carry a transgene in all or most of its cells. Preferably, the transgene is at least in the oviduct cells of the recipient chick. Following maturation, the cloned avian may express a desired phenotype or may be able to lay eggs that contain one or more desired, heterologous protein(s).

5.1.6 Sperm-mediated Integration of Heterologous Transgenes

Detailed descriptions of methods of sperm-mediated transfer of nucleic acid suitable for use in the present invention are described in the PCT Publication WO 00/697257, incorporated herein by reference in its entirety. The first method of incorporating heterologous genetic material into the genome of an avian delivers a nucleic acid using known gene delivery systems to male germ cells in situ in the testis of the male avian (e.g., by in vivo transfection or transduction). The second, in vitro, method of incorporating heterologous genetic material into the genome of an avian involves isolating male germ cells ex corpora, delivering a polynucleotide thereto and then returning the transfected cells to the testes of a recipient male bird.

In vivo Method

The in vivo method employs injection of the gene delivery mixture, preferably into the seminiferous tubules, or into the pete testis, and most preferably into the vas efferens or vasa efferentia, using, for example, a micropipette and a picopump delivering a precise measured volume under controlled amounts of pressure. A small amount of a suitable, non-toxic dye can be added to the gene delivery mixture (fluid) to confirm delivery and dissemination to the seminiferous tubules of the testis. The genetically modified germ cells differentiate in their own milieu. Progeny animals exhibiting the nucleic acid's integration into its germ cells (transgenic animals) are selected. The selected progeny can then be mated, or their sperm utilized for insemination or in vitro fertilization to produce further generations of transgenic progeny.

In vitro Method

Male germ cells are obtained or collected from the donor male bird by any means known in the art such as, for example, transection of the testes. The germ cells are then exposed to a gene delivery mixture, preferably within several hours, or cryopreserved for later use. When the male germ cells are obtained from the donor vertebrate by transection of the testes, the cells can be incubated in an enzyme mixture known for gently breaking up the tissue matrix and releasing undamaged cells such as, for example, pancreatic trypsin, collagenase type I, pancreatic DNAse type I, as well as bovine serum albumin and a modified DMEM medium. After washing the cells, they can be placed in an incubation medium such as DMEM, and the like, and plated on a culture dish for genetic modification by exposure to a gene delivery mixture.

Whether employed in the in vivo method or in vitro method, the gene delivery mixture, once in contact with the male germ cells, facilitates the uptake and transport of heterologous genetic material into the appropriate cell location for integration into the genome and expression. A number of known gene delivery methods can be used for the uptake of nucleic acid sequences into the cell. Such methods include, but are not limited to viral vectors, liposomes, electroporation and Restriction Enzyme Mediated Integration (REMI) (discussed below). In both the in vivo or in vitro method, a gene delivery mixture typically comprises a polynucleotide encoding the desired trait or product (for example, immunoglobulin polypeptides) and a suitable promoter sequence such as, for example, a tissue-specific promoter, an IRES or the like and optionally agents that increase the uptake of or comprise the polynucleotide sequence, such as liposomes, retroviral vectors, adenoviral vectors, adenovirus enhanced gene delivery systems and the like, or combinations thereof. A reporter construct, including a genetic selection marker, such as the gene encoding for Green Fluorescent Protein, can further be added to the gene delivery mixture. Targeting molecules, such as the c-kit ligand, can be added to the gene delivery mixture to enhance the transfer of genetic material into the male germ cell. An immunosuppressing agent, such as cyclosporin or a corticosteroid may also be added to the gene delivery mixture as known in the art.

Any of a number of commercially available gene delivery mixtures can be used, to which the polynucleotide encoding a desired trait or product is further admixed. The final gene delivery mixture comprising the polynucleotide can then be admixed with the cells and allowed to interact for a period of between about 2 hours to about 16 hours, at a temperature of between about 33° C. to about 37° C. After this period, the cells are preferably placed at a lower temperature of about 33° C. to about 34° C., for about 4 hours to about 20 hours, preferably about 16 to 18 hrs.

Isolating and/or selecting genetically transgenic germ cells (and transgenic somatic cells, and of transgenic vertebrates) is by any suitable means, such as, but not limited to, physiological and/or morphological phenotypes of interest using any suitable means, such as biochemical, enzymatic, immunochemical, histologic, electrophysiologic, biometric or like methods, and analysis of cellular nucleic acids, for example the presence or absence of specific DNAs or RNAs of interest using conventional molecular biological techniques, including hybridization analysis, nucleic acid amplification including, but not limited to, polymerase chain reaction, transcription-mediated amplification, reverse transcriptase-mediated ligase chain reaction, and/or electrophoretic technologies.

A preferred method of isolating or selecting male germ cell populations comprises obtaining specific male germ cell populations, such as spermatogonia, from a mixed population of testicular cells by extrusion of the cells from the seminiferous tubules and enzyme digestion. The spermatogonia, or other male germ cell populations, can be isolated from a mixed cell population by methods such as the utilization of a promoter sequence that is specifically or selectively active in cycling male germ line stem cell populations. Suitable promoters include B-Myb or a specific promoter, such as the c-kit promoter region, c-raf-1 promoter, ATM (ataxia-telangiectasia) promoter, vasa promoter, RBM (ribosome binding motif) promoter, DAZ (deleted in azoospermia) promoter, XRCC-1 promoter, HSP 90 (heat shock gene) promoter, cyclin A1 promoter, or FRMI (from Fragile X site) promoter and the like. A selected promoter may be linked to a reporter construct, for example, a construct comprising a gene encoding Green Fluorescent Protein (or EGFP), Yellow Fluorescent Protein, Blue Fluorescent Protein, a phycobiliprotein, such as phycoerythrin or phycocyanin, or any other protein which fluoresces under suitable wave-lengths of light, or encoding a light-emitting protein, such as luciferase or apoaequorin. The unique promoter sequences drive the expression of the reporter construct only during specific stages of male germ cell development (e.g., Mailer et al., J. Biol. Chem. 276(16), 11220-28 (1999); Schrans-Stassen et al., Endocrinology 140, 5894-5900 (1999)) incorporated herein by reference in their entireties. In the cast of a fluorescent reporter construct, the cells can be sorted with the aid of, for example, a FACS set at the appropriate wavelength(s), or they can be selected by chemical methods.

Male germ cells that have the DNA modified in the desired manner are isolated or selected, and transferred to the testis of a suitable recipient animal. Further selection can be attempted after biopsy of one or both of the recipient male's testes, or after examination of the animal's ejaculate amplified by the polymerase chain reaction to confirm that the desired nucleic acid sequence had been incorporated.

The genetically modified germ cells isolated or selected as described above are preferably transferred to a testis of a recipient male avian, preferably a chicken, that can be, but need not be, the same donor animal. Before transferring the genetically modified male germ cells to the recipient animal, the testes of the recipient can be depopulated of endogenous germ cells, thereby facilitating the colonization of the recipient testis by the genetically modified germ cells, by any suitable means, including by gamma irradiation, by chemical treatment, by means of infectious agents such as viruses, or by autoimmune depletion or by combinations thereof, preferably by a combined treatment of the vertebrate with an alkylating agent and gamma irradiation.

The basic rigid architecture of the gonad should not be destroyed, nor significantly damaged. Disruption of tubules may lead to impaired transport of testicular sperm and result in infertility. Sertoli cells should not be irreversibly damaged, as they provide a base for development of the germ cells during maturation, and for preventing the host immune defense system from destroying grafted foreign spermatogonia.

In a preferred method, a cytotoxic alkylating agent, such as, but not limited to, bisulfan (1,4-butanediol dimethanesulphonate), chlorambucil, cyclophosphamide, melphalan, or ethyl ethanesulfonic acid, is combined with gamma irradiation, to be administered in either sequence. The dose of the alkylating agent and the dose of gamma radiation are in an amount sufficient to substantially depopulate the testis. The alkylating agent can be administered by any pharmaceutically acceptable delivery system, including but not limited to, intraperitoneal, intravenous, or intramuscular injection, intravenous drip, implant, transdermal or transmucosal delivery systems.

The isolated or selected genetically modified germ cells are transferred into the recipient testis by direct injection using a suitable micropipette. Support cells, such as Leydig or Sertoli cells, that can be unmodified or genetically modified, can be transferred to a recipient testis along with the modified germ cells.

A union of male and female gametes to form a transgenic zygote is brought about by copulation of the male and female vertebrates of the same species, or by in vitro or in vivo artificial means. If artificial means are chosen, then incorporating into the genome a genetic selection marker that is expressed in male germ cells is particularly useful.

Suitable artificial means include, but are not limited to, artificial insemination, in vitro fertilization (IVF) and/or other artificial reproductive technologies, such as intracytoplasmic sperm injection (ICSI), subzonal insemination (SUZI), or partial zona dissection (PZD). Also others, such as cloning and embryo transfer, cloning and embryo splitting, and the like, can be employed.

The transgenic vertebrate progeny can, in turn, be bred by natural mating, artificial insemination, or by in vitro fertilization (IVF) and/or other artificial reproductive technologies, such as intracytoplasmic sperm injection (ICSI) and chicken intracytoplasmic sperm injection (CHICSI™), subzonal insemination (SUZI), or partial zona dissection (PZD), to obtain further generations of transgenic progeny. Although the genetic material is originally inserted solely into the germ cells of a parent animal, it will ultimately be present in the germ cells of future progeny and subsequent generations thereof. In addition, the genetic material will also be present in cells of the progeny other than germ cells, i.e., somatic cells.

5.1.7 Generation of Transgenic Avian Zygotes by Restriction Enzyme-mediated Integration (REMI)

The REMI method for stably integrating heterologous DNA into the genomic DNA of a recipient cell is described by Shemesh et al. in PCT Publication No. WO 99/42569 and incorporated herein by reference in its entirety. This REMI method comprises in part an adaptation of the REMI technique disclosed by Schiest and Petes (Proc. Nat. Acad. Sci. U.S.A. 88, 7585-7589 (1991)) and Kuspa and Loomis (Proc. Nat. Acad. Sci. U.S.A., 89, 8803-8807 (1992)) both incorporated herein by reference in their entireties.

The REMI method is suitable for introducing heterologous DNA into the genome nucleic acid of sperm and sperm precursor cells, or ovum, embryonic cell, or somatic cell of an animal, preferably an avian, more preferably a chicken.

The heterologous nucleic acid to be integrated into, for example, the sperm nuclear DNA is converted to a linear double stranded DNA possessing single-stranded cohesive ends by contacting the heterologous DNA with a type II restriction enzyme that upon scission, generates such ends. The nucleic acid to be cut can be a circular nucleic acid such as in a plasmid or a viral vector or a linear nucleic acid that possesses at least one recognition and cutting site outside of the genes or regulatory regions critical to the desired post-integration function of the nucleic acid, and no recognition and cutting sites within the critical regions.

Alternatively the heterologous DNA to be integrated into the sperm nuclear DNA can be prepared by chemically and/or enzymatically adding cohesive ends to a linear DNA (see, for example Sambrook et al., *Molecular Cloning: A Laboratory Manual*. 3rd ed., Cold Spring Harbor Laboratory, Cold Spring Harbor, N.Y. (2001) incorporated herein by reference in its entirety). The added cohesive ends must be able to hybridize to the cohesive ends characteristic of a nucleic acid cleaved by a type II restriction endonuclease.

Alternatively the cohesive ends can be added by combining the methods based on type II restriction enzyme cutting and chemical and/or enzymatic addition.

According to the present invention, a heterologous nucleic acid encoding at least one polypeptide, and the appropriate restriction enzyme can be introduced into sperm cells together or sequentially by way of, for example, electroporation, or lipofection. Preferably electroporation may be used, and most preferably lipofection is used. However, the present invention contemplates that any technique capable of transferring heterologous material into sperm could be used so long as the technique preserves enough of the sperm's motility and fertilization functions, such that the resultant sperm will be able to fertilize the appropriate oocytes. It is understood that the heterologous nucleic acid may be integrated into the genome of a recipient cell such as a spermatogonial cell or a spermatogonial precursor cell for subsequent transfer to an embryo or the testicular material of the recipient male animal, preferably a chicken. It is further understood that the heterologous nucleic acid may not be integrated into the genome of the recipient cell.

The combination of REMI as described in the present application, plus a relatively benign method of transferring heterologous material into a cell may result in heterologous nucleic acid being stably integrated into genomic DNA of a high fraction of the treated sperm, while not diminishing to any great extent, the viability of the sperm or their ability to fertilize oocytes. Examples of suitable methods for the introduction of the genetically modified sperm, spermatogonial cells or precuror spermatogonial cells into a recipient avian, preferably a chicken, are as described above.

5.1.8 Breeding and Maintenance of Transgenic Avians

A union of male and female gametes from transgenic birds generated by the cytoplasmically microinjected embryos, thereby forming a transgenic zygote, is brought about by copulation of the male and female vertebrates of the same species, or by in vitro or in vivo artificial means. Suitable artificial means include, but are not limited to, artificial insemination, in vitro fertilization (IVF) and/or other artificial reproductive technologies, such as intracytoplasmic sperm injection (ICSI), subzonal insemination (SUZI), or partial zona dissection (PZD). Also others, such as cloning and embryo transfer, cloning and embryo splitting, and the like, can be employed.

The transgenic avian progeny can, in turn, be bred by natural mating, artificial insemination, or by in vitro fertilization (IVF) and/or other artificial reproductive technologies, such as intracytoplasmic sperm injection (ICSI) and chicken intracytoplasmic sperm injection (CHICSrrM), subzonal insemination (SUZI), or partial zona dissection (PZD), to obtain further generations of transgenic progeny.

Using the methods of the invention for producing transgenic avians, particularly methods using vectors that are not derived from eukaryotic viruses, and, preferably, the methods of cytoplasmic micro-injection described herein, the level of mosaicism of the transgene (percentage of cells containing the transgene) in avians hatched from microinjected embryos (i.e., the $G_0$s) is greater than 5%, 10%, 25%, 50%, 75% or 90%, or is the equivalent of one copy per one genome, two genomes, five genomes, seven genomes or eight genomes, as determined by any number of techniques known in the art and described infra. In additional particular embodiments, the percentage of $G_0$s that transmit the transgene to progeny ($G_1$s) is greater than 5%, preferably, greater than 10%, 20%, 30%, 40%, and, most preferably, greater than 50%, 60%, 70%, 80%, 90%. In other embodiments, the transgene is detected in 10%, 20%, 30%, 40%, and most preferably, greater than 50%, 60%, 70%, 80%, 90% of chicks hatching from embryos into which nucleic acids have been introduced using methods of the invention.

5.2 Vectors

A variety of vectors useful in carrying out the methods of the present invention are described herein. These vectors may be used for stable introduction of a selected heterologous polypeptide-coding sequence (and/or regulatory sequences) into the genome of an avian, in particular, to generate transgenic avians that produce exogenous proteins in specific tissues of an avian, and in the oviduct in particular, or in the serum of an avian. In still further embodiments, the vectors are used in methods to produce avian eggs containing exogenous protein.

In particular embodiments, preferably for use in the microinjection, sperm-mediated transgenesis, and nuclear transfer methods described herein, the vectors of the invention are not derived from eukaryotic viral vectors or retroviral vectors (except in certain embodiments for containing eukaryotic viral regulatory elements such as promoters, origins of replication, etc). In particular embodiments, the vector is not an REV, ALV or MuLV vector. In particular, useful vectors include, bacteriophages such as lambda derivatives, such as λgt11, λgt WES.tB, Charon 4, and plasmid vectors such as pBR322, pBR325, pACYC177, pACYC184, pUC8, pUC9, pUC18, pUC19, pLG339, pR290, pKC37, pKC101, SV40, PBLUESCRIPT® II SK+/− or KS+/− (see "Stratagene Cloning Systems" Catalog (1993) from STRATAGENE®, La Jolla, Calif., which is hereby incorporated by reference), pQE, pIH821, pGEX, pET series (see Studier, F. W. et. al., 1990, "Use of T7 RNA Polymerase to Direct Expression of Cloned Genes" *Gene Expression Technology* 185, which is hereby incorporated by reference) and any derivatives thereof, cosmid vectors and, in preferred embodiments, artificial chromosomes, such as, but not limited to, YACs, BACs, BBPACs or PACs. Such artificial chromosomes are useful in that a large nucleic acid insert can be propagated and introduced into the avian cell.

In other particular embodiments, as detailed above in section 5.2, infra, the vectors of the invention are derived from eukaryotic viruses, preferably avian viruses, and can be replication competent or, preferably, replication deficient. In particular embodiments, the vectors are derived from REV, ALV or MuLV. Nucleic acid sequences or derivative or truncated variants thereof, may be introduced into viruses such as vaccinia virus. Methods for making a viral recombinant vector useful for expressing a protein under the control of the lysozyme promoter are analogous to the methods disclosed in U.S. Pat. Nos. 4,603,112; 4,769,330; 5,174,993; 5,505,941; 5,338,683; 5,494,807; 4,722,848; Paoletti, E., 1996, *Proc. Natl. Acad. Sci.* 93: 11349-11353; Moss, 1996, *Proc. Natl. Acad. Sci.* 93: 11341-11348; Roizman, 1996, *Proc. Natl. Acad. Sci.* 93: 11307-11302; Frolov et al., 1996, *Proc. Natl. Acad. Sci.* 93: 11371-11377; Grunhaus et al., 1993, *Seminars in Virology* 3: 237-252 and U.S. Pat. Nos. 5,591,639; 5,589,466; and 5,580,859 relating to DNA expression vectors, inter alia; the contents of which are incorporated herein by reference in their entireties.

Recombinant viruses can also be generated by transfection of plasmids into cells infected with virus.

Preferably, vectors can replicate (i.e., have a bacterial origin of replication) and be manipulated in bacteria (or yeast) and can then be introduced into avian cells. Preferably, the vector comprises a marker that is selectable and/or detectable in bacteria or yeast cells and, preferably, also in avian cells, such markers include, but are not limited to, Amp$^r$, tet$^r$, LacZ, etc. Preferably, such vectors can accommodate (i.e., can be used to introduce into cells and replicate) large pieces of DNA such as genomic sequences, for example, large pieces of DNA consisting of at least 25 kb, 50 kb, 75 kb, 100 kb, 150 kb, 200 kb or 250 kb, such as BACs, YACs, cosmids, etc.

The insertion of a DNA fragment into a vector can, for example, be accomplished by ligating the DNA fragment into a vector that has complementary cohesive termini. However, if the complementary restriction sites used to fragment the DNA are not present in the vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and the transgene may be modified by homopolymeric tailing.

The vector can be cloned using methods known in the art, e.g., by the methods disclosed in Sambrook et al., 2001, Molecular Cloning, A Laboratory Manual, Third Edition, Cold Spring Harbor Laboratory Press, N.Y.; Ausubel et al., 1989, Current Protocols in Molecular Biology, Green Publishing Associates and Wiley Interscience, N.Y., both of which are hereby incorporated by reference in their entireties. Preferably, the vectors contain cloning sites, for example, restriction enzyme sites that are unique in the sequence of the vector and insertion of a sequence at that site would not disrupt an essential vector function, such as replication.

As discussed above, vectors used in certain methods of the invention preferably can accommodate, and in certain embodiments comprise, large pieces of heterologous DNA such as genomic sequences, particularly avian genomic sequences. Such vectors can contain an entire genomic locus, or at least sufficient sequence to confer endogenous regulatory expression pattern, e.g., high level of expression in the magnum characteristic of lysozyme, ovalbumin, ovomucoid, ovotransferrin, etc, and to insulate the expression of the transgene sequences from the effect of regulatory sequences surrounding the site of integration of the transgene in the genome. Accordingly, as detailed below, in preferred embodiments, the transgene is inserted in an entire genomic loci or significant portion thereof.

To manipulate large genomic sequences contained in, for example, a BAC, nucleotide sequences coding for the heterologous protein to be expressed and/or other regulatory elements may be inserted into the BAC by directed homologous recombination in bacteria, e.g., the methods of Heintz WO 98/59060; Heintz et al., WO 01/05962; Yang et al., 1997, *Nature Biotechnol.* 15: 859-865; Yang et al., 1999, *Nature Genetics* 22: 327-35; which are incorporated herein by reference in their entireties.

Alternatively, the BAC can also be engineered or modified by "E-T cloning," as described by Muyrers et al. (1999, *Nucleic Acids Res.* 27(6): 1555-57, incorporated herein by reference in its entirety). Using these methods, specific DNA may be engineered into a BAC independently of the presence of suitable restriction sites. This method is based on homologous recombination mediated by the recE and recT proteins ("ET-cloning") (Zhang et al., 1998, Nat. Genet. 20(2): 123-28; incorporated herein by reference in its entirety). Homologous recombination can be performed between a PCR fragment flanked by short homology arms and an endogenous intact recipient such as a BAC. Using this method, homologous recombination is not limited by the disposition of restriction endonuclease cleavage sites or the size of the target DNA. A BAC can be modified in its host strain using a plasmid, e.g., pBAD-αβγ, in which recE and recT have been replaced by their respective functional counterparts of phage lambda (Muyrers et al., 1999, *Nucleic Acids Res*. 27(6): 1555-57). Preferably, a BAC is modified by recombination with a PCR product containing homology arms ranging from 27-60 bp. In a specific embodiment, homology arms are 50 bp in length.

In another embodiment, a transgene is inserted into a yeast artificial chromosome (YAC) (Burke et al., 1987, *Science* 236: 806-12; and Peterson et al., 1997, *Trends Genet.* 13:61, both of which are incorporated by reference herein in their entireties).

In other embodiments, the transgene is inserted into another vector developed for the cloning of large segments of genomic DNA, such as a cosmid or bacteriophage P1 (Sternberg et al., 1990, *Proc. Natl. Acad. Sci. USA* 87: 103-07). The approximate maximum insert size is 30-35 kb for cosmids and 100 kb for bacteriophage P1. In another embodiment, the transgene is inserted into a P-1 derived artificial chromosome (PAC) (Mejia et al., 1997, *Genome Res* 7:179-186). The maximum insert size is 300 kb.

Vectors containing the appropriate heterologous sequences may be identified by any method well known in the art, for example, by sequencing, restriction mapping, hybridization, PCR amplification, etc.

The vectors of the invention comprise one or more nucleotide sequences encoding a heterologous protein desired to be expressed in the transgenic avian, as well as regulatory elements such as promoters, enhancers, MARs, IRES's and other translation control elements, transcriptional termination elements, polyadenylation sequences, etc, as discussed infra. In particular embodiments, the vector of the invention contains at least two nucleotide sequences coding for heterologous proteins, for example, but not limited to, the heavy and light chains of an immunoglobulin.

In a preferred embodiment, the nucleotide sequence encoding the heterologous protein is inserted into all or a significant portion of a nucleic acid containing the genomic sequence of an endogenous avian gene, preferably an avian gene that is expressed in the magnum, e.g., lysozyme, ovalbumin, ovomucoid, conalbumin, ovotransferrin, etc. For example, the heterologous gene sequence may be inserted into or replace a portion of the 3' untranslated region (UTR) or 5' untranslated region (UTR) or an intron sequence of the endogenous gene genomic sequence. Preferably, the heterologous gene coding sequence has its own IRES. For descriptions of IRESes, see, e.g., Jackson et al., 1990, *Trends Biochem Sci*. 15(12):477-83; Jang et al., 1988, *J. Virol*. 62(8):2636-43; Jang et al., 1 *Enzyme* 44(1-4):292-309; and Martinez-Salas, 1999, *Curr. Opin. Biotechnol*. 10(5):458-64; Palmenberg et al., U.S. Pat. No. 4,937,190, which are incorporated by reference herein in their entireties. In another embodiment, the heterologous protein coding sequence is inserted at the 3' end of the endogenous gene coding sequence. In another preferred embodiment, the heterologous gene coding sequences are inserted using 5' direct fusion wherein the heterologous gene coding sequences are inserted in-frame adjacent to the initial ATG sequence (or adjacent the nucleotide sequence encoding the first two, three, four, five, six, seven or eight amino acids) of the endogenous gene or replacing some or all of the sequence of the endogenous gene coding sequence. In yet another specific embodiment, the heterologous gene coding sequence is inserted into a separate cistron in the 5' region of the endogenous gene genomic sequence and has an independent IRES sequence.

The present invention further relates to nucleic acid vectors (preferably, not derived from eukaryotic viruses, except, in certain embodiments, for eukaryotic viral promoters and/or enhancers) and transgenes inserted therein that incorporate multiple polypeptide-encoding regions, wherein a first polypeptide-encoding region is operatively linked to a transcription promoter and a second polypeptide-encoding region is operatively linked to an IRES. For example, the vector may contain coding sequences for two different heterologous proteins (e.g., the heavy and light chains of an immunoglobulin) or the coding sequences for all or a significant part of the genomic sequence for the gene from which the promoter driving expression of the transgene is derived, and the heterologous protein desired to be expressed (e.g., a construct containing the genomic coding sequences, including introns, of the avian lysozyme gene when the avian lysozyme promoter is used to drive expression of the transgene, an IRES, and the coding sequence for the heterologous protein desired to be expressed downstream (i.e., 3' on the RNA transcript of the IRES)). Thus, in certain embodiments, the nucleic acid encoding the heterologous protein is introduced into the 5' untranslated or 3' untranslated regions of an endogenous gene, such as but not limited to, lysozyme, ovalbumin, ovotransferrin, and ovomucoid, with an IRES sequence directing translation of the heterologous sequence.

Such nucleic acid constructs, when inserted into the genome of a bird and expressed therein, will generate individual polypeptides that may be post-translationally modified, for example, glycosylated or, in certain embodiments, form complexes, such as heterodimers with each other in the white of the avian egg. Alternatively, the expressed polypeptides may be isolated from an avian egg and combined in vitro, or expressed in a non-reproductive tissue such as serum. In other embodiments, for example, but not limited to, when expression of both heavy and light chains of an antibody is desired, two separate constructs, each containing a coding sequence for one of the heterologous proteins operably linked to a promoter (either the same or different promoters), are introduced by microinjection into cytoplasm of one or more embryonic cells and transgenic avians harboring both transgenes in their genomes and expressing both heterologous proteins are identified. Alternatively, two transgenic avians each containing one of the two heterologous proteins (e.g., one transgenic avian having a transgene encoding the light chain of an antibody and a second transgenic avian having a transgene encoding the heavy chain of the antibody) can be bred to obtain an avian containing both transgenes in its germline and expressing both transgene encoded proteins, preferably in eggs.

Recombinant expression vectors can be designed for the expression of the encoded proteins in eukaryotic cells. Useful vectors may comprise constitutive or inducible promoters to direct expression of either fusion or non-fusion proteins. With fusion vectors, a number of amino acids are usually added to the expressed target gene sequence such as, but not limited to, a protein sequence for thioredoxin, a polyhistidine, or any other amino acid sequence that facilitates purification of the expressed protein. A proteolytic cleavage site may further be introduced at a site between the target recombinant protein and the fusion sequence. Additionally, a region of amino acids such as a polymeric histidine region may be introduced to allow binding of the fusion protein to metallic ions such as nickel bonded to a solid support, and thereby allow purification of the fusion protein. Once the fusion protein has been purified, the cleavage site allows the target recombinant protein to be separated from the fusion sequence. Enzymes suitable for use in cleaving the proteolytic cleavage site include, but are not limited to, Factor Xa and thrombin. Fusion expression vectors that may be useful in the present invention include pGex (AMRAD® Corp., Melbourne, Australia), pRIT5 (PHARMACIA®, Piscataway, N.J.) and pMAL (NEW ENGLAND BIOLABS®, Beverly, Mass.), fusingglutathione S-transferase, protein A, or maltose E binding protein, respectively, to the target recombinant protein.

Once a promoter and a nucleic acid encoding a heterologous protein of the present invention have been cloned into a vector system, it is ready to be incorporated into a host cell. Such incorporation can be carried out by the various forms of transformation noted above, depending upon the vector/host cell system. It is contemplated that the incorporation of the DNA of the present invention into a recipient cell may be by any suitable method such as, but not limited to, viral transfer, electroporation, gene gun insertion, sperm-mediated transfer to an ovum, microinjection and the like. Suitable host cells include, but are not limited to, bacteria, virus, yeast, mammalian cells, and the like. In particular, the present invention contemplates the use of recipient avian cells, such as chicken cells or quail cells.

Another aspect of the present invention, therefore, is a method of expressing a heterologous polypeptide in a eukaryotic cell by transfecting an avian cell with a recombinant DNA comprising an avian tissue-specific promoter operably linked to a nucleic acid insert encoding a polypeptide and, optionally, a polyadenylation signal sequence, and culturing the transfected cell in a medium suitable for expression of the heterologous polypeptide under the control of the avian lysozyme gene expression control region.

Yet another aspect of the present invention is a eukaryotic cell transformed with an expression vector according to the present invention and described above. In one embodiment of the present invention, the transformed cell is a chicken oviduct cell and the nucleic acid insert comprises the chicken lysozyme gene expression control region, a nucleic acid insert encoding a human interferon α2b and codon optimized for expression in an avian cell, and an SV40 polyadenylation sequence.

In another embodiment, the transformed cell is a quail oviduct cell and the nucleic acid insert comprises the artificial avian promoter construct MDOT (SEQ ID NO.:11) operably linked to an interferon-encoding sequence, as described in Example 34 below.

In yet another embodiment of the present invention, a quail oviduct cell is transfected with the nucleic acid insert comprising the MDOT artificial promoter construct operably linked to an erythropoietin (EPO)-encoding nucleic acid, wherein the transfected quail produces heterologous erythropoietin.

5.2.1 Promoters

The vectors of the invention contain promoters that function in avian cells, preferably, that are tissue-specific and, in preferred embodiments, direct expression in the magnum or serum or other tissue such that expressed proteins are deposited in eggs, more preferably, that are specific for expression in the magnum. Alternatively, the promoter directs expression of the protein in the serum of the transgenic avian. Introduction of the vectors of the invention, preferably, generate transgenics that express the heterologous protein in tubular gland cells where it is secreted into the oviduct lumen and deposited, e.g., into the white of an egg. In preferred embodiments, the promoter directs a level of expression of the heterologous protein in the egg white of eggs laid by $G_0$ and/or $G_1$ chicks and/or their progeny that is greater than 5 µg, 10 µg, 50 µg, 100 µg, 250 µg, 500 µg, or µg, more preferably greater than 1 mg, 2 mg, 5 mg, 10 mg, 20 mg, 50 mg, 100 mg, 200 mg, 500 mg, 700 mg, 1 gram, 2 grams, 3 grams, 4 grams or 5 grams. Such levels of expression can be obtained using the promoters of the invention.

In preferred embodiments, the promoters of the invention are derived from genes that express proteins present in significant levels in the egg white and/or the serum. For example, the promoter comprises regions of an ovomucoid, ovalbumin, conalbumin, lysozyme or ovotransferrin promoter or any other promoter that directs expression of a gene in an avian, particularly in a specific tissue of interest, such as the magnum or in the serum. Alternatively, the promoter used in the expression vector may be derived from that of the lysozyme gene that is expressed in both the oviduct and macrophages. Portions of two or more of these, and other promoters that function in avians, may be combined to produce effective synthetic promoter.

The promoter may optionally be a segment of the ovalbumin promoter region that is sufficiently large to direct expression of the coding sequence in the tubular gland cells. Other exemplary promoters include the promoter regions of the ovalbumin, lysozyme, ovomucoid, ovotransferrin or ovomucin genes (for example, but not limited to, as disclosed in U.S. patent application Ser. Nos. 09/922,549, filed Aug. 3, 2001 now U.S. Pat. No. 7,176,300 and 10/114,739 now U.S. Pat. No. 7,199,270, filed Apr. 1, 2002, both entitled "Avian Lysozyme Promoter", by Rapp, and U.S. patent application Ser. No. 09/998,716 now U.S. Pat. No. 6,875, 588, filed Nov. 30, 2001, entitled "Ovomucoid Promoter and Methods of Use," by Harvey et al., all of which are incorporated by reference herein in their entireties). Alternatively, the promoter may be a promoter that is largely, but not entirely, specific to the magnum, such as the lysozyme promoter. Other suitable promoters may be artificial constructs such as a combination of nucleic acid regions derived from at least two avian gene promoters. One such embodiment of the present invention is the MDOT construct (SEQ ID NO: 11) comprising regions derived from the chicken ovomucin and ovotransferrin promoters, including but not limited to promoters altered, e.g., to increase expression, and inducible promoters, e.g., the tetr system.

The ovalbumin gene encodes a 45 kD protein that is also specifically expressed in the tubular gland cells of the magnum of the oviduct (Beato, 1989, *Cell* 56:335-344). Ovalbumin is the most abundant egg white protein, comprising over 50 percent of the total protein produced by the tubular gland cells, or about 4 grams of protein per large Grade A egg (Gilbert, "Egg albumen and its formation" in *Physiology and Biochemistry of the Domestic Fowl*, Bell and Freeman, eds., Academic Press, London, New York, pp. 1291-1329). The ovalbumin gene and over 20 kb of each flanking region have been cloned and analyzed (Lai et al., 1978, *Proc. Natl. Acad. Sci. USA* 75:2205-2209; Gannon et al., 1979, *Nature* 278:428-424; Roop et al., 1980, *Cell* 19:63-68; and Royal et al., 1975, *Nature* 279:125-132).

The ovalbumin gene responds to steroid hormones such as estrogen, glucocorticoids, and progesterone, which induce the accumulation of about 70,000 ovalbumin mRNA transcripts per tubular gland cell in immature chicks and 100, 000 ovalbumin mRNA transcripts per tubular gland cell in the mature laying hen (Palmiter, 1973, *J. Biol. Chem.* 248:8260-8270; Palmiter, 1975, *Cell* 4:189-197). The 5' flanking region contains four DNAse I-hypersensitive sites centered at −0.25, −0.8, −3.2, and −6.0 kb from the transcription start site. These sites are called HS-I, -II, -III, and -IV, respectively. Promoters of the invention may contain one, all, or a combination of HS-I, HS-II, HS-III and HS0IV. Hypersensitivity of HS-II and -III are estrogen-induced, supporting a role for these regions in hormone-induction of ovalbumin gene expression.

HS-I and HS-II are both required for steroid induction of ovalbumin gene transcription, and a 1.4 kb portion of the 5' region that includes these elements is sufficient to drive steroid-dependent ovalbumin expression in explanted tubular gland cells (Sanders and McKnight, 1988, *Biochemistry* 27: 6550-6557). HS-I is termed the negative-response element ("NRE") because it contains several negative regulatory elements which repress ovalbumin expression in the absence of hormone (Haekers et al., 1995, *Mol. Endo.* 9:1113-1126). Protein factors bind these elements, including some factors only found in oviduct nuclei suggesting a role in tissue-specific expression. HS-II is termed the steroid-dependent response element ("SDRE") because it is required to promote steroid induction of transcription. It binds a protein or protein complex known as Chirp-I. Chirp-I is induced by estrogen and turns over rapidly in the presence of cyclohexamide (Dean et al., 1996, *Mol. Cell. Biol.* 16:2015-2024). Experiments using an explanted tubular gland cell culture system defined an additional set of factors that bind SDRE in a steroid-dependent manner, including a NFκB-like factor (Nordstrom et al., 1993, *J. Biol. Chem.* 268:13193-13202; Schweers and Sanders, 1991, *J. Biol. Chem.* 266: 10490-10497).

Less is known about the function of HS-III and HS-IV. HS-III contains a functional estrogen response element and confers estrogen inducibility to either the ovalbumin-proximal promoter or a heterologous promoter when co-transfected into HeLa cells with an estrogen receptor cDNA. These data imply that HS-II may play a functional role in the overall regulation of the ovalbumin gene. Little is known about the function of HS-IV, except that it does not contain a functional estrogen-response element (Kato et al., 1992, *Cell* 68: 731-742).

In an alternative embodiment of the invention, transgenes containing constitutive promoters are used, but the transgenes are engineered so that expression of the transgene effectively becomes magnum-specific. Thus, a method for producing an exogenous protein in an avian oviduct provided by the present invention involves generating a transgenic avian having two transgenes in its tubular gland cells. One transgene comprises a first coding sequence operably linked to a constitutive promoter. The second transgene comprises a second coding sequence that is operably linked to a magnum-specific promoter, where expression of the first coding sequence is either directly or indirectly dependent upon the cellular presence of the protein expressed by the second coding sequence.

Additional promoters useful in the present invention include inducible promoters, such as the tet operator and the metallothionein promoter which can be induced by treatment with tetracycline and zinc ions, respectively (Gossen et al., 1992, *Proc. Natl. Acad. Sci.* 89: 5547-5551 and Walden et al., 1987, *Gene* 61: 317-327; incorporated herein by reference in their entireties).

Chicken Lysozyme Gene Expression Control Region Nucleic Acid Sequences:

The chicken lysozyme gene is highly expressed in the myeloid lineage of ematopoietic cells, and in the tubular glands of the mature hen oviduct (Hauser et al., 1981, *Hematol. and Blood Transfusion* 26: 175-178; Schutz et al., 1978, Cold Spring Harbor Symp. Quart. Biol. 42: 617-624) and is therefore a suitable candidate for an efficient promoter for heterologous protein production in transgenic animals. The regulatory region of the lysozyme locus extends over at least 12 kb of DNA 5' upstream of the transcription start site, and comprises a number of elements that have been individually isolated and characterized. The known elements include three enhancer sequences at about −6.1 kb, −3.9 kb, and −2.7 kb (Grewal et al., 1992, *Mol. Cell Biol.* 12: 2339-2350; Bonifer et al., 1996, *J. Mol. Med.* 74: 663-671), a hormone responsive element (Hecht et al., 1988, *E.M.B.O.J.* 7: 2063-2073), a silencer element and a complex proximal promoter. The constituent elements of the lysozyme gene expression control region are identifiable as DNAase 1 hypersensitive chromatin sites (DHS). They may be differentially exposed to nuclease digestion depending upon the differentiation stage of the cell. For example, in the multipotent progenitor stage of myelomoncytic cell development, or in erythroblasts, the silencer element is a DHS. At the myeloblast stage; a transcription enchancer located −6.1 kb upstream from the gene transcription start site is a DHS, while at the later monocytic stage another enhancer, at −2.7 kb becomes DNAase sensitive (Huber et al., 1995, DNA and *Cell Biol.* 14: 397-402).

This invention also envisions the use of promoters other than the lysozyme promoter, including but not limited to, a cytomegalovirus promoter, an ovomucoid, conalbumin or ovotransferrin promoter or any other promoter that directs expression of a gene in an avian, particularly in a specific tissue of interest, such as the magnum.

Another aspect of the methods of the present invention is the use of combinational promoters comprising an artificial nucleic acid construct having at least two regions wherein the regions are derived from at least two gene promoters, including but not limited to a lysozyme, ovomucoid, conalbumin or ovotransferrin promoter. In one embodiment of the present invention, the promoter may comprise a region of an avian ovomucoid promoter and a region of an avian oxotransferrin promoter, thereby generating the MDOT avian artificial promoter construct as described in Example 12, below. The avian MDOT promoter construct of the present invention has the nucleic acid sequence SEQ ID NO: 11 and is illustrated in FIG. 14. This promoter is useful for allowing expression of a heterologous protein in chicken oviduct cells and may be operably linked to any nucleic acid encoding a heterologous polypeptide of interest including, for example, a cytokine, growth hormone, growth factor, enzyme, structural protein or the like.

5.2.2 Matrix Attachment Regions

In preferred embodiments of the invention, the vectors contain matrix attachment regions (MARs) that preferably flank the transgene sequences to reduce position effects on expression when integrated into the avian genome. In fact, 5' MARs and 3' MARs (also referred to as "scaffold attachment regions" or SARs) have been identified in the outer boundaries of the chicken lysozyme locus (Phi-Van et al., 1988, *E.M.B.O.J.* 7: 655-664; Phi-Van, L. and Stratling, W. H., 1996, *Biochem*. 35: 10735-10742). Deletion of a 1.32 kb or a 1.45 kb halves region, each comprising half of a 5' MAR, reduces positional variation in the level of transgene expression (Phi-Van and Stratling, supra).

The 5' matrix-associated region (5' MAR), located about −11.7 kb upstream of the chicken lysozyme transcription start site, can increase the level of gene expression by limiting the positional effects exerted against a transgene (Phi-Van et al., 1988, supra). At least one other MAR is located 3' downstream of the protein encoding region. Although MAR nucleic acid sequences are conserved, little cross-hybridization is seen, indicating significant overall sequence variation. However, MARs of different species can interact with the nucleomatrices of heterologous species, to the extent that the chicken lysozyme MAR can associate with the plant tobacco nucleomatrix as well as that of the chicken oviduct cells (Mlynarona et al., 1994, *Cell* 6: 417-426; von Kries et al., 1990, *Nucleic Acids Res*. 18: 3881-3885).

Gene expression must be considered not only from the perspective of cis-regulatory elements associated with a gene, and their interactions with trans-acting elements, but also with regard to the genetic environment in which they are located. Chromosomal positioning effects (CPEs), therefore, are the variations in levels of transgene expression associated with different locations of the transgene within the recipient genome. An important factor governing CPE upon the level of transgene expression is the chromatin structure around a transgene, and how it cooperates with the cis-regulatory elements. The cis-elements of the lysozyme locus are confined within a single chromatin domain (Bonifer et al., 1996, supra; Sippel et al., pgs. 133-147 in Eckstein F. & Lilley D. M. J. (eds), "Nucleic Acids and Molecular Biology", Vol. 3, 1989, Springer.

The lysozyme promoter region of chicken is active when transfected into mouse fibroblast cells and linked to a reporter gene such as the bacterial chloramphenicol acetyltransferase (CAT) gene. The promoter element is also effective when transiently transfected into chicken promacrophage cells. In each case, however, the presence of a 5' MAR element increased positional independency of the level of transcription (Stief et al., 1989, *Nature* 341: 343-345; Sippel et al., pgs. 257-265 in Houdebine L. M. (ed), "Transgenic Animals: Generation and Use").

The ability to direct the insertion of a transgene into a site in the genome of an animal where the positional effect is limited offers predictability of results during the development of a desired transgenic animal, and increased yields of the expressed product. Sippel and Steif disclose, in U.S. Pat. No. 5,731,178, which is incorporated by reference herein in its entirety, methods to increase the expression of genes introduced into eukaryotic cells by flanking a transcription unit with scaffold attachment elements, in particular the 5' MAR isolated from the chicken lysozyme gene. The transcription unit disclosed by Sippel and Steif was an artificial construct that combined only the −6.1 kb enhancer element and the proximal promoter element (base position −579 to +15) from the lysozyme gene. Other promoter associated elements were not included. However, although individual cis-regulatory elements have been isolated and sequenced, together with short regions flanking DNA, the entire nucleic acid sequence comprising the functional 5' upstream region of the lysozyme gene has not been determined in its entirety and therefore not employed as a functional promoter to allow expression of a heterologous transgene.

Accordingly, vectors of the invention comprise MARs, preferably both 5' and 3' MARs that flank the transgene, including the heterologous protein coding sequences and the regulatory sequences.

5.2.3 Nuclear Localization Signal Peptides

Targeting of the nucleic acids introduced into embryonic cells using methods of the invention may be enhanced by mixing the nucleic acid to be introduced with a nuclear localization signal (NLS) peptide prior to introduction, e.g., microinjection, of the nucleic acid. Nuclear localization signal (NLS) sequences are a class of short amino acid sequences which may be exploited for cellular import of linked cargo into a nucleus. The present invention envisions the use of any NLS peptide, including but not limited to, the NLS peptide of SV40 virus T-antigen.

An NLS sequence of the invention is an amino acid sequence which mediates nuclear transport into the nucleus, wherein deletion of the NLS prevents nuclear transport. In particular embodiments, a NLS is a highly cationic peptide. The present invention envisions the use of any NLS sequence, including but not limited to, SV40 virus T-antigen. NLSs known in the art include, but are not limited to those discussed in Cokol et al., 2000, *EMBO Reports*, 1(5):411-415, Boulikas, T., 1993, *Crit. Rev. Eukaryot. Gene Expr.*, 3:193-227, Collas, P. et al., 1996, *Transgenic Research*, 5: 451-458, Collas and Alestrom, 1997, *Biochem. Cell Biol.* 75: 633-640, Collas and Alestrom, 1998, *Transgenic Resarch*, 7: 303-309, Collas and Alestrom, *Mol. Reprod. Devel.*, 1996, 45:431-438, all of which are incorporated by reference in their entireties.

5.2.4 Codon-optimized Gene Expression

Another aspect of the present invention provides nucleic acid sequences encoding heterologous polypeptides that are codon-optimized for expression in avian cells, and derivatives and fragments thereof. When a heterologous nucleic acid is to be delivered to a recipient cell for expression therein, the sequence of the nucleic acid sequence may be modified so that the codons are optimized for the codon usage of the recipient species. For example, if the heterologous nucleic acid is transfected into a recipient chicken cell, the sequence of the expressed nucleic acid insert is optimized for chicken codon usage. This may be determined from the codon usage of at least one, and preferably more than one, protein expressed in a chicken cell. For example, the codon usage may be determined from the nucleic acid sequences encoding the proteins ovalbumin, lysozyme, ovomucin and ovotransferrin of chicken. Briefly, the DNA sequence for the target protein may be optimized using the BACKTRANSLATE® program of the Wisconsin Package, version 9.1 (Genetics Computer Group, Inc., Madison, Wis.) with a codon usage table compiled from the chicken (*Gallus gallus*) ovalbumin, lysozyme, ovomucoid, and ovotransferrin proteins. The template and primer oligonucleotides are then amplified, by any means known in the art, including but not limited to PCR with Pfu polymerase (STRATAGENE®, La Jolla Calif.).

In one exemplary embodiment of a heterologous nucleic acid for use by the methods of the present invention, a nucleic acid insert encoding the human interferon α2b polypeptide optimized for codon-usage by the chicken is microinjected into the cytoplasm of a stage 1 embryo. Optimization of the sequence for codon usage is useful in elevating the level of translation in avian eggs.

It is contemplated to be within the scope of the present invention for any nucleic acid encoding a polypeptide to be optimized for expression in avian cells. It is further contemplated that the codon usage may be optimized for a particular avian species used as a source of the host cells. In one embodiment of the present invention, the heterologous polypeptide is encoded using the codon-usage of a chicken.

5.2.5 Specific Vectors of the Invention

In a preferred embodiment, a transgene of the invention comprises a chicken, or other avian, lysozyme control region sequence which directs expression of the coding sequence within the transgene. A series of PCR amplifications of template chicken genomic DNA are used to isolate the gene expression control region of the chicken lysozyme locus. Two amplification reactions used the PCR primer sets 5pLMAR2 (5'-TGCCGCCTTCTTTGATATTC-3') (SEQ ID NO: 1) and LE-6.1kbrev1 (5'-TTGGTGGTAAGGC-CTTTTTG-3') (SEQ ID NO: 2) (Set 1) and lys-6.1 (5'-CTGGCAAGCTGTCAAAAACA-3') (SEQ ID NO: 3) and LysE1 Rev (5'-CAGCTCACATCGTCCAAAGA-3') (SEQ ID NO: 4) (Set 2). The amplified PCR products were united as a contiguous isolated nucleic acid by a third PCR amplification step with the primers SEQ ID NOS: 1 and 4, as described in Example 9 below.

The isolated PCR-amplified product, comprising about 12 kb of the nucleic acid region 5' upstream of the native chicken lysozyme gene locus, was cloned into the plasmid pCMV-LysSPIFNMM. pCMV-LysSPIFNMM comprises a modified nucleic acid insert encoding a human interferon α2b sequence and an SV40 polyadenylation signal sequence (SEQ ID NO: 8) 3' downstream of the interferon encoding nucleic acid. The sequence SEQ ID NO: 5 of the nucleic acid insert encoding human interferon α2b was in accordance with avian cell codon usage, as determined from the nucleotide sequences encoding chicken ovomucin, ovalbumin, ovotransferrin and lysozyme.

The nucleic acid sequence (SEQ ID NO: 6) (GenBank Accession No. AF405538) of the insert in pAVIJCR-A115.93.1.2 is shown in FIGS. 1A-E. The modified human interferon α2b encoding nucleotide sequence SEQ ID NO: 5 (GenBank Accession No. AF405539) and the novel chicken lysozyme gene expression control region SEQ ID NO: 7 (GenBank Accession No. AF405540), shown in FIGS. 2 and 3A-E respectively. A polyadenylation signal sequence that is suitable for operably linking to the polypeptide-encoding nucleic acid insert is the SV40 signal sequence SEQ ID NO: 8, as shown in FIG. 4.

The plasmid pAVIJCR-A115.93.1.2 was restriction digested with enzyme FseI to isolate a 15.4 kb DNA containing the lysozyme 5' matrix attachment region (MAR) and the −12.0 kb lysozyme promoter during the expression of the interferon-encoding insert, as described in Example 10, below. Plasmid pIIIilys was restriction digested with MluI and XhoI to isolate an approximately 6 kb nucleic acids, comprising the 3' lysozyme domain, the sequence of which (SEQ ID NO: 9) is shown in FIGS. 5A-C. The 15.4 kb and 6 kb nucleic acids were ligated and the 21.4 kb nucleic acid comprising the nucleic acid sequence SEQ ID NO: 10 as shown in FIGS. 6A-J was transformed into recipient STBL4 cells as described in Example 10, below.

The inclusion of the novel isolated avian lysozyme gene expression control region of the present invention upstream of a codon-optimized interferon-encoding sequence in pAVIJCR-A115.93.1.2 allowed expression of the interferon polypeptide in avian cells transfected by cytoplasmic microinjection, as described in Examples 3 and 4, below. The 3' lysozyme domain SEQ ID NO: 9, when operably linked downstream of a heterologous nucleic acid insert, also allows expression of the nucleic acid insert as described in Example 11, below. For example, the nucleic acid insert may encode a heterologous polypeptide such as the α2b interferon encoded by the sequence SEQ ID NO: 5.

It is further contemplated that any nucleic acid sequence encoding a polypeptide may be operably linked to the novel isolated avian lysozyme gene expression control region (SEQ ID NO: 7) and optionally operably linked to the 3' lysozyme domain SEQ ID NO. 9 so as to be expressed in a transfected avian cell. The plasmid construct pAVIJCR-Al 15.93.1.2 when transfected into cultured quail oviduct cells, which were then incubated for about 72 hours. ELISA assays of the cultured media showed that the transfected cells synthesized a polypeptide detectable with anti-human interferon α2b antibodies. Plasmid construct pAVIJCR-A212.89.2.1 and pAVIJCR-A212.89.2.3 transfected into chicken myelomonocytic HD11 cells yield detectable human α2b interferon, as described in Example 3 and 4 below, and shown in FIGS. 8-12.

The isolated chicken lysozyme gene expression control region (SEQ ID NO: 7) for use in the methods of the present invention comprises the nucleotide elements that are positioned 5' upstream of the lysozyme-encoding region of the native chicken lysozyme locus and which are necessary for the regulated expression of a downstream polypeptide-encoding nucleic acid. While not wishing to be bound by any one theory, the inclusion of at least one 5' MAR sequence of or reference element in the isolated control region may confer positional independence to a transfected gene operably linked to the novel lysozyme gene expression control region.

The isolated lysozyme gene expression control region (SEQ ID NO: 7) of the present invention is useful for reducing the chromosomal positional effect of a transgene operably linked to the lysozyme gene expression control region and transfected into a recipient avian cell. By isolating a region of the avian genome extending from a point 5' upstream of a 5' MAR of the lysozyme locus to the junction between the signal peptide sequence and a polypeptide-encoding region, cis-regulatory elements are also included that may allow gene expression in a tissue-specific manner.

The lysozyme promoter region of the present invention, therefore, will allow expression of an operably linked heterologous nucleic acid insert in a transfected avian cell such as, for example, an oviduct cell.

It is further contemplated that a recombinant DNA of the present invention may further comprise the chicken lysozyme 3' domain (SEQ. ID NO: 9) linked downstream of the nucleic acid insert encoding a heterologous polypeptide. The lysozyme 3' domain (SEQ ID NO: 9) includes a nucleic acid sequence encoding a 3' MAR domain that may cooperate with a 5' MAR to direct the insertion of the construct of the present invention into the chromosome of a transgenic avian, or may act independently of the 5' MAR.

Fragments of a nucleic acid encoding a portion of the subject lysozyme gene expression control region may also be useful as an autonomous gene regulatory element that may itself be operably linked to a polypeptide-encoding nucleic acid. Alternatively, the fragment may be combined with fragments derived from other gene promoters, such as an avian ovalbumin or ovomucoid promoter, thereby generating novel promoters having new properties or a combination of properties. As used herein, a fragment of the nucleic acid encoding an active portion of a lysozyme gene expression control region refers to a nucleotide sequence having fewer nucleotides than the nucleotide sequence encoding the entire nucleic acid sequence of the lysozyme gene expression control region, but at least 200 nucleotides.

The present invention also contemplates the use of antisense nucleic acid molecules that are designed to be complementary to a coding strand of a nucleic acid (i.e., complementary to an endogenous DNA or an mRNA sequence) or, alternatively, complimentary to a 5' or 3' untranslated region of the mRNA and therefore useful for regulating the expression of a gene by the lysozyme promoter.

Synthesized oligonucleotides can be produced in variable lengths when for example, non-naturally occurring polypeptide sequences are desired. The number of bases synthesized will depend upon a variety of factors, including the desired use for the probes or primers. Additionally, sense or antisense nucleic acids or oligonucleotides can be chemically synthesized using modified nucleotides to increase the biological stability of the molecule or of the binding complex formed between the anti-sense and sense nucleic acids. For example, acridine substituted nucleotides can be synthesized. Protocols for designing isolated nucleotides, nucleotide probes, and/or nucleotide primers are well-known to those of ordinary skill, and can be purchased commercially from a variety of sources (e.g., SIGMA GENOSYS®, The Woodlands, Tex. or The Great American Gene Co., Ramona, Calif.).

5.2.6 Recombinant Expression Vectors

A useful application of the novel promoters of the present invention, such as the avian lysozyme gene expression control region (SEQ ID NO: 7) or the MDOT promoter construct (SEQ ID NO: 11, Example 12, below) is the possibility of increasing the amount of a heterologous protein present in a bird, especially a chicken, by gene transfer. In most instances, a heterologous polypeptide-encoding nucleic acid insert transferred into the recipient animal host will be operably linked with a gene expression control region to allow the cell to initiate and continue production of the genetic product protein. A recombinant DNA molecule of the present invention can be transferred into the extra-chromosomal or genomic DNA of the host.

Figure 10:
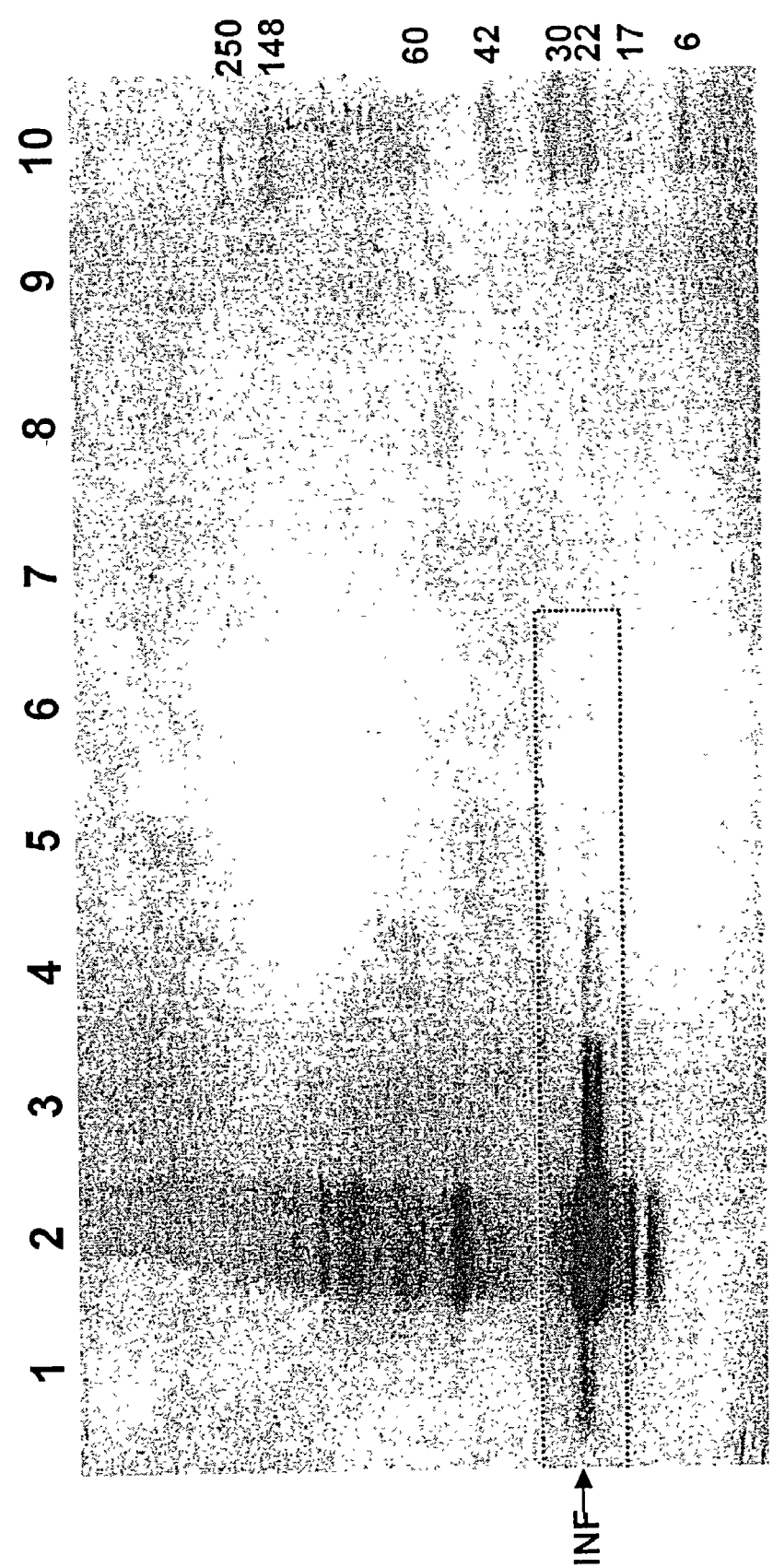
FIG. 10 illustrates the results of SDS-PAGE analysis of human IFN-α2b purified from the pooled egg whites obtained from transgenic chicken AVI-029.1, molecular weight markers; 2, transferrin/avidin markers; 3, ovalbumin/lysozyme markers; 4, ovoglobulins; 5, pooled egg white; 6, solubilized egg white; 7, cation exchange Pool #1; 8, cation exchange Pool #2; 9, HIC pool.

Expression of a foreign gene in an avian cell permits partial or complete post-translational modification such as, but not only, glycosylation, as shown, for example, in FIGS. 10-12, and/or the formation of the relevant inter- or intra-chain disulfide bonds. Examples of vectors useful for expression in the chicken *Gallus gallus* include pYepSec1 (Baldari et al., 1987, *E.M.B.O.J.*, 6: 229-234; incorporated herein by reference in its entirety) and pYES2 (INVITROGEN® Corp., San Diego, Calif.).

The present invention contemplates that the injected cell may transiently contain the injected DNA, whereby the recombinant DNA or expression vector may not be integrated into the genomic nucleic acid. It is further contemplated that the injected recombinant DNA or expression vector may be stably integrated into the genomic DNA of the recipient cell, thereby replicating with the cell so that each daughter cell receives a copy of the injected nucleic acid. It is still further contemplated for the scope of the present invention to include a transgenic animal producing a heterologous protein expressed from an injected nucleic acid according to the present invention.

Heterologous nucleic acid molecules can be delivered to cells using the cytoplasmic microinjection method or any other method of the present invention. The nucleic acid molecule may be inserted into a cell to which the nucleic acid molecule (or promoter coding region) is heterologous (i.e., not normally present). Alternatively, the recombinant DNA molecule may be introduced into cells which normally contain the recombinant DNA molecule or the particular coding region, as, for example, to correct a deficiency in the expression of a polypeptide, or where over-expression of the polypeptide is desired.

Another aspect of the present invention, therefore, is a method of expressing a heterologous polypeptide in an avian cell by transfecting the avian cell with a selected heterologous nucleic acid comprising an avian promoter operably linked to a nucleic acid insert encoding a polypeptide and, optionally, a polyadenylation signal sequence. The transfected cell, which may be an avian embryonic cell microinjected with a heterologous nucleic acid, will generate a transgenic embryo that after introduction into a recipient hen will be laid as a hard-shell egg and develop into a transgenic chick.

In another embodiment of the present invention, the nucleic acid insert comprises the chicken lysozyme gene expression control region, a nucleic acid insert encoding a human interferon α2b and codon optimized for expression in an avian cell, and a chicken 3' domain, i.e., downstream enhancer elements.

In one embodiment of the present invention, the transgenic animal is an avian selected from a turkey, duck, goose, quail, pheasant, ratite, and ornamental bird or a feral bird. In another embodiment, the avian is a chicken and the heterologous polypeptide produced under the transcriptional control of the avian promoter is produced in the white of an egg. In yet another embodiment of the present invention, the heterologous polypeptide is produced in the serum of a bird.

5.3 Heterologous Proteins Produced by Transgenic Avians

Methods of the present invention, providing for the production of heterologous protein in the avian oviduct (or other tissue leading to deposition of the protein into the egg) and the production of eggs containing heterologous protein, involve providing a suitable vector coding for the heterologous protein and introducing the vector into embryonic cells such as a single cell embryo such that the vector is integrated into the avian genome. A subsequent step involves deriving a mature transgenic avian from the transgenic embryonic cells produced in the previous steps by transferring the injected cell or cells into the infundibulum of a recipient hen;

producing a hard shell egg from that hen; and allowing the egg to develop and hatch to produce a transgenic bird.

A transgenic avian so produced from transgenic embryonic cells is known as a founder. Such founders may be mosaic for the transgene (in certain embodiments, the founder has 5%, 10%, 20%, 30%, 40%, 50%, 60%, 70%, 90%, 100% of the cells containin the transgene. The invention further provides production of heterologous proteins in other tissues of the transgenic avians. Some founders will carry the transgene in the tubular gland cells in the magnum of their oviducts. These birds will express the exogenous protein encoded by the transgene in their oviducts. If the exogenous protein contains the appropriate signal sequences, it will be secreted into the lumen of the oviduct and into the white of an egg.

Some founders are germ-line founders. A germ-line founder is a founder that carries the transgene in genetic material of its germ-line tissue, and may also carry the transgene in oviduct magnum tubular gland cells that express the exogenous protein. Therefore, in accordance with the invention, the transgenic bird may have tubular gland cells expressing the exogenous protein and the offspring of the transgenic bird will also have oviduct magnum tubular gland cells that express the exogenous protein. Alternatively, the offspring express a phenotype determined by expression of the exogenous gene in a specific tissue of the avian. In preferred embodiments, the heterologous proteins are produced from transgenic avians that were not (or the founder ancestors were not) using a eukaryotic viral vector, or a retroviral vector.

The present invention can be used to express, in large yields and at low cost, a wide range of desired proteins including those used as human and animal pharmaceuticals, diagnostics, and livestock feed additives. Proteins such as growth hormones, cytokines, structural proteins and enzymes, including human growth hormone, interferon, lysozyme, and β-casein, are examples of proteins that are desirably expressed in the oviduct and deposited in eggs according to the invention. Other possible proteins to be produced include, but are not limited to, albumin, α-1 antitrypsin, antithrombin III, collagen, factors VIII, IX, X (and the like), fibrinogen, hyaluronic acid, insulin, lactoferrin, protein C, erythropoietin (EPO), granulocyte colony-stimulating factor (G-CSF), granulocyte macrophage colony-stimulating factor (GM-CSF), tissue-type plasminogen activator (tPA), feed additive enzymes, somatotropin, and chymotrypsin. Immunoglobulins and genetically engineered antibodies, including immunotoxins that bind to surface antigens on human tumor cells and destroy them, can also be expressed for use as pharmaceuticals or diagnostics. It is contemplated that immunoglobulin polypeptides expressed in avian cells following transfection by the methods of the present invention may include monomeric heavy and light chains, single-chain antibodies or multimeric immunoglobulins comprising variable heavy and light chain regions, i.e., antigen-binding domains, or intact heavy and light immunoglobulin chains.

5.3.1 Protein Recovery

The protein of the present invention may be produced in purified form by any known conventional technique. For example, chicken cells may be homogenized and centrifuged. The supernatant can then be subjected to sequential ammonium sulfate precipitation and heat treatment. The fraction containing the protein of the present invention is subjected to gel filtration in an appropriately sized dextran or polyacrylamide column to separate the proteins. If necessary, the protein fraction may be further purified by HPLC. In another embodiment, an affinity column is used, wherein the protein is expressed with a tag.

Accordingly, the invention provides proteins that are produced by transgenic avians of the invention. In a preferred embodiment, the protein is produced and isolated from an avian egg. In another embodiment, the protein is produced and isolated from avian serum.

5.3.2 Multimeric Proteins

The invention, in preferred embodiments, provides methods for producing multimeric proteins, preferably immunoglobulins, such as antibodies, and antigen binding fragments thereof.

In one embodiment of the present invention, the multimeric protein is an immunoglobulin, wherein the first and second heterologous polypeptides are an immunoglobulin heavy and light chains respectively. Illustrative examples of this and other aspects and embodiments of the present invention for the production of heterologous multimeric polypeptides in avian cells are fully disclosed in U.S. patent application Ser. No. 09/877,374, filed Jun. 8, 200', by Rapp, which is incorporated herein by reference in its entirety. In one embodiment of the present invention, therefore, the multimeric protein is an immunoglobulin wherein the first and second heterologous polypeptides are an immunoglobulin heavy and light chain respectively. Accordingly, the invention provides immunoglobulin and other multimeric proteins that have been produced by transgenic avians of the invention.

In the various embodiments of this aspect of the present invention, an immunoglobulin polypeptide encoded by the transcriptional unit of at least one expression vector may be an immunoglobulin heavy chain polypeptide comprising a variable region or a variant thereof, and may further comprise a D region, a J region, a C region, or a combination thereof. An immunoglobulin polypeptide encoded by the transcriptional unit of an expression vector may also be an immunoglobulin light chain polypeptide comprising a variable region or a variant thereof, and may further comprise a J region and a C region. It is also contemplated to be within the scope of the present invention for the immunoglobulin regions to be derived from the same animal species, or a mixture of species including, but not only, human, mouse, rat, rabbit and chicken. In preferred embodiments, the antibodies are human or humanized.

In other embodiments of the present invention, the immunoglobulin polypeptide encoded by the transcriptional unit of at least one expression vector comprises an immunoglobulin heavy chain variable region, an immunoglobulin light chain variable region, and a linker peptide thereby forming a single-chain antibody capable of selectively binding an antigen.

Another aspect of the present invention provides a method for the production in an avian of an heterologous protein capable of forming an antibody suitable for selectively binding an antigen comprising the step of producing a transgenic avian incorporating at least one transgene, wherein the transgene encodes at least one heterologous polypeptide selected from an immunoglobulin heavy chain variable region, an immunoglobulin heavy chain comprising a variable region and a constant region, an immunoglobulin light chain variable region, an immunoglobulin light chain comprising a variable region and a constant region, and a single-chain antibody comprising two peptide-linked immunoglobulin variable regions. Preferably, the antibody is expressed such that it is deposited in the white of the developing eggs of the avian. The hard shell avian eggs thus produced can be harvested and the heterologous polypeptide capable of forming or which formed an antibody can be isolated from the harvested egg. It is also understood that the heterologous polypeptides may also be expressed under the transcrinptional control of promoters that allow for release of the polypeptides into the serum of the transgenic animal. Exemplary promoters for non-tissue specific production of a heterologous protein are the CMV promoter and the RSV promoter.

In one embodiment of this method of the present invention, the transgene comprises a transcription unit encoding a first and a second immunoglobulin polypeptide operatively linked to a transcription promoter, a transcription terminator and, optionally, an internal ribosome entry site (IRES)(see, for example, U.S. Pat. No. 4,937,190 to Palmenberg et al., the contents of which is incorporated herein by reference in its entirety).

In an embodiment of this method of the present invention, the isolated heterologous protein is an antibody capable of selectively binding to an antigen. In this embodiment, the antibody may be generated within the serum of an avian or within the white of the avian egg by combining at least one immunoglobulin heavy chain variable region and at least one immunoglobulin light chain variable region, preferably cross-linked by at least one di-sulfide bridge. The combination of the two variable regions will generate a binding site capable of binding an antigen using methods for antibody reconstitution that are well known in the art.

It is, however, contemplated to be within the scope of the present invention for immunoglobulin heavy and light chains, or variants or derivatives thereof, to be expressed in separate transgenic avians, and therefore isolated from separate media including serum or eggs, each isolate comprising a single species of immunoglobulin polypeptide. The method may further comprise the step of combining a plurality of isolated heterologous immunoglobulin polypeptides, thereby producing an antibody capable of selectively binding to an antigen. In this embodiment, two individual transgenic avians may be generated wherein one transgenic produces serum or eggs having an immunoglobulin heavy chain variable region, or a polypeptide comprising such, expressed therein. A second transgenic animal, having a second transgene, produces serum or eggs having an immunoglobulin light chain variable region, or a polypeptide comprising such, expressed therein. The polypeptides may be isolated from their respective sera and eggs and combined in vitro to generate a binding site capable of binding an antigen.

Examples of therapeutic antibodies that can be used in methods of the invention include but are not limited to HERCEPTIN® (Trastuzumab) (Genentech, Calif.) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath IH/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); ICM3 is a humanized anti-ICAM3 antibody (ICOS Pharm); IDEC-114 is a primatied anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-a IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); and CAT-152 is a human anti-TGF-$β_2$ antibody (Cambridge Ab Tech).

5.4 Pharmaceutical Compositions

The present invention further provides pharmaceutical compositions, formulations, dosage units and methods of administration comprising the heterologous proteins produced by the transgenic avians using methods of the invention. Preferably, compositions of the invention comprise a prophylactically or therapeutically effective amount of a the heterologous protein, and a pharmaceutically acceptable carrier.

The term "carrier" refers to a diluent, adjuvant, excipient, or vehicle with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabliizing, thickening, lubricating and coloring agents may be used. When administered to a patient, the compounds of the invention and pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propyleneglycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in "Remington's Pharmaceutical Sciences" by E. W. Martin.

In a preferred embodiment, the heterologous proteins are formulated in accordance with routine procedures as a pharmaceutical composition adapted for intravenous administration to human beings. Typically, compounds of the invention for intravenous administration are solutions in sterile isotonic aqueous buffer. Where necessary, the compositions may also include a solubilizing agent. Compositions for intravenous administration may optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the heterologous protein of the invention is to be administered by infusion, it can be dispensed, for example, with an infusion bottle containing sterile pharmaceutical grade water or saline. Where the composition of the invention is administered by injection, an ampoule of sterile water for injection or saline can be provided so that the ingredients may be mixed prior to administration.

Compositions for oral delivery may be in the form of tablets, lozenges, aqueous or oily suspensions, granules, powders, emulsions, capsules, syrups, or elixirs, for example. Orally administered compositions may contain one or more optional agellis, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharin, cellulose, magnesium carbonate, etc. Such vehicles are preferably of pharmaceutical grade.

Further, the effect of the heterologous proteins may be delayed or prolonged by proper formulation. For example, a slowly soluble pellet of the compound may be prepared and incorporated in a tablet or capsule. The technique may be improved by making pellets of several different dissolution rates and filling capsules with a mixture of the pellets. Tablets or capsules may be coated with a film which resists dissolution for a predictable period of time. Even the parenteral preparations may be made long-acting, by dissolving or suspending the compound in oily or emulsified vehicles which allow it to disperse only slowly in the serum.

5.5 Transgenic Avians

Another aspect of the present invention concerns transgenic avians, preferably chicken or quail, produced by methods of the invention described in section 5.1 infra, preferably by microinjecting a nucleic acid comprising a transgene into an avian embryo by the cytoplasmic microinjection methods of the present invention. Following introduction of the selected nucleic acid into an early stage avian embryo by the methods of the present invention, the embryo is transferred into the reproductive tract of a recipient hen. The embryo containing the transgene then develops inside the recipient hen and travels through the oviduct thereof, where it is encapsulated by natural egg white proteins and a natural egg shell. The egg is laid and can be incubated and hatched to produce a transgenic chick. The resulting transgenic avian chick (i.e, the G0) will carry one or more desired transgene(s) some or all of its cells, preferably in its germ line. These G0 transgenic avians can be bred using methods well known in the art to generate second generation (i.e., G1s) transgenic avians that carry the transgene, i.e., achieve germline transmission of the transgene. In preferred embodiments, the methods of the invention result in germline transmission, i.e., percentage of G0s that transmit the transgene to progeny (G1s), that is greater than 5%, preferably, greater than 10%, 20%, 30%, 40%, and, most preferably, greater than 50%, 60%, 70%, 80%, 90% or even 100%. In other embodiments, the efficiency of transgenesis (i.e., number of G0s containing the transgene) is greater than 2%, 5%, 10%, 20%, 30%, 40%, 50%, 60%, 70%, 80% or 99%.

Following maturation, the transgenic avian and/or transgenic progeny thereof, may lay eggs containing one or more desired heterologous protein(s) expressed therein and that can be easily harvested therefrom. The G1 chicks, when sexually mature, can then be bred to produce progeny that are homozygous or heterozygous for the transgene.

A transgenic avian of the invention may contain at least one transgene, at least two transgenes, at least 3 transgenes, at least 4 transgenes, at least 5 transgenes, and preferably, though optionally, may express the subject nucleic acid encoding a polypeptide in one or more cells in the animal, such as the oviduct cells of the chicken. In embodiments of the present invention, the expression of the transgene may be restricted to specific subsets of cells, tissues, or developmental stages utilizing, for example, cis-acting sequences that control expression in the desired pattern. Toward this end, it is contemplated that tissue-specific regulatory sequences, or tissue-specific promoters, and conditional regulatory sequences may be used to control expression of the transgene in certain spatial patterns. Moreover, temporal patterns of expression can be provided by, for example, conditional recombination systems or prokaryotic transcriptional regulatory sequences. The inclusion of a 5' MAR region, and optionally the 3' MAR on either end of the sequence, in the expression cassettes suitable for use in the methods of the present invention may allow the heterologous expression unit to escape the chromosomal positional effect (CPE) and therefore be expressed at a more uniform level in transgenic tissues that received the transgene by a route other than through germ line cells.

The transgenes may, in certain embodiments, be expressed conditionally, e.g., the heterologous protein coding sequence is under the control of an inducible promoter, such as a prokaryotic promoter or operator that requires a prokaryotic inducer protein to be activated. Operators present in prokaryotic cells have been extensively characterized in vivo and in vitro and can be readily manipulated to place them in any position upstream from or within a gene by standard techniques. Such operators comprise promoter regions and regions thai specifically bind proteins such as activators and repressors. One example is the operator region of the lexA gene of *E. coli* to which the LexA polypeptide binds. Other exemplary prokaryotic regulatory sequences and the corresponding trans-activating prokaryotic proteins are disclosed by Brent and Ptashne in U.S. Pat. No. 4,833,080 (the contents of which is herein incorporated by reference in its entirety). Transgenic animals can be created which harbor the subject transgene under transcriptional control of a prokaryotic sequence or other activator sequence that is not appreciably activated by avian proteins. Breeding of this transgenic animal with another animal that is transgenic for the corresponding trans-activator can be used to activate of the expression of the transgene. Moreover, expression of the conditional transgenes can also be induced by gene therapy-like methods wherein a gene encoding the trans-activating protein, e.g., a recombinase or a prokaryotic protein, is delivered to the tissue and caused to be expressed, such as in a cell-type specific manner.

Transactivators in these inducible or repressible transcriptional regulation systems are designed to interact specifically with sequences engineered into the transgene. Such systems include those regulated by tetracycline ("tet systems"), interferon, estrogen, ecdysone, Lac operator, progesterone antagonist RU486, and rapamycin (FK506) with tet systems being particularly preferred (see, e.g., Gingrich and Roder, 1998, Annu. Rev. Neurosci. 21: 377-405; incorporated herein by reference in its entirety). These drugs or hormones (or their analogs) act on modular transactivators composed of natural or mutant ligand-binding domains and intrinsic or extrinsic DNA binding and transcriptional activation domains. In certain embodiments, expression of the heterologous peptidecan be regulated by varying the concentration of the drug or hormone in medium in vitro or in the diet of the transgenic animal in vivo.

In a preferred embodiment, the control elements of the tetracycline-resistance operon of E. coli is used as an inducible or repressible transactivator or transcriptional regulation system ("tet system") for conditional expression of the transgene. A tetracycline-controlled transactivator can require either the presence or absence of the antibiotic tetracycline, or one of its derivatives, e.g., doxycycline (dox), for binding to the tet operator of the tet system, and thus for the activation of the tet system promoter (Ptet).

In a specific embodiment, a tetracycline-repressed regulatable system (TrRS) is used (Agha-Mohammadi and Lotze, 2000, J. Clin. Invest. 105(9): 1177-83; Shockett et al., 1995, Proc. Natl. Acad. Sci. USA 92: 6522-26 and Gossen and Bujard, 1992, Proc. Natl. Acad. Sci. USA 89: 5547-51; incorporated herein by reference in their entireties).

In another embodiment, a reverse tetracycline-controlled transactivator, e.g., rtTA2 S-M2, is used. rtTA2S-M2 transactivator has reduced basal activity in the absence doxycycline, increased stability in eukaryotic cells, and increased doxycycline sensitivity (Urlinger et al., 2000, Proc. Natl. Acad. Sci. USA 97(14): 7963-68; incorporated herein by reference in its entirety). In another embodiment, the tet-repressible system described by Wells et al. (1999, Transgenic Res. 8(5): 371-81; incorporated herein by reference in its entirety) is used. In one aspect of the embodiment, a single plasmid Tet-repressible system is used. In another embodiment, the GAL4-UAS system (Ornitz et al., 1991, Proc. Natl. Acad. Sci. USA 88:698-702; Rowitch et al., 1999, J. Neuroscience 19(20):8954-8965; Wang et al., 1999, Proc. Natl. Acad. Sci. USA 96:8483-8488; Lewandoski, 2001, Nature Reviews (Genetics) 2:743-755) or a GAL4-VP16 fusion protein system (Wang et al., 1999, Proc. Natl. Acad. Sci. USA 96:8483-8488) is used.

In other embodiments, conditional expression of a transgene is regulated by using a recombinase system that is used to turn on or off the gene's expression by recombination in the appropriate region of the genome in which the potential drug target gene is inserted. The transgene is flanked by recombinase sites, e.g., FRT sites. Such a recombinase system can be used to turn on or off expression a transgene (for review of temporal genetic switches and "tissue scissors" using recombinases, see Hennighausen & Furth, 1999, Nature Biotechnol. 17: 1062-63). Exclusive recombination in a selected cell type may be mediated by use of a site-specific recombinase such as Cre, FLP-wild type (wt), FLP-L or FLPe. Recombination may be effected by any art-known method, e.g., the method of Doetschman et al. (1987, Nature 330: 576-78; incorporated herein by reference in its entirety); the method of Thomas et al., (1986, Cell 44: 419-28; incorporated herein by reference in its entirety); the Cre-loxP recombination system (Sternberg and Hamilton, 1981, J. Mol. Biol. 150: 467-86; Lakso et al., 1992, Proc. Natl. Acad. Sci. USA 89: 6232-36; which are both incorporated herein by reference in their entireties); the FLP recombinase system of Saccharomyces cerevisiae (O'Gorman et al., 1991, Science 251: 1351-55); the Cre-loxP-tetracycline control switch (Gossen and Bujard, 1992, Proc. Natl. Acad. Sci. USA 89: 5547-51, incorporated herein by reference in its entirety); and ligand-regulated recombinase system (Kellendonk et al., 1999, J. Mol. Biol. 285: 175-82; incorporated herein by reference in its entirety). Preferably, the recombinase is highly active, e.g., the Cre-loxP or the FLPe system, and has enhanced thermostability (Rodriguez et al., 2000, Nature Genetics 25: 139-40; incorporated herein by reference in its entirety).

In a specific embodiment, the ligand-regulated recombinase system of Kellendonk et al. (1999, J. Mol. Biol. 285: 175-82; incorporated herein by reference in its entirety) can be used. In this system, the ligand-binding domain (LBD) of a receptor, e.g., the progesterone or estrogen receptor, is fused to the Cre recombinase to increase specificity of the recombinase.

In the case of an avian, a heterologous polypeptide or polypeptides encoded by the transgenic nucleic acid may be secreted into the oviduct lumen of the mature animal and deposited as a constituent component of the egg white into eggs laid by the animal. It is also contemplated to be within the scope of the present invention for the heterologous polypeptides to be produced in the serum of a transgenic avian.

A leaky promoter such as the CMV promoter may be operably linked to a transgene, resulting in expression of the transgene in all tissues of the transgenic avian, resulting in production of, for example, immunoglobulin polypeptides in the serum. Alternatively, the transgene may be operably linked to an avian promoter that may express the transgene in a restricted range of tissues such as, for example, oviduct cells and macrophages so that the heterologous protein may be identified in the egg white or the serum of a transgenic avian. Transgenic avians produced by the cytoplasmic microinjection method of the present invention will have the ability to lay eggs that contain one or more desired heterologous protein(s) or variant thereof.

One embodiment of the present invention, therefore, is a transgenic avian produced by the cytoplasmic microinjection methods of the present invention and having a heterologous polynucleotide sequence comprising a nucleic acid insert encoding a heterologous polypeptide and operably linked to an avian lysozyme gene expression control region, the gene expression control region comprising at least one 5' matrix attachment region, an intrinsically curved DNA region, at least one transcription enhancer, a negative regulatory element, at least one hormone responsive element, at least one avian CR1 repeat element, and a proximal lysozyme promoter and signal peptide-encoding region.

Another embodiment of the present invention provides a transgenic avian further comprising a transgene with a lysozyme 3' domain.

Accordingly, the invention provides transgenic avians produced by methods of the invention, preferably by cytoplasmic microinjection as described infra. In preferred embodiments, the transgenic avian contains a transgene comprising a heterologous peptide coding sequence operably linked to a promoter and, in certain embodiments, other regulatory elements. In more preferred embodiments, the transgenic avians of the invention produce heterologous proteins, preferably in a tissue specific manner, more preferably such that they are deposited in the serum and, most preferably, such that the heterologous protein is deposited into the egg, particularly in the egg white. In preferred embodiments, the transgenic avians produce eggs containing greater than 5 µg, 10 µg, 50 µg, 100 µg, 250 µg, 500 µg, or 750 µg, more preferably greater than 1 mg, 2 mg, 5 mg, 10 mg, 20 mg, 50 mg, 100 mg, 200 mg, 500 mg, 700 mg, 1 gram, 2 grams, 3 grams, 4 grams or 5 grams of the heterologous protein. In preferred embodiments, the transgenic avians produce an immunoglobulin molecule and deposit the immunoglobulin in the egg or serum of the avian, and preferably, the immunoglobulin isolated from the egg or serum specifically binds its cognate antigen. The antibody so produced may bind the antigen with the same, greater or lesser affinity than the antibody produced in a mammalian cell, such as a myeloma or CHO cell.

In specific embodiments, the transgenic avians of the invention were not produced or are not progeny of a transgenic ancestor produced using a eukaryotic viral vector, more particularly, not a retroviral vector (although, in certain embodiments, the vector may contain sequences derived from a eukaryotic viral vector, such as promoters, origins of replication, etc.). The transgenic avians of the invention include G0 avians, founder transgenic avians, G1 transgenic avians, avians containing the transgene in the sperm or ova, avians mosaic for the transgene and avians containing copies of the transgene in most or all of the cells. Contemplated by the invention are transgenic avians in which the transgene is episomal. In more preferred embodiments, the transgenic avians have the transgene integrated into one or more chromosomes. Chromosomal integration can be detected using a variety of methods well known in the art, such as, but not limited to, Southern blotting, PCR, etc.

6. EXAMPLES

The present invention is further illustrated by the following examples. Each example is provided by way of explanation of the invention, and is not intended to be a limitation of the invention. In fact, it will be apparent to those skilled in the art that various modifications, combination, additions, deletions and variations can be made in the present invention without departing from the scope or spirit of the invention. For instance, features illustrated or described as part of one embodiment can be used in another embodiment to yield a still further embodiment. It is intended that the present invention covers such modifications, combinations, additions, deletions and variations as come within the scope of the appended claims and their equivalents.

The contents of all references, published patent applications, and patents cited throughout the present application are hereby incorporated by reference in their entirety.

6.1 Example 1

Cytoplasmic Microinjections (a) Preparation of DNA for microinjection: The plasmid pAVIJCR-A115.93.1.2 (containing the −12.0 kb lysozyme promoter controlling expression of human interferon α2b) was purified with a QIAGEN® Plasmid Maxi Kit (QIAGEN®, Valencia, Calif.), and 100 µg of the plasmid were restriction digested with NotI restriction enzyme. The digested DNA was phenol/$CHCl_3$ extracted and ethanol precipitated. Recovered DNA was resuspended in 1 mM Tris-HCl (pH 8.0) and 0.1 mM EDTA, then placed overnight at 4° C. DNA was quantified by spectrophotometry and diluted to the appropriate concentration. DNA samples which were bound with the SV40 T antigen nuclear localization signal peptide (NLS peptide, amino acid sequence CGGPKKKRKVG (SEQ ID NO: 12)) were first resuspended in 0.25 M KCl, and NLS peptide was added to achieve a peptide DNA molar ratio of 100:1 (Collas and Alestrom, 1996, *Mol. Reprod. Develop.* 45: 431-438, the contents of which are incorporated by reference in its entirety). The DNA samples were bound to the SV40 T antigen NLS peptide by incubation for 15 minutes.

(b) Cytoplasmic microinjections: The germinal disc of the avian egg was positioned in, and illuminated by the incident light beam, then the micropipette was moved to a position whereby the tip of the micropipette was over the area of the germinal disc and therefore optimally placed for the insertion of the micropipette into the germinal disc. The tip of the micropipette was then pressed onto the vitelline membrane of the avian egg, to a depth of about 20 microns below the general plane of the membrane. The vitelline membrane resisted penetration by the micropipette and therefore the tip indented the vitelline membrane without piercing the membrane. The depth of the indentation formed by the pressure of the tip of the micropipette on the vitelline membrane can be determined by two methods. The micropipette may be pre-marked about 20 microns from the tip. When the mark is about level with the general plane of the membrane, the tip will enter the germinal disc once the vitelline membrane is penetrated. The distance for the micropipette to be depressed may also be controlled by using the micropipette bevel as reference. In this method, the injection needle penetrates the vitelline membrane up to a point where only the apical end of the opening of the bevel is visible above the vitelline membrane, while the remaining of the opening is located inside the germinal disk. The movement of the micropipette relative to an avian germinal disc is monitored by the obliquely angled macro monitoring unit, comprising a focusable macro lens capable of delivering a focused magnified image of the avian germinal disc to an electronic camera for display by a monitor. The oblique angle of the macro lens shows the depth of movement of the micropipette relative to the vitelline membrane and the degree of indentation thereof, more distinctly than if a vertical microscope objective-is used to monitor the microinjection. Pulses of piezo-electric induced oscillations were applied to the micropipette once it was in contact with the indented vitelline membrane. The vibrating tip of the micropipette drills through the vitelline membrane. The fluid contents of the micropipette are then injected into the germinal disc by positive hydraulic pressure exerted on the lumen and the contents therein, by the pressure-regulating system.

Approximately 100 nanoliters of DNA were injected into a germinal disc of stage 1 White Leghorn embryos obtained two hours after oviposition of the previous egg. DNA amounts per injection ranged from 1 nanoliter to 100 nanoliters.

Injected embryos were surgically transferred to recipient hens via ovum transfer according to the method of Christmann et al. (PCT/US01/26723, the contents of which are incorporated by reference in its entirety), and hard shell eggs were incubated and hatched (Olsen and Neher, 1948, *J. Exp. Zoo.* 109: 355-366).

6.2 Example 2

PCR Analysis of Chick Blood DNA (a) DNA extraction. Whole blood from one-week old chicks was collected with heparinized capillary tubes. Red blood cell (RBC) nuclei were released and washed with lysis buffer solution. DNA's from RBC nuclei were extracted by digestion with proteinase K (1 mg/ml) and precipitated with ethanol. Purified DNA was resuspended in 1 mM Tris-HCl (pH 8.0) and 0.1 mM EDTA and quantitated.

Figure 7:
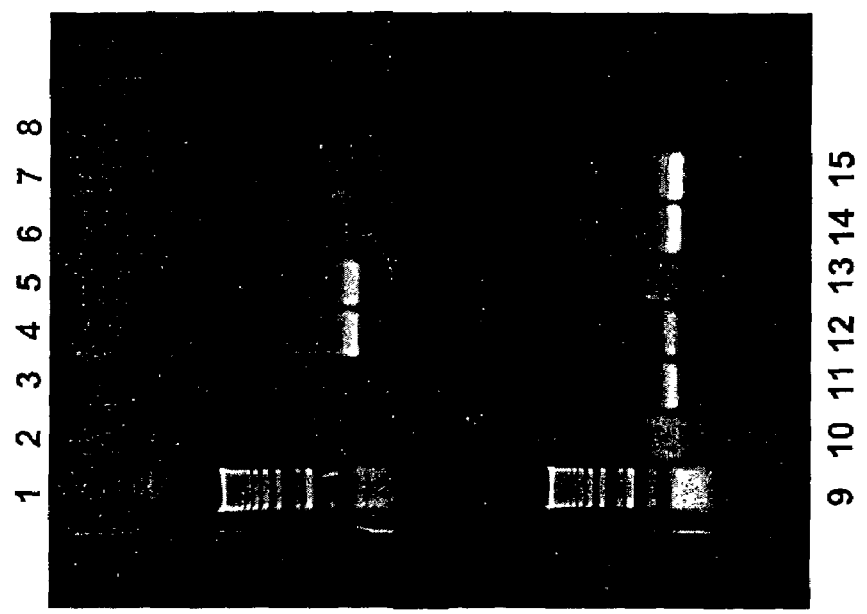

(b) PCR analysis of chick blood DNA. Genomic DNA samples from one-week old chicks were analyzed by PCR using primers LYS051 for (5'-TGCATCCTTCAGCACT-TGAG-3')(SEQ ID NO: 13) and IFN-3 (5'-AACTCCTCT-TGAGGAAAGCC-3')(SEQ ID NO: 14)). This primer set amplifies a 584 bp region of the transgene carried by the pAVIJCR-A115.93.1.2 plasmid. Three hundred nanograms of genomic DNA were added to a 50 µl reaction mixture (1×Promega PCR Buffer with 1.5 mM $MgCl_2$, 200 µM of each dNTP, 5 µM primers) and 1.25 units of Taq DNA polymerase (Promega). The reaction mixtures were heated for 4 minutes at 94° C., and then amplified for 34 cycles at 94° C. for 1 min, 60°for 1 min and 72° C. for 1 min. The samples were heated in a final cycle for 4 minutes at 72° C. PCR products were detected on a 0.8% agarose gel with ethidium bromide staining, as shown in FIG. 7.

6.3 Example 3

Human Interferon α2b Expression in Chick Serum

Figure 8:
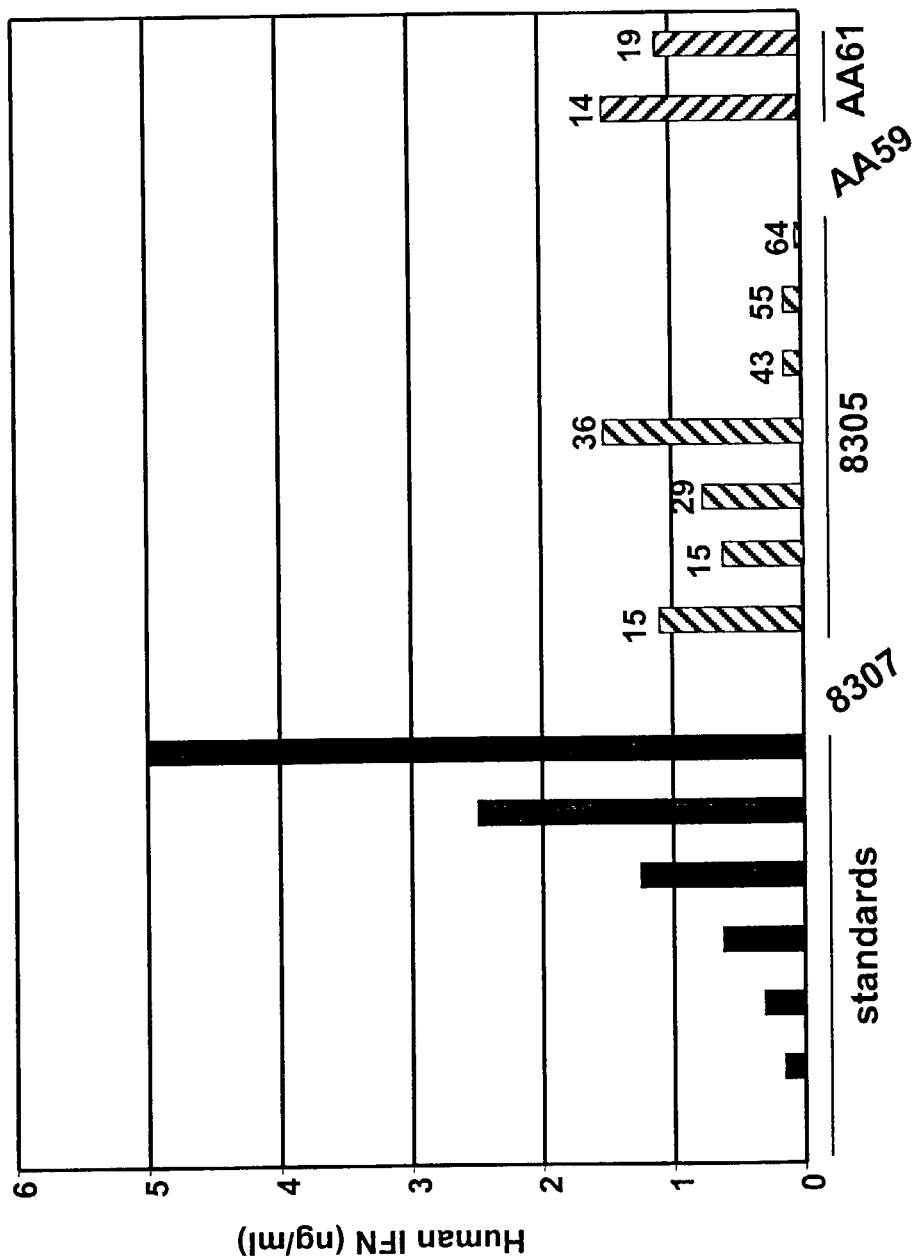
FIG. 8 illustrates the results of ELISA for human IFN α2b in transgenic hen serum. 8307 and AA59 are serum samples collected from negative control birds. Numbers on top of the bars represent the number of days after hatching that the serum was collected.
Figure 9:
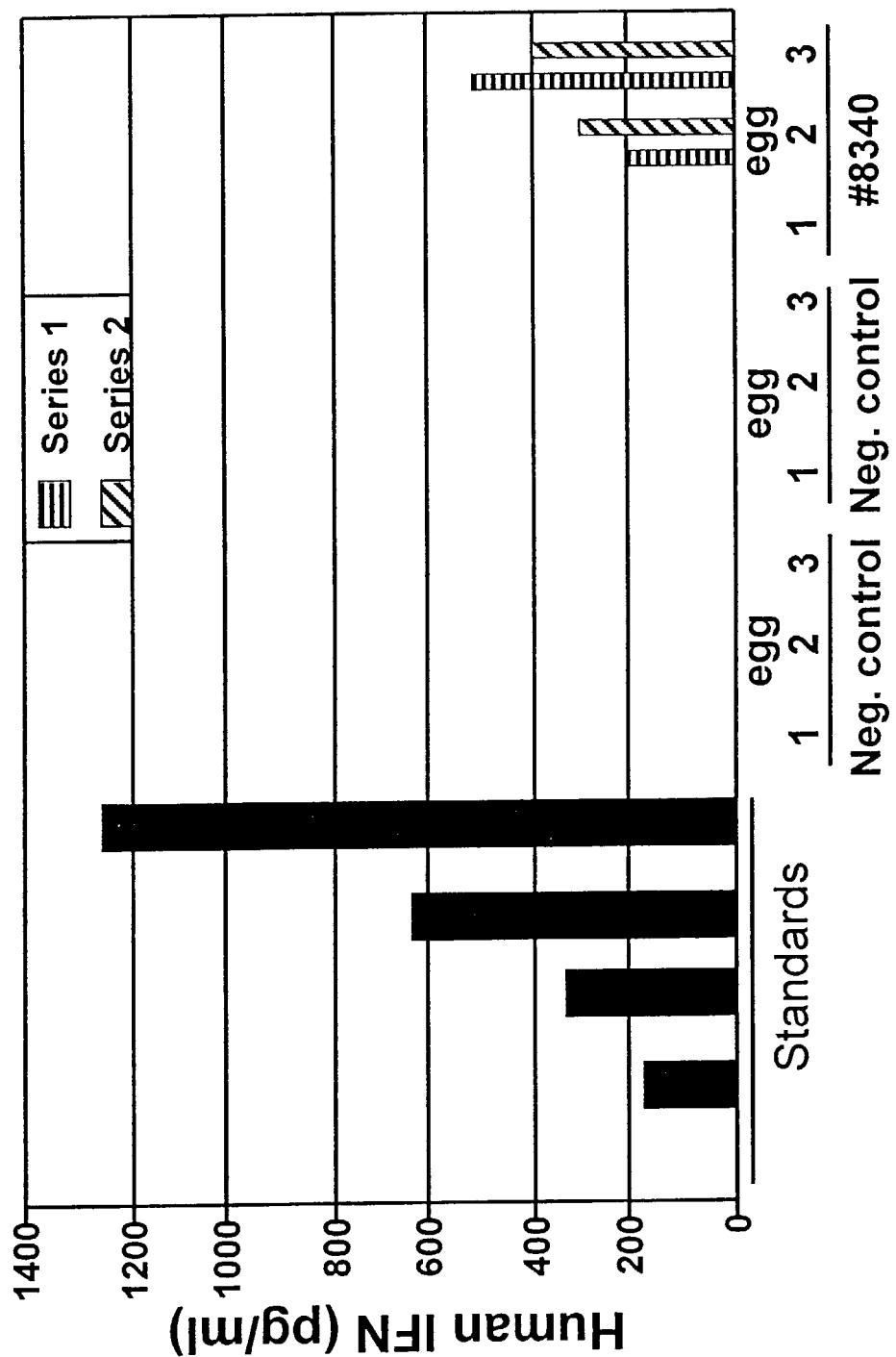
FIG. 9 illustrates the results of ELISA for human IFN α2b in transgenic hen egg white. Three eggs from each hen were assayed.

One week after hatching, blood was collected from chicks using heparinized capillary tubes. Blood was then added to an equal volume of phosphate buffered saline, centrifuged at 200×g, and 100 microliters of the supernatant were assayed by human IFN ELISA (PBL Biomedical Laboratories, New Brunswick, N.J.), as shown in FIGS. 8 and 9.

6.4 Example 4

Human Interferon α2b Expression in Egg White of Transgenic Hens

Once hens have reached sexual maturity and began to lay (approximately 22-24 weeks of age), eggs were collected and the egg whites were assayed by ELISA using human IFN ELISA (PBL Biomedical Laboratories, New Brunswick, N.J.) according to the manufacturer's instructions. The results of PCR and ELISA analysis of blood and egg white are given in Table 1 below that summarizes results of PCR and ELISA analysis.

TABLE 1

Analysis of Transgene Presence and Interferon Expression

| Bird # | Nuclear Localization Signal | Sex | PCR (Blood) | ELISA (Blood) | ELISA (egg white) |
|---|---|---|---|---|---|
| 8305 | −NLS | M | + | + | NA |
| 8331 |  | F | − | − | + |
| 8340 | −NLS | F | − | − | + |
| AA123 | +NLS | F | + | + | NA |
| AA61 | +NLS | M | + | + |  |
| AA105 | +NLS | F | − | + |  |
| AA115 | +NLS | M | + | − | NA |

−NLS: DNA injected without NLS peptide;
+NLS: DNA injected with NLS peptide;
NA: not applicable.

As shown in Table 1, one bird (#8305) of 69 produced using microinjection of DNA without the NLS peptide was positive for both the presence of the transgene and the expression of interferon in the blood. Because this bird is a male, he can be bred to a non-transgenic hen to establish germline transmission of the transgene.

FIGS. 8 and 9 demonstrate the expression of human interferon in the blood of #8305, as compared to standards. FIG. 7 illustrates the PCR results from the serum of for several birds, including bird 8305, obtained at different intervals after hatching. As can be seen in lanes 4, 5, 11, and 12 of FIG. 7, positive signal indicated the presence of the transgene at two different collection periods. Other PCR positive bands were seen in birds produced by microinjection of DNA covalently linked to the NLS peptide as described above. Table 1 shows that 4 birds, AA123, AA61, AA105 and AA115, of 43 tested were PCR positive, ELISA positive or both. Expression levels of human IFN in bird AA61, as compared to standards, are also illustrated in FIGS. 8 and 9. PCR-positive male birds can be bred to determine germline transmission, and eggs collected from transgeiiic females to assay for IFN expression, as described above, as chicks reach sexual maturity

6.5 Example 5

Purification and Identification of Human Interfcron-α2b from Transgenic Eggs

One hundred eggs were cracked and the egg whites separated from the yolks by manual manipulation and pooled. The pooled egg white was solubilized by adding 3 volumes of deionized water per volume of egg white, followed by adjusting the pH to 5.0 with the drop-wise addition of 1N HCl. The solubilized egg white was clarified by centrifugation at 3750 g for 20 minutes at 4° C.

The solubilized egg white was fractionated by cation exchange chromatography using SP-Sepharose HP. Two chromatographic runs were performed, the first in 50 mM sodium acetate at pH 5.0, the second in 50 mM sodium acetate at pH 4.0. A commercially available ELISA kit specific for human interferon-α was used to identify interferon-containing fractions.

The cation-exchange purified material was further purified by hydrophobic interaction chromatography on Phenyl-Sepharose, with the interferon fraction eluting after the addition of 1M acetic acid, pH 4.5, containing 0.5% triton X-100.

The results of SDS-PAGE and Western Blot analyses of the products at each step of the purification procedure are shown in FIGS. 10 and 11 respectively. A peak of interferon with a molecular weight of approximately. 22,000 daltons was seen following the hydrophobic interaction chromatography step. The purity of the interferon at this stage was estimated to be approximately 50%, based on the intensity of staining.

An analysis of the carbohydrate content of the human IFN-α2b purified from the transgenic chicken AVI-029 is shown in FIG. 12. Bands 1, 2 and 3 are the unsialyated, mono- and disialylated saccharides. Sialic acid linkage is alpha 2-3 to galactose and alpha 2-6 to N-acetylgalactosamine. The glycosylation of the human IFN-α2b produced by human cells is compared to that produced in chicken cells, as shown in FIG. 13.

6.6 Example 6

Construction of Lysozyme Promoter Plasmids

The chicken lysozyme gene expression control region was isolated by PCR amplification. Ligation and reamplification of the fragments thereby obtained yielded a contiguous nucleic acid construct comprising the chicken lysozyme gene expression control region operably linked to a nucleic acid sequence optimized for codon usage in the chicken (SEQ ID NO: 5) and encoding a human interferon α2b polypeptide optimized for expression in an avian cell.

White Leghorn Chicken (*Gallus gallus*) genomic DNA was PCR amplified using the primers 5pLMAR2 (SEQ ID NO: 1) and LE-6.1kbrev1 (SEQ ID NO: 2) in a first reaction, and Lys-6.1 (SEQ ID NO: 3) and LysElrev (SEQ ID NO: 4) as primers in a second reaction. PCR cycling steps were: denaturation at 94° C. for 1 minute; annealing at 60° C. for 1 minute; extension at 72° C. for 6 minutes, for 30 cycles using TAQ PLUS PRECISION DNA polymerase (STRATAGENE®, LaJolla, Calif.). The PCR products from these two reactions were gel purified, and then united in a third PCR reaction using only 5pLMAR2 (SEQ ID NO: 1) and LysElrev (SEQ ID NO: 4) as primers and a 10-minute extension period. The resulting DNA product was phosphorylated, gel-purified, and cloned into the EcoR V restriction site of the vector PBLUESCRIPT® KS, resulting in the plasmid p12.0-lys.

p12.0-lys was used as a template in a PCR reaction with primers 5pLMAR2 (SEQ ID NO: 1) and LYSBSU (5'-CCCCCCCCTAAGGCAGCCAGGGGCAGGAAGCAAA-3') (SEQ ID NO: 5) and a 10 minute extension time. The resulting DNA was phosphorylated, gel-purified, and cloned into the EcoR V restriction site of PBLUESCRIPT® KS, forming plasmid p12.0lys-B.

p12.0lys-B was restriction digested with Not I and Bsu36 I, gel-purified, and cloned into Not I and Bsu36 I digested pCMV-LysSPIFNMM, resulting in pl2.0-lys-LSPIFNMM. p12.0-lys-LSPIFNMM was digested with Sal I and the SalItoNotI primer (5'-TCGAGCGGCCGC-3') (SEQ ID NO: 16) was annealed to the digested plasmid, followed by Not I digestion. The resulting 12.5 kb Not I fragment, comprising the lysozyme promoter region linked to IFNMAGMAX-encoding region and an SV40 polyadenylation signal sequence, was gel-purified and ligated to Not I cleaved and dephosphorylated PBLUESCRIPT® KS, thereby forming the plasmid pAVIJCR-A115.93.1.2, which was then sequenced.

6.7 Example 7

Construction of Plasmids which Contain the 3' Lysozyme Domain

The plasmid pAVIJCR-A115.93.1.2 was restriction digested with FseI and blunt-ended with T4 DNA polymerase. The linearized, blunt-ended pAVIJCR-A115.93.1.2 plasmid was then digested with XhoI restriction enzyme, followed by treatment with alkaline phosphatase. The resulting 15.4 kb DNA band containing the lysozyme 5' matrix attachment region (MAR) and –12.0 kb lysozyme promoter driving expression of a human interferon was gel purified by electroelution.

The plasmid pIIIilys was restriction digested with MluI, then blunt-ended with the Klenow fragment of DNA polymerase. The linearized, blunt-ended pIIIilys plasmid was digested with XhoI restriction enzyme and the resulting 6 kb band containing the 3' lysozyme domain from exon 3 to the 3' end of the 3' MAR was gel purified by electroelution. The 15.4 kb band from pAVIJCR-A115.93.1.2 and the 6 kb band from pIIIilys were ligated with T4 DNA ligase and transformed into STBL4 cells (Invitrogen Life Technologies, Carlsbad, Calif.) by electroporation. The resulting 21.3 kb plasmids from two different bacterial colonies were named pAVIJCR-A212.89.2.1 and pAVIJCR-A212.89.2.3 respectively.

6.8 Example 8

Transfection of Chicken HD11 Cells with pAVIJCR-A212.89.2.1 and pAVIJCR-A212.89.2.3

Chicken cells transfected with plasmids having the 3' lysozyme domain linked to a nucleic acid expressing human α2b interferon express the heterologous polypeptide. Chicken myelomonocytic HD11 cells were transfected with plasmid pAVIJCR-A212.89.2.1 and pAVIJCR-A212.89.2.3 to test the functionality of the plasmids. One million HD11 cells were plated per each well of a 24-well dish. The next day, HD11 cells were transfected with 1 µg of plasmid DNA per 4 µl of LIPOFECTAMINE 2000 (Invitrogen Life Technologies). For comparison, independent wells were also transfected with the parent vector pAVIJCR-A115.93.1.2. After 5 hours of transfection, the cell medium was changed with fresh medium. 48 hours later, cell medium was harvested by centrifugation at 110×g for 5 min and assayed for human interferon by ELISA (PBL Biomedicals, Flanders, N.J.).

The transfected cells expressed the heterologous human α2b interferon at least to the level seen with a plasmid not having the 3' lysozyme domain operably linked to the human α2b interferon encoding nucleic acid.

6.9 Example 9

Cytoplasmic Microelectroporation

The application of electrical current has been shown to enhance the uptake of exogenous DNA fragments by cultured cells. The DNA fragments will be injected into the germinal disk according to the above-described methods. Enhancement of nuclear uptake of the heterologous DNA will promote earlier chromosomal integration of the exogenous DNA molecules, thus reducing the degree of genetic mosaicism observed in transgenic avian founders.

A sample of nucleic acid will be microinjected into the cytoplasm of a recipient stage 1 avian cell, and delivered to a recipient cell nucleus by microelectroporation. In a system suitable for use in microelectroporating early stage avian cells, a cathode will be located within the lumen of the DNA delivery micropipette. Another possible location for the electrode is on the exterior surface of the micropipette. For either option, the electrode is situated close or adjacent to the exit orifice of the pipette so that the electrode and the micropipette may be introduced into the recipient cell together. Alternatively, the micropipette will be introduced into the cytoplasm and used to guide a cathode to make electrical contact with the cytoplasm of the targeted cell.

The placement of the anode is optional. In one arrangement of the electrodes of the microelectroporation system, the anode is located on the micropipette and, therefore, will enter the cell or cells with the micropipette and the cathode. In another arrangement, an anode is in electrical contact with the Ringers solution that will surround the targeted recipient early stage avian cell. In yet another version, the anode is individually positioned within the cytoplasm, or the nucleus, of the recipient stage 1 cell. The anode and cathode are electrically connected to an electrical impulse generator capable of delivering a timed electrical pulse to the electrodes. One suitable apparatus for generating a timed electrical pulse according to the present invention is a Kation Scientific Iontaphorsis pump BAB-500.

A solution of a selected nucleic acid will be microinjected through the inserted micropipette into the recipient cell according to the protocols described in the examples above. The recipient cell will be pulsed at least once with about 0.1 to about 20.0 microamps for about 0.1 to about 60 secs.

This novel intracellular DNA microelectroporation method will enhance the efficiency of transgenesis, increase the efficiency of chromosomal integration of heterologous transgenic DNA, and reduce mosaicism of the transgenic founder animal by ensuring that more recipient cells receive and incorporate the nucleic acid at each delivery to a cell than is the case with non-electroporated microinjection.

6.10 Example 10

Construction of an ALV-based Vector Having β-lactamase Encoding Sequences

The lacZ gene of pNLB, a replication-deficient avian leukosis virus (ALV)-based vector (Cosset et al., *J. Virol.* 65: 3388-94 (1991)), was replaced with an expression cassette consisting of a cytomegalovirus (CMV) promoter and the reporter gene β-lactamase (β-La or BL).

To efficiently replace the lacZ gene of pNLB with a transgene, an intermediate adaptor plasmid was first created, pNLB-Adapter. pNLB-Adapter was created by inserting the chewed back ApaI/ApaI fragment of pNLB (Cosset et al., 1991, *J. Virol.* 65:3388-94) (in pNLB, the 5' ApaI sites reside 289 bp upstream of lacZ and the 3' ApaI sites reside 3' of the 3' LTR and Gag segments) into the chewed-back KpnI/SacI sites of PBLUESCRIPT®KS(-). The filled-in MluI/XbaI fragment of pCMV-BL (Moore et al., *Anal. Biochem.* 247: 203-9 (1997)) was inserted into the chewed-back KpnI/NdeI sites of pNLB-Adapter, replacing lacZ with the CMV promoter arid the BL gene (in pNLB, KpnI resides 67 bp upstream of lacZ and NdeI resides 100 bp upstream of the lacZ stop codon), thereby creating pNLB-Adapter-CMV-BL. To create pNLB-CMV-BL, the HindIII/BlpI insert of pNLB (containing lacZ) was replaced with the HindIII/BlpI insert of pNLB-Adapter-CMV-BL. This two step cloning was necessary because direct ligation of blunt-ended fragments into the HindIII/BlpI sites of pNLB yielded mostly rearranged subclones, for unknown reasons.

6.11 Example 11

Production of Transduction Particles having an ALV-based Vector having β-lactamase Encoding Sequences Sentas and Isoldes were cultured in F10 (GIBCO®), 5% newborn calf serum (GIBCO®), 1% chicken serum (GIBCO®), 50 μg/ml phleomycin (Cayla Laboratories) and 50 μg/ml hygromycin (SIGMA®). Transduction particles were produced as described in Cosset et al., 1991, herein incorporated by reference, with the following exceptions. Two days after transfection of the retroviral vector pNLB-CMV-BL (from Example 10, above) into $9\times10^5$ Sentas, virus was harvested in fresh media for 6-16 hours and filtered. All of the media was used to transduce $3\times10^6$ Isoldes in three 100 mm plates with polybrene added to a final concentration of 4 μg/ml. The following day the media was replaced with media containing 50 μg/ml phleomycin, 50 μg/ml hygromycin and 200 μg/ml G418 (SIGMA®). After 10-12 days, single G418 colonies were isolated and transferred to 24-well plates. After 7-10 days, titers from each colony was determined by transduction of Sentas followed by G418 selection. Typically 2 out of 60 colonies gave titers at $1-3\times10^5$. Those colonies were expanded and the virus concentrated to $2-7\times10^7$ as described in Allioli et al., 1994, *Dev. Biol.* 165:30-7, herein incorporated by reference. The integrity of the CMV-BL expression cassette was confirmed by assaying for β-lactamase in the media of cells transduced with NLB-CMV-BL transduction particles.

6.12 Example 12

Production of Chickens Transgenic for β-lactamase

Stage X embryos in freshly laid eggs were transduced with NLB-CMV-BL transduction particles (from Example 11, above) as described in Thoraval et al., 1995, *Transgenic Res.* 4:369-377, herein incorporated by reference, except that the eggshell hole was covered with 1-2 layers of eggshell membrane and, once dry, DUCO® model cement.

Approximately 120 White Leghorns were produced by transduction of the stage X embryos with NLB-CMV-BL transduction particles. These birds constitute chimeric founders, not fully transgenic birds. Extensive analysis of DNA in the blood and sperm from the transduced chickens indicates that 10-20% of the birds had detectable levels of the transgene in any given tissue. Of those birds carrying the transgene, approximately 2-15% of the cells in any given tissue were actually transgenic.

6.13 Example 13

β-lactamase Activity Assay in Blood and Egg White

When hens produced in Example 12, above, began to lay eggs, the egg whites of those eggs were assayed for the presence of β-lactamase. The β-lactamase assay was carried out as described in Moore et al., 1997, *Anal. Biochem.* 247:203-9, herein incorporated by reference, with the following modifications.

To assay blood from two to ten day old chicks, the leg vein was pricked with a scalpel. 50 μl of blood was collected in a heparinized capillary tube (Fisher), of which 25 μl was transferred to 100 μl phosphate-buffered saline (PBS) in a 96-well plate. Various dilutions of purified β-lactamase (CALBIOCHEM®) was added to some wells prior to addition of blood from control (non-transduced) chicks to establish a β-lactamase standard curve. After one day at 4° C., the plate was centrifuged for 10 minutes at 730×g. 25 μl of the supernatant was added to 75 μl of PBS. 100 μl of 20 μM 7-(thienyl-2-acetamido)-3-[2-(4-N,N-dimethylaminophenylazo)pyridinium-methyl]-3-cephem-4-carboxylic acid (PADAC, from CALBIOCHEM®) in PBS was added, and the wells were read immediately on a plate reader in a 10 minute kinetic read at 560 nm or left overnight in the dark at room temperature. Wells were scored positive if the well had turned from purple to yellow. To assay blood from older birds, the same procedure was followed except that 200-300 μl blood was drawn from the wing vein using a syringe primed with 50 μl of heparin (SIGMA®).

Analysis of the NLB-CMV-BL transduced flock revealed nine chickens that had significant levels of β-lactamase in their blood. Three of these chickens were males and these were the only three males that had significant levels of the NLB-CMV-BL transgene in their sperm as determined by PCR analysis. Thus, these are the males to be outbred to obtain fully transgenic $G_1$ offspring. The other six chickens were the hens that expressed α-lactamase in their magnum tissue (see below). Other birds had low levels of β-lactamase (just above the level of detection) in their blood but did not have transgenic sperm or eggs containing β-lactamase. Thus β-lactamase expression in blood is a strong indicator of whether a chicken was successfully transduced.

To assay β-lactamase in egg white, freshly laid eggs were transferred that day to a 4° C. cooler, at which point the β-lactamase is stable for at least one month. (Bacterially-expressed, purified β-lactamase added to egg white was determined to lose minimal activity over several weeks at 4° C., confirming the stability of β-lactamase in egg white.) To collect egg white samples, eggs were cracked onto plastic wrap. The egg white was pipetted up and down several times to mix the thick and thin egg whites. A sample of the egg white was transferred to a 96-well plate. 10 μl of the egg white sample was transferred to a 96-well plate containing 100 μl of PBS supplemented with 1.5 μl of 1 M $NaH_2PO_4$, pH 5.5 per well. After addition of 100 μl of 20 μM PADAC, the wells were read immediately on a plate reader in a 10 minute or 12 hour kinetic read at 560 nm. Various dilutions of purified β-lactamase was added to some wells along with 10 μl of egg white from control (non-transduced) hens to establish a β-lactamase standard curve. Egg white from both untreated and NLB-CMV-BL transduced hens were assayed for the presence of β-lactamase.

Significant levels of β-lactamase were detected in the egg white of six hens, as shown in Table 2, below. Eggs laid by Hen 1522, the first hen to demonstrate expression in eggs, have 0.3 mg or higher of active β-lactamase per egg. Also shown is β-lactamase production from three other NLB-CMV-BL transduced hens (Hen 1549, Hen 1790 and Hen 1593). Every hen that laid eggs containing β-lactamase also had significant levels of β-lactamase in its blood.

TABLE 2

Expression of β-lactamase in eggs of NLB-CMV-BL treated hens.

| Hen # | Average mg of β-lactamase per egg | # of eggs assayed |
|---|---|---|
| Control | 0.1 ± 0.07 | 29 |
| 1522 | 0.31 ± 0.07 | 20 |
| 1549 | 0.96 ± 0.15 | 22 |
| 1581 | 1.26 ± 0.19 | 12 |
| 1587 | 1.13 ± 0.13 | 15 |
| 1790 | 0.68 ± 0.15 | 13 |
| 1793 | 1.26 ± 0.18 | 12 |

Controls were eggs from untreated hens. The low level of BL in these eggs was due to spontaneous breakdown of PADAC during the course of the kinetic assay. The other hens were transduced with NLB-CMV-BL as described in Example 3. Egg white from each egg was assayed in triplicate.

Based on the β-lactamase activity assay, the expression levels of β-lactamase appeared to range from 0.1 to 1.3 mg per egg (assuming 40 milliliters of egg white per egg). However, these assay quantities were significantly less than the quantities obtained by western blot assay and were determined to be deceptively lower than the true values. The difference in results between the enzymatic activity assay and a western blot analysis was due to a β-lactamase inhibitor in egg white. The activity of purified β-lactamase was inhibited by egg white such that 50 μl of egg white in a 200 μl reaction resulted in nearly 100% inhibition, whereas 10 μl of egg white in a 200 μl reaction resulted in only moderate inhibition. Furthermore, spontaneous breakdown of the enzymatic substrate, PADAC, during the course of the assay also contributed to the erroneously low calculation of β-lactamase concentration.

6.14 Example 14

Isolation and ex vivo Transfection of Blastodermal Cells

Donor blastodermal cells are isolated from fertilized eggs of Barred Plymouth Rock hens using a sterile annular ring of Whatman filter paper which is placed over a blastoderm and lifted after cutting through the yolk membrane of the ring. The ring bearing the attached blastoderm is transferred to phosphate-buffered saline (PBS) in a petri dish ventral side up, and adhering yolk is removed by gentle pipetting. The area opaca is dissected away with a hair loop and the translucent stage X blastoderm is transferred via a large-bore pipette tip to a microfuge tube. About 30,000-40,000 cells are isolated per blastoderm and for a typical experiment 10 blastoderms are collected.

Cells are dispersed by brief trypsin (0.2%) digestion, washed once by low speed centrifugation in Dulbecco's modified Eagle's medium (DMEM) and then transfected with linearized plasmids via lipofectin (16 mg/200 ml, BRL) for 3 hours at room temperature. Cells are washed free of lipofectin with medium and then 400-600 cells are injected into g-irradiated (650 rads) recipient stage X embryos from the Athens-Canadian randombred line (AC line). Injection is through a small window (~0.5 cm) into the subgerminal cavity beneath the recipient blastoderms. Windows are sealed with fresh egg shell membrane and DUCO® plastic cement. Eggs are then incubated at 39.1° C. in a humidified incubator with 90° rotation every 2 hr.

6.15 Example 15

Identification of Transgenic Mosaics by PCR Assay

Among the chicks which hatch from embryos containing transfected or transduced blastodermal cells, only those exhibiting Barred Plymouth Rock feather mosaicism are retained. Even if no reporter gene is present in the transgene, transgenic mosaics can be identified by PCR assay.

To identify transgenic mosaics, DNA blood and black feather pulp of individual chicks are assayed by PCR for the presence of the transgene using a primer pair specific to the transgene as described by Love et al., 1994, *Bio/Technology* 12:60-63. Transgene chimeras are induced, withdrawn and re-induced with diethylstilbestrol (DES) pellets and excised magnums analyzed for expression of reporter activity. Blood and liver are assayed to monitor tissue specificity.

Male and female blood DNA was collected at 10 to 20 days post-hatch. Blood is drawn from a wing vein into a heparinized syringe and one drop is immediately dispensed into one well of a flat-bottom 96-well dish containing a buffer which lyses cytoplasmic membranes exclusively. The plate is then briefly centrifuged, which pellets the nuclei. The supernatant is removed and a second lysis buffer is added which releases genomic DNA from nuclei and degrades nucleases. The DNA is ethanol precipitated in the plate, washed with 70% ethanol, dried and resuspended in 100 µl of water per well. As much as 80 µg of DNA suitable for PCR and TAQMAN™ (Perkin Elmer/Applied Biosystems) analysis can be obtained from one drop (8 µl) of chick blood.

The isolated DNA is tested for the presence of the transgenes using the TAQMAN® sequence detection assay to evaluate the efficiency of the embryo transduction process. The TAQMAN® sequence detection system allows the direct detection of a specific sequence. A fluorescently-labeled oligonucleotide probe complementary to an internal region of a desired PCR product only fluoresces when annealed to the desired PCR product, which in this case is complementary to the transgene. Because all of the detection occurs in the PCR tube during the cycling process, the TAQMAN® system allows high-throughput PCR (no gel electrophoresis is need) as well as sequence detection analogous to and as sensitive as Southern analysis. 1 µl of the isolated DNA, which contains 600-800 ng of DNA, is used for the TAQMAN® reaction. Each reaction contains two sets of primer pairs and TAQMAN® probes. The first set detects the chicken glyceraldehyde 3-phosphate dehydrogenase gene (GAPDH) and is used as an internal control for the quality of the genomic DNA and also serves as a standard for quantitation of the transgene dosage. The second set is specific for the desired transgene. Fluorescence is detected in a dissecting stereomicroscope equipped with epifluorescence detection. The two TAQMAN® probes are attached to different dyes that fluoresce at unique wavelengths: thus both PCR products are detected simultaneously in an ABI/PE 7700 Sequence Detector. It is estimated that up to 180 birds will hatch, and 20% (36 birds) will contain the transgene in their blood.

6.16 Example 16

Production of Fully Transgenic $G_1$ Chickens Expressing β-Lactamase

Males are selected for breeding as a single male can give rise to 20 to 30 $G_1$ offspring per week as opposed to 6 $G_1$ offspring per female per week, thereby speeding the expansion of $G_1$ transgenics. The feed of $G_0$ males is supplemented with sulfamethazine, which accelerates the sexual maturation of males such that they can start producing sperm at 10-12 weeks of age instead of 20-22 weeks without influencing their health or fertility.

Sperm DNA of all males are screened for the presence of the transgene. Sperm are collected and the DNA extracted using Chelex-100. Briefly, 3 µl of sperm and 200 µl of 5% Chelex-100 are mixed, followed by addition of 2 µl of 10 mg/ml proteinase K and 7 µl of 2 M DTT. Samples are incubated at 56° C. for 30-60 minutes. Samples are boiled for 8 minutes and vortexed vigorously for 10 seconds. After centrifugation at 10 to 15 kG for 2-3 minutes, the supernatant is ready for PCR or TAQMAN® analysis. The DNAs are analyzed by the TAQMAN® assay using a TAQMAN® probe and primers complementary to the transgene. Of the 90 $G_0$ males, it is estimated that 5%, or 4 to 5, will have the transgene in their sperm DNA.

As noted above in Example 13, the NLB-CMV-BL transduced flock included three males that had significant levels of the NLB-CMV-BL transgene in their sperm as determined by PCR analysis. Thus, these males are chosen for further breeding to obtain fully transgenic $G_1$ offspring.

By breeding germline transgenic males to 90 non-transgenic White Leghorn females per week, about 16 $G_1$ offspring per week will be obtained. Hatched chicks are vent-sexed and screened for the presence of the transgene in their blood DNA by the TAQMAN® assay. Twenty male and female $G_1$ transgenics will be obtained or 40 total, which will take up to 3 weeks.

Males will be kept for further breeding and females tested for expression of transgenes in the egg.

6.17 Example 17 pNLB-CMV-IFN Vector having an IFN Encoding Sequence

The DNA sequence for human interferon α2b based on hen oviduct optimized codon usage was created using the BACKTRANSLATE program of the Wisconsin Package, version 9.1 (Genetics Computer Group. Inc., Madison, Wis.) with a codon usage table compiled from the chicken (*Gallus gallus*) ovalbumin, lysozyme, ovomucoid, and ovotransferrin proteins. The template and primer oligonucleotides (SEQ ID NOS: 17-34) shown in FIGS. 15A-B were amplified by PCR with Pfu polymerase (STRATAGENE®, La Jolla, Calif.) using 20 cycles of 94° C. for 1 min., 50° C. for 30 sec., and 72° C. for 1 sec.

PCR products were purified from a 12% polyacrylamide-TBE gel by the "crush and soak" method (Maniatis et al. 1982), then combined as templates in an amplification reaction using only IFN-1 (SEQ ID NO: 24) and IFN-8 (SEQ ID NO: 34) as primers. The resulting PCR product was digested with Hind III and Xba I and gel purified from a 2% agarose-TAE gel, then ligated into Hind III and Xba I digested, alkaline phosphatase-treated, PBLUESCRIPT® KS (STRATAGENE®), resulting in the plasmid pBluKSP-IFNMagMax. Both strands were sequenced by cycle sequencing on an ABI PRISM 377 DNA Sequencer (Perkin-Elmer, Foster City, Calif.) using universal T7 or T3 primers. Mutations in pBluKSP-IFN derived from the original oligonucleotide templates were corrected by site-directed mutagenesis with the Transformer Site-Directed Mutagenesis Kit (Clontech, Palo Alto, Calif.). The interferon coding sequence was then removed from the corrected pBluKSP- IFN with Hind III and Xba I, purified from a 0.8% agarose-TAE Gel, and ligated to Hind III and Xba I digested, alkaline phosphatase-treated pCMV-BetaLa-3B-dH. The resulting plasmid was pCMV-IFN which contained IFN coding sequence controlled by the cytomegalovirus immediate early promoter/enhancer and SV40 polyA site.

To clone the IFN coding sequence controlled by the CMV promoter/enhancer into the NLB retroviral plasmid, pCMV-IFN was first digested with ClaI and XbaI, then both ends were filled in with Klenow fragment of DNA polymerase (New England BioLabs, Beverly, Mass.). pNLB-adapter was digested with Nde I and Kpn I, and both ends were made blunt by T4 DNA polymerase (New England BioLabs). Appropriate DNA fragments were purified on a 0.8% agarose-TAE gel, then ligated and transformed into DH5α cells. The resulting plasmid was pNLB-adapter-CMV-IFN.

This plasmid was then digested with Mlu I and partially digested with Blp I and the appropriate fragment was gel purified. pNLB-CMV-EGFP was digested with Mlu I and Blp I, then alkaline-phosphatase treated and gel purified. The Mlu I/Blp I partial fragment of pNLB-adapter-CMV-IFN was ligated to the large fragment derived from the Mlu I/Blp I digest of pNLB-CMV-EGFP, creating pNLB-CMV-IFN.

6.18 Example 18

Production of pNLB-CMV-IFN Transduction Particles

Senta packaging cells (Cosset et al., 1991) were plated at a density of $3 \times 10^5$ cells/35 mm tissue culture dish in F-10 medium (Life Technologies) supplemented with 50% calf serum (Atlanta Biologicals), 1% chicken serum (Life Technologies), 50 µg/ml hygromycin (SIGMA®), and 50 µg/ml phleomycin (CAYLA, Toulouse, France). These cells were transfected 24 h after plating with 2 µg of CsCl-purified pNLB-CMV-IFN DNA and 6 µl of Lipofectin liposomes (Life Technologies) in a final volume of 500 µl Optimem (Life Technologies): The plates were gently rocked for four hours at 37° C. in a 5% $CO_2$ incubator. For each well, the media was removed, washed once with 1 ml of Optimem and re-fed with 2 mls of F-10 medium supplemented with 50% calf serum, 1% chicken serum, 50 µg/ml hygromycin, and 50 µg/ml phleomycin. The next day, medium from transfected Sentas was recovered and filtered through a 0.45 micron filter.

This medium was then used to transduce Isolde cells. 0.3 ml of the filtered medium recovered from Senta cells was added to 9.6 ml of F-10 (Life Technologies) supplemented as described above, in addition to polybrene (SIGMA®) at a final concentration of 4 µg/ml. This mixture was added to $10^6$ Isolde packaging cells (Cosset et al., 1991) plated on a 100 mm dish the previous day, then replaced with fresh F-10 medium (as described for Senta growth) 4 hours later.

The next day, the medium was replaced with fresh medium which also contained 200 µg/ml neomycin (G418, SIGMA®). Every other day, the medium was replaced with fresh F-10 medium supplemented with 50% calf serum, 1% chicken serum, 50 µg/ml hygromycin, 50 µg/ml phleomycin, and 200 µg/ml neomycin. Eleven to twelve days later, single colonies were visible by eye, and these were picked and placed into 24 well dishes. When some of the 24 well dishes became confluent, medium was harvested and titered to determine the cell lines with the highest production of retrovirus.

Titering was performed by plating $7.5 \times 10^4$ Senta cells per well in 24 well plates on the day prior to viral harvest and transduction. The next day 1 ml of fresh F-10 medium supplemented with 50% calf serum, 1% chicken serum, 50 µg/ml hygromycin, and 50 µg/ml phleomycin was added to each well of the isolated Isolde colonies. Virus was harvested for 8-10 hours. The relative density of each well of Isoldes was noted. After 8-10 hours, 2 and 20 µl of media from each well of Isoldes was added directly to the media of duplicate wills of the Sentas. Harvested medium was also tested for the presence of interferon by IFN ELISA and for interferon bioreactivity. The next day the media was replaced with F-10 medium supplemented with 50% calf serum, 1% chicken serum, 50 µg/ml hygromycin, 50 µg/ml phleomycin, and 200 µg/ml neomycin. When obvious neomycin-resistant colonies were evident in the wells of transduced Sentas, the number of colonies was counted for each well.

The Isolde colony producing the highest titer was determined by taking into account the number of colonies and correcting for the density of the Isolde cells when the viral particles were harvested (i.e., if two Isolde colonies gave rise to media with the same titer, but one was at a 5% density and the other was at a 50% density at the time of viral harvest, the one at the 5% density was chosen for further work, as was the case in the present example).

The Isolde cell line producing the highest titer of IFN-encoding transducing particles was scaled up to six T-75 tissue culture flasks. When flasks were confluent, cells were washed with F-10 medium (unsupplemented) and transducing particles were then harvested for 16 hours in 14 ml/flask of F-10 containing 1% calf serum (Atlanta Biologicals) and 0.2% chicken serum (Life Technologies). Medium was harvested, filtered through a 0.45 micron syringe filter, then centrifuged at 195,000×g in a Beckman 60Ti rotor for 35 min. Liquid was removed except for 1 ml, and this was incubated with the pellet at 37° C. with gentle shaking for one hour. Aliquots were frozen at −70° C. Transducing particles were then titered on Senta cells to determine concentrations used to inject embryos.

6.19 Example 19

Production of Chimeric Transgenic Chickens

Approximately 300 White Leghorn (strain Line 0) eggs were windowed according to the Speksnijder procedure described in U.S. Pat. No. 5,897,998, incorporated herein by reference in its entirety, then injected with about $7 \times 10^4$ transducing particles per egg. Eggs hatched 21 days after injection and human interferon levels were measured by IFN ELISA from serum samples collected from chicks one week after hatch.

6.20 Example 20

Production of Fully Transgenic $G_1$ Chickens for Selective Breeding from Males Expressing Human Interferon To screen for $G_0$ roosters which contained the interferon transgene in their sperm, DNA was extracted from rooster sperm samples by Chelex-100 extraction (Walsh et al., 1991). DNA samples were then subjected to TAQMAN® analysis on a 7700 Sequence Detector (Perkin Elmer) using the "neo for-1" (5'-TGGATTGCACGCAGGTTCT-3') (SEQ ID NO: 35) and "neo rev-1" (5'-GTGCCCAGTCATAGC- CGAAT-3') (SEQ ID NO: 36) primers and FAM labeled NEO-PROBE1 (5'-CCTCTCCACCCAAGCGGCCG-3') (SEQ ID NO: 37) to detect the transgene. Three $G_0$ roosters with the highest levels of the transgene in their sperm samples were bred to nontransgenic SPAFAS (White Leghorn) hens by artificial insemination.

Blood DNA samples were screened for the presence of the transgene by TAQMAN® analysis as described in Example 14, above. Out of 1,597 offspring, one rooster was found to be transgenic (a.k.a. "Alphie"). Alphie's serum was tested for the presence of human interferon by hIFN ELISA. hIFN was present at 200 nanograms/ml.

Alphie's sperm was used for artificial insemination of nontransgenic SPAFAS (White Leghorn) hens. To date, 106 out of 202 (about 52%) offspring contain the transgene as detected by TAQMAN® analysis. These breeding results follow a Mendelian inheritance pattern and indicate that Alphie is transgenic.

6.21 Example 21

Production of Human Interferon α2b in the Egg White of $G_2$ Transgenic Hens

Human lung carcinoma cells were incubated with diluted egg white samples, then washed and challenged with mengovirus. After incubation, cells were stained with crystal violet to assess viral interference.

Expression levels of human IFN α2b in egg white produced by $G_2$ hens as determined by ELISA are shown in FIG. 16. The bioactivity versus the mass of human IFN α2b produced in $G_2$ hen egg white is shown in FIG. 17. Bioactivity was determined by a viral inhibition assay, and mass was determined by IFN ELISA. Bird number 53 was a control bird and represented egg white from a non-transgenic hen.

6.22 Example 22

Transfection of Cultured Quail Oviduct Cells

The oviduct was removed from a Japanese quail (*Coturnix coturnix* japonica) and the magnum portion was minced and enzymatically dissociated with 0.8 mg/ml collagenase (SIGMA® Chemical Co., St. Louis, Mo.) and 1.0 mg/ml dispase (ROCHE® Molecular Biochemicals, Indianapolis, Ind.) by shaking and titurating for 30 min at 37° C. The cell suspension was then filtered through sterile surgical gauze, washed three times with F-12 medium (Life Technologies, Grand Island, N.Y.) by centrifugation at 200×g, and resuspended in OPTIMEM™ (Life Technologies) such that the $OD_{600}$ was approximately 2. 300 µl of cell suspension was plated per well of a 24-well dish. For each transfection, 2.5 µl of DMRIE-C liposomes (Life Technologies) and 1 µg of DNA were preincubated 15 minutes at room temperature in 100 µl of OPTIMEM™, then added to the oviduct cells. Cells with DNA/liposomes were incubated for 5 hours at 37° C. in 5% $CO_2$. Next, 0.75 ml of DMEM (Life Technologies) supplemented with 15% fetal bovine serum (FBS) (Atlanta Biologicals, Atlanta, Ga.), 2×penicillin/streptomycin (Life Technologies), $10^{-6}$ M insulin (SIGMA®), $10^{-8}$ M β-estradiol (SIGMA®), and $10^{-7}$ M corticosterone (SIGMA®) was added to each well, and incubation continued for 72 hours. Medium was then harvested and centrifuged at 110×g for 5 minutes.

6.23 Example 23

Transfection of Cultured Chicken Whole Embryo Fibroblasts

To obtain whole embryo fibroblasts (WEFs), fertile chicken eggs were incubated for approximately 65 hours. Embryos were collected using filter paper rings, then washed three times in phosphate buffered saline with glucose (PBS-G) followed by a wash in calcium- and magnesium-free EDTA (CMF-EDTA). Embryos were then incubated in fresh CMF-EDTA at 4° C. with gentle shaking for 30 minutes. CMF-EDTA was removed, and replaced with 0.5% trypsin solution (no EDTA) at 37° C. for 3 minutes. Cells were titurated 10 times, then 5% chicken serum was added to inhibit the trypsin reaction. The cell suspension was then added to α-MEM (Life Technologies) supplemented with 2.2 g/l $NaHCO_3$, 2.52 g/L EPPS, 0.18 g/l D-glucose, 5% FBS, 5% chick serum (heat inactivated at 55° C. for 1 hour), $5\times10^{-5}$M β-mercaptoethanol, 0.2 mM L-glutamine, 2×penicillin/streptomycin and centrifuged. Cells were resuspended in a-MEM supplemented as described above, and plated on 6-well dishes at a density of $2\times10^5$ cells per well.

For each transfection, 6 µl of FuGene 6 liposomes (ROCHE® Molecular Biochemicals) and 2 µg of DNA were preincubated 15 min at room temperature in 100 µl of OPTIMEM™, then added to the WEFs. WEFs with DNA/liposomes were incubated 5 hours at 37° C. in 5% $CO_2$. The transfection medium was then removed and replaced with 2 ml of α-MEM supplemented as described above. Medium was removed 72 hours after transfection and centrifuged at 110×g for 5 minutes.

WEFs were transfected either with the heavy and light immunoglobulin polypeptides encoded by separate plasmids (p1083 and p1086 respectively) each under the control of the CMV promoter or encoded on the same reactor under the transcriptional control of a CMV promoter and including an IRES translational element as described in U.S. patent application Ser. No. 09/977,374, filed Jun. 8, 2001 and incorporated herein by reference in its entirety. The supernatants were analyzed for antibody content by ELISA and FACs.

6.24 Example 24

Generation of Transgenic Chickens Expressing Antibodies

A retroviral vector, based on either avian leukosis virus (ALV) or Moloney murine leukemia virus (MoMLV), will be constructed such that the light (L) and heavy (H) chains of a monoclonal antibody (MAb) will be linked by an internal ribosome entry site (IRES) element. Both genes will then be transcriptionally regulated by a promoter such as the cytomegalovirus (CMV) immediate early promoter/enhancer or a promoter that demonstrates tissue specificity for the hen oviduct (for example, the lysozyme promoter, ovalbumin promoter, an artificial promoter construct such as MDOT, and the like). The promoter-L chain-IRES-H chain DNA expression cassette will be flanked by the long terminal repeats (LTRs) of the retrovirus. Stage X chicken embryos will be injected with transducing particles containing the above construct to generate transgenic chickens.

Alternatively, the heavy and light chains will be included in separate retroviral vectors and separate lines of transgenic chickens will be generated. Each line will either express the heavy or light chain of the MAb. Once germline transmission of the transgene is established in the two lines, they will be bred to each other to express heavy and light chains together to make functional MAbs in the offspring.

The above DNA constructs can also be integrated into a chicken genome by sperm-mediated transgenesis (SMT). SMT may involve transfection, electroporation, or incubation of sperm with the desired DNA construct (for example, the lysozyme promoter controlling expression of heavy and light chains of the MAb) and fertilization of ovum with the treated sperm by artificial insemination or by chicken intracytoplasmic sperm injection (ChICSI™).

6.25 Example 25

Preparation of Recipient Avian Cytoplasts by TPLSM

Incubation

Ova were isolated from euthanized hens between 2-4 hours after oviposition of the previous egg. Alternatively, eggs were isolated from hens whose oviducts have been fistulated (Gilbert & Woodgush, 1963, *J Reprod. & Fertility* 5: 451-453) and (Pancer et al., 1989, *Br. Poult. Sci.* 30: 953-7). Before generating images of the avian early embryo, DNA was incubated with a specific dye according to the following protocol.

The albumen capsule was removed and the ovum placed in a dish with the germinal disk facing the top. Remnants of the albumen capsule were removed from the top of the germinal disk. Phosphate buffered saline was added to the dish to prevent drying of the ovum. A cloning cylinder was placed around the germinal disk and 1.0 µg/ml of DAPI in PBS was added to the cylinder. Visualization was performed after approximately 15 minutes of incubation.

Injection

Preparation of the egg was done as described for incubation. Following removal of the capsule, 10-50 nanoliters of a 0.1 µg/ml solution of DAPI in PBS was injected into the germinal disk using a glass pipette. Visualization was performed approximately 15 minutes after injection.

Visualization

Following incubation, images of the inside of the avian early embryo were generated through the use of TPLSM. The germinal disk was-placed under the microscope objective, and the pronuclear structures were searched within the central area of the disk, to a depth of 60 µm using low laser power of 3-6 milliwatts at a wavelength of 750 nm. Once the structures were found they were subsequently ablated.

Nuclear Ablation and Enucleation

Pronuclear structures were subjected to laser-mediated ablation. In these experiments, an Olympus 20x/0.5NA (Numerical Aperture) water immersion lens was used. The x and y planes to be ablated were defined with the two photon software, while the z plane (depth) was just under 10 µm for this type of objective. Since the pronuclear structure was about 20 µm in diameter, the ablation comprised two steps (2 times 10 µm). The focal point was lowered to visualize the remaining of the pronucleus, which was subsequently ablated. The laser power used to ablate the pronuclei was between 30 to 70 milliwatts at a wavelength of 750 nm. For the ablation experiments, the image was zoomed by a factor of 4 to 5, giving an area compression of 16-25 fold. Then the power was increased 10-12 fold for a total intensity increase of 160-300 fold compared to the visualization intensity of 3-6 milliwatts. The ablation intensity (power density) is the functional parameter, i.e. the power increase of 10-12 fold results in ablation power of 30-70 milliwatts, but the zoom factor compressed this power into an area 16-25×smaller giving a power density increase of 160-300 fold.

6.26 Example 26

Preparation of the Nuclear Donor Cell and Isolation of the Donor Nucleus

Avian fibroblast cells in culture were trypsinized (0.25% Trypsin and 1 µM EDTA), centrifuged twice in PBS containing 5% of fetal calf serum (FCS) and placed in a 60 mm plastic dish in PBS containing 5% of FCS. Using the microscope/micromanipulation unit described in Example 27 below, under transmission light, the nuclear donors were then isolated by repeated pipetting of the cells, which disrupted the cytoplasmic membrane and released the nucleus from inside the cell.

6.27 Example 27

Preparation of the Reconstructed Zygote

A micromanipulation unit, comprising an IM-16 microinjector and a MM-188NE micromanipulator, both from NIKON®/MARISHIGE, were adapted to an upright NIKON® Eclipse E800. This microscope was adapted to operate under both transmission and reflective light conditions. This unique configuration has allowed as to morphologically examine and prepare (isolate the nuclei, as described above) somatic cells in suspension and to load the injection pipette using dry or water immersion senses under diascopic illumination or transmitted light. This was followed by prompt localization and positioning of the germinal disk under the microscope and subsequent guided injection of the somatic cells, using dry and long distance lenses under fiber optic as well as episcopic illumination (light coming from the side and through the objectives onto the sample respectively).

6.28 Example 28

Production of Transgenic Chickens by Direct Pronuclear DNA Injection

Production of transgenic chickens by direct DNA injection can be by two methods: (a) injection of a DNA directly into the germinal disk, commonly described as cytoplasmic injection, as described for avian species by Sang & Perry, 1989, *Mol. Reprod. Dev.* 1: 98-106, and Love et al., 1994, *Biotechnology* (N.Y.) 12: 60-3, incorporated herein by reference in their entireties. Sang & Perry described only episomal replication of the injected cloned DNA. Love et al. suggested that the injected DNA becomes integrated into the cell's genome. In both cases, injection was into pronuclear stage eggs. This procedure, therefore, is cytoplasmic injection of pronuclear stage eggs, not pronuclear injection; and (b) imaging of the egg using multiphoton microscopy to allow localization of the pronuclear structures. The DNA solution is then injected directly into the pronucleus.

DNA Preparation

The plasmid pAVIJCR-A115.93.1.2 containing the chicken lysozyme promoter region, and controlling expression of human interferon α2b, was purified with a QIAGEN® Plasmid Maxi Kit (QIAGEN®, Valencia, Calif.), and 5 μg of the plasmid DNA were restriction digested with the restriction enzyme Not I. A 12.7 kb fragment was purified by gel electrophoresis and electroelution, pheno/chloroform extraction, and ethanol precipitation. The DNA was resuspended in 1 mM Tris-HCl, pH 8.0 and 0.1 mM EDTA (0.1×TE) to a final concentration of 5pg/nl and then used for microinjections.

Pronuclear Injection (i) Preparation of ova. Ova were isolated from euthanized hens between two and four hours after oviposition of the previous egg. Alternatively, eggs were isolated from hens whose oviducts have been fistulated as described by Gilbert & Woodgush, 1963, *J. of Reprod. and Fertility* 5: 451-453 and Pancer et al., 1989, *Br. Poult. Sci.* 30: 953-7 and incorporated herein in their entireties.

The albumen capsule was removed and the ovum placed in a dish with the germinal disk facing upwards. Remnants of the albumen capsule were removed from over the germinal disk. Phosphate buffered saline (PBS) was added to the dish to prevent drying of the ovum. A cloning cylinder could be placed around the germinal disk to reduce the depression of the ooplasmic membrane formed during subsequent pipette penetration, thereby facilitating the injection.

(ii) Injection. Between about 1-100 nanoliters of DNA solution was injected into a germinal disk using a glass pipette after removal of the capsule. The microinjection assembly and methods for microinjecting and reimplanting avian eggs are fully described in U.S. patent application Ser. No. 09/919,143, filed Jul. 31, 2001.

Briefly, the microscope/micromanipulation unit is an IM-16 microinjector and a MM-188NE micromanipulator, both from NIKON®/MARISHIGE, adapted to an upright NIKON® Eclipse E800 microscope adapted to operate under both transmitted and reflected light conditions. This unique configuration allows the loading of a DNA solution into a micropipette while observed with a pipette dry or water immersion lenses under diascopic illumination or transmitted light. Pipette loading is followed by the prompt localization and positioning of the germinal disk under the microscope and subsequent guided injection of DNA solution into the germinal disk using dry and long working distance lenses under fiber optic as well as episcopic illumination (side illumination and directly through the objectives and onto the sample, respectively).

(iii) Localization of the Avian Embryo. A cloning cylinder is placed around the germinal disk and MITOTRACKER® (300 nM) in PBS was added to the cylinder. Visualization is performed after approximately 20 minutes of incubation. Imaging using this dye shows intense labeling of the region around the nucleus while the nucleus itself does not take up the dye. This will allow localization of the pronucleus for injection while not causing excessive damage to its structure, since the content of the pronuclei are not labeled and therefore are bleached during imaging. Once the pronucleus is localized, the DNA solution can be delivered into it using a microinjector. Cytoplasmic or pronuclear injected eggs can then be surgically transferred to a recipient hen.

(iv) Ovum transfer. At the time of laying, recipient hens are gas anesthetized using Isofluorine. At this time, the infundibulum is receptive to receiving a donor ovum but has not yet ovulated. Feathers are removed from the abdominal area, and the area is scrubbed with betadine, and rinsed with 70% ethanol. The bird is placed in a supine position and a surgical drape is placed over the bird with the surgical area exposed. An incision approximately 2 inches long is made beginning at the junction of the sternal rib to the breastbone and running parallel to the breastbone and through the smooth muscle layers and the peritoneum, to locate the infundibulum. The infundibulum is externalized and opened using gloved hands and the donor ovum is gently applied to the open infundibulum. The ovum is allowed to move into the infundibulum and into the anterior magnum by gravity feed. The infundibulum is returned to the body cavity and the incision closed using interlocking stitches both for the smooth muscle layer and the skin. The recipient hen is returned to her cage and allowed to recover with free access to both feed and water. Recovery time for the bird to be up, moving and feeding is usually within 45 minutes. Eggs laid by the recipient hens are collected the next day, set, and incubated. They will hatch 21 days later.

The procedure described by Love et al., 1994, in *Biotechnology* N.Y.) 12: 60-63, resulted in 5.5% survival to sexual maturity using the Perry ex ovo procedure. Following injection and surgical transfer by the methods described herein, however, a survival rate between about 50% and about 70% is expected, i.e., hatching, and most of the hatched birds should reach maturity.

6.29 Example 29

MuLV and VSV Viral Transfection of Avian Eggs

Preparation of MuLV/VSVg viral stocks. GP-293 cells at 70-80% confluence were transfected with 10 μg of the plasmid pVSVg or pLNHX-CMVE-MDOT-IFN. Sixty hours after transfection, the supernatant was collected and centrifuged at 1000 rpm for 5 minutes to remove cells. The supernatant was filtered through a 0.45 micron filter and the filtrate was centrifuged at 20,000 rpm to pellet the virus. The viral pellet was resuspended in 400 ml of STE buffer. To determine the viral titer, a 100-fold dilution of the viral stock was made and 5 μl of the serially diluted stock was used to infect Sentas cells. Forty-eight hours after infection, the cells were grown in medium containing 100 μg/ml G418. Colonies that were formed after two weeks in the selection medium were counted to determine the viral titer.

Isolation of blastodermal cells from stage X Barred Plymouth Rock (BPR) embryos. Freshly laid eggs were collected. The embryo at this stage consists of about 50,000-60,000 cells in a small circular area called the blastodermal disc. The discs from about 30 embryos were dissected from the eggs and the cells dissociated using 1×PBS (phosphate buffer saline) containing 0.05% trypsin. The cells were centrifuged at 500 rpm for 5 minutes. The pellet was gently washed with 1×PBS and pelleted again and counted using a hemocytometer.

Interferon (IFN) assay. Blood samples were collected from 6 wk old chicks and the interferon levels in the serum were measured using the hu-IFN-α ELISA Kit (PBL Biomedical Lab., New Brunswick, N.J.).

119 WL stage X eggs were injected with 5 μl of pLNHX-MDOT-IFN/VSVg virus with a titer $6 \times 10^4$/ml). 53 injected eggs survived, of which 20 hatched. Sperm samples were tested from the males at sexual maturity. Two males, # A 24 and A 34, showed the presence of the transgene and therefore were used for further breeding for testing the germ-line transmission.

Freshly isolated $2 \times 10^5$ BRD cells from stage X embryos were infected with $1.5 \times 10^4$ pLNHX-MDOT-IFN/VSVg virus at 37° C. for 1 hour. The cells were gently stirred every 10-15 minutes. While the blastodermal cells were being thus processed, 150 freshly laid WL (stage X) eggs were irradiated at 600 rads and set aside for the injections. A 5 µl cell suspension containing about 4000-5000 blastodermal cells were injected into each of 85 irradiated stage X WL eggs through a hole drilled in the shell. The eggs were sealed and incubated to hatch. Out of 85 stage X WL eggs that were injected with the BRD cells infected with pLNHX-MDOT-IFN/VSVg virus, 47 survived and 15 of these hatched. The feather chimerism in these birds was between 5-85%.

In an alternative experiment, freshly isolated 6×10$^5$ BRD cells from stage X embryos were mixed with 4×10$^5$ pLNHX-CMVE-MDOT-IFN viral particle and incubated at 37° C. for 1 hour. The cells were gently stirred every 10-15 minutes. While the blastodermal cells were being processed, 150 freshly laid WL (stage X) eggs were collected and irradiated at 600 rads and set aside for the injections. A 5 µl cell suspension containing about 4000-5000 cells was injected into each of 107 irradiated stage X WL eggs through a small hole drilled in the shell. The eggs were sealed and incubated to hatch.

Out of 107 stage X WL eggs injected with the BPR cells infected with the pLNHX-CMVE-MDOT-IFN virus, 53 of these survived, of which 17 hatched. These birds showed varying degree of feather chimerism that ranged from 2-85%, as shown in Table 3 below.

TABLE 3

Chimera distribution of chicks transgenic for pLNHX-CMVE-MDOT-IFN virus

| Bird # | Chimerism % Black | Status | Sex |
| --- | --- | --- | --- |
| 457 | 75% | | Male |
| 458 | 15% | DEAD | |
| 459 | | | Female |
| 460 | | | |
| 461 | 85% | DEAD | |
| 462 | | | Female |
| 463 | 45% | | Male |
| 464 | 20% | | Male |
| 465 | 30% | DEAD | |
| 466 | | | Male |
| 467 | | | Female |
| 468 | | | |
| 469 | 30% | DEAD | |
| 470 | 2% | DEAD | |
| 471 | | DEAD | |
| 472 | | DEAD | |
| 473 | | DEAD | |

Blood samples were collected from these chicks when they were 6wk old. Interferon levels in 100 µl serum sample was analyzed using the h-IFN-ELISA Kit. Results of the assay are shown in FIG. 18. The successful detection of the transgene-encoded product (i.e. interferon) indicates that the BPR-injected cells were stably integrated into different tissues and thereby demonstrating that Moloney leukemia viruses pseudotyped with VSVg can be used for generating transgenic birds.

In a parallel experiment with a different MuLV/VSVg pseudotyped virus (PLNHX-MDOT-IFN), feather chimeric chicks that did not hatch (i.e. died during the incubation period) were collected. Three tissues, skin heart and lung, from these birds were analyzed for the presence of the transgene by TAQMAN® analysis. In three chicks, all three tissues showed the presence of the transgene. In the fourth chick, as shown in FIGS. 19 and 20, the transgene was detected in two of the tissues. These results show that the injected BPR cells infected with Moloney viruses pseudotyped with VSVg are stably integrated into different tissues of the chick.

6.30 Example 30

Construction of Lysozyme Promoter Plasmids

The chicken lysozyme gene expression control region isolated by PCR amplification is fully disclosed in U.S. patent application Ser. No. 09/922,549, filed Aug. 3, 2001 now U.S. Pat. No. 7,176,300 and incorporated herein by reference in its entirety. Ligation and reamplification of the fragments thereby obtained yielded a functionally contiguous nucleic acid construct comprising the chicken lysozyme gene expression control region operably linked to a nucleic acid sequence encoding a human interferon α2b polypeptide and optimized for codon usage in the chicken. Briefly, chicken (*Gallus gallus* (White Leghorn)) genomic DNA was PCR amplified using the primers 5pLMAR2 and LE-6.1kbrev1 in a first reaction, and Lys-6.1 and LysE1rev as primers in a second reaction. PCR cycling steps were: denaturation at 94° C. for 1 minute; annealing at 60° C. for 1 minute; extension at 72° C. for 6 minutes, for 30 cycles using TAQ PLUS PRECISION™ DNA polymerase (STRATAGENE®, LaJolla, Calif.). The PCR products from these two reactions were gel purified, and then united in a third PCR reaction using only 5pLMAR2 and LysE1rev as primers and a 10 minute extension period. The resulting DNA product was phosphorylated, gel-purified, and cloned into the EcoR V restriction site of the vector PBLUESCRIPT® KS, resulting in the plasmid p12.0-lys.

p12.0-lys was used as a template in a PCR reaction with primers 5pLMAR2 and LYSBSU and a 10 minute extension time. The resulting DNA was phosphorylated, gel-purified, and cloned into the EcoR V restriction site of PBLUESCRIPT® KS, forming plasmid p12.0lys-B.

p12.0lys-B was restriction digested with Not I and Bsu36 I, gel-purified, and cloned into Not I and Bsu36 I digested pCMV-LysSPIFNMM, resulting in p12.0-lys-LSPIFNMM. p12.0-lys-LSPIFNMM was digested with Sal I and the SalItoNotI primer was annealed to the digested plasmid, followed by Not I digestion. The resulting 12.5 kb Not I fragment, comprising the lysozyme promoter region linked to IFNMAGMAX-encoding region and an SV40 polyadenylation signal sequence, was gel-purified and ligated to Not I cleaved and dephosphorylated PBLUESCRIPT® KS, thereby forming the plasmid pAVIJCR-A115.93.1.2.

6.31 Example 31

Complete Lysozyme Promoter and IFNMAGMAX Sequences

The complete sequences of the lysozyme gene promoter and the codon-optimized human interferon α2b nucleic acid are fully disclosed in U.S. patent application Ser. No. 09/922,549, filed Aug. 3, 2001 and incorporated herein by reference in its entirety. The complete nucleotide sequence of the approximately 12.5 kb chicken lysozyme promoter region/IFNMAGMAX construct spans the 5' matrix attachment region (5' MAR), through the lysozyme signal peptide, to the sequence encoding the gene IFNMAGMAX and the subsequent polyadenylation signal sequence. The IFNMAGMAX nucleic acid sequence had been synthesized as described in Example 17 above. The expressed IFN α2b sequence within plasmid pAVIJCR-A115.93.1.2 functioned as a reporter gene for lysozyme promoter activity. This plasmid construct may also be used for production of interferon α2b in the egg white of transgenic chickens.

6.32 Example 32

Expression in Transfected Cultured Avian Oviduct Cells of Human Interferon α2b Regulated by the 12 kb Lysozyme Promoter The oviduct was removed from a Japanese quail (*Coturnix coturnix* japonica) and the oviduct cells transfected with the lysozyme promoter-IFNMAGMAX as described in Example 21, above. The supernatant was analyzed by ELISA for human interferon α2b content.

The human interferon α2b contents of medium derived from cultured oviduct cells transfected with either pAVIJCR-A115.93.1.2 or the negative control plasmid pCMV-EGFP, as shown in FIG. 16. Bars to the right of the figure represent the standards for the IFN ELISA.

6.33 Example 33

Production of Heterologous GM-CSF in Serum of Transgenic Chickens

Seventy-three birds were injected with CMV-GMCSF (ALV) wherein a nucleic acid encoding GM-CSF was functionally linked to the cytomegalovirus promoter. All were subsequently tested. Three control birds that had nothing injected were also included. For each bird tested, approximately 100 μl of blood was collected with heparinized tubes then diluted into 100 μl of PBS solution and spun to remove red blood cells. 100 μl of the plasma was then assayed.

As shown in Table 2 (below), three of the experimental birds had GM-CSF plasma levels that were higher than the highest available standard of 500 pg/ml used in the ELISAs.

TABLE 2 production of heterologous GM-CSF by heterologous chickens

| Band # | Diluted sample 100 μl dilutent/ 100 μl blood ng/ml | corrected results ng/ml | M/F | Transgene in sperm | Sperm Transgene +/− evaluation | Confor- mation | Egg Weight sample 1 (g) | Protein in egg sample 1 (pg/ml) | Egg Weight sample 2 (g) | Protein in egg sample 2 (pg/ml) |
|---|---|---|---|---|---|---|---|---|---|---|
| 1210 | 0.002 | 0.004 | F | | | | | | | |
| 1212 | 0 | 0 | M | | | | | | | |
| 4545 | 0 | 0 | M | NT | | | | | | |
| 5488 | 0.031 | 0.062 | M | NT | | | | | | |
| 8371 | 0 | 0 | M | 0 | | | | | | |
| 8374 | 0.03 | 0.06 | M | 0 | | | | | | |
| 8375 | 0 | 0 | M | 0 | | | | | | |
| 8376 | 0.003 | 0.006 | F | | | | 53.40 | 0.00 | 53.90 | 0.00 |
| 8380 | 0 | 0 | M | 0 | | | | | | |
| 8387 | 0 | 0 | M | NT | − | | | | | |
| 8389 | 0 | 0 | F | | | | 45.70 | 0.00 | 41.90 | 0.00 |
| 8391 | 0 | 0 | F | | | | 47.20 | 0.00 | 48.90 | 0.00 |
| 8392 | 0.007 | 0.014 | M | 0 | | | | | | |
| 8397 | 0 | 0 | M | NT | − | | | | | |
| 8400 | 0 | 0 | M | 0 | | | | | | |
| 8401 | 0 | 0 | M | NT | − | | | | | |
| 8402 | 0.674 | 1.348 | M | 50 copies | | | | | | |
| 8403 | 0 | 0 | M | 50 copies | | | | | | |
| 8406 | 0 | 0 | F | | | | | | | |
| 8410 | 0 | 0 | F | | | | 45.90 | 0.00 | 47.40 | 0.00 |
| 8413 | 0.003 | 0.006 | F | | | | 41.50 | 0.00 | 43.70 | 0.00 |
| 8415 | 0 | 0 | M | 0 | | | | | | |
| 8416 | 0.039 | 0.078 | M | 50 copies | | | | | | |
| 8417 | 0 | 0 | M | NT | − | | | | | |
| 8424 | 0 | 0 | M | NT | + | + | | | | |
| 8425 | 0 | 0 | F | | | | 44.80 | 0.00 | 44.10 | 0.00 |
| 8426 | 0 | 0 | M | 50 copies | | | | | | |
| 8429 | 0 | 0 | M | 500 copies | − | | | | | |
| 8430 | 0.091 | 0.182 | M | NT | | | | | | |
| 8432 | 0 | 0 | M | 0 | + | | | | | |
| 8433 | 0 | 0 | M | >500 copies | − | − | | | | |
| 8440 | 0 | 0 | M | NT | − | | | | | |
| 8444 | 0 | 0 | M | 0 | − | | | | | |
| 8447 | 0 | 0 | F | | | | 35.60 | 0.00 | 58.90 | 0.00 |
| 8448 | 0 | 0 | M | NT | − | | | | | |
| 8449 | 0 | 0 | F | | | | 49.60 | 0.00 | 46.80 | 0.00 |
| 8452 | 0.706 | 1.412 | F | | | | 41.70 | 4117.25 | 39.80 | 4051.31 |
| 8454 | 0 | 0 | M | 0 | − | | | | | |
| 8455 | 0 | 0 | M | NT | | | | | | |
| 8456 | 0 | 0 | F | | | | | | | |
| 8460 | 0.027 | 0.054 | M | 500 copies | − | − | | | | |
| 8461 | 0 | 0 | M | 500 copies | − | − | | | | |
| 8462 | 0.063 | 0.126 | F | | | | 45.80 | 0.00 | 54.40 | 0.00 |
| 8463 | 0 | 0 | M | 0 | − | | | | | |
| 8464 | 0.057 | 0.114 | M | 0 | − | | | | | |
| 8467 | 0 | 0 | F | | | | 53.90 | 0.00 | 51.50 | 0.00 |

TABLE 2-continued production of heterologous GM-CSF by heterologous chickens

| Band # | Diluted sample 100 μl dilutent/ 100 μl blood ng/ml | corrected results ng/ml | M/F | Transgene in sperm | Sperm Transgene +/− evaluation | Confor- mation | Egg Weight sample 1 (g) | Protein in egg sample 1 (pg/ml) | Egg Weight sample 2 (g) | Protein in egg sample 2 (pg/ml) |
|---|---|---|---|---|---|---|---|---|---|---|
| 8468 | 0 | 0 | M | 0 | | | | | | |
| 8470 | 0 | 0 | M | 0 | | − | | | | |
| 8473 | 0 | 0 | F | | | | 40.70 | 0.02 | 56.80 | 0.00 |
| 8475 | 0 | 0 | F | | | | 41.50 | 0.00 | 41.00 | 0.00 |
| 8478 | 0 | 0 | M | 500 copies | − | − | | | | |
| 8482 | 0 | 0 | F | | | | 38.10 | 0.00 | | |
| 8483 | 0 | 0 | M | 50 copies | | | | | | |
| 8485 | 0 | 0 | M | NT | | | | | | |
| 8489 | 0 | 0 | M | 500 copies | + | + | | | | |
| 8490 | 0 | 0 | M | 0 | − | | | | | |
| 8497 | 0 | 0 | M | NT | − | | | | | |
| 8499 | 0 | 0 | M | 500 copies | − | − | | | | |
| 8500 | 0 | 0 | M | 0 | − | | | | | |
| 8501 | 0 | 0 | F | | | | 38.10 | 0.00 | 37.60 | 0.00 |
| 8502 | 0 | 0 | F | | | | 44.10 | 0.01 | 47.10 | 0.00 |
| 8508 | 0.086 | 0.172 | M | NT | + | + | | | | |
| 8509 | 1.068 | 2.136 | F | | | | 72.30 | 0.00 | 48.50 | 0.00 |
| 8514 | 0 | 0 | F | | | | 45.30 | 0.00 | 44.70 | 0.00 |
| 8518 | 0 | 0 | F | | | | 48.70 | 0.00 | 47.30 | 0.00 |
| 8521 | 0 | 0 | F | | | | 49.00 | 0.00 | 47.70 | 0.00 |
| 8525 | 0.016 | 0.032 | F | | | | 54.10 | 0.00 | 49.10 | 0.01 |
| 8526 | 0 | 0 | M | 500 copies | + | ++ | | | | |
| 8528 | 0.013 | 0.026 | M | 500 copies | + | ++ | | | | |
| 8531 | 0 | 0 | M | 0 | − | | | | | |
| 8650 | 0.001 | 0.002 | F | | | | 45.60 | 16.55 | 46.50 | 0.04 |
| 8653 | 0.045 | 0.09 | F | | | | 44.60 | 0.00 | 44.30 | 0.00 |
| 8720 | 0 | 0 | M | NT | | | | | | |
| S8484(c) | 0 | 0 | F | | | | | | | |
| S8507(c) | 0 | 0 | F | | | | | | | |
| S8508(c) | 0 | 0 | F | | | | | | | |

When the dilution is factored in, three birds had greater than approximately 1 ng/ml. Eleven additional birds had GM-CSF levels within the range detectable by ELISA, from 26 pg/ml to 182 pg/ml (with the dilution factored in). Control birds S8484, S8507 and S8508 were negative.

6.34 Example 34

Synthesis of the MDOT Promoter Construct

Amplification of the Ovomucoid and Ovotransferrin Promoter Sequences

Oligonucleotide primers 1 (SEQ ID NO: 38) and 2 (SEQ ID NO: 39), as shown in FIG. 22 were used to amplify the ovomucoid sequences. Oligonucleotide primers 3 (SEQ ID NO: 40) and 4 (SEQ ID NO: 41) were used to amplify the ovotransferrin sequence by PCR. The primers were designed such that the PCR-amplified ovomucoid sequences contained an Xho I restriction cleavage site at the 5' end and a Cla I site at the 3' end. Similarly, the PCR-amplified ovotransferrin product had a Cla I restriction site at the 5' end and a Hind III site at the 3' end. The overlapping Cla I site was used to splice the two-PCR products to create the MDOT promoter construct. The nucleic acid sequence SEQ ID NO: 11 of the MDOT promoter construct is shown in FIG. 14. The final product was cloned in a bluescript vector between the Xho I and Hind III sites. From the bluescript vector the promoter region was released by Kpn I/Hind III restriction digestion and cloned into the prc-CMV-IFN vector to replace the CMV promoter to create MDOT-IFN (clone #10). This plasmid was tested in vitro.

Interferon Synthesis Directed by the MDOT Promoter in Transfected Oviduct Cells.

The promoter activity was tested in vitro by transfecting the plasmid construct into tubular gland cells isolated from the quail oviduct. The transfected cells were treated with hormones (progesterone, estrogen and insulin). At 72 hrs after transfection, the supernatant media of the transfected cells were collected and the interferon levels analyzed using an ELISA assay. The results, as shown in FIG. 23 show a significant induction of interferon α2b expression in hormonally treated cells.

6.35 Example 35

Production of Erythropoietin in the Serum of Transgenic Chickens

Sixty birds were injected with a nucleic acid construct comprising a nucleic acid region encoding erythropoietin (EPO) 3' of, and operably linked to, the MDOT artificial promoter in the ALV vector (MDOT-EPO (ALV)) described in Example 34, above. All birds were subsequently tested. Two control birds that had nothing injected were also tested. Approximately 100 μl of blood from each bird was diluted into 100 μl of PBS/EDTA solution and spun to remove red blood cells. 100 μl of the plasma was then assayed.

As shown in Table 4 below, twenty-three of the experimental birds had EPO levels in their plasma higher than the highest available ELISA standard of 1540 pg/ml.

TABLE 4

Production of erythropietin under the control of promoter MDOT

| | ELISA | | | Taqman ® | | EGG | | EGG | | EGG | |
| | Diluted sample | | | Sperm | | ELISA | | ELISA | | ELISA | |
| | (100 ul | | | | | | | | | | |
| | dilutent/ 100 ul | corrected results | | Transgene +/− | Confirm- | Protein in egg | | Protein in egg | | Protein in egg | |
| Band # | blood) ng/ml | ng/ml | M/F | evaluation | ation | (pg/ml) | | (pg/ml) | | (pg/ml) | |
|---|---|---|---|---|---|---|---|---|---|---|---|
| 300 | 6.067 | 12.134 | F | | | 1011.403 | 697.186 | 2792.153 | 1848.942 | 2529.037 | 1711.554 |
| 301 | 0.45 | 0.9 | M | + | ++ | | | | | | |
| 302 | 6.187 | 12.374 | M | ++ | ++ | | | | | | |
| 303 | 0.771 | 1.542 | M | +++ | +++ | | | | | | |
| 304 | 0.56 | 1.12 | M | − | | | | | | | |
| 305 | 0.545 | 1.09 | F | | | 1562.893 | | 1859.896 | 2405.046 | 1702.548 | 1926.763 | 2108.639 |
| 306 | 0.682 | 1.364 | M | + | | | | | | | |
| 307 | 6.245 | 12.49 | M | + | | | | | | | |
| 308 | 6.24 | 12.48 | F | | | NT | | 17918.84 | 24599.5 | 17378.85 | 25764.39 |
| 309 | 6.211 | 12.422 | M | − | − | | | | | | |
| 310 | 6.25 | 12.5 | M | − | − | | | | | | |
| 311 | 6.245 | 12.49 | M | ++ | ++ | | | | | | |
| 312 | 2.239 | 4.478 | M | + | | | | | | | |
| 314 | 4.545 | 9.09 | F | | | 691.466 | | 1979.496 | 2203.295 | 2128.271 | 1869.904 |
| 316 | 4.738 | 9.476 | M | − | | | | | | | |
| 317 | 1.841 | 3.682 | F | | | 0 | | 149.161 | 0 | | |
| 320 | 1.028 | 2.056 | M | ++ | | | | | | | |
| 321 | 0.029 | 0.058 | M | − | | | | | | | |
| 322 | 0 | 0 | M | − | | | | | | | |
| 323 | 6.148 | 12.296 | M | ++ | ++ | | | | | | |
| 324 | 0 | 0 | F | | | NT | | 0 | 0 | | |
| 325 | 1.683 | 3.366 | F | | | NT | | | | | |
| 327 | 0 | 0 | M | NT | | | | | | | |
| 328 | 0 | 0 | M | − | | | | | | | |
| 329 | 0.975 | 1.95 | M | NT | | | | | | | |
| 330 | 6.263 | 12.526 | F | | | 4118.945 | 2592.05 | 7515.93 | 5638.896 | | |
| 331 | 0.533 | 1.066 | M | + | | | | | | | |
| 332 | 0.319 | 0.638 | M | + | | | | | | | |
| 333 | 1.969 | 3.938 | M | redo | − | | | | | | |
| 334 | 0 | 0 | F | | | | | 0 | 0 | | |
| 335 | 0 | 0 | F | | | NT | | 0 | 0 | | |
| 336 | 0.356 | 0.712 | F | | | NT | | 1800.975 | 2360.708 | 1536.928 | 2551.83 |
| 337 | 0.437 | 0.874 | M | − | | | | | | | |
| 338 | 0.306 | 0.612 | F | | | NT | | 0 | 0 | 0 | |
| 339 | 6.255 | 12.51 | M | ++ | ++ | | | | | | |
| 340 | 0.009 | 0.018 | M | − | | | | | | | |
| 341 | 0.436 | 0.872 | M | ++ | ++ | | | | | | |
| 342 | 2.314 | 4.628 | M | ++ | ++ | | | | | | |
| 343 | 0.083 | 0.166 | M | − | | | | | | | |
| 344 | 0.219 | 0.438 | M | ++ | + | | | | | | |
| 345 | 0.195 | 0.39 | F | | | 0 | | 375.962 | 1465.576 | 349.881 | 1936.851 |
| 346 | 0.429 | 0.858 | F | | | NT | | | | | |
| 348 | 0.422 | 0.844 | M | + | | | | | | | |
| 349 | 1.199 | 2.398 | M | − | | | | | | | |
| 350 | 0.1 | 0.2 | M | +++ | +++ | | | | | | |
| 352 | 0.29 | 0.58 | F | | | NT | | 141.163 | 296.148 | | |
| 353 | 0.572 | 1.144 | F | | | NT | | 802.981 | 747.527 | | |
| 354 | 6.243 | 12.486 | F | | | NT | | 0 | | | |
| 356 | 1.225 | 2.45 | M | + | | | | | | | |
| 357 | 0.038 | 0.076 | F | | | NT | | 118.717 | 0 | | |
| 359 | 0.002 | 0.004 | F | | | NT | | 52.913 | 38.691 | | |
| 360 | 2.318 | 4.636 | M | + | | | | | | | |
| 362 | 1.055 | 2.11 | F | | | NT | | 0 | 0 | | |
| 363 | 6.242 | 12.484 | F | | | 517.406 | | 1005.69 | 2033.381 | 747.537 | 1980.494 |
| 365 | 0.446 | 0.892 | M | ++ | ++ | | | | | | |
| 367 | | | | | | | | 0 | 92.454 | | |
| 368 | | | | | | | | 0 | 69.274 | | |
| 369 | | | M | − | | | | | | | |
| 608 | 6.191 | 12.382 | M | NT | ++ | | | | | | |
| 609 | 0 | 0 | M | NT | | | | 0 | 0 | | |
| 1173 | 0 | 0 | M | NT | − | | | | | | |
| 1174 | 1.614 | 3.228 | M | NT | ++ | | | | | | |
| 1175 | 6.252 | 12.504 | M | NT | − | | | | | | |
| 1204 | 0 | 0 | F | | | NT | | | | | |
| 367 | 0 | 0 | F | | | NT | | | | | |

When the dilution is factored in, 23 birds have greater than approximately 3080 pg/ml. An additional 27 birds had EPO levels within the range detectable by ELISA, from 58 pg/ml to 2450 pg/ml (with the dilution factored in). Control birds were negative.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged both in whole or in part.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. A method of producing a transgenic avian comprising:
   microinjecting into a cell of an avian embryo a nucleic acid comprising a transgene comprising a nucleotide sequence encoding a heterologous polypeptide;
   introducing the microinjected avian embryo into an oviduct of a recipient hen, such that the recipient hen lays a shelled egg containing the microinjected avian embryo;
   incubating the shelled egg containing the microinjected avian embryo until the egg hatches;
   testing a hatched chick for the presence of the transgene; and
   developing a chick that tests positive for the transgene to sexual maturity.

2. The method of claim 1 wherein the embryo is isolated from a hen.

3. The method of claim 1 wherein the embryo is a stage I embryo.

4. The method of claim 1 wherein the coding sequence is expressed in one or more cells of the transgenic avian.

5. The method of claim 1 where in the heterologous polypeptide is present in the serum of the transgenic avian.

6. The method of claim 1 where in the heterologous polypeptide is expressed in the magnum of the transgenic avian.

7. The method of 1 wherein the heterologous polypeptide is present in the white of an egg produced by the transgenic avian.

8. The method of claim 1 wherein the coding sequence is operably linked to a transcriptional regulatory element that can direct gene expression in one or more cells of the tranagenic avian.

9. The method of claim 8 wherein the transcriptional regulatory element is a promoter region of an avian gene which encodes a protein selected from the group consisting of ovalbumin, lysozyme, ovomucoid, ovomucin, conalbumin and ovotransferrin.

10. The method of claim 8 wherein the transcriptional regulatory element is a regulatable promoter.

11. The method of claim 8 wherein the transcriptional regulatory element is a tissue specific promoter.

12. The method of claim 8 wherein the transcriptional regulatory element comprises at least two regions derived from the promoter of an avian gene, the regions being from different promoters.

13. The method of claim 1 wherein the nucleotide sequence comprises at least one cytomegalovirus promoter.

14. The method of claim 1 wherein the nucleotide sequence comprises at least one matrix attachment region (MAR).

15. The method of claim 14 wherein the nucleotide sequence comprises a 5' MAR and a 3' MAR which flank the nucleotide sequence.

16. The method of claim 1 wherein the nucleotide sequence is bound to a nuclear localization signal (NLS) peptide during microinjection.

17. The method of claim 1 wherein the heterologous polypeptide is selected from the group consisting of a cytokine, a hormone, an enzyme and an immunolobulin polypeptide.

18. The method of claim 1 wherein the heterologous polypeptide is selected from the group consisting of interferon, interleukin, granulocyte colony-stimulating factor, granulocyte-macrophage colony-stimulating factor, erythropoietin, thrombopoietin and stem cell factor.

19. The method of claim 1 wherein the transgene comprises an internal ribosome entry site (IRES).

20. The method of claim 1 wherein the transgene comprises at least two coding sequences each encoding a heterologous polypeptide.

21. The method of claim 20 wherein the at least two nucleotide sequences encode at least two heterologous peptides that form a multimeric protein.

22. The method of claim 21 wherein the multimeric protein specifically binds a ligand.

23. The method of claim 21 wherein the multimeric protein is an antibody.

24. The method of claim 1 wherein the heterologous polypeptide comprises a peptide region useful for isolation of the heterologous polypeptide.

25. The method of claim 1 wherein the nucleotide sequence comprises a vector.

26. The method of claim 1 wherein the nucleotide sequence comprises a plasmid vector.

27. The method of claim 1 wherein the nucleotide sequence is not a eukaryotic viral vector.

28. The method of claim 1 wherein the transgenic avian is not produce using a eukaryotic viral vector.

29. The method of claim 1 comprising isolating the heterologous peptide from the transgenic avian or from an egg laid by the transgenic avian.

30. A method of producing a transgenic avian comprising:
microinjecting into a cell of an avian embryo a nucleic acid comprising a transgene comprising a nucleotide sequence encoding a pharmaceutical protein;
introducing the microinjected avian embryo into an oviduct of a recipient hen, such that the recipient hen lays a shelled egg containing the microinjected avian embryo;
incubating the shelled egg containing the microinjected avian embryo until the egg hatches;
testing a hatched chick for the presence of the transgene; and
developing a chick that tests positive for the transgene to sexual maturity.

31. The method of claim 1 or 30 wherein the avian is a chicken.

32. The method of claim 30 wherein the coding sequence is expressed in one or more cells of the transgenic avian.

33. The method of claim 30 wherein the heterologous polypeptide is present in the white of an egg produced by the transgenic avian.

34. The method of claim 30 wherein the coding sequence is operably linked to transcriptional regulatory element that can direct gene expression in one or more cells of the transgenic avian.

35. The method of claim 34 wherein the transcriptional regulatory element is a promoter region of an avian gene which encodes a protein selected from the group consisting of ovalbumin, lysozyme, ovomucoid, ovomucin, conalbumin and ovotransferrin.

36. The method of claim 30 wherein the heterologous polypeptide is selected from the group consisting of a cytokine, a hormone, an enzyme, an immunoglobulin polypeptide, interferon, interleukin, granulocyte colony-stimulating factor, granulocyte-macrophage colony-stimulating factor, erythropoietin, thrombopoietin and stem cell factor.

37. The method of claim 30 wherein the transgene comprises at least two coding sequences each encoding a heterologous polypeptide.

38. The method of claim 30 wherein the nucleotide sequence comprises a vector.

39. The method of claim 30 comprising isolating the heterologous peptide from the transgenic avian or from an egg laid by the transgenic avian.

40. A method of producing a transgenic chicken comprising:
microinjecting into a cell of an embryo of a chicken a nucleic acid comprising a transgene comprising a nucleotide sequence encoding a heterologous polypeptide;
introducing the chicken embryo into an oviduct of a recipient chicken, such that the recipient chicken lays a shelled egg containing the microinjected chicken embryo;
incubating the shelled egg containing the microinjected chicken embryo until the egg hatches;

testing a hatched chick for the presence of the transgene; and developing a chick that tests positive for the transgene to sexual maturity.

41. The method as in any one of claims 1, 30 or 40 wherein the nucleic acid is DNA.

* * * * *